US011446375B2

(12) United States Patent
Chuah et al.

(10) Patent No.: US 11,446,375 B2
(45) Date of Patent: Sep. 20, 2022

(54) ENDOTHELIUM-SPECIFIC NUCLEIC ACID REGULATORY ELEMENTS AND METHODS AND USE THEREOF

(71) Applicant: Vrije Universiteit Brussel, Brussels (BE)

(72) Inventors: Marinee Chuah, Bierbeek (BE); Thierry Vandendriessche, Bierbeek (BE)

(73) Assignee: Vrije Universiteit Brussel, Brussels (BE)

(*) Notice: Subject to any disclaimer, the term of this patent is extended or adjusted under 35 U.S.C. 154(b) by 330 days.

(21) Appl. No.: 16/065,629

(22) PCT Filed: Dec. 22, 2016

(86) PCT No.: PCT/EP2016/082314
§ 371 (c)(1),
(2) Date: Jun. 22, 2018

(87) PCT Pub. No.: WO2017/109039
PCT Pub. Date: Jun. 29, 2017

(65) Prior Publication Data

US 2020/0237900 A1 Jul. 30, 2020

(30) Foreign Application Priority Data

Dec. 22, 2015 (WO) ................ PCT/EP2015/081075

(51) Int. Cl.
*A61K 39/23* (2006.01)
*C12N 15/86* (2006.01)
*C12N 15/67* (2006.01)

(52) U.S. Cl.
CPC .............. *A61K 39/23* (2013.01); *C12N 15/67* (2013.01); *C12N 15/86* (2013.01);
(Continued)

(58) Field of Classification Search
CPC .................... A61K 39/23; C12N 15/86; C12N 2740/15043; C12N 2750/14143; C12N 2830/008
See application file for complete search history.

(56) References Cited

U.S. PATENT DOCUMENTS

| | | | |
|---|---|---|---|
| 5,656,454 A | 8/1997 | Lee et al. | |
| 6,524,815 B1 * | 2/2003 | Huber .................... | A61P 35/00 435/69.1 |

(Continued)

FOREIGN PATENT DOCUMENTS

| | | |
|---|---|---|
| EP | 1 264 892 | 12/2002 |
| JP | 2005204549 | 8/2005 |

(Continued)

OTHER PUBLICATIONS

Sequence Alignment SEQ 9 (RAFFI) and SEQ 1 (U.S. Appl. No. 16/065,629) (Year: 2020).*

(Continued)

*Primary Examiner* — Kevin K Hill
*Assistant Examiner* — Anjeanette Roberts
(74) *Attorney, Agent, or Firm* — McDonnell Boehnen Hulbert & Berghoff LLP

(57) ABSTRACT

The present invention relates to nucleic acid regulatory elements that are able to enhance endothelial cell-specific expression of genes, methods employing these regulatory elements and uses of these elements. Expression cassettes and vectors containing these nucleic acid regulatory elements are also disclosed. The present invention is particularly useful for applications using gene therapy, more particularly endothelial cell-directed gene therapy, and for vaccination purposes.

21 Claims, 11 Drawing Sheets

Specification includes a Sequence Listing.

(52) U.S. Cl.
CPC .............. *C12N 2740/15043* (2013.01); *C12N 2750/14143* (2013.01); *C12N 2830/00* (2013.01); *C12N 2830/008* (2013.01)

(56) References Cited

U.S. PATENT DOCUMENTS

| | | | | |
|---|---|---|---|---|
| 2005/0112110 | A1 | 5/2005 | Harats et al. | |
| 2007/0161031 | A1 | 7/2007 | Trinklein et al. | |
| 2011/0065100 | A1 | 3/2011 | Aldred et al. | |
| 2012/0301443 | A1 * | 11/2012 | Raffi ...................... | C12N 5/069 424/93.7 |
| 2014/0017215 | A1 | 1/2014 | Ayares et al. | |

FOREIGN PATENT DOCUMENTS

| | | | | |
|---|---|---|---|---|
| JP | 2015-109833 A | | 6/2015 | |
| WO | WO-2008073303 A2 | * | 6/2008 | ......... C12N 15/1051 |
| WO | WO 2011/090684 A2 | | 7/2011 | |

OTHER PUBLICATIONS

Nabel EG. Gene therapy for cardiovascular disease. Circulation. Jan. 15, 1995;91(2):541-8. (Year: 1995).*

Luckow B, Schütz G. CAT constructions with multiple unique restriction sites for the functional analysis of eukaryotic promoters and regulatory elements. Nucleic Acids Research. Jul. 10, 1987;15(13):5490. (Year: 1987).*

Izsvák Z, Ivics Z. Sleeping beauty transposition: biology and applications for molecular therapy. Molecular Therapy. Feb. 1, 2004;9(2):147-56. (Year: 2004).*

Bio Cat webpage (dated Aug. 16, 2015 biocat.com/genomics/piggybac-transposon-system) retrieved via Wayback Machine Apr. 9, 2021. (Year: 2015).*

Kren, B. T., Unger, G. M., Sjeklocha, L., et al. Nanocapsule-delivered Sleeping Beauty mediates therapeutic Factor VIII expression in liver sinusoidal endothelial cells of hemophilia A mice. The Journal of clinical investigation, 2009; 119(7), 2086-2099. (Year: 2009).*

Zheng C, Baum BJ. Evaluation of promoters for use in tissue-specific gene delivery. Gene Therapy Protocols 2008 (pp. 205-219). Humana Press. (Year: 2008).*

De Palma M, Venneri MA, Naldini L. In vivo targeting of tumor endothelial cells by systemic delivery of lentiviral vectors. Human gene therapy. Aug. 10, 2003; 14(12):1193-206. (Year: 2003).*

Dull T, Zufferey R, Kelly M, Mandel RJ, Nguyen M, Trono D, Naldini L. A third-generation lentivirus vector with a conditional packaging system. Journal of virology. Nov. 1, 1998;72(11):8463-71. (Year: 1998).*

De Wet JR, Wood KV, Helinski DR, DeLuca M. Cloning of firefly luciferase cDNA and the expression of active luciferase in *Escherichia coli*. Proceedings of the National Academy of Sciences. Dec. 1, 1985;82(23):7870-3. (Year: 1985).*

Bert AG, Burrows J, Osborne CS, Cockerill PN. Generation of an improved luciferase reporter gene plasmid that employs a novel mechanism for high-copy replication. Plasmid. Sep. 1, 2000;44(2):173-82. (Year: 2000).*

Prandini MH, Dreher I, Bouillot S, Benkerri S, Moll T, Huber P. The human VE-cadherin promoter is subjected to organ-specific regulation and is activated in tumour angiogenesis. Oncogene. Apr. 2005;24(18):2992-3001. (Year: 2005).*

Papac-Milicevic N, Breuss JM, Zaujec J, Ryban L, Plyushch T, Wagner GA, Fenzl S, Dremsek P, Cabaravdic M, Steiner M, Glass CK. The interferon stimulated gene 12 inactivates vasculoprotective functions of NR4A nuclear receptors. Circulation research. Apr. 13, 2012;110(8):e50-63. (Year: 2012).*

Rafii S, Kloss CC, Butler JM, et al. Human ESC-derived hemogenic endothelial cells undergo distinct waves of endothelial to hematopoietic transition. Blood, The Journal of the American Society of Hematology. Jan. 31, 2013;121(5):770-80. (Year: 2013).*

Abel et al.,"Specific gene delivery to liver sinusoidal and artery endothelial cells." Blood. 122(12):2030-8 (Sep. 2013).

Altshcul et al., "Basic Local Alignment Search Tool," J Mol Biol 215:403-10 (1990).

Anliker et al., "Specific gene transfer to neurons, endothelial cells and hematopoietic progenitors with lentiviral vectors." Nat Methods. 7(11):929-35 (Nov. 2010; Epub Oct. 10, 2010).

Bhasin et al., "Bioinformatic identification and characterization of human endothelial cell-restricted genes," BMC Genomics, 11:342, pp. 1-18 (May 2010).

Buchholz et al. "Surface-Engineered Viral Vectors for Selective and Cell Type-Specific Gene Delivery." Trends Biotechnol. 33(12):777-90 (Dec. 2015; Epub Oct. 20, 2015).

Dai et al., "Identification of Synthetic Endothelial Cell-Specific Promoters by Use of a High-Throughput Screen," Journal of Virology 87(12):6209-21 (Jun. 2004).

DeLeve et al., "Liver sinusoidal endothelial cells and liver regeneration," J Clin. Invest. 123(5):1861-66 (May 2013 Epub May 1, 2013).

De Leeuw et al., "Sinusoidal endothelial cells of the liver: fine structure and function in relation to age." J Electron Microsc Tech. 14(3):218-36 (Mar. 1990).

Flynn et al., "Helper-dependent Adenoviral Vectors are Superior In Vitro to First-generation Vectors for Endothelial Cell-targeted Gene Therapy," Mol Ther. 18(12):2121-9 (Dec. 2010).

Godwin et al., "Towards endothelial cell-specific transgene expression in pigs: characterization of the pig ICAM-2 promoter," Xenotransplantation 13(6):515-21 (Nov. 2006).

Levitt et al., "Definition of an efficient synthetic poly(A) site." Genes Dev 3(7):1019-1025 (Jul. 1989).

Mavria et al., "Generation of a high title retroviral vector for endothelial cell-specific gene expression in vivo," Gene Therapy 7(5):368-76 (Mar. 2000).

McCarty et al., "Self-complementary recombinant adeno-associated virus (scAAV) vectors promote efficient transduction independently of DNA synthesis," Gene Therapy 8(16):1248-54 (Aug. 2001).

McCarty et al., "Adeno-associated virus terminal repeat (TR) mutant generates self-complementary vectors to overcome the rate-limiting step to transduction in vivo," Gene Therapy 10(26):2112-8 (Dec. 2003).

Modlich et al., "Increasing endothelial cell specific expression by the use of heterologous hypoxic and cytokine-inducible enhancers," Gene Therapy 7(10):896-902 (May 2000).

Munch et al., "DARPins: an efficient targeting domain for lentiviral vectors." Mol Ther. 9(4):686-93 (Apr. 2011; Epub Jan. 11, 2011).

Munch et al., "Off-target-free gene delivery by affinity-purified receptor-targeted viral vectors." Nat Commun. 10;6:6246 (Feb. 2015).

Munch et al., "Overexpression of ABCG1 protein attenuates arteriosclerosis and endothelial dysfunction in atherosclerotic rabbits," Heart Int. 7(2): e12, pp. 108 (Jun. 2012).

Nathwani et al., "Sustained high-level expression of human factor IX (hFIX) after liver-targeted delivery of recombinant adeno-associated virus encoding the hFIX gene in rhesus macaques," Blood 100(5): 1662-9 (Sep. 2002).

Nathwani et al., "Self-complementary adeno-associated virus vectors containing a novel liver-specific human factor IX expression cassette enable highly efficient transduction of murine and nonhuman primate liver," Blood 107(7):2653-61 (Apr. 2006; Epub Dec. 1, 2005).

Nathwani et al., "Adenovirus-Associated Virus Vector-Mediated Gene Transferin Hemophilia B," N. Engl. J. Med. 365(25):2357-65 (Dec. 2011; Epub Dec. 10, 2011).

Neumann et al., "Liver sinusoidal endothelial cells induce immunosuppressive IL-10-producing Th1 cells via the Notch pathway." Eur J Immunol. 45(7):2008-16 (Jul. 2015; Epub May 12, 2015).

Nicol et al., "Use of in vivo phage display to engineer novel adenoviruses for targeted delivery to the cardiac vasculature." FEBS Lett. 583(12):2100-7 (Jun. 2009; Epub May 28, 2009).

Nicklin & Baker, "Efficient vascular endothelial gene transfer following intravenous adenovirus delivery." Mol Ther. 16(12):1904-5 (Dec. 2008).

(56) References Cited

OTHER PUBLICATIONS

Shahani et al., "Human liver sinusoidal endothelial cells but not hepatocytes contain factor VIII." J. Thromb. Hemost 12(1):36-42 (Jan. 2014).
Shahani et al., "Activation of human endothelial cells from specific vascular beds induces the release of a FVIII storage pool." Blood. 115(23):4902-9 (Jun. 2010; Epub Mar. 29, 2010).
Tatusov & Madden, "Blast 2 Sequences, a new tool for comparing protein and nucleotide sequences," FEMS Microbiol Lett 174:247-50 (1999).
Vandendriessche et al., "Lentiviral vectors containing the human immunodeficiency virus type-1 central polypurine tract can efficiently transduce nondividing hepatocytes and antigen-presenting cells in vivo." Blood 100(3):813-22 (Aug. 2002).
Vandendriessche et al., "Efficacy and safety of adeno-associated viral vectors based on serotype 8 and 9 vs. lentiviral vectors for hemophilia B gene therapy." J Thromb Haemost. 5(1):16-24 (Jan. 2007; Epub Sep. 26, 2006).
Vandendriessche & Chuah, "Targeting endothelial cells by gene therapy." 122(12):1993-4 (Sep. 2013).
White et al., "Assessment of a novel, capsid-modified adenovirus with an improved vascular gene transfer profile." J Cardiothorac Surg. 8:183 pp. 1-8 (Aug. 2013).
White et al., "Targeted gene delivery to vascular tissue in vivo by tropism-modified adeno-associated virus vectors." Circulation. 109(4):513-9 (Feb. 2004; Epub Jan. 19, 2004).
Work et al., "Improved gene delivery to human saphenous vein cells and tissue using a peptide-modified adenoviral vector." Genet Vaccines Ther. 2(1):14 (Oct. 2004).
Work et al., "In vivo biopanning: A methodological approach to identifying novel targeting ligands for delivery of biological agents to the vasculature." Methods Mol Med. 108:395-413 (2005).
Work et al., "Vascular bed-targeted in vivo gene delivery using tropism-modified adeno-associated viruses." Mol Ther. 13(4):683-93 (Apr. 2006; Epub Jan. 4, 2006).
Wu et al., "Optimization of self-complementary AAV vectors for liver-directed expression results in sustained correction of hemophilia B at low vector dose," Mol Ther. 16(2):280-9 (Feb. 2009; Epub Dec. 4, 2007).
GenBank: CE 213087.1 "tigr-gss-dog-17000372777183 Dog Canine lupus familiaris genomic, genomic survey sequence" Entry created Sep. 25, 2003, one page.
The International Search Report from International Application No. PCT/EP2016/082314; dated Mar. 3, 2017, pp. 1-4.
Martensen et al., "The interferon alpha induced protein ISG12 is localized to the nuclear membrane," Eur J Biochem. 268(22):5947-54 (2001).
Genbank Accession No. AJ296088.1 "Homo sapiens promoter region of ISG12 gene," published on Jan. 7, 2002 [retrieved from the internet https://www.ncbi.nlm.nih.gov/nuccore/AJ296088.1] [1 page].

* cited by examiner

SEQUENCE LISTING

<160> NUMBER OF SEQ ID NOS: 56

<210> SEQ ID NO 1
<211> LENGTH: 76
<212> TYPE: DNA
<213> ORGANISM: Homo sapiens

<400> SEQUENCE: 1
gccctcacaa aggaacaata acaggaaacc atcccagggg gaagtgggcc agggccagct 60
ggaaaacctg aagggg 76

<210> SEQ ID NO 2
<211> LENGTH: 277
<212> TYPE: DNA
<213> ORGANISM: Homo sapiens

<400> SEQUENCE: 2
ggccgaggca gccgcccacc gcagggcctg cctatctgca gccagcccag ccctcacaaa 60
ggaacaataa caggaaacca tcccaggggg aagtgggcca gggccagctg gaaaacctga 120
aggggaggca gccaggcctc cctcgccagc ggggtgtggc tcccctccaa agacggtcgg 180
ctgacaggct ccacagagct ccactcacgc tcagccctgg acggacaggc agtccaacgg 240
aacagaaaca tccctcagcc cacaggcacg gtgagtg 277

<210> SEQ ID NO 3
<211> LENGTH: 408
<212> TYPE: DNA
<213> ORGANISM: Homo sapiens

<400> SEQUENCE: 3
gcttcctcct ctgctactaa tctggtctca cagaccatcc catttcctgc tagcccacca 60
gccgccttcc ttgctcccaa tgacacttcc tggccttgtg ccctcctgtt acctcctttg 120
cctccagaga ggttggagca gaggctgggc agtgccagaa atcaggcatg aaatcctcag 180
ggggaccaag gaggcaccag cctccctccc acagtctcag ctacctctgc tacggtgacc 240
cccagcccca cccctggggc ccacagctca tgcctggctc accattcctt tgtttatgga 300
ccacaggaac agtcgttttc agggcagagt caacttcctc atggactggg agtacaaagg 360
gaattggcag atggtgccag gacaggccct gtccccatct gccacagc 408

<210> SEQ ID NO 4
<211> LENGTH: 173
<212> TYPE: DNA
<213> ORGANISM: Homo sapiens

<400> SEQUENCE: 4
gcttcctcct ctgctactaa tctggtctca cagaccatcc catttcctgc tagcccacca 60
gccgccttcc ttgctcccaa tgacacttcc tggccttgtg ccctcctgtt acctcctttg 120
cctccagaga ggttggagca gaggctgggc agtgccagaa atcaggcatg aaa 173

<210> SEQ ID NO 5
<211> LENGTH: 307
<212> TYPE: DNA
<213> ORGANISM: Homo sapiens

<400> SEQUENCE: 5
cccagctgag ggctggtgcc agagccgtgt ctgcttgccc catcaagagg tgggagggat 60
tgatccacct tcctgcccca cagatggtgc agcctccaac ctattgtttt ccaggacgct 120

-continued tcggtggaga gcacaaggaa tgtagggtct agaaacagga agccctggct tccgctggac 180
aaggtttcct ccagactcag gcctgccctc cagacaacaa ggcagggccc ttggtcccac 240
cctgccctgc ctggctcact gggccacccc aaggaaggcc ttgccctctc tgggcttctg 300
catgtga 307

<210> SEQ ID NO 6
<211> LENGTH: 450
<212> TYPE: DNA
<213> ORGANISM: Homo sapiens

<400> SEQUENCE: 6
aggtatccac caaggggccc aagagctgct gagcccctga gcagccctac caatttcagc 60
ttatggtggt gaggggtagg ggaggtgtat actggcctgg aaggggttaa gctgcccgcc 120
tgcagcctca gcctgagcta ttgtgttgcc aaacaagggc cggacatgag ggcaggaagc 180
cagcaggggc cacacatttt ctgcaaagtt ggatgattca ctgctgactt ggggacaccc 240
aggggacaga ggggacacca tcccaggaag aatcttaggc tcattttgcc cacatggacc 300
catgactgtt ccctgtatcc tctctctgca ccccctcagt cacactgaag caactatgag 360
aattcccatt tgacagatgg gaccatcgag gctgagggaa gctgtgcagc cagtccaagg 420
tcacacaacc aacacaaggt agaagcaggg 450

<210> SEQ ID NO 7
<211> LENGTH: 123
<212> TYPE: DNA
<213> ORGANISM: Homo sapiens

<400> SEQUENCE: 7
agggcccctg gagctggtcc caatgtgttt ccttctattc ttttgacagg aagctcctgg 60
agagccagtc cccaccccca tcccgcccca gcactccctc tctcttctcc actatggaca 120
gag 123

<210> SEQ ID NO 8
<211> LENGTH: 499
<212> TYPE: DNA
<213> ORGANISM: Homo sapiens

<400> SEQUENCE: 8
tagggcctct ctgaaagatg tggggagtcc tatctgcatt gggatccctg aggagggaga 60
ggaatgtgga gaattcaggg tccagggagc atgggtgact ggtgggctgg gcttccaggc 120
tgaatcatgg gaaaggagaa cctggtctga aacagtactg ggcgggattg gtgttagatt 180
ccaggaaaac ccccaggcgg tctgtggtgg aacctgatgg accctcagaa gggaagagaa 240
tggggatggg gccaggttgc catggttggt cattgtgcat aggcactaga ggccatgctg 300
ggtgggcaca gtcgctgctg cagcctcaca tcctcatctg gacatggctg agcagggccc 360
ctggagctgg tcccaatgtg tttccttcta ttcttttgac aggaagctcc tggagagcca 420
gtccccaccc ccatcccgcc ccagcactcc ctctctcttc tccactatgg acagagcctc 480
cactgagctg ctgcctgcc 499

<210> SEQ ID NO 9
<211> LENGTH: 455
<212> TYPE: DNA
<213> ORGANISM: Homo sapiens

<400> SEQUENCE: 9
gagacataaa aggaaaatga agcgagcaac aattaaaaaa aattccccgc acacaacaat 60
acaatctatt taaactgtgg ctcatacttt tcataccaat ggtatgactt tttttctgga 120
gtcccctctt ctgattcttg aactccgggg ctggcagctt gcaaagggga agcggactcc 180
agcactgcac gggcaggttt agcaaaggtc tctaatgggt attttctttt tcttagccct 240
gcccccgaat tgtcagacgg cgggcgtctg cctctgaagt tagcagtgat ttcctttcgg 300
gcctggcctt atctccggct gcacgttgcc tgttggtgac taataacaca ataacattgt 360
ctggggctgg aataaagtcg gagctgttta cccccactct aataggggtt caatataaaa 420
agccggcaga gagctgtcca agtcagacgc gcctc 455

<210> SEQ ID NO 10
<211> LENGTH: 153
<212> TYPE: DNA
<213> ORGANISM: Homo sapiens

<400> SEQUENCE: 10
tgtccacttc tcctgacccc tcggccgcca ccccagaagg ctggagcagg gacgccgtcg 60
ctccggccgc ctgctcccct cgggtccccg tgcgagccca cgccggcccc ggtgcccgcc 120
cgcagccctg ccactggaca caggataagg ccc 153

<210> SEQ ID NO 11
<211> LENGTH: 125
<212> TYPE: DNA
<213> ORGANISM: Homo sapiens

<400> SEQUENCE: 11
gggcccccca cccagtgaca aagcccgtgg cacttcctct acccggttgg caggcggcct 60
ggcccagccc cttctctaag gaagcgcatt tcctgcctcc ctgggccggc cgggctggat 120
gagcc 125

<210> SEQ ID NO 12
<211> LENGTH: 498
<212> TYPE: DNA
<213> ORGANISM: Homo sapiens

<400> SEQUENCE: 12
gggatgggag ggtggggtgc ttggggagac aagcctagag cctgggccct cccaccccac 60
tgcctccccc catcccaggg ccccccaccc agtgacaaag cccgtggcac ttcctctacc 120
cggttggcag gcggcctggc ccagcccctt ctctaaggaa gcgcatttcc tgcctccctg 180
ggccggccgg gctggatgag ccaggagctc cctgctgccg gtcataccac agccttcatc 240
tgcgccctgg ggccaggact gctgctgtca ctgccatcca ttggagccca gcacccccctc 300 cccgcccatc cttcggacag caactccagc ccagccccgc gtccctgtgt ccacttctcc 360
tgacccctcg gccgccaccc cagaaggctg gagcagggac gccgtcgctc cggccgcctg 420
ctcccctcgg gtccccgtgc gagcccacgc cggccccggt gcccgcccgc agccctgcca 480
ctggacacag gataaggc 498

<210> SEQ ID NO 13
<211> LENGTH: 136
<212> TYPE: DNA
<213> ORGANISM: Homo sapiens

<400> SEQUENCE: 13

```
agcggtgacg tcaaggggcg cgctgtggca gcacctcccc gcgcgctagt taaaaagaag     60

aagaaaagag ggaacgaaac atgagaggct gtgtgagaag ctgcagccgc cggcagagga    120

gacctcagca tcatct                                                    136


<210> SEQ ID NO 14
<211> LENGTH: 574
<212> TYPE: DNA
<213> ORGANISM: Homo sapiens

<400> SEQUENCE: 14

ctgggcgggg gcgcgcgaga agcggtgacg tcaaggggcg cgctgtggca gcacctcccc     60

gcgcgctagt taaaaagaag aagaaaagag ggaacgaaac atgagaggct gtgtgagaag    120

ctgcagccgc cggcagagga gacctcagca tcatctagag cccagcgctg gccctgcctc    180

cgcctgcccc gccgccgccg tcgccgtttc tgttcctgct actgtcccac ctaaacaact    240

cccgttacac ggacaagtga acatctgtgg ctgtcctctc cttttcttcc tcctcttcca    300

actccttctc ctcctcccac ttcccagccg cagcagaaag cccccaaccc aactgacact    360

ggcacaactg caaacggtgt catccgcaca actttatctc gctcctcggg ctcccctaag    420

gcattggacc catcgccgcg tcttttattt tttgcaaagt tgcatcgctg tacatatttt    480

tgtccccgcc acctccctct gtctctggag tgccctacag ccccgcaaac tcctcctgga    540

gctgcgccct agtgcccctg ctgggcagtg gcgt                                574


<210> SEQ ID NO 15
<211> LENGTH: 170
<212> TYPE: DNA
<213> ORGANISM: Homo sapiens

<400> SEQUENCE: 15

agggaactcc ctgtgctggg cctacccagc tgaccccatc gctggaaaca atgggggtca     60

ggcaacactt ccccactctc tcccgccggg ctgtgctcac ttccttcctg ctggctgcct    120

gaggaagtgt ccctgccctg ggacagtctg gcctagcctt tgtttccccg               170


<210> SEQ ID NO 16
<211> LENGTH: 470
<212> TYPE: DNA
<213> ORGANISM: Homo sapiens

<400> SEQUENCE: 16

gacaggcttc tgagtgtagg gagctggtct gccagtcttt cggaggtttg aacttgtcaa     60

ggctagggca ggatcaccat atccagcctg gacttgcagt tctgtggggt gcctccccat    120

acccccataa gatgccaaac atgaggccct gtcatcctcc atggtccccc tctactggct    180

gttcaaggcc cagggctctc ccatgccaga tagcatcctg tctcctacca ccactgtccc    240

agcctgaggg aactccctgt gctgggccta cccagctgac cccatcgctg gaaacaatgg    300

gggtcaggca acacttcccc actctctccc gccgggctgt gctcacttcc ttcctgctgg    360

ctgcctgagg aagtgtccct gccctgggac agtctggcct agcctttgtt tccccggggg    420

tccccaccca tggagctttc aaggcttctg gcccctgtga agccagcaca               470


<210> SEQ ID NO 17
<211> LENGTH: 602
<212> TYPE: DNA
<213> ORGANISM: Homo sapiens
```

-continued

<400> SEQUENCE: 17
cagtggaaaa aaacggactc agctactgga agtccccccg accctccccc caaggctagt 60
tcccttcttg ggcacctgct ctgggggacc atcagctgaa cgacccccaa gtattttgac 120
tcccaaaagc accaccacct gaccccatcc tctcacaccc tactggattt gaggatgggc 180
cccaatccta gggaaggagt gaagaggttc cctagtgttg gaagctgtgg gtgtggggga 240
gattggcacc tgatcctgag cccatagcct tcctgtcacc tggcgcagct ggcggggcca 300
gatcctactc gggaagggtg gggagggcag ccagccagca gggcattctg gagggaaaca 360
gggtcaaggc gatctcctcc cccacgcctg ttcctggccc tttcctctca gggggcagca 420
ggaagtgagg agaaagggct gggatgggag gcgggagcgg atgggaggga atggggttta 480
tcaagtcctc ggcgagctgc ccaacgggca gcagctggcg caagtagcct agctggagag 540
gctcacccca ggaaggaggg aggccaccga cctactgggc cgacggactc ccacacaggt 600
ga 602

<210> SEQ ID NO 18
<211> LENGTH: 265
<212> TYPE: DNA
<213> ORGANISM: Homo sapiens

<400> SEQUENCE: 18
cttgcataga tggccagcgt tcatactttc tgcttgtttg tacaaagtca ttcttctaga 60
gtaattgttg taaaattgct aggcaaggtg gcaggtctga taagatttga tgacgtaatg 120
gctcttagtc gctaataaga ggcttttgtg gagtggcgtg tcacagccag cgaaggctca 180
gctctgtgat cttcgcctgc ctcacttggg ggaccagaag gcagcttgtc ttggaactgc 240
ctcattcaca gaagacccca ttgag 265

<210> SEQ ID NO 19
<211> LENGTH: 545
<212> TYPE: DNA
<213> ORGANISM: Homo sapiens

<400> SEQUENCE: 19
tttacctagc atgatcttgg cagttcaaag aggaatgtgc cagaaaccaa gcaaagaaga 60
aaaagaaata aatggaaatg gaaagtgatc tgctcagagg ccacaaagtt gagggaggag 120
gtttccagag tgggatttgg cccaaatgtt gcctgaggaa gtacgtaaag gggtctcaac 180
tctggctaca caacagaaca gcaggactgt gtgtgcagct cacgaagtgg gtacacaggg 240
taatctgcaa gttctgggtg gatctagcac ctggattgtt aaaacttgca tagatggcca 300
gcgttcatac tttctgcttg tttgtacaaa gtcattcttc tagagtaatt gttgtaaaat 360
tgctaggcaa ggtggcaggt ctgataagat ttgatgacgt aatggctctt agtcgctaat 420
aagaggcttt tgtggagtgg cgtgtcacag ccagcgaagg ctcagctctg tgatcttcgc 480
ctgcctcact tgggggacca gaaggcagct tgtcttggaa ctgcctcatt cacagaagac 540
cccat 545

<210> SEQ ID NO 20
<211> LENGTH: 554
<212> TYPE: DNA
<213> ORGANISM: Homo sapiens

<400> SEQUENCE: 20
atggcagctg gcaggtgcct tcacgtccag ggtttccaga gagaaagcat ctctcctccg 60

-continued

```
cagagaccct cccacgctct ccctccctca aattagtgca tctacataga ccgccctcct    120

tataaacagt ctctcagggg atcctagccc attccaaatc tacctgtgat tgcagaatcg    180

caaggaatgt gatttaccgc agatcgcggg gcgtcgtgtc ttttagggga cctgctcact    240

ttggccacta ggtggcgggc agtgcagccc ctgctcctgt cgaccctgag cgttcagcgt    300

ttccgccgcc tccgccccac tccgtagggg gagctgatga gatgaggttg aggtccagga    360

agacgtcaag ggcttggttt tgtaaacaac tccattcctc gctcgctgat aagttttcta    420

agtgatgcat attcacaacc ttgtcccatc caaggaccca agaattaaca cattacataa    480

tatggacagc cccctcctgt ccaacgggca tgattttggg gtctgatatt ctgtggatct    540

gtgcaatagt caac                                                      554
```

<210> SEQ ID NO 21
<211> LENGTH: 450
<212> TYPE: DNA
<213> ORGANISM: Homo sapiens

<400> SEQUENCE: 21

```
agactttttt tgaaaaacgg aacatctgcc tatcgcaagg actactatta ttctgaaaat     60

caccttcttc attagaaagt aatatttatc attttattat agaactttga tcttacttct    120

tgtgacttca ttctgcgtag agcacactcc catccttgaa ttaaatgaca aagcatttta    180

tattaactga caatgactga tgccatgggc aaatcctatt tctgtaaata actgaatttt    240

cttctggact gcgcatgagg ggagaaagat gtctgcagtt tcggtttcct ggaaaatgaa    300

acctatctca tttgttgcct gtgtcaaggg gcagtgcttc agtcggggtg gagctgctta    360

aaaggcctgg gatcacaccc tttgggaaca catccaagct taagacggtg aggtcagctt    420

cacattctca ggaactctcc ttctttgggt                                     450
```

<210> SEQ ID NO 22
<211> LENGTH: 570
<212> TYPE: DNA
<213> ORGANISM: Homo sapiens

<400> SEQUENCE: 22

```
gagacttttt ttgaaaaacg gaacatctgc ctatcgcaag gactactatt attctgaaaa     60

tcaccttctt cattagaaag taatatttat cattttatta tagaactttg atcttacttc    120

ttgtgacttc attctgcgta gagcacactc ccatccttga attaaatgac aaagcatttt    180

atattaactg acaatgactg atgccatggg caaatcctat ttctgtaaat aactgaattt    240

tcttctggac tgcgcatgag gggagaaaga tgtctgcagt ttcggtttcc tggaaaatga    300

aacctatctc atttgttgcc tgtgtcaagg ggcagtgctt cagtcggggt ggagctgctt    360

aaaaggcctg ggatcacacc ctttgggaac acatccaagc ttaagacggt gaggtcagct    420

tcacattctc aggaactctc cttctttggg taagactggg agggtgggca ggagctaccc    480

ttcccgtggc cccggacctt gggtgggctg tgggctcagg gagcggaggg gaggccttaa    540

gcatccactc tctgcccggt gtttttgttc                                     570
```

<210> SEQ ID NO 23
<211> LENGTH: 513
<212> TYPE: DNA
<213> ORGANISM: Homo sapiens

<400> SEQUENCE: 23

-continued

```
aggtggggat gaggggctaa gtatgaacca aggagctaga aatacagcac tggaagctgg      60

aagcaggggg cttggagact gggagctgga gtgcgtgtgg gcagggtgtg gcagcagccg     120

gcagaggcca tttccccttg gcagaacatt caccatgtga ccctgagcat gtctttgaac     180

tcctctgagc tcctgtttcc tctccagaga aaaggctggt aatgcccatt cagggttatg     240

gtcaggattg catagggtga aacaatagag attgaacaca gtagacatga aagagatgcc     300

agggctcagc tccctttggt ttagttgctt ccagtgtgct ctgtggcaac accacggagc     360

cctagagctg tctctttgag ccgctctgaa tgtgcctctt acataatctc ctgggcaaca     420

tctgctcccc taatgagatt tgctccccag caaagataag aaacttgcca accactcccc     480

tggtccagca tttggccaag gcagacactg agg                                  513


<210> SEQ ID NO 24
<211> LENGTH: 217
<212> TYPE: DNA
<213> ORGANISM: Homo sapiens

<400> SEQUENCE: 24

acctcactca atgcatggaa gttgacacaa tggctcaaca ttagcgttgg gctgattcat      60

catttggctg ttgacaccag cctctggccc agccaggaca gaaaaagggc ccctgaggaa     120

cttctggctc tgttccctct atgggggagg ggcagtggac ttgtgataag acagggtgtt     180

agggtgaggt ggacttgggg aaacaggata tttctaa                              217


<210> SEQ ID NO 25
<211> LENGTH: 97
<212> TYPE: DNA
<213> ORGANISM: Homo sapiens

<400> SEQUENCE: 25

ggggggaggg gagaccccag aacaatgtcc cccaccccac ccccctcctc aataggcgga      60

agccactggc ttcctccctt tcctgcctcc tgcctcc                               97


<210> SEQ ID NO 26
<211> LENGTH: 427
<212> TYPE: DNA
<213> ORGANISM: Homo sapiens

<400> SEQUENCE: 26

gtgtgtttgt gccgggggga ggggagaccc cagaacaatg tcccccaccc cacccccctc      60

ctcaataggc ggaagccact ggcttcctcc ctttcctgcc tcctgcctcc tttgtgccag     120

caagactgag tactggagag agacagggga tgggaaaaat cagtccagct gtccccaggt     180

ctgcccttac cataaccttc cccccacctc aagtgactcc tcccaggcca cacccatccc     240

cagccttgtg gggccagat tgggggcct agaggctcaa aggcagaatg agtcctccca     300

ccccctaccc tgccacccct cccacccaag ccacctcatt tcctcttcct ccccagcacc     360

gacccacact gaccaacaca ggctgagcag tcaggcccac agcatctgac cccaggccca     420

gctcgtc                                                               427


<210> SEQ ID NO 27
<211> LENGTH: 119
<212> TYPE: DNA
<213> ORGANISM: Homo sapiens

<400> SEQUENCE: 27

ctacaaagct ttatcagctt ggaggtactt ctaataccat ttcctttcat tgtttccttt      60
```

tggtaattaa aaggaggcca atcccctgtt gtggcagctc acagctattg tggtgggaa 119

<210> SEQ ID NO 28
<211> LENGTH: 385
<212> TYPE: DNA
<213> ORGANISM: Homo sapiens

<400> SEQUENCE: 28
ctgccaggag gtctccctcc aaactctaca aagctttatc agcttggagg tacttctaat 60
accatttcct ttcattgttt ccttttggta attaaaagga ggccaatccc ctgttgtggc 120
agctcacagc tattgtggtg ggaaagggag ggtggttggt ggatgtcaca gcttgggctt 180
tatctccccc agcagtgggg actccacagc ccctgggcta cataacagca agacagtccg 240
gagctgtagc agacctgatt gagcctttgc agcagctgag agcatggcct agggtgggcg 300
gcaccattgt ccagcagctg agtttcccag ggaccttgga gatagccgca gccctcattt 360
gcaggggaag gtatggcctt tggaa 385

<210> SEQ ID NO 29
<211> LENGTH: 517
<212> TYPE: DNA
<213> ORGANISM: Homo sapiens

<400> SEQUENCE: 29
gccattggct ggtccttcac tgacagcaga aacttggcca atggcaatca atcagggggc 60
ccgcgctgcc ttaaatacca gcagagcaaa cagcctcaga caaagctgcg ccgtgtatca 120
attaccgaga ggctgcgtgc tcctctgggc ggagggagcc ggagcgagcg gccagggctg 180
ctgccccagc tgataagggc ccgcattgtt cggggacagc tggcagcccg ataagggcct 240
gctcgcccga gataatggca gtgggcaggc gcctcgcggc agtttagaat ttcttgggtc 300
tccaagaaag gttctattaa gcccactgac cccaattgaa tattaattag ctaattaacg 360
gatttattgt tccacgccat ttctggagag gccatttttt ttcgagtgcc attatttttg 420
taaatgattt ttcgcattgt tcataattga atctttgcag ctgccagcat cttctgcatg 480
atttggcaaa aaaaaggaag cagaagcact tagggtt 517

<210> SEQ ID NO 30
<211> LENGTH: 511
<212> TYPE: DNA
<213> ORGANISM: Homo sapiens

<400> SEQUENCE: 30
cccctaataa acaggaaggc atccgcgcca ttagtatcca tccttttcag agcatctgag 60
acctgtctgg accatcaaag ccatccccag cccccaggag cctactggag gagacaccag 120
cctcgccaaa acaattctcc attgtgttct tccccttaga aatcatgggt ttgtaaacag 180
gcccttacat ttcagcaggt cctgccctgg ctttgtgctg gtgtgttgtt ttttcttccc 240
tgaacaatgt cctttccagt agggccagcc gttcacacca ttgtctgaga cccttggact 300
acaggaaaca tcaccagatt cttatcagtt gggggcagga gtggggggt gaacagatga 360 gatcatgtcc acagagcaag tggctggtgt gccacgtcat tccccatgcc ttcatctgtg 420
agagcagagc ccgctcgccc tccatcaatc tgggcttcat gtgtccagag tccagtcccc 480
tctatttggt ggtagacacc tggactctgt t 511

<210> SEQ ID NO 31

```
<211> LENGTH: 390
<212> TYPE: DNA
<213> ORGANISM: Homo sapiens

<400> SEQUENCE: 31

tcctacagtt atgggtctgt ctttcctgct agatcagaag ctccagggac ctgtctgtct     60

tattaacctt tcttcccctc atgatgcctg gcccaggact ccacgttcag aggcagttta    120

atgtctacag aactgatgga tgctccatac cctgtattca taagcctgtg ttttgctgcc    180

aaacaccaga gggcactgtt agcatgtcga tgaagattat aaaccctcag acctggaagg    240

ctgggaaagg cttatgaaaa tcttgcttct gttttgggat tacataagac ttattgcgcc    300

tcaattgttc taaacacatc tgttcgagtt tattcatgag gcacgttcct gttggggtta    360

gagatgagtt tgaaagctcc ccgtcacagg                                      390

<210> SEQ ID NO 32
<211> LENGTH: 573
<212> TYPE: DNA
<213> ORGANISM: Homo sapiens

<400> SEQUENCE: 32

agggactgtt gggcagcccc agactggcac aggtggatcg ggtgcctagg caggggggtgg     60

tgagttatgg cgcagctgtc ttggtggctg gggggagcag ggataagggt ggacttctta    120

gtgaccgctc tctgccccag gaggtagagt cctgggggct gggctggcct gagagacgcc    180

ccctcatcct ttccagggtg aggtacgagg gctccgcccc ctcctgatat caccaggcct    240

agggcagcat cctgatgggg gaggggcaag tgacccgggc cctggactgc aggaacagcc    300

cctcctccac tggtggagtt cccacttcct gcggaaggaa ctatgttaga agttgtgtat    360

atggggtggg ggttgggtgt gggtggcggg gggcctgggt ggggtccact gagtcgcctc    420

ccctgtctcc ctgcacttcc tcctggagga aatggggaca acaggatgaa gtgagggcct    480

gctgagccca gggctgccac ctgggagtga agccggggca ggctgcaggg tccgggccct    540

tctgtgtggg caggtggaag tggtggggat gca                                  573

<210> SEQ ID NO 33
<211> LENGTH: 441
<212> TYPE: DNA
<213> ORGANISM: Homo sapiens

<400> SEQUENCE: 33

ggggagaggg tgtggggtgg ggtggggaga gggtgtgggg tggggtgggg agaggggatg     60

ggatggcatg gggggatgtg gcagtgagga ggctgggccc ttggagctgc cgagtgcagg    120

ggcctggagg actccgggaa ggcgtcctag tgcatcaagc gtgggcttgg cctgcttggg    180

tctcccctcc tggcccccct agcaatgggc ggacttgggc ccgctctggg aggattccag    240

gaacggctcc tgcctggtta taaatagact tctccgaaag gcctggggct gtgccagctg    300

cagcaggtgc ctcccaggcc cggccagagg gccccaggca agggggtgga gcccgggtgg    360

gggtgatgag gatgctgggg tccacttttg tagcgccaga ggcgacgggc tctgtctggt    420

tgtagcatca cagagcttga t                                               441

<210> SEQ ID NO 34
<211> LENGTH: 1303
<212> TYPE: DNA
<213> ORGANISM: Homo sapiens

<400> SEQUENCE: 34
```

gcttgcccag ctatataata aaacaagttt gggacttccc aaccattcac ccatggaaaa 60
acagaagcaa ctcttcaaag gacagattcc caggatctgc cctgggagat tccaaatcag 120
ttgatctggg gtgagcccag tcctctgtag tttttagaag ctcctcctat gtctctcctg 180
gtcagcagaa tcttggcccc tcccttcccc ccagcctctt ggttcttctg ggctctgatc 240
cagcctcagc gtcactgtct tccacgcccc tctttgattc tcgtttatgt caaaagcctt 300
gtgaggatga ggctgtgatt atccccattt tacagatgag gaaactgtgg ctccaggatg 360
acacaactgg ccagaggtca catcagaagc agagctgggt cacttgactc cacccaatat 420
ccctaaatgc aaacatcccc tacagaccga ggctggcacc ttagagctgg agtccatgcc 480
cgctctgacc aggagaagcc aacctggtcc tccagagcca agagcttctg tccctttccc 540
atctcctgaa gcctccctgt cacctttaaa gtccattccc acaaagacat catgggatca 600
ccacagaaaa tcaagctctg gggctaggct gaccccagct agatttttgg ctcttttata 660
ccccagctgg gtggacaagc accttaaacc cgctgagcct cagcttcccg ggctataaaa 720
tgggggtgat gacacctgcc tgtagcattc caaggagggt taaatgtgat gctgcagcca 780
agggtcccca cagccaggct ctttgcaggt gctgggttca gagtcccaga gctgaggccg 840
ggagtagggg ttcaagtggg gtgccccagg cagggtccag tgccagccct ctgtggagac 900
agccatccgg ggccgaggca gccgcccacc gcagggcctg cctatctgca gccagcccag 960
ccctcacaaa ggaacaataa caggaaacca tcccaggggg aagtgggcca gggccagctg 1020
gaaaacctga aggggaggca gccaggcctc cctcgccagc ggggtgtggc tcccctccaa 1080
agacggtcgg ctgacaggct ccacagagct ccactcacgc tcagccctgg acggacaggc 1140
agtccaacgg aacagaaaca tccctcagcc cacaggcacg gtgagtgggg gctcccacac 1200
tcccctccac cccaaacccg ccaccctgcg cccaagatgg gagggtcctc agcttcccca 1260
tctgtagaat gggcatcgtc ccactcccat gacagagagg ctc 1303

<210> SEQ ID NO 35
<211> LENGTH: 455
<212> TYPE: DNA
<213> ORGANISM: Homo sapiens

<400> SEQUENCE: 35
gagacataaa aggaaaatga agcgagcaac aattaaaaaa aattccccgc acacaacaat 60
acaatctatt taaactgtgg ctcatacttt tcataccaat ggtatgactt tttttctgga 120
gtcccctctt ctgattcttg aactccgggg ctggcagctt gcaaagggga agcggactcc 180
agcactgcac gggcaggttt agcaaaggtc tctaatgggt attttctttt tcttagccct 240
gcccccgaat tgtcagacgg cgggcgtctg cctctgaagt tagcagtgat ttcctttcgg 300
gcctggcctt atctccggct gcacgttgcc tgttggtgac taataacaca ataacattgt 360
ctggggctgg aataaagtcg gagctgttta cccccactct aataggggtt caatataaaa 420
agccggcaga gagctgtcca agtcagacgc gcctc 455

<210> SEQ ID NO 36
<211> LENGTH: 888
<212> TYPE: DNA
<213> ORGANISM: Homo sapiens

<400> SEQUENCE: 36
cgccttgctg tgccactttg ggacttccct ccctagcctg agcttcagtt ttcctgcctg 60

-continued ttaggcagcc ccatgtcaac tgcacttagt aggccgggtt tgatgcccga caagacgtga 120
agtggtggag gtgggcagga tcccagcgct accatcttct tgaaccagtg atctcaacac 180
atcggatttc tgtttcctca tctgcaaaat gggatcagtg agctcaggtg ggtcacaaat 240
tctacaggaa ctactttagc caagcccggc cccctgaaag ttcccctcgg tgggctgtta 300
gggtgattgt tttcatctgt ggggctccct gatgcgtccc acccaccagc cttggagagg 360
gtgggatggg agggtggggt gcttggggag acaagcctag agcctgggcc ctcccacccc 420
actgcctccc cccatcccag ggccccccac ccagtgacaa agcccgtggc acttcctcta 480
cccggttggc aggcggcctg gcccagcccc ttctctaagg aagcgcattt cctgcctccc 540
tgggccggcc gggctggatg agccgggagc tccctgctgc cggtcatacc acagccttca 600
tctgcgccct ggggccagga ctgctgctgt cactgccatc cattggagcc cagcaccccc 660
tccccgccca tccttcggac agcaactcca gcccagcccc gcgtccctgt gtccacttct 720
cctgacccct cggccgccac cccagaaggc tggagcaggg acgccgtcgc tccggccgcc 780
tgctcccctc gggtccccgt gcgagcccac gccggccccg gtgcccgccc gcagccctgc 840
cactggacac aggataaggc ccagcgcaca ggcccccacg tggacacc 888

<210> SEQ ID NO 37
<211> LENGTH: 1037
<212> TYPE: DNA
<213> ORGANISM: Homo sapiens

<400> SEQUENCE: 37
tttgcttcta ggaagcagaa gactgaggaa atgacttggg cgggtgcatc aatgcggcca 60
aaaaagacac ggacacgctc ccctgggacc tgagctggtt cgcagtcttc ccaaaggtgc 120
caagcaagcg tcagttcccc tcaggcgctc caggttcagt gccttgtgcc gagggtctcc 180
ggtgccttcc tagacttctc gggacagtct gaaggggtca ggagcggcgg gacagcgcgg 240
gaagagcagg caaggggaga cagccggact gcgcctcagt cctccgtgcc aagaacaccg 300
tcgcggaggc gcggccagct tcccttggat cggactttcc gcccctaggg ccaggcggcg 360
gagcttcagc cttgtccctt ccccagtttc gggcggcccc cagagctgag taagccgggt 420
ggagggagtc tgcaaggatt tcctgagcgc gatgggcagg aggaggggca agggcaagag 480
ggcgcggagc aaagaccctg aacctgccgg ggccgcgctc ccgggcccgc gtcgccagca 540
cctccccacg cgcgctcggc cccgggccac ccgccctcgt cggcccccgc ccctctccgt 600
agccgcaggg aagcgagcct gggaggaaga agagggtagg tggggaggcg gatgaggggt 660
gggggacccc ttgacgtcac cagaaggagg tgccggggta ggaagtgggc tggggaaagg 720
ttataaatcg cccccgccct cggctgctct tcatcgaggt ccgcgggagg ctcggagcgc 780
gccaggcgga cactcctctc ggctcctccc cggcagcggc ggcggctcgg agcgggctcc 840
ggggctcggg tgcagcggcc agcgggcgcc tggcggcgag gattacccgg ggaagtggtt 900
gtctcctggc tggagccgcg agacgggcgc tcagggcgcg gggccggcgg cggcgaacaa 960
gaggacggac tctggcggcc gggtcgttgg ccgcggggag cgcgggcacc gggcgagcag 1020
gccgcgtcgc gctcacc 1037

<210> SEQ ID NO 38
<211> LENGTH: 399
<212> TYPE: DNA
<213> ORGANISM: Homo sapiens

<400> SEQUENCE: 38
gtctcccagg catgactcca acaatgcatc ccatgggatt tggggttccc cagatctggg 60
gcttgtaggc ctgactctcc cctgtgcaca cgtctcatac acgcatgcgt gcacccattg 120
cctgccccgc cccttgcaca gggagtcagc agggaggact gggttatgcc ctgcttatca 180
gcagcttccc agcttcctct gcctggattc ttagaggcct ggggtcctag aacgagctgg 240
tgcacgtggc ttcccaaaga tctctcagat aatgagagga aatgcagtca tcagtttgca 300
gaaggctagg gattctgggc catagctcag acctgcgccc accatctccc tccaggcagc 360
ccttggctgg tccctgcgag cccgtggaga ctgccagtc 399

<210> SEQ ID NO 39
<211> LENGTH: 6
<212> TYPE: DNA
<213> ORGANISM: Homo sapiens

<400> SEQUENCE: 39 gccacc 6

<210> SEQ ID NO 40
<211> LENGTH: 8834
<212> TYPE: DNA
<213> ORGANISM: Artificial Sequence
<220> FEATURE:
<223> OTHER INFORMATION: vector

<400> SEQUENCE: 40
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320

-continued

```
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga actacaaaaa caaattacaa aaattcaaaa ttttcgggtt tattacaggg   2160
acagcagaga tccagtttat cgataagctt gggagttccg cgttacataa cttacggtaa   2220
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaactgccca cttggcagta catcaagtgt atcatatgcc aagtacgccc cctattgacg   2400
tcaatgacgg taaatggccc gcctggcatt atgcccagta catgacctta cgggactttc   2460
ctacttggca gtacatctac gtattagtca tcgctattac catggtgatg cggttttggc   2520
agtacaccaa tgggcgtgga tagcggtttg actcacgggg atttccaagt ctccacccca   2580
ttgacgtcaa tgggagtttg ttttggcacc aaaatcaacg ggactttcca aaatgtcgta   2640
acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
tccatagaag acaccgactc tagctagagg atctaccggt cgccaccatg gtgagcaagg   2820
gcgccgagct gttcaccggc atcgtgccca tcctgatcga gctgaatggc gatgtgaatg   2880
gccacaagtt cagcgtgagc ggcgagggcg agggcgatgc cacctacggc aagctgaccc   2940
tgaagttcat ctgcaccacc ggcaagctgc ctgtgccctg gcccaccctg gtgaccaccc   3000
tgagctacgg cgtgcagtgc ttctcacgct accccgatca catgaagcag cacgacttct   3060
tcaagagcgc catgcctgag ggctacatcc aggagcgcac catcttcttc gaggatgacg   3120
gcaactacaa gtcgcgcgcc gaggtgaagt tcgagggcga taccctggtg aatcgcatcg   3180
agctgaccgg caccgatttc aaggaggatg gcaacatcct gggcaataag atggagtaca   3240
actacaacgc ccacaatgtg tacatcatga ccgacaaggc caagaatggc atcaaggtga   3300
acttcaagat ccgccacaac atcgaggatg gcagcgtgca gctggccgac cactaccagc   3360
agaatacccc catcggcgat ggccctgtgc tgctgcccga taaccactac ctgtccaccc   3420
agagcgccct gtccaaggac cccaacgaga agcgcgatca catgatctac ttcggcttcg   3480
tgaccgccgc cgccatcacc cacggcatgg atgagctgta caagtccgga ctcagatctc   3540
gagctcaagc ttcgaattct gcagtcgacg gtaccgcggg cccgggatcc accggatcta   3600
gataactgat cataattcta ccgggtaggg gaggcgcttt tcccaaggca gtctggagca   3660
tgcgctttag cagccccgct gggcacttgg cgctacacaa gtggcctctg gcctcgcaca   3720
```

-continued

```
cattccacat ccaccggtag gcgccaaccg gctccgttct ttggtggccc cttcgcgcca   3780
ccttctactc ctcccctagt caggaagttc ccccccgccc cgcagctcgc gtcgtgcagg   3840
acgtgacaaa tggaagtagc acgtctcact agtctcgtgc agatggacag caccgctgag   3900
caatggaagc gggtaggcct ttggggcagc ggccaatagc agctttgctc cttcgctttc   3960
tgggctcaga ggctgggaag gggtgggtcc gggggcgggc tcaggggcgg gctcaggggc   4020
ggggcgggcg cccgaaggtc ctccggaggc ccggcattct gcacgcttca aaagcgcacg   4080
tctgccgcgc tgttctcctc ttcctcatct ccgggccttt cgacctgcag cccaagctta   4140
ccatgaccga gtacaagccc acggtgcgcc tcgccacccg cgacgacgtc cccagggccg   4200
tacgcaccct cgccgccgcg ttcgccgact accccgccac gcgccacacc gtcgatccgg   4260
accgccacat cgagcgggtc accgagctgc aagaactctt cctcacgcgc gtcgggctcg   4320
acatcggcaa ggtgtgggtc gcggacgacg gcgccgcggt ggcggtctgg accacgccgg   4380
agagcgtcga agcgggggcg gtgttcgccg agatcggccc gcgcatggcc gagttgagcg   4440
gttcccggct ggccgcgcag caacagatgg aaggcctcct ggcgccgcac cggcccaagg   4500
agcccgcgtg gttcctggcc accgtcggcg tctcgcccga ccaccagggc aagggtctgg   4560
gcagcgccgt cgtgctcccc ggagtggagg cggccgagcg cgccggggtg cccgccttcc   4620
tggagacctc cgcgccccgc aacctcccct tctacgagcg gctcggcttc accgtcaccg   4680
ccgacgtcga ggtgcccgaa ggaccgcgca cctggtgcat gacccgcaag cccggtgcct   4740
gaccgcgtct ggaacaatca acctctggat tacaaaattt gtgaaagatt gactggtatt   4800
cttaactatg ttgctccttt tacgctatgt ggatacgctg ctttaatgcc tttgtatcat   4860
gctattgctt cccgtatggc tttcattttc tcctccttgt ataaatcctg gttgctgtct   4920
ctttatgagg agttgtggcc cgttgtcagg caacgtggcg tggtgtgcac tgtgtttgct   4980
gacgcaaccc ccactggttg gggcattgcc accacctgtc agctcctttc cgggactttc   5040
gctttccccc tccctattgc cacggcggaa ctcatcgccg cctgccttgc ccgctgctgg   5100
acaggggctc ggctgttggg cactgacaat tccgtggtgt tgtcggggaa gctgacgtcc   5160
tttccatggc tgctcgcctg tgttgccacc tggattctgc gcgggacgtc cttctgctac   5220
gtcccttcgg ccctcaatcc agcggacctt ccttcccgcg gcctgctgcc ggctctgcgg   5280
cctcttccgc gtcttcgcct tcgccctcag acgagtcgga tctccctttg ggccgcctcc   5340
ccgcctggaa ttaattctgc agtcgagacc tagaaaaaca tggagcaatc acaagtagca   5400
atacagcagc taccaatgct gattgtgcct ggctagaagc acaagaggag gaggaggtgg   5460
gtttttccag tcacacctca ggtaccttta agaccaatga cttacaaggc agctgtagat   5520
cttagccact ttttaaaaga aaagagggga ctggaagggc taattcactc ccaacgaaga   5580
caagatatcc ttgatctgtg gatctaccac acacaaggct acttccctga ttagcagaac   5640
tacacaccag ggccaggggt cagatatcca ctgacctttg gatggtgcta caagctagta   5700
ccagttgagc cagataaggt agaagaggcc aataaaggag agaacaccag cttgttacac   5760
cctgtgagcc tgcatgggat ggatgacccg gagagagaag tgttagagtg gaggtttgac   5820
agccgcctag catttcatca cgtggcccga gagctgcatc cggagtactt caagaactgc   5880
tgatatcgag cttgctacaa gggactttcc gctggggact ttccagggag gcgtggcctg   5940
ggcgggactg gggagtggcg agccctcaga tcctgcatat aagcagctgc tttttgcctg   6000
tactgggtct ctctggttag accagatctg agcctgggag ctctctggct aactagggaa   6060
```

-continued

```
cccactgctt aagcctcaat aaagcttgcc ttgagtgctt caagtagtgt gtgcccgtct   6120
gttgtgtgac tctggtaact agagatccct cagacccttt tagtcagtgt ggaaaatctc   6180
tagcagtagt agttcatgtc atcttattat tcagtattta taacttgcaa agaaatgaat   6240
atcagagagt gagaggcctt gacattgcta gcgttttacc gtcgacctct agctagagct   6300
tggcgtaatc atggtcatag ctgtttcctg tgtgaaattg ttatccgctc acaattccac   6360
acaacatacg agccggaagc ataaagtgta aagcctgggg tgcctaatga gtgagctaac   6420
tcacattaat tgcgttgcgc tcactgcccg ctttccagtc gggaaacctg tcgtgccagc   6480
tgcattaatg aatcggccaa cgcgcgggga gaggcggttt gcgtattggg cgctcttccg   6540
cttcctcgct cactgactcg ctgcgctcgg tcgttcggct gcggcgagcg gtatcagctc   6600
actcaaaggc ggtaatacgg ttatccacag aatcagggga taacgcagga aagaacatgt   6660
gagcaaaagg ccagcaaaag gccaggaacc gtaaaaaggc cgcgttgctg gcgtttttcc   6720
ataggctccg cccccctgac gagcatcaca aaaatcgacg ctcaagtcag aggtggcgaa   6780
acccgacagg actataaaga taccaggcgt ttccccctgg aagctccctc gtgcgctctc   6840
ctgttccgac cctgccgctt accggatacc tgtccgcctt tctcccttcg ggaagcgtgg   6900
cgctttctca tagctcacgc tgtaggtatc tcagttcggt gtaggtcgtt cgctccaagc   6960
tgggctgtgt gcacgaaccc cccgttcagc ccgaccgctg cgccttatcc ggtaactatc   7020
gtcttgagtc caacccggta agacacgact tatcgccact ggcagcagcc actggtaaca   7080
ggattagcag agcgaggtat gtaggcggtg ctacagagtt cttgaagtgg tggcctaact   7140
acggctacac tagaagaaca gtatttggta tctgcgctct gctgaagcca gttaccttcg   7200
gaaaaagagt tggtagctct tgatccggca aacaaaccac cgctggtagc ggtttttttg   7260
tttgcaagca gcagattacg cgcagaaaaa aaggatctca agaagatcct ttgatctttt   7320
ctacggggtc tgacgctcag tggaacgaaa actcacgtta agggattttg gtcatgagat   7380
tatcaaaaag gatcttcacc tagatccttt taaattaaaa atgaagtttt aaatcaatct   7440
aaagtatata tgagtaaact tggtctgaca gttaccaatg cttaatcagt gaggcaccta   7500
tctcagcgat ctgtctattt cgttcatcca tagttgcctg actccccgtc gtgtagataa   7560
ctacgatacg ggagggctta ccatctggcc ccagtgctgc aatgataccg cgagacccac   7620
gctcaccggc tccagattta tcagcaataa accagccagc cggaagggcc gagcgcagaa   7680
gtggtcctgc aactttatcc gcctccatcc agtctattaa ttgttgccgg gaagctagag   7740
taagtagttc gccagttaat agtttgcgca acgttgttgc cattgctaca ggcatcgtgg   7800
tgtcacgctc gtcgtttggt atggcttcat tcagctccgg ttcccaacga tcaaggcgag   7860
ttacatgatc ccccatgttg tgcaaaaaag cggttagctc cttcggtcct ccgatcgttg   7920
tcagaagtaa gttggccgca gtgttatcac tcatggttat ggcagcactg cataattctc   7980
ttactgtcat gccatccgta agatgctttt ctgtgactgg tgagtactca accaagtcat   8040
tctgagaata gtgtatgcgg cgaccgagtt gctcttgccc ggcgtcaata cgggataata   8100
ccgcgccaca tagcagaact ttaaaagtgc tcatcattgg aaaacgttct tcggggcgaa   8160
aactctcaag gatcttaccg ctgttgagat ccagttcgat gtaacccact cgtgcaccca   8220
actgatcttc agcatctttt actttcacca gcgtttctgg gtgagcaaaa acaggaaggc   8280
aaaatgccgc aaaaaaggga ataagggcga cacggaaatg ttgaatactc atactcttcc   8340
tttttcaata ttattgaagc atttatcagg gttattgtct catgagcgga tacatatttg   8400
aatgtattta gaaaaataaa caaatagggg ttccgcgcac atttccccga aaagtgccac   8460
```

-continued

```
ctgacgtcga cggatcggga gatcaacttg tttattgcag cttataatgg ttacaaataa   8520

agcaatagca tcacaaattt cacaaataaa gcattttttt cactgcattc tagttgtggt   8580

ttgtccaaac tcatcaatgt atcttatcat gtctggatca actggataac tcaagctaac   8640

caaaatcatc ccaaacttcc caccccatac cctattacca ctgccaatta cctagtggtt   8700

tcatttactc taaacctgtg attcctctga attattttca ttttaaagaa attgtatttg   8760

ttaaatatgt actacaaact tagtagtttt taaagaaatt gtatttgtta aatatgtact   8820

acaaacttag tagt                                                     8834
```

```
<210> SEQ ID NO 41
<211> LENGTH: 11329
<212> TYPE: DNA
<213> ORGANISM: Artificial Sequence
<220> FEATURE:
<223> OTHER INFORMATION: vector

<400> SEQUENCE: 41

tggaagggct aattcactcc caaagaagac aagatatcct tgatctgtgg atctaccaca     60

cacaaggcta cttccctgat tagcagaact acacaccagg gccaggggtc agatatccac    120

tgacctttgg atggtgctac aagctagtac cagttgagcc agataaggta gaagaggcca    180

ataaaggaga gaacaccagc ttgttacacc ctgtgagcct gcatgggatg gatgacccgg    240

agagagaagt gttagagtgg aggtttgaca gccgcctagc atttcatcac gtggcccgag    300

agctgcatcc ggagtacttc aagaactgct gatatcgagc ttgctacaag ggactttccg    360

ctggggactt tccagggagg cgtggcctgg gcgggactgg ggagtggcga gccctcagat    420

cctgcatata agcagctgct ttttgcctgt actgggtctc tctggttaga ccagatctga    480

gcctgggagc tctctggcta actagggaac ccactgctta agcctcaata aagcttgcct    540

tgagtgcttc aagtagtgtg tgcccgtctg ttgtgtgact ctggtaacta gagatccctc    600

agaccctttt agtcagtgtg gaaaatctct agcagtggcg cccgaacagg gacttgaaag    660

cgaaagggaa accagaggag ctctctcgac gcaggactcg gcttgctgaa gcgcgcacgg    720

caagaggcga ggggcggcga ctggtgagta cgccaaaaat tttgactagc ggaggctaga    780

aggagagaga tgggtgcgag agcgtcagta ttaagcgggg gagaattaga tcgcgatggg    840

aaaaaattcg gttaaggcca gggggaaaga aaaaatataa attaaaacat atagtatggg    900

caagcaggga gctagaacga ttcgcagtta atcctggcct gttagaaaca tcagaaggct    960

gtagacaaat actgggacag ctacaaccat cccttcagac aggatcagaa gaacttagat   1020

cattatataa tacagtagca accctctatt gtgtgcatca aaggatagag ataaaagaca   1080

ccaaggaagc tttagacaag atagaggaag agcaaaacaa aagtaagacc accgcacagc   1140

aagcggccgg ccgctgatct tcagacctgg aggaggagat atgagggaca attggagaag   1200

tgaattatat aaatataaag tagtaaaaat tgaaccatta ggagtagcac ccaccaaggc   1260

aaagagaaga gtggtgcaga gagaaaaaag agcagtggga ataggagctt tgttccttgg   1320

gttcttggga gcagcaggaa gcactatggg cgcagcgtca atgacgctga cggtacaggc   1380

cagacaatta ttgtctggta tagtgcagca gcagaacaat ttgctgaggg ctattgaggc   1440

gcaacagcat ctgttgcaac tcacagtctg gggcatcaag cagctccagg caagaatcct   1500

ggctgtggaa agatacctaa aggatcaaca gctcctgggg atttggggtt gctctggaaa   1560

actcatttgc accactgctg tgccttggaa tgctagttgg agtaataaat ctctggaaca   1620
```

-continued

```
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgataagctt gggagttccg cgttacataa cttacggtaa   2220
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaactgccca cttggcagta catcaagtgt atcatatgcc aagtacgccc cctattgacg   2400
tcaatgacgg taaatggccc gcctggcatt atgcccagta catgacctta tgggactttc   2460
ctacttggca gtacatctac gtattagtca tcgctattac catggtgatg cggttttggc   2520
agtacatcaa tgggcgtgga tagcggtttg actcacgggg atttccaagt ctccacccca   2580
ttgacgtcaa tgggagtttg ttttggcacc aaaatcaacg ggactttcca aaatgtcgta   2640
acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
tccatagaag acaccgactc tactagagga tcgctagcgc taccggactc agatctcgag   2820
ctcaagcttc gaattctgca gtcgacggta ccgcgggccc ggatgcagat cgagctgtcc   2880
acctgctttt ttctgtgcct gctgcggttc tgcttcagcg ccacccggcg gtactacctg   2940
ggcgccgtgg agctgtcctg ggactacatg cagagcgacc tgggcgagct gcccgtggac   3000
gcccggttcc cccccagagt gcccaagagc ttccccttca acaccagcgt ggtgtacaag   3060
aaaaccctgt tcgtggagtt caccgaccac ctgttcaata tcgccaagcc caggcccccc   3120
tggatgggcc tgctgggccc caccatccag gccgaggtgt acgacaccgt ggtgatcacc   3180
ctgaagaaca tggccagcca ccccgtgagc ctgcacgccg tgggcgtgag ctactggaag   3240
gccagcgagg gcgccgagta cgacgaccag accagccagc gggagaaaga agatgacaag   3300
gtgttccctg gcggcagcca cacctacgtg tggcaggtgc tgaaagaaaa cggccccatg   3360
gcctccgacc ccctgtgcct gacctacagc tacctgagcc acgtggacct ggtgaaggac   3420
ctgaacagcg gcctgatcgg cgctctgctc gtctgccggg agggcagcct ggccaaagag   3480
aaaacccaga ccctgcacaa gttcatcctg ctgttcgccg tgttcgacga gggcaagagc   3540
tggcacagcg agacaaagaa cagcctgatg caggaccggg acgccgcctc tgccagagcc   3600
tggcccaaga tgcacaccgt gaacggctac gtgaacagaa gcctgcccgg cctgattggc   3660
tgccaccgga agagcgtgta ctggcacgtg atcggcatgg gcaccacacc cgaggtgcac   3720
agcatctttc tggaagggca cacctttctg gtccggaacc accggcaggc cagcctggaa   3780
atcagcccta tcaccttcct gaccgcccag acactgctga tggacctggg ccagttcctg   3840
ctgttttgcc acatcagctc tcaccagcac gacggcatgg aagcctacgt gaaggtggac   3900
tcttgccccg aggaacccca gctgcggatg aagaacaacg aggaagccga ggactacgac   3960
gacgacctga ccgacagcga gatggacgtg gtgcggttcg acgacgacaa cagccccagc   4020
```

ttcatccaga tcagaagcgt ggccaagaag caccccaaga cctgggtgca ctatatcgcc 4080
gccgaggaag aggactggga ctacgccccc ctggtgctgg cccccgacga cagaagctac 4140
aagagccagt acctgaacaa tggcccccag cggatcggcc ggaagtacaa gaaagtgcgg 4200
ttcatggcct acaccgacga gacattcaag acccgggagg ccatccagca cgagagcggc 4260
atcctgggcc ccctgctgta cggcgaagtg ggcgacacac tgctgatcat cttcaagaac 4320
caggctagcc ggccctacaa catctacccc cacggcatca ccgacgtgcg gcccctgtac 4380
agcaggcggc tgcccaaggg cgtgaagcac ctgaaggact tccccatcct gcccggcgag 4440
atcttcaagt acaagtggac cgtgaccgtg gaggacggcc ccaccaagag cgaccccaga 4500
tgcctgaccc ggtactacag cagcttcgtg aacatggaac gggacctggc ctccgggctg 4560
atcggacctc tgctgatctg ctacaaagaa agcgtggacc agcggggcaa ccagatcatg 4620
agcgacaagc ggaacgtgat cctgttcagc gtgttcgatg agaaccggtc ctggtatctg 4680
accgagaaca tccagcggtt tctgcccaac cctgccggcg tgcagctgga agatcccgag 4740
ttccaggcca gcaacatcat gcactccatc aatggctacg tgttcgactc tctgcagctc 4800
tccgtgtgtc tgcacgaggt ggcctactgg tacatcctga gcatcggcgc ccagaccgac 4860
ttcctgagcg tgttcttcag cggctacacc ttcaagcaca agatggtgta cgaggacacc 4920
ctgaccctgt tccctttcag cggcgagaca gtgttcatga gcatggaaaa ccccggcctg 4980
tggattctgg gctgccacaa cagcgacttc cggaaccggg gcatgaccgc cctgctgaag 5040
gtgtccagct gcgacaagaa caccggcgac tactacgagg acagctacga ggatatcagc 5100
gcctacctgc tgtccaagaa caacgccatc gaaccccgga gcttcagcca gaaccccccc 5160
gtgctgacgc gtcaccagcg ggagatcacc cggacaaccc tgcagtccga ccaggaagag 5220
atcgattacg acgacaccat cagcgtggag atgaagaaag aggatttcga tatctacgac 5280
gaggacgaga accagagccc cagaagcttc cagaagaaaa cccggcacta cttcattgcc 5340
gccgtggaga ggctgtggga ctacggcatg agttctagcc cccacgtgct gcggaaccgg 5400
gcccagagcg gcagcgtgcc ccagttcaag aaagtggtgt tccaggaatt cacagacggc 5460
agcttcaccc agcctctgta tagaggcgag ctgaacgagc acctggggct gctggggccc 5520
tacatcaggg ccgaagtgga ggacaacatc atggtgacct tccggaatca ggccagcaga 5580
ccctactcct tctacagcag cctgatcagc tacgaagagg accagcggca gggcgccgaa 5640
ccccggaaga acttcgtgaa gcccaacgaa accaagacct acttctggaa agtgcagcac 5700
cacatggccc ccaccaagga cgagttcgac tgcaaggcct gggcctactt cagcgacgtg 5760
gatctggaaa aggacgtgca ctctggactg attggcccac tcctggtctg ccacactaac 5820
accctcaacc ccgcccacgg ccgccaggtg accgtgcagg aattcgccct gttcttcacc 5880
atcttcgacg agacaaagtc ctggtacttc accgagaata tggaacggaa ctgcagagcc 5940
ccctgcaaca tccagatgga agatcctacc ttcaaagaga actaccggtt ccacgccatc 6000
aacggctaca tcatggacac cctgcctggc ctggtgatgg cccaggacca gagaatccgg 6060
tggtatctgc tgtccatggg cagcaacgag aatatccaca gcatccactt cagcggccac 6120
gtgttcaccg tgcggaagaa agaagagtac aagatggccc tgtacaacct gtaccccggc 6180
gtgttcgaga cagtggagat gctgcccagc aaggccggca tctggcgggt ggagtgtctg 6240
atcggcgagc acctgcacgc tggcatgagc accctgtttc tggtgtacag caacaagtgc 6300
cagaccccac tgggcatggc ctctggccac atccgggact tccagatcac cgcctccggc 6360

-continued

```
cagtacggcc agtgggcccc caagctggcc agactgcact acagcggcag catcaacgcc   6420
tggtccacca aagagccctt cagctggatc aaggtggacc tgctggcccc tatgatcatc   6480
cacggcatta agacccaggg cgccaggcag aagttcagca gcctgtacat cagccagttc   6540
atcatcatgt acagcctgga cggcaagaag tggcagacct accggggcaa cagcaccggc   6600
accctgatgg tgttcttcgg caatgtggac agcagcggca tcaagcacaa catcttcaac   6660
ccccccatca ttgcccggta catccggctg caccccaccc actacagcat tagatccaca   6720
ctgagaatgg aactgatggg ctgcgacctg aactcctgca gcatgcctct gggcatggaa   6780
agcaaggcca tcagcgacgc ccagatcaca gccagcagct acttcaccaa catgttcgcc   6840
acctggtccc cctccaaggc caggctgcac ctgcagggcc ggtccaacgc ctggcggcct   6900
caggtcaaca accccaaaga atggctgcag gtggactttc agaaaaccat gaaggtgacc   6960
ggcgtgacca cccagggcgt gaaaagcctg ctgaccagca tgtacgtgaa agagtttctg   7020
atcagcagct ctcaggatgg ccaccagtgg accctgttct ttcagaacgg caaggtgaaa   7080
gtgttccagg gcaaccagga ctccttcacc cccgtggtga actccctgga cccccccctg   7140
ctgacccgct acctgagaat ccacccccag tcttgggtgc accagatcgc cctcaggatg   7200
gaagtcctgg gatgtgaggc ccaggatctg tactgatgac gtctggaaca atcaacctct   7260
ggattacaaa atttgtgaaa gattgactgg tattcttaac tatgttgctc cttttacgct   7320
atgtggatac gctgctttaa tgcctttgta tcatgctatt gcttcccgta tggctttcat   7380
tttctcctcc ttgtataaat cctggttgct gtctctttat gaggagttgt ggcccgttgt   7440
caggcaacgt ggcgtggtgt gcactgtgtt tgctgacgca acccccactg gttggggcat   7500
tgccaccacc tgtcagctcc tttccgggac tttcgctttc cccctcccta ttgccacggc   7560
ggaactcatc gccgcctgcc ttgcccgctg ctggacaggg gctcggctgt tgggcactga   7620
caattccgtg gtgttgtcgg ggaagctgac gtcctttcca tggctgctcg cctgtgttgc   7680
cacctggatt ctgcgcggga cgtccttctg ctacgtccct tcggccctca atccagcgga   7740
ccttccttcc cgcggcctgc tgccggctct gcggcctctt ccgcgtcttc gccttcgccc   7800
tcagacgagt cggatctccc tttgggccgc ctccccgcct ggaattaatt ctgcagtcga   7860
gacctagaaa aacatggagc aatcacaagt agcaatacag cagctaccaa tgctgattgt   7920
gcctggctag aagcacaaga ggaggaggag gtgggttttc cagtcacacc tcaggtacct   7980
ttaagaccaa tgacttacaa ggcagctgta gatcttagcc actttttaaa agaaaagagg   8040
ggactggaag ggctaattca ctcccaacga agacaagata tccttgatct gtggatctac   8100
cacacacaag gctacttccc tgattagcag aactacacac cagggccagg ggtcagatat   8160
ccactgacct ttggatggtg ctacaagcta gtaccagttg agccagataa ggtagaagag   8220
gccaataaag gagagaacac cagcttgtta caccctgtga gcctgcatgg gatggatgac   8280
ccggagagag aagtgttaga gtggaggttt gacagccgcc tagcatttca tcacgtggcc   8340
cgagagctgc atccggagta cttcaagaac tgctgatatc gagcttgcta caagggactt   8400
tccgctgggg actttccagg gaggcgtggc ctgggcggga ctggggagtg gcgagccctc   8460
agatcctgca tataagcagc tgctttttgc ctgtactggg tctctctggt tagaccagat   8520
ctgagcctgg gagctctctg gctaactagg gaacccactg cttaagcctc aataaagctt   8580
gccttgagtg cttcaagtag tgtgtgcccg tctgttgtgt gactctggta actagagatc   8640
cctcagaccc ttttagtcag tgtggaaaat ctctagcagt agtagttcat gtcatcttat   8700
tattcagtat ttataacttg caaagaaatg aatatcagag agtgagaggc cttgacattg   8760
```

ctagcgtttt accgtcgacc tctagctaga gcttggcgta atcatggtca tagctgtttc 8820
ctgtgtgaaa ttgttatccg ctcacaattc cacacaacat acgagccgga agcataaagt 8880
gtaaagcctg gggtgcctaa tgagtgagct aactcacatt aattgcgttg cgctcactgc 8940
ccgctttcca gtcgggaaac ctgtcgtgcc agctgcatta atgaatcggc caacgcgcgg 9000
ggagaggcgg tttgcgtatt gggcgctctt ccgcttcctc gctcactgac tcgctgcgct 9060
cggtcgttcg gctgcggcga gcggtatcag ctcactcaaa ggcggtaata cggttatcca 9120
cagaatcagg ggataacgca ggaaagaaca tgtgagcaaa aggccagcaa aaggccagga 9180
accgtaaaaa ggccgcgttg ctggcgtttt tccataggct ccgcccccct gacgagcatc 9240
acaaaaatcg acgctcaagt cagaggtggc gaaacccgac aggactataa agataccagg 9300
cgtttccccc tggaagctcc ctcgtgcgct ctcctgttcc gaccctgccg cttaccggat 9360
acctgtccgc ctttctccct tcgggaagcg tggcgctttc tcatagctca cgctgtaggt 9420
atctcagttc ggtgtaggtc gttcgctcca agctgggctg tgtgcacgaa ccccccgttc 9480
agcccgaccg ctgcgcctta tccggtaact atcgtcttga gtccaacccg gtaagacacg 9540
acttatcgcc actggcagca gccactggta acaggattag cagagcgagg tatgtaggcg 9600
gtgctacaga gttcttgaag tggtggccta actacggcta cactagaaga acagtatttg 9660
gtatctgcgc tctgctgaag ccagttacct tcggaaaaag agttggtagc tcttgatccg 9720
gcaaacaaac caccgctggt agcggtggtt tttttgtttg caagcagcag attacgcgca 9780
gaaaaaaagg atctcaagaa gatcctttga tcttttctac ggggtctgac gctcagtgga 9840
acgaaaactc acgttaaggg attttggtca tgagattatc aaaaaggatc ttcacctaga 9900
tccttttaaa ttaaaaatga agttttaaat caatctaaag tatatatgag taaacttggt 9960
ctgacagtta ccaatgctta atcagtgagg cacctatctc agcgatctgt ctatttcgtt 10020
catccatagt tgcctgactc cccgtcgtgt agataactac gatacgggag ggcttaccat 10080
ctggccccag tgctgcaatg ataccgcgag acccacgctc accggctcca gatttatcag 10140
caataaacca gccagccgga agggccgagc gcagaagtgg tcctgcaact ttatccgcct 10200
ccatccagtc tattaattgt tgccgggaag ctagagtaag tagttcgcca gttaatagtt 10260
tgcgcaacgt tgttgccatt gctacaggca tcgtggtgtc acgctcgtcg tttggtatgg 10320
cttcattcag ctccggttcc caacgatcaa ggcgagttac atgatccccc atgttgtgca 10380
aaaaagcggt tagctccttc ggtcctccga tcgttgtcag aagtaagttg gccgcagtgt 10440
tatcactcat ggttatggca gcactgcata attctcttac tgtcatgcca tccgtaagat 10500
gcttttctgt gactggtgag tactcaacca agtcattctg agaatagtgt atgcggcgac 10560
cgagttgctc ttgcccggcg tcaatacggg ataataccgc gccacatagc agaactttaa 10620
aagtgctcat cattggaaaa cgttcttcgg ggcgaaaact ctcaaggatc ttaccgctgt 10680
tgagatccag ttcgatgtaa cccactcgtg cacccaactg atcttcagca tcttttactt 10740
tcaccagcgt ttctgggtga gcaaaaacag gaaggcaaaa tgccgcaaaa aagggaataa 10800
gggcgacacg gaaatgttga atactcatac tcttcctttt tcaatattat tgaagcattt 10860
atcagggtta ttgtctcatg agcggataca tatttgaatg tatttagaaa aataaacaaa 10920
taggggttcc gcgcacattt ccccgaaaag tgccacctga cgtcgacgga tcgggagatc 10980
aacttgttta ttgcagctta taatggttac aaataaagca atagcatcac aaatttcaca 11040
aataaagcat ttttttcact gcattctagt tgtggtttgt ccaaactcat caatgtatct 11100
tatcatgtct ggatcaactg gataactcaa gctaaccaaa atcatcccaa acttcccacc 11160
ccatacccta ttaccactgc caattacctg tggtttcatt tactctaaac ctgtgattcc 11220
tctgaattat tttcatttta aagaaattgt atttgttaaa tatgtactac aaacttagta 11280
gtttttaaag aaattgtatt tgttaaatat gtactacaaa cttagtagt 11329

<210> SEQ ID NO 42
<211> LENGTH: 11220
<212> TYPE: DNA
<213> ORGANISM: Artificial Sequence
<220> FEATURE:
<223> OTHER INFORMATION: vector

<400> SEQUENCE: 42
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860

-continued

```
actttctata gtgaatagag ttaggcaggg atattcacca ttatcgtttc agacccacct   1920
cccaaccccg aggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aaggggggat tggggggtac agtgcagggg aaagaatagt   2100
agacataata gcaacagaca tacaaactaa agaattacaa aaacaaatta caaaaattca   2160
aaattttcgg gtttattaca gggacagcag agatccagtt tggatcgata agcttgatat   2220
cgaattcctg cgcggccgct tcgaacgcgc gcgatgcatc atatgcgtac gcggtctaga   2280
actagtgaga cataaaagga aaatgaagcg agcaacaatt aaaaaaaatt ccccgcacac   2340
aacaatacaa tctatttaaa ctgtggctca tacttttcat accaatggta tgactttttt   2400
tctggagtcc cctcttctga ttcttgaact ccggggctgg cagcttgcaa aggggaagcg   2460
gactccagca ctgcacgggc aggtttagca aaggtctcta atgggtattt tctttttctt   2520
agccctgccc ccgaattgtc agacggcggg cgtctgcctc tgaagttagc agtgatttcc   2580
tttcgggcct ggccttatct ccggctgcac gttgcctgtt ggtgactaat aacacaataa   2640
cattgtctgg ggctggaata aagtcggagc tgtttacccc cactctaata ggggttcaat   2700
ataaaaagcc ggcagagagc tgtccaagtc agacgcgcct cagcgctgga tccatgcaga   2760
tcgagctgtc cacctgcttt tttctgtgcc tgctgcggtt ctgcttcagc gccacccggc   2820
ggtactacct gggcgccgtg gagctgtcct gggactacat gcagagcgac ctgggcgagc   2880
tgcccgtgga cgcccggttc ccccccagag tgcccaagag cttccccttc aacaccagcg   2940
tggtgtacaa gaaaaccctg ttcgtggagt tcaccgacca cctgttcaat atcgccaagc   3000
ccaggccccc ctggatgggc ctgctgggcc ccaccatcca ggccgaggtg tacgacaccg   3060
tggtgatcac cctgaagaac atggccagcc accccgtgag cctgcacgcc gtgggcgtga   3120
gctactggaa ggccagcgag ggcgccgagt acgacgacca gaccagccag cgggagaaag   3180
aagatgacaa ggtgttccct ggcggcagcc acacctacgt gtggcaggtg ctgaaagaaa   3240
acggccccat ggcctccgac cccctgtgcc tgacctacag ctacctgagc cacgtggacc   3300
tggtgaagga cctgaacagc ggcctgatcg gcgctctgct cgtctgccgg gagggcagcc   3360
tggccaaaga gaaaacccag accctgcaca agttcatcct gctgttcgcc gtgttcgacg   3420
agggcaagag ctggcacagc gagacaaaga acagcctgat gcaggaccgg gacgccgcct   3480
ctgccagagc ctggcccaag atgcacaccg tgaacggcta cgtgaacaga agcctgcccg   3540
gcctgattgg ctgccaccgg aagagcgtgt actggcacgt gatcggcatg ggcaccacac   3600
ccgaggtgca cagcatcttt ctggaagggc acacctttct ggtccggaac caccggcagg   3660
ccagcctgga aatcagccct atcaccttcc tgaccgccca gacactgctg atggacctgg   3720
gccagttcct gctgttttgc cacatcagct ctcaccagca cgacggcatg gaagcctacg   3780
tgaaggtgga ctcttgcccc gaggaacccc agctgcggat gaagaacaac gaggaagccg   3840
aggactacga cgacgacctg accgacagcg agatggacgt ggtgcggttc gacgacgaca   3900
acagccccag cttcatccag atcagaagcg tggccaagaa gcaccccaag acctgggtgc   3960
actatatcgc cgccgaggaa gaggactggg actacgcccc cctggtgctg gcccccgacg   4020
acagaagcta caagagccag tacctgaaca atggccccca gcggatcggc cggaagtaca   4080
agaaagtgcg gttcatggcc tacaccgacg agacattcaa gacccgggag gccatccagc   4140
acgagagcgg catcctgggc cccctgctgt acggcgaagt gggcgacaca ctgctgatca   4200
```

-continued tcttcaagaa ccaggctagc cggccctaca acatctaccc ccacggcatc accgacgtgc 4260
ggcccctgta cagcaggcgg ctgcccaagg gcgtgaagca cctgaaggac ttccccatcc 4320
tgcccggcga gatcttcaag tacaagtgga ccgtgaccgt ggaggacggc cccaccaaga 4380
gcgaccccag atgcctgacc cggtactaca gcagcttcgt gaacatggaa cgggacctgg 4440
cctccgggct gatcggacct ctgctgatct gctacaaaga aagcgtggac cagcggggca 4500
accagatcat gagcgacaag cggaacgtga tcctgttcag cgtgttcgat gagaaccggt 4560
cctggtatct gaccgagaac atccagcggt ttctgcccaa ccctgccggc gtgcagctgg 4620
aagatcccga gttccaggcc agcaacatca tgcactccat caatggctac gtgttcgact 4680
ctctgcagct ctccgtgtgt ctgcacgagg tggcctactg gtacatcctg agcatcggcg 4740
cccagaccga cttcctgagc gtgttcttca gcggctacac cttcaagcac aagatggtgt 4800
acgaggacac cctgaccctg ttccctttca gcggcgagac agtgttcatg agcatggaaa 4860
accccggcct gtggattctg ggctgccaca acagcgactt ccggaaccgg ggcatgaccg 4920
ccctgctgaa ggtgtccagc tgcgacaaga acaccggcga ctactacgag gacagctacg 4980
aggatatcag cgcctacctg ctgtccaaga acaacgccat cgaaccccgg agcttcagcc 5040
agaacccccc cgtgctgacg cgtcaccagc gggagatcac ccggacaacc ctgcagtccg 5100
accaggaaga gatcgattac gacgacacca tcagcgtgga gatgaagaaa gaggatttcg 5160
atatctacga cgaggacgag aaccagagcc ccagaagctt ccagaagaaa acccggcact 5220
acttcattgc cgccgtggag aggctgtggg actacggcat gagttctagc cccccacgtgc 5280 tgcggaaccg ggcccagagc ggcagcgtgc cccagttcaa gaaagtggtg ttccaggaat 5340
tcacagacgg cagcttcacc cagcctctgt atagaggcga gctgaacgag cacctggggc 5400
tgctggggcc ctacatcagg gccgaagtgg aggacaacat catggtgacc ttccggaatc 5460
aggccagcag accctactcc ttctacagca gcctgatcag ctacgaagag gaccagcggc 5520
agggcgccga accccggaag aacttcgtga agcccaacga aaccaagacc tacttctgga 5580
aagtgcagca ccacatggcc cccaccaagg acgagttcga ctgcaaggcc tgggcctact 5640
tcagcgacgt ggatctggaa aaggacgtgc actctggact gattggccca ctcctggtct 5700
gccacactaa caccctcaac cccgcccacg gccgccaggt gaccgtgcag gaattcgccc 5760
tgttcttcac catcttcgac gagacaaagt cctggtactt caccgagaat atggaacgga 5820
actgcagagc cccctgcaac atccagatgg aagatcctac cttcaaagag aactaccggt 5880
tccacgccat caacggctac atcatggaca ccctgcctgg cctggtgatg gcccaggacc 5940
agagaatccg gtggtatctg ctgtccatgg gcagcaacga gaatatccac agcatccact 6000
tcagcggcca cgtgttcacc gtgcggaaga aagaagagta caagatggcc ctgtacaacc 6060
tgtaccccgg cgtgttcgag acagtggaga tgctgcccag caaggccggc atctggcggg 6120
tggagtgtct gatcggcgag cacctgcacg ctggcatgag caccctgttt ctggtgtaca 6180
gcaacaagtg ccagacccca ctgggcatgg cctctggcca catccgggac ttccagatca 6240
ccgcctccgg ccagtacggc cagtgggccc ccaagctggc cagactgcac tacagcggca 6300
gcatcaacgc ctggtccacc aaagagccct tcagctggat caaggtggac ctgctggccc 6360
ctatgatcat ccacggcatt aagacccagg gcgccaggca gaagttcagc agcctgtaca 6420
tcagccagtt catcatcatg tacagcctgg acggcaagaa gtggcagacc taccggggca 6480
acagcaccgg caccctgatg gtgttcttcg gcaatgtgga cagcagcggc atcaagcaca 6540
acatcttcaa ccccccccatc attgcccggt acatccggct gcaccccacc cactacagca 6600

```
ttagatccac actgagaatg gaactgatgg gctgcgacct gaactcctgc agcatgcctc   6660
tgggcatgga aagcaaggcc atcagcgacg cccagatcac agccagcagc tacttcacca   6720
acatgttcgc cacctggtcc ccctccaagg ccaggctgca cctgcagggc cggtccaacg   6780
cctggcggcc tcaggtcaac aaccccaaag aatggctgca ggtggacttt cagaaaacca   6840
tgaaggtgac cggcgtgacc acccagggcg tgaaaagcct gctgaccagc atgtacgtga   6900
aagagtttct gatcagcagc tctcaggatg gccaccagtg gaccctgttc tttcagaacg   6960
gcaaggtgaa agtgttccag ggcaaccagg actccttcac ccccgtggtg aactccctgg   7020
acccccccct gctgacccgc tacctgagaa tccaccccca gtcttgggtg caccagatcg   7080
ccctcaggat ggaagtcctg ggatgtgagg cccaggatct gtactgatga cgtctggaac   7140
aatcaacctc tggattacaa aatttgtgaa agattgactg gtattcttaa ctatgttgct   7200
ccttttacgc tatgtggata cgctgcttta atgcctttgt atcatgctat tgcttcccgt   7260
atggctttca ttttctcctc cttgtataaa tcctggttgc tgtctcttta tgaggagttg   7320
tggcccgttg tcaggcaacg tggcgtggtg tgcactgtgt ttgctgacgc aacccccact   7380
ggttggggca ttgccaccac ctgtcagctc ctttccggga ctttcgcttt ccccctccct   7440
attgccacgg cggaactcat cgccgcctgc cttgcccgct gctggacagg ggctcggctg   7500
ttgggcactg acaattccgt ggtgttgtcg gggaagctga cgtcctttcc atggctgctc   7560
gcctgtgttg ccacctggat tctgcgcggg acgtccttct gctacgtccc ttcggccctc   7620
aatccagcgg accttccttc ccgcggcctg ctgccggctc tgcggcctct tccgcgtctt   7680
cgccttcgcc ctcagacgag tcggatctcc ctttgggccg cctccccgcc tggaattaat   7740
tctgcagtcg agacctagaa aaacatggag caatcacaag tagcaataca gcagctacca   7800
atgctgattg tgcctggcta gaagcacaag aggaggagga ggtgggtttt ccagtcacac   7860
ctcaggtacc tttaagacca atgacttaca aggcagctgt agatcttagc cactttttaa   7920
aagaaaagag gggactggaa gggctaattc actcccaacg aagacaagat atccttgatc   7980
tgtggatcta ccacacacaa ggctacttcc ctgattagca gaactacaca ccagggccag   8040
gggtcagata tccactgacc tttggatggt gctacaagct agtaccagtt gagccagata   8100
aggtagaaga ggccaataaa ggagagaaca ccagcttgtt acaccctgtg agcctgcatg   8160
ggatggatga cccggagaga gaagtgttag agtggaggtt tgacagccgc ctagcatttc   8220
atcacgtggc ccgagagctg catccggagt acttcaagaa ctgctgatat cgagcttgct   8280
acaagggact ttccgctggg gactttccag ggaggcgtgg cctgggcggg actggggagt   8340
ggcgagccct cagatcctgc atataagcag ctgctttttg cctgtactgg gtctctctgg   8400
ttagaccaga tctgagcctg ggagctctct ggctaactag ggaacccact gcttaagcct   8460
caataaagct tgccttgagt gcttcaagta gtgtgtgccc gtctgttgtg tgactctggt   8520
aactagagat ccctcagacc cttttagtca gtgtggaaaa tctctagcag tagtagttca   8580
tgtcatctta ttattcagta tttataactt gcaaagaaat gaatatcaga gagtgagagg   8640
ccttgacatt gctagcgttt taccgtcgac ctctagctag agcttggcgt aatcatggtc   8700
atagctgttt cctgtgtgaa attgttatcc gctcacaatt ccacacaaca tacgagccgg   8760
aagcataaag tgtaaagcct ggggtgccta atgagtgagc taactcacat taattgcgtt   8820
gcgctcactg cccgctttcc agtcgggaaa cctgtcgtgc cagctgcatt aatgaatcgg   8880
ccaacgcgcg gggagaggcg gtttgcgtat tgggcgctct tccgcttcct cgctcactga   8940
```

-continued

```
ctcgctgcgc tcggtcgttc ggctgcggcg agcggtatca gctcactcaa aggcggtaat   9000
acggttatcc acagaatcag gggataacgc aggaaagaac atgtgagcaa aaggccagca   9060
aaaggccagg aaccgtaaaa aggccgcgtt gctggcgttt ttccataggc tccgcccccc   9120
tgacgagcat cacaaaaatc gacgctcaag tcagaggtgg cgaaacccga caggactata   9180
aagataccag gcgtttcccc ctggaagctc cctcgtgcgc tctcctgttc cgaccctgcc   9240
gcttaccgga tacctgtccg cctttctccc ttcgggaagc gtggcgcttt ctcatagctc   9300
acgctgtagg tatctcagtt cggtgtaggt cgttcgctcc aagctgggct gtgtgcacga   9360
accccccgtt cagcccgacc gctgcgcctt atccggtaac tatcgtcttg agtccaaccc   9420
ggtaagacac gacttatcgc cactggcagc agccactggt aacaggatta gcagagcgag   9480
gtatgtaggc ggtgctacag agttcttgaa gtggtggcct aactacggct acactagaag   9540
aacagtattt ggtatctgcg ctctgctgaa gccagttacc ttcggaaaaa gagttggtag   9600
ctcttgatcc ggcaaacaaa ccaccgctgg tagcggtggt ttttttgttt gcaagcagca   9660
gattacgcgc agaaaaaaag gatctcaaga agatcctttg atcttttcta cggggtctga   9720
cgctcagtgg aacgaaaact cacgttaagg gattttggtc atgagattat caaaaaggat   9780
cttcacctag atccttttaa attaaaaatg aagttttaaa tcaatctaaa gtatatatga   9840
gtaaacttgg tctgacagtt accaatgctt aatcagtgag gcacctatct cagcgatctg   9900
tctatttcgt tcatccatag ttgcctgact ccccgtcgtg tagataacta cgatacggga   9960
gggcttacca tctggcccca gtgctgcaat gataccgcga gacccacgct caccggctcc  10020
agatttatca gcaataaacc agccagccgg aagggccgag cgcagaagtg gtcctgcaac  10080
tttatccgcc tccatccagt ctattaattg ttgccgggaa gctagagtaa gtagttcgcc  10140
agttaatagt ttgcgcaacg ttgttgccat tgctacaggc atcgtggtgt cacgctcgtc  10200
gtttggtatg gcttcattca gctccggttc ccaacgatca aggcgagtta catgatcccc  10260
catgttgtgc aaaaaagcgg ttagctcctt cggtcctccg atcgttgtca gaagtaagtt  10320
ggccgcagtg ttatcactca tggttatggc agcactgcat aattctctta ctgtcatgcc  10380
atccgtaaga tgcttttctg tgactggtga gtactcaacc aagtcattct gagaatagtg  10440
tatgcggcga ccgagttgct cttgcccggc gtcaatacgg gataataccg cgccacatag  10500
cagaacttta aaagtgctca tcattggaaa acgttcttcg gggcgaaaac tctcaaggat  10560
cttaccgctg ttgagatcca gttcgatgta acccactcgt gcacccaact gatcttcagc  10620
atcttttact ttcaccagcg tttctgggtg agcaaaaaca ggaaggcaaa atgccgcaaa  10680
aaagggaata agggcgacac ggaaatgttg aatactcata ctcttccttt ttcaatatta  10740
ttgaagcatt tatcagggtt attgtctcat gagcggatac atatttgaat gtatttagaa  10800
aaataaacaa ataggggttc cgcgcacatt tccccgaaaa gtgccacctg acgtcgacgg  10860
atcgggagat caacttgttt attgcagctt ataatggtta caaataaagc aatagcatca  10920
caaatttcac aaataaagca tttttttcac tgcattctag ttgtggtttg tccaaactca  10980
tcaatgtatc ttatcatgtc tggatcaact ggataactca agctaaccaa aatcatccca  11040
aacttcccac cccataccct attaccactg ccaattacct gtggtttcat ttactctaaa  11100
cctgtgattc ctctgaatta ttttcatttt aaagaaattg tatttgttaa atatgtacta  11160
caaacttagt agtttttaaa gaaattgtat ttgttaaata tgtactacaa acttagtagt  11220
```

<210> SEQ ID NO 43
<211> LENGTH: 11236

<212> TYPE: DNA
<213> ORGANISM: Artificial Sequence
<220> FEATURE:
<223> OTHER INFORMATION: vector

<400> SEQUENCE: 43
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920
cccaaccccg aggggggacc cgacaggccc gaaggaatag aagaagaagg tggagagaga 1980
gacagagaca gatccattcg attagtgaac ggatctcgac ggtcgccaaa tggcagtatt 2040
catccacaat tttaaaagaa aaggggggat tggggggtac agtgcagggg aaagaatagt 2100
agacataata gcaacagaca tacaaactaa agaattacaa aaacaaatta caaaaattca 2160

-continued

```
aaattttcgg gtttattaca gggacagcag agatccagtt tggatcgata agcttgatat   2220
cgaattcctg cgcggccgct tcgaacgcgc gcgatgcatc atatgcgtac gcggtctaga   2280
actagtgaga cataaaagga aaatgaagcg agcaacaatt aaaaaaaatt ccccgcacac   2340
aacaatacaa tctatttaaa ctgtggctca tacttttcat accaatggta tgactttttt   2400
tctggagtcc cctcttctga ttcttgaact ccggggctgg cagcttgcaa aggggaagcg   2460
gactccagca ctgcacgggc aggtttagca aaggtctcta atgggtattt tctttttctt   2520
agccctgccc ccgaattgtc agacggcggg cgtctgcctc tgaagttagc agtgatttcc   2580
tttcgggcct ggccttatct ccggctgcac gttgcctgtt ggtgactaat aacacaataa   2640
cattgtctgg ggctggaata aagtcggagc tgtttacccc cactctaata ggggttcaat   2700
ataaaaagcc ggcagagagc tgtccaagtc agacgcgcct cagcgctgga tctcgggctc   2760
gaggccacca tgcagatcga gctgtccacc tgcttttttc tgtgcctgct gcggttctgc   2820
ttcagcgcca cccggcggta ctacctgggc gccgtggagc tgtcctggga ctacatgcag   2880
agcgacctgg gcgagctgcc cgtggacgcc cggttccccc ccagagtgcc caagagcttc   2940
cccttcaaca ccagcgtggt gtacaagaaa accctgttcg tggagttcac cgaccacctg   3000
ttcaatatcg ccaagcccag gcccccctgg atgggcctgc tgggccccac catccaggcc   3060
gaggtgtacg acaccgtggt gatcaccctg aagaacatgg ccagccaccc cgtgagcctg   3120
cacgccgtgg gcgtgagcta ctggaaggcc agcgagggcg ccgagtacga cgaccagacc   3180
agccagcggg agaaagaaga tgacaaggtg ttccctggcg gcagccacac ctacgtgtgg   3240
caggtgctga aagaaaacgg ccccatggcc tccgaccccc tgtgcctgac ctacagctac   3300
ctgagccacg tggacctggt gaaggacctg aacagcggcc tgatcggcgc tctgctcgtc   3360
tgccgggagg gcagcctggc caaagagaaa acccagaccc tgcacaagtt catcctgctg   3420
ttcgccgtgt tcgacgaggg caagagctgg cacagcgaga caaagaacag cctgatgcag   3480
gaccgggacg ccgcctctgc cagagcctgg cccaagatgc acaccgtgaa cggctacgtg   3540
aacagaagcc tgcccggcct gattggctgc caccggaaga gcgtgtactg gcacgtgatc   3600
ggcatgggca ccacacccga ggtgcacagc atctttctgg aagggcacac ctttctggtc   3660
cggaaccacc ggcaggccag cctggaaatc agccctatca ccttcctgac cgcccagaca   3720
ctgctgatgg acctgggcca gttcctgctg ttttgccaca tcagctctca ccagcacgac   3780
ggcatggaag cctacgtgaa ggtggactct tgccccgagg aaccccagct gcggatgaag   3840
aacaacgagg aagccgagga ctacgacgac gacctgaccg acagcgagat ggacgtggtg   3900
cggttcgacg acgacaacag ccccagcttc atccagatca gaagcgtggc caagaagcac   3960
cccaagacct gggtgcacta tatcgccgcc gaggaagagg actgggacta cgcccccctg   4020
gtgctggccc ccgacgacag aagctacaag agccagtacc tgaacaatgg cccccagcgg   4080
atcggccgga agtacaagaa agtgcggttc atggcctaca ccgacgagac attcaagacc   4140
cgggaggcca tccagcacga gagcggcatc ctgggccccc tgctgtacgg cgaagtgggc   4200
gacacactgc tgatcatctt caagaaccag gctagccggc cctacaacat ctacccccac   4260
ggcatcaccg acgtgcggcc cctgtacagc aggcggctgc ccaagggcgt gaagcacctg   4320
aaggacttcc ccatcctgcc cggcgagatc ttcaagtaca agtggaccgt gaccgtggag   4380
gacggcccca ccaagagcga ccccagatgc ctgacccggt actacagcag cttcgtgaac   4440
atggaacggg acctggcctc cgggctgatc ggacctctgc tgatctgcta caaagaaagc   4500
gtggaccagc ggggcaacca gatcatgagc gacaagcgga acgtgatcct gttcagcgtg   4560
```

```
ttcgatgaga accggtcctg gtatctgacc gagaacatcc agcggtttct gcccaaccct   4620

gccggcgtgc agctggaaga tcccgagttc caggccagca acatcatgca ctccatcaat   4680

ggctacgtgt tcgactctct gcagctctcc gtgtgtctgc acgaggtggc ctactggtac   4740

atcctgagca tcggcgccca gaccgacttc ctgagcgtgt tcttcagcgg ctacaccttc   4800

aagcacaaga tggtgtacga ggacaccctg accctgttcc ctttcagcgg cgagacagtg   4860

ttcatgagca tggaaaaccc cggcctgtgg attctgggct gccacaacag cgacttccgg   4920

aaccggggca tgaccgccct gctgaaggtg tccagctgcg acaagaacac cggcgactac   4980

tacgaggaca gctacgagga tatcagcgcc tacctgctgt ccaagaacaa cgccatcgaa   5040

ccccggagct tcagccagaa cccccccgtg ctgacgcgtc accagcggga gatcacccgg   5100

acaaccctgc agtccgacca ggaagagatc gattacgacg acaccatcag cgtggagatg   5160

aagaaagagg atttcgatat ctacgacgag gacgagaacc agagccccag aagcttccag   5220

aagaaaaccc ggcactactt cattgccgcc gtggagaggc tgtgggacta cggcatgagt   5280

tctagccccc acgtgctgcg gaaccgggcc cagagcggca gcgtgcccca gttcaagaaa   5340

gtggtgttcc aggaattcac agacggcagc ttcacccagc ctctgtatag aggcgagctg   5400

aacgagcacc tggggctgct ggggccctac atcagggccg aagtggagga caacatcatg   5460

gtgaccttcc ggaatcaggc cagcagaccc tactccttct acagcagcct gatcagctac   5520

gaagaggacc agcggcaggg cgccgaaccc cggaagaact tcgtgaagcc caacgaaacc   5580

aagacctact tctggaaagt gcagcaccac atggccccca ccaaggacga gttcgactgc   5640

aaggcctggg cctacttcag cgacgtggat ctggaaaagg acgtgcactc tggactgatt   5700

ggcccactcc tggtctgcca cactaacacc ctcaaccccg cccacggccg ccaggtgacc   5760

gtgcaggaat tcgccctgtt cttcaccatc ttcgacgaga caaagtcctg gtacttcacc   5820

gagaatatgg aacggaactg cagagccccc tgcaacatcc agatggaaga tcctaccttc   5880

aaagagaact accggttcca cgccatcaac ggctacatca tggacaccct gcctggcctg   5940

gtgatggccc aggaccagag aatccggtgg tatctgctgt ccatgggcag caacgagaat   6000

atccacagca tccacttcag cggccacgtg ttcaccgtgc ggaagaaaga agagtacaag   6060

atggccctgt acaacctgta ccccggcgtg ttcgagacag tggagatgct gcccagcaag   6120

gccggcatct ggcgggtgga gtgtctgatc ggcgagcacc tgcacgctgg catgagcacc   6180

ctgtttctgg tgtacagcaa caagtgccag accccactgg gcatggcctc tggccacatc   6240

cgggacttcc agatcaccgc ctccggccag tacggccagt gggcccccaa gctggccaga   6300

ctgcactaca gcggcagcat caacgcctgg tccaccaaag agcccttcag ctggatcaag   6360

gtggacctgc tggcccctat gatcatccac ggcattaaga cccagggcgc caggcagaag   6420

ttcagcagcc tgtacatcag ccagttcatc atcatgtaca gcctggacgg caagaagtgg   6480

cagacctacc ggggcaacag caccggcacc ctgatggtgt tcttcggcaa tgtggacagc   6540

agcggcatca agcacaacat cttcaacccc cccatcattg cccggtacat ccggctgcac   6600

cccacccact acagcattag atccacactg agaatggaac tgatgggctg cgacctgaac   6660

tcctgcagca tgcctctggg catggaaagc aaggccatca gcgacgccca gatcacagcc   6720

agcagctact tcaccaacat gttcgccacc tggtccccct ccaaggccag gctgcacctg   6780

cagggccggt ccaacgcctg gcggcctcag gtcaacaacc ccaaagaatg gctgcaggtg   6840

gactttcaga aaccatgaa ggtgaccggc gtgaccaccc agggcgtgaa aagcctgctg   6900
```

-continued accagcatgt acgtgaaaga gtttctgatc agcagctctc aggatggcca ccagtggacc 6960
ctgttctttc agaacggcaa ggtgaaagtg ttccagggca accaggactc cttcaccccc 7020
gtggtgaact ccctggaccc ccccctgctg acccgctacc tgagaatcca cccccagtct 7080
tgggtgcacc agatcgccct caggatggaa gtcctgggat gtgaggccca ggatctgtac 7140
tgatgacgtc tggaacaatc aacctctgga ttacaaaatt tgtgaaagat tgactggtat 7200
tcttaactat gttgctcctt ttacgctatg tggatacgct gctttaatgc ctttgtatca 7260
tgctattgct tcccgtatgg ctttcatttt ctcctccttg tataaatcct ggttgctgtc 7320
tctttatgag gagttgtggc ccgttgtcag gcaacgtggc gtggtgtgca ctgtgtttgc 7380
tgacgcaacc cccactggtt ggggcattgc caccacctgt cagctccttt ccgggacttt 7440
cgctttcccc ctccctattg ccacggcgga actcatcgcc gcctgccttg cccgctgctg 7500
gacaggggct cggctgttgg gcactgacaa ttccgtggtg ttgtcgggga agctgacgtc 7560
ctttccatgg ctgctcgcct gtgttgccac ctggattctg cgcgggacgt ccttctgcta 7620
cgtcccttcg gccctcaatc cagcggacct tccttcccgc ggcctgctgc cggctctgcg 7680
gcctcttccg cgtcttcgcc ttcgccctca gacgagtcgg atctcccttt gggccgcctc 7740
cccgcctgga attaattctg cagtcgagac ctagaaaaac atggagcaat cacaagtagc 7800
aatacagcag ctaccaatgc tgattgtgcc tggctagaag cacaagagga ggaggaggtg 7860
ggttttccag tcacacctca ggtaccttta agaccaatga cttacaaggc agctgtagat 7920
cttagccact ttttaaaaga aaagaggggga ctggaagggc taattcactc ccaacgaaga 7980
caagatatcc ttgatctgtg gatctaccac acacaaggct acttccctga ttagcagaac 8040
tacacaccag ggccaggggt cagatatcca ctgacctttg gatggtgcta caagctagta 8100
ccagttgagc cagataaggt agaagaggcc aataaaggag agaacaccag cttgttacac 8160
cctgtgagcc tgcatgggat ggatgacccg gagagagaag tgttagagtg gaggtttgac 8220
agccgcctag catttcatca cgtggcccga gagctgcatc cggagtactt caagaactgc 8280
tgatatcgag cttgctacaa gggactttcc gctggggact ttccagggag gcgtggcctg 8340
ggcgggactg gggagtggcg agccctcaga tcctgcatat aagcagctgc tttttgcctg 8400
tactgggtct ctctggttag accagatctg agcctgggag ctctctggct aactagggaa 8460
cccactgctt aagcctcaat aaagcttgcc ttgagtgctt caagtagtgt gtgcccgtct 8520
gttgtgtgac tctggtaact agagatccct cagacccttt tagtcagtgt ggaaaatctc 8580
tagcagtagt agttcatgtc atcttattat tcagtattta taacttgcaa agaaatgaat 8640
atcagagagt gagaggcctt gacattgcta gcgttttacc gtcgacctct agctagagct 8700
tggcgtaatc atggtcatag ctgtttcctg tgtgaaattg ttatccgctc acaattccac 8760
acaacatacg agccggaagc ataaagtgta aagcctgggg tgcctaatga gtgagctaac 8820
tcacattaat tgcgttgcgc tcactgcccg ctttccagtc gggaaacctg tcgtgccagc 8880
tgcattaatg aatcggccaa cgcgcgggga gaggcggttt gcgtattggg cgctcttccg 8940
cttcctcgct cactgactcg ctgcgctcgg tcgttcggct gcggcgagcg gtatcagctc 9000
actcaaaggc ggtaatacgg ttatccacag aatcagggga taacgcagga aagaacatgt 9060
gagcaaaagg ccagcaaaag gccaggaacc gtaaaaaggc cgcgttgctg gcgtttttcc 9120
ataggctccg cccccctgac gagcatcaca aaaatcgacg ctcaagtcag aggtggcgaa 9180
acccgacagg actataaaga taccaggcgt ttccccctgg aagctccctc gtgcgctctc 9240
ctgttccgac cctgccgctt accggatacc tgtccgcctt tctcccttcg ggaagcgtgg 9300

```
cgctttctca tagctcacgc tgtaggtatc tcagttcggt gtaggtcgtt cgctccaagc   9360

tgggctgtgt gcacgaaccc cccgttcagc ccgaccgctg cgccttatcc ggtaactatc   9420

gtcttgagtc caacccggta agacacgact tatcgccact ggcagcagcc actggtaaca   9480

ggattagcag agcgaggtat gtaggcggtg ctacagagtt cttgaagtgg tggcctaact   9540

acggctacac tagaagaaca gtatttggta tctgcgctct gctgaagcca gttaccttcg   9600

gaaaaagagt tggtagctct tgatccggca aacaaaccac cgctggtagc ggtggttttt   9660

ttgtttgcaa gcagcagatt acgcgcagaa aaaaaggatc tcaagaagat cctttgatct   9720

tttctacggg gtctgacgct cagtggaacg aaaactcacg ttaagggatt ttggtcatga   9780

gattatcaaa aaggatcttc acctagatcc ttttaaatta aaaatgaagt tttaaatcaa   9840

tctaaagtat atatgagtaa acttggtctg acagttacca atgcttaatc agtgaggcac   9900

ctatctcagc gatctgtcta tttcgttcat ccatagttgc ctgactcccc gtcgtgtaga   9960

taactacgat acgggagggc ttaccatctg gccccagtgc tgcaatgata ccgcgagacc  10020

cacgctcacc ggctccagat ttatcagcaa taaaccagcc agccggaagg gccgagcgca  10080

gaagtggtcc tgcaacttta tccgcctcca tccagtctat taattgttgc cgggaagcta  10140

gagtaagtag ttcgccagtt aatagtttgc gcaacgttgt tgccattgct acaggcatcg  10200

tggtgtcacg ctcgtcgttt ggtatggctt cattcagctc cggttcccaa cgatcaaggc  10260

gagttacatg atcccccatg ttgtgcaaaa aagcggttag ctccttcggt cctccgatcg  10320

ttgtcagaag taagttggcc gcagtgttat cactcatggt tatggcagca ctgcataatt  10380

ctcttactgt catgccatcc gtaagatgct tttctgtgac tggtgagtac tcaaccaagt  10440

cattctgaga atagtgtatg cggcgaccga gttgctcttg cccggcgtca atacgggata  10500

ataccgcgcc acatagcaga actttaaaag tgctcatcat tggaaaacgt tcttcggggc  10560

gaaaactctc aaggatctta ccgctgttga gatccagttc gatgtaaccc actcgtgcac  10620

ccaactgatc ttcagcatct tttactttca ccagcgtttc tgggtgagca aaaacaggaa  10680

ggcaaaatgc cgcaaaaaag ggaataaggg cgacacggaa atgttgaata ctcatactct  10740

tcctttttca atattattga agcatttatc agggttattg tctcatgagc ggatacatat  10800

ttgaatgtat ttagaaaaat aaacaaatag gggttccgcg cacatttccc cgaaaagtgc  10860

cacctgacgt cgacggatcg ggagatcaac ttgtttattg cagcttataa tggttacaaa  10920

taaagcaata gcatcacaaa tttcacaaat aaagcatttt tttcactgca ttctagttgt  10980

ggtttgtcca aactcatcaa tgtatcttat catgtctgga tcaactggat aactcaagct  11040

aaccaaaatc atcccaaact tcccacccca taccctatta ccactgccaa ttacctgtgg  11100

tttcatttac tctaaacctg tgattcctct gaattatttt cattttaaag aaattgtatt  11160

tgttaaatat gtactacaaa cttagtagtt tttaaagaaa ttgtatttgt taaatatgta  11220

ctacaaactt agtagt                                                  11236
```

```
<210> SEQ ID NO 44
<211> LENGTH: 11177
<212> TYPE: DNA
<213> ORGANISM: Artificial Sequence
<220> FEATURE:
<223> OTHER INFORMATION: vector

<400> SEQUENCE: 44

tggaagggct aattcactcc caaagaagac aagatatcct tgatctgtgg atctaccaca     60
```

-continued

```
cacaaggcta cttccctgat tagcagaact acacaccagg gccaggggtc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aaggggggat tggggggtac agtgcagggg aaagaatagt   2100
agacataata gcaacagaca tacaaactaa agaattacaa aaacaaatta caaaaattca   2160
aaattttcgg gtttattaca gggacagcag agatccagtt tggatcgata agcttgatat   2220
cgaattcctg cgcggccgct tcgaacgcgc gcgatgcatc atatgcgtac gcggtctaga   2280
attcctgcag ggcccactag tctcccaggc atgactccaa caatgcatcc catgggattt   2340
ggggttcccc agatctgggg cttgtaggcc tgactctccc ctgtgcacac gtctcataca   2400
cgcatgcgtg cacccattgc ctgccccgcc ccttgcacag ggagtcagca gggaggactg   2460
```

```
ggttatgccc tgcttatcag cagcttccca gcttcctctg cctggattct tagaggcctg   2520
gggtcctaga acgagctggt gcacgtggct tcccaaagat ctctcagata atgagaggaa   2580
atgcagtcat cagtttgcag aaggctaggg attctgggcc atagctcaga cctgcgccca   2640
ccatctccct ccaggcagcc cttggctggt ccctgcgagc ccgtggagac tgccagtcag   2700
cgctggatcc atgcagatcg agctgtccac ctgctttttt ctgtgcctgc tgcggttctg   2760
cttcagcgcc acccggcggt actacctggg cgccgtggag ctgtcctggg actacatgca   2820
gagcgacctg ggcgagctgc ccgtggacgc ccggttcccc cccagagtgc ccaagagctt   2880
ccccttcaac accagcgtgg tgtacaagaa aaccctgttc gtggagttca ccgaccacct   2940
gttcaatatc gccaagccca ggcccccctg gatgggcctg ctgggcccca ccatccaggc   3000
cgaggtgtac gacaccgtgg tgatcaccct gaagaacatg gccagccacc ccgtgagcct   3060
gcacgccgtg ggcgtgagct actggaaggc cagcgagggc gccgagtacg acgaccagac   3120
cagccagcgg gagaaagaag atgacaaggt gttccctggc ggcagccaca cctacgtgtg   3180
gcaggtgctg aaagaaaacg gccccatggc ctccgacccc ctgtgcctga cctacagcta   3240
cctgagccac gtggacctgg tgaaggacct gaacagcggc ctgatcggcg ctctgctcgt   3300
ctgccgggag ggcagcctgg ccaaagagaa aacccagacc ctgcacaagt tcatcctgct   3360
gttcgccgtg ttcgacgagg gcaagagctg gcacagcgag acaaagaaca gcctgatgca   3420
ggaccgggac gccgcctctg ccagagcctg gcccaagatg cacaccgtga acggctacgt   3480
gaacagaagc ctgcccggcc tgattggctg ccaccggaag agcgtgtact ggcacgtgat   3540
cggcatgggc accacacccg aggtgcacag catctttctg gaagggcaca cctttctggt   3600
ccggaaccac cggcaggcca gcctggaaat cagccctatc accttcctga ccgcccagac   3660
actgctgatg gacctgggcc agttcctgct gttttgccac atcagctctc accagcacga   3720
cggcatggaa gcctacgtga aggtggactc ttgccccgag gaaccccagc tgcggatgaa   3780
gaacaacgag gaagccgagg actacgacga cgacctgacc gacagcgaga tggacgtggt   3840
gcggttcgac gacgacaaca gccccagctt catccagatc agaagcgtgg ccaagaagca   3900
ccccaagacc tgggtgcact atatcgccgc cgaggaagag gactgggact acgccccccct   3960
ggtgctggcc cccgacgaca gaagctacaa gagccagtac ctgaacaatg gcccccagcg   4020
gatcggccgg aagtacaaga aagtgcggtt catggcctac accgacgaga cattcaagac   4080
ccgggaggcc atccagcacg agagcggcat cctgggcccc ctgctgtacg gcgaagtggg   4140
cgacacactg ctgatcatct tcaagaacca ggctagccgg ccctacaaca tctaccccca   4200
cggcatcacc gacgtgcggc ccctgtacag caggcggctg cccaagggcg tgaagcacct   4260
gaaggacttc cccatcctgc ccggcgagat cttcaagtac aagtggaccg tgaccgtgga   4320
ggacggcccc accaagagcg accccagatg cctgacccgg tactacagca gcttcgtgaa   4380
catggaacgg gacctggcct ccgggctgat cggacctctg ctgatctgct acaaagaaag   4440
cgtggaccag cggggcaacc agatcatgag cgacaagcgg aacgtgatcc tgttcagcgt   4500
gttcgatgag aaccggtcct ggtatctgac cgagaacatc cagcggtttc tgcccaaccc   4560
tgccggcgtg cagctggaag atcccgagtt ccaggccagc aacatcatgc actccatcaa   4620
tggctacgtg ttcgactctc tgcagctctc cgtgtgtctg cacgaggtgg cctactggta   4680
catcctgagc atcggcgccc agaccgactt cctgagcgtg ttcttcagcg gctacacctt   4740
caagcacaag atggtgtacg aggacaccct gaccctgttc cctttcagcg gcgagacagt   4800
```

-continued

```
gttcatgagc atggaaaacc ccggcctgtg gattctgggc tgccacaaca gcgacttccg   4860
gaaccggggc atgaccgccc tgctgaaggt gtccagctgc gacaagaaca ccggcgacta   4920
ctacgaggac agctacgagg atatcagcgc ctacctgctg tccaagaaca acgccatcga   4980
accccggagc ttcagccaga acccccccgt gctgacgcgt caccagcggg agatcacccg   5040
gacaaccctg cagtccgacc aggaagagat cgattacgac gacaccatca gcgtggagat   5100
gaagaaagag gatttcgata tctacgacga ggacgagaac cagagcccca gaagcttcca   5160
gaagaaaacc cggcactact tcattgccgc cgtggagagg ctgtgggact acggcatgag   5220
ttctagcccc cacgtgctgc ggaaccgggc ccagagcggc agcgtgcccc agttcaagaa   5280
agtggtgttc caggaattca cagacggcag cttcacccag cctctgtata gaggcgagct   5340
gaacgagcac ctggggctgc tggggcccta catcagggcc gaagtggagg acaacatcat   5400
ggtgaccttc cggaatcagg ccagcagacc ctactccttc tacagcagcc tgatcagcta   5460
cgaagaggac cagcggcagg gcgccgaacc ccggaagaac ttcgtgaagc ccaacgaaac   5520
caagacctac ttctggaaag tgcagcacca catggccccc accaaggacg agttcgactg   5580
caaggcctgg gcctacttca gcgacgtgga tctggaaaag gacgtgcact ctggactgat   5640
tggcccactc ctggtctgcc acactaacac cctcaacccc gcccacggcc gccaggtgac   5700
cgtgcaggaa ttcgccctgt tcttcaccat cttcgacgag acaaagtcct ggtacttcac   5760
cgagaatatg gaacggaact gcagagcccc ctgcaacatc cagatggaag atcctacctt   5820
caaagagaac taccggttcc acgccatcaa cggctacatc atggacaccc tgcctggcct   5880
ggtgatggcc caggaccaga gaatccggtg gtatctgctg tccatgggca gcaacgagaa   5940
tatccacagc atccacttca gcggccacgt gttcaccgtg cggaagaaag aagagtacaa   6000
gatggccctg tacaacctgt accccggcgt gttcgagaca gtggagatgc tgcccagcaa   6060
ggccggcatc tggcgggtgg agtgtctgat cggcgagcac ctgcacgctg gcatgagcac   6120
cctgtttctg gtgtacagca acaagtgcca gaccccactg ggcatggcct ctggccacat   6180
ccgggacttc cagatcaccg cctccggcca gtacggccag tgggccccca agctggccag   6240
actgcactac agcggcagca tcaacgcctg gtccaccaaa gagcccttca gctggatcaa   6300
ggtggacctg ctggccccta tgatcatcca cggcattaag acccagggcg ccaggcagaa   6360
gttcagcagc ctgtacatca gccagttcat catcatgtac agcctggacg gcaagaagtg   6420
gcagacctac cggggcaaca gcaccggcac cctgatggtg ttcttcggca atgtggacag   6480
cagcggcatc aagcacaaca tcttcaaccc ccccatcatt gcccggtaca tccggctgca   6540
ccccacccac tacagcatta gatccacact gagaatggaa ctgatgggct gcgacctgaa   6600
ctcctgcagc atgcctctgg gcatggaaag caaggccatc agcgacgccc agatcacagc   6660
cagcagctac ttcaccaaca tgttcgccac ctggtccccc tccaaggcca ggctgcacct   6720
gcagggccgg tccaacgcct ggcggcctca ggtcaacaac cccaaagaat ggctgcaggt   6780
ggactttcag aaaaccatga aggtgaccgg cgtgaccacc cagggcgtga aaagcctgct   6840
gaccagcatg tacgtgaaag agtttctgat cagcagctct caggatggcc accagtggac   6900
cctgttcttt cagaacggca aggtgaaagt gttccagggc aaccaggact ccttcacccc   6960
cgtggtgaac tccctggacc ccccccctgct gacccgctac ctgagaatcc acccccagtc   7020
ttgggtgcac cagatcgccc tcaggatgga agtcctggga tgtgaggccc aggatctgta   7080
ctgatgacgt ctggaacaat caacctctgg attacaaaat ttgtgaaaga ttgactggta   7140
ttcttaacta tgttgctcct tttacgctat gtggatacgc tgctttaatg cctttgtatc   7200
```

```
atgctattgc ttcccgtatg gctttcattt tctcctcctt gtataaatcc tggttgctgt   7260
ctctttatga ggagttgtgg cccgttgtca ggcaacgtgg cgtggtgtgc actgtgtttg   7320
ctgacgcaac ccccactggt tggggcattg ccaccacctg tcagctcctt tccgggactt   7380
tcgctttccc cctccctatt gccacggcgg aactcatcgc cgcctgcctt gcccgctgct   7440
ggacaggggc tcggctgttg ggcactgaca attccgtggt gttgtcgggg aagctgacgt   7500
cctttccatg gctgctcgcc tgtgttgcca cctggattct gcgcgggacg tccttctgct   7560
acgtcccttc ggccctcaat ccagcggacc ttccttcccg cggcctgctg ccggctctgc   7620
ggcctcttcc gcgtcttcgc cttcgccctc agacgagtcg gatctccctt tgggccgcct   7680
ccccgcctgg aattaattct gcagtcgaga cctagaaaaa catggagcaa tcacaagtag   7740
caatacagca gctaccaatg ctgattgtgc ctggctagaa gcacaagagg aggaggaggt   7800
gggttttcca gtcacacctc aggtaccttt aagaccaatg acttacaagg cagctgtaga   7860
tcttagccac tttttaaaag aaaagagggg actggaaggg ctaattcact cccaacgaag   7920
acaagatatc cttgatctgt ggatctacca cacacaaggc tacttccctg attagcagaa   7980
ctacacacca gggccagggg tcagatatcc actgaccttt ggatggtgct acaagctagt   8040
accagttgag ccagataagg tagaagaggc caataaagga gagaacacca gcttgttaca   8100
ccctgtgagc ctgcatggga tggatgaccc ggagagagaa gtgttagagt ggaggtttga   8160
cagccgccta gcatttcatc acgtggcccg agagctgcat ccggagtact tcaagaactg   8220
ctgatatcga gcttgctaca agggactttc cgctggggac tttccaggga ggcgtggcct   8280
gggcgggact ggggagtggc gagccctcag atcctgcata taagcagctg ctttttgcct   8340
gtactgggtc tctctggtta gaccagatct gagcctggga gctctctggc taactaggga   8400
acccactgct taagcctcaa taaagcttgc cttgagtgct tcaagtagtg tgtgcccgtc   8460
tgttgtgtga ctctggtaac tagagatccc tcagaccctt ttagtcagtg tggaaaatct   8520
ctagcagtag tagttcatgt catcttatta ttcagtattt ataacttgca aagaaatgaa   8580
tatcagagag tgagaggcct tgacattgct agcgttttac cgtcgacctc tagctagagc   8640
ttggcgtaat catggtcata gctgtttcct gtgtgaaatt gttatccgct cacaattcca   8700
cacaacatac gagccggaag cataaagtgt aaagcctggg gtgcctaatg agtgagctaa   8760
ctcacattaa ttgcgttgcg ctcactgccc gctttccagt cgggaaacct gtcgtgccag   8820
ctgcattaat gaatcggcca acgcgcgggg agaggcggtt tgcgtattgg gcgctcttcc   8880
gcttcctcgc tcactgactc gctgcgctcg gtcgttcggc tgcggcgagc ggtatcagct   8940
cactcaaagg cggtaatacg gttatccaca gaatcagggg ataacgcagg aaagaacatg   9000
tgagcaaaag gccagcaaaa ggccaggaac cgtaaaaagg ccgcgttgct ggcgtttttc   9060
cataggctcc gcccccctga cgagcatcac aaaaatcgac gctcaagtca gaggtggcga   9120
aacccgacag gactataaag ataccaggcg tttccccctg gaagctccct cgtgcgctct   9180
cctgttccga ccctgccgct taccggatac ctgtccgcct ttctcccttc gggaagcgtg   9240
gcgctttctc atagctcacg ctgtaggtat ctcagttcgg tgtaggtcgt tcgctccaag   9300
ctgggctgtg tgcacgaacc ccccgttcag cccgaccgct gcgccttatc cggtaactat   9360
cgtcttgagt ccaacccggt aagacacgac ttatcgccac tggcagcagc cactggtaac   9420
aggattagca gagcgaggta tgtaggcggt gctacagagt tcttgaagtg gtggcctaac   9480
tacggctaca ctagaagaac agtatttggt atctgcgctc tgctgaagcc agttaccttc   9540
```

-continued

```
ggaaaaagag ttggtagctc ttgatccggc aaacaaacca ccgctggtag cggtggtttt   9600
tttgtttgca agcagcagat tacgcgcaga aaaaaaggat ctcaagaaga tcctttgatc   9660
ttttctacgg ggtctgacgc tcagtggaac gaaaactcac gttaagggat tttggtcatg   9720
agattatcaa aaaggatctt cacctagatc cttttaaatt aaaaatgaag ttttaaatca   9780
atctaaagta tatatgagta aacttggtct gacagttacc aatgcttaat cagtgaggca   9840
cctatctcag cgatctgtct atttcgttca tccatagttg cctgactccc cgtcgtgtag   9900
ataactacga tacgggaggg cttaccatct ggccccagtg ctgcaatgat accgcgagac   9960
ccacgctcac cggctccaga tttatcagca ataaaccagc cagccggaag ggccgagcgc  10020
agaagtggtc ctgcaacttt atccgcctcc atccagtcta ttaattgttg ccgggaagct  10080
agagtaagta gttcgccagt taatagtttg cgcaacgttg ttgccattgc tacaggcatc  10140
gtggtgtcac gctcgtcgtt tggtatggct tcattcagct ccggttccca acgatcaagg  10200
cgagttacat gatcccccat gttgtgcaaa aaagcggtta gctccttcgg tcctccgatc  10260
gttgtcagaa gtaagttggc cgcagtgtta tcactcatgg ttatggcagc actgcataat  10320
tctcttactg tcatgccatc cgtaagatgc ttttctgtga ctggtgagta ctcaaccaag  10380
tcattctgag aatagtgtat gcggcgaccg agttgctctt gcccggcgtc aatacgggat  10440
aataccgcgc cacatagcag aactttaaaa gtgctcatca ttggaaaacg ttcttcgggg  10500
cgaaaactct caaggatctt accgctgttg agatccagtt cgatgtaacc cactcgtgca  10560
cccaactgat cttcagcatc ttttactttc accagcgttt ctgggtgagc aaaaacagga  10620
aggcaaaatg ccgcaaaaaa gggaataagg gcgacacgga aatgttgaat actcatactc  10680
ttcctttttc aatattattg aagcatttat cagggttatt gtctcatgag cggatacata  10740
tttgaatgta tttagaaaaa taaacaaata ggggttccgc gcacatttcc ccgaaaagtg  10800
ccacctgacg tcgacggatc gggagatcaa cttgtttatt gcagcttata atggttacaa  10860
ataaagcaat agcatcacaa atttcacaaa taaagcattt ttttcactgc attctagttg  10920
tggtttgtcc aaactcatca atgtatctta tcatgtctgg atcaactgga taactcaagc  10980
taaccaaaat catcccaaac ttcccacccc ataccctatt accactgcca attacctgtg  11040
gtttcattta ctctaaacct gtgattcctc tgaattattt tcattttaaa gaaattgtat  11100
ttgttaaata tgtactacaa acttagtagt ttttaaagaa attgtatttg ttaaatatgt  11160
actacaaact tagtagt                                                 11177
```

<210> SEQ ID NO 45
<211> LENGTH: 11196
<212> TYPE: DNA
<213> ORGANISM: Artificial Sequence
<220> FEATURE:
<223> OTHER INFORMATION: vector

<400> SEQUENCE: 45

```
tggaagggct aattcactcc caaagaagac aagatatcct tgatctgtgg atctaccaca     60
cacaaggcta cttccctgat tagcagaact acacaccagg gccaggggtc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
```

-continued

```
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aaggggggat tggggggtac agtgcagggg aaagaatagt   2100
agacataata gcaacagaca tacaaactaa agaattacaa aaacaaatta caaaaattca   2160
aaattttcgg gtttattaca gggacagcag agatccagtt tggatcgata agcttgatat   2220
cgaattcctg cgcggccgct tcgaacgcgc gcgatgcatc atatgcgtac gcggtctaga   2280
attcctgcag ggcccactag tctcccaggc atgactccaa caatgcatcc catgggattt   2340
ggggttcccc agatctgggg cttgtaggcc tgactctccc ctgtgcacac gtctcataca   2400
cgcatgcgtg cacccattgc ctgccccgcc ccttgcacag ggagtcagca gggaggactg   2460
ggttatgccc tgcttatcag cagcttccca gcttcctctg cctggattct tagaggcctg   2520
gggtcctaga acgagctggt gcacgtggct tcccaaagat ctctcagata atgagaggaa   2580
atgcagtcat cagtttgcag aaggctaggg attctgggcc atagctcaga cctgcgccca   2640
ccatctccct ccaggcagcc cttggctggt ccctgcgagc ccgtggagac tgccagtcag   2700
cgctgctgga tctcgggctc gaggccacca tgcagatcga gctgtccacc tgcttttttc   2760
```

-continued

```
tgtgcctgct gcggttctgc ttcagcgcca cccggcggta ctacctgggc gccgtggagc   2820
tgtcctggga ctacatgcag agcgacctgg gcgagctgcc cgtggacgcc cggttccccc   2880
ccagagtgcc caagagcttc cccttcaaca ccagcgtggt gtacaagaaa accctgttcg   2940
tggagttcac cgaccacctg ttcaatatcg ccaagcccag gccccccctgg atgggcctgc   3000
tgggccccac catccaggcc gaggtgtacg acaccgtggt gatcaccctg aagaacatgg   3060
ccagccaccc cgtgagcctg cacgccgtgg gcgtgagcta ctggaaggcc agcgagggcg   3120
ccgagtacga cgaccagacc agccagcggg agaaagaaga tgacaaggtg ttccctggcg   3180
gcagccacac ctacgtgtgg caggtgctga aagaaaacgg ccccatggcc tccgaccccc   3240
tgtgcctgac ctacagctac ctgagccacg tggacctggt gaaggacctg aacagcggcc   3300
tgatcggcgc tctgctcgtc tgccgggagg gcagcctggc caaagagaaa acccagaccc   3360
tgcacaagtt catcctgctg ttcgccgtgt tcgacgaggg caagagctgg cacagcgaga   3420
caaagaacag cctgatgcag gaccgggacg ccgcctctgc cagagcctgg cccaagatgc   3480
acaccgtgaa cggctacgtg aacagaagcc tgcccggcct gattggctgc caccggaaga   3540
gcgtgtactg gcacgtgatc ggcatgggca ccacacccga ggtgcacagc atctttctgg   3600
aagggcacac ctttctggtc cggaaccacc ggcaggccag cctggaaatc agccctatca   3660
ccttcctgac cgcccagaca ctgctgatgg acctgggcca gttcctgctg ttttgccaca   3720
tcagctctca ccagcacgac ggcatggaag cctacgtgaa ggtggactct tgccccgagg   3780
aaccccagct gcggatgaag aacaacgagg aagccgagga ctacgacgac gacctgaccg   3840
acagcgagat ggacgtggtg cggttcgacg acgacaacag ccccagcttc atccagatca   3900
gaagcgtggc caagaagcac cccaagacct gggtgcacta tatcgccgcc gaggaagagg   3960
actgggacta cgcccccctg gtgctggccc ccgacgacag aagctacaag agccagtacc   4020
tgaacaatgg cccccagcgg atcggccgga agtacaagaa agtgcggttc atggcctaca   4080
ccgacgagac attcaagacc cgggaggcca tccagcacga gagcggcatc ctgggccccc   4140
tgctgtacgg cgaagtgggc gacacactgc tgatcatctt caagaaccag gctagccggc   4200
cctacaacat ctacccccac ggcatcaccg acgtgcggcc cctgtacagc aggcggctgc   4260
ccaagggcgt gaagcacctg aaggacttcc ccatcctgcc cggcgagatc ttcaagtaca   4320
agtggaccgt gaccgtggag gacggcccca ccaagagcga ccccagatgc ctgacccggt   4380
actacagcag cttcgtgaac atggaacggg acctggcctc cgggctgatc ggacctctgc   4440
tgatctgcta caaagaaagc gtggaccagc ggggcaacca gatcatgagc gacaagcgga   4500
acgtgatcct gttcagcgtg ttcgatgaga accggtcctg gtatctgacc gagaacatcc   4560
agcggtttct gcccaaccct gccggcgtgc agctggaaga tcccgagttc caggccagca   4620
acatcatgca ctccatcaat ggctacgtgt tcgactctct gcagctctcc gtgtgtctgc   4680
acgaggtggc ctactggtac atcctgagca tcggcgccca gaccgacttc ctgagcgtgt   4740
tcttcagcgg ctacaccttc aagcacaaga tggtgtacga ggacaccctg accctgttcc   4800
ctttcagcgg cgagacagtg ttcatgagca tggaaaaccc cggcctgtgg attctgggct   4860
gccacaacag cgacttccgg aaccggggca tgaccgccct gctgaaggtg tccagctgcg   4920
acaagaacac cggcgactac tacgaggaca gctacgagga tatcagcgcc tacctgctgt   4980
ccaagaacaa cgccatcgaa ccccggagct tcagccagaa cccccccgtg ctgacgcgtc   5040
accagcggga gatcacccgg acaaccctgc agtccgacca ggaagagatc gattacgacg   5100
acaccatcag cgtggagatg aagaaagagg atttcgatat ctacgacgag gacgagaacc   5160
```

agagccccag aagcttccag aagaaaaccc ggcactactt cattgccgcc gtggagaggc 5220
tgtgggacta cggcatgagt tctagccccc acgtgctgcg gaaccgggcc cagagcggca 5280
gcgtgcccca gttcaagaaa gtggtgttcc aggaattcac agacggcagc ttcacccagc 5340
ctctgtatag aggcgagctg aacgagcacc tggggctgct ggggccctac atcagggccg 5400
aagtggagga caacatcatg gtgaccttcc ggaatcaggc cagcagaccc tactccttct 5460
acagcagcct gatcagctac gaagaggacc agcggcaggg cgccgaaccc cggaagaact 5520
tcgtgaagcc caacgaaacc aagacctact tctggaaagt gcagcaccac atggccccca 5580
ccaaggacga gttcgactgc aaggcctggg cctacttcag cgacgtggat ctggaaaagg 5640
acgtgcactc tggactgatt ggcccactcc tggtctgcca cactaacacc ctcaaccccg 5700
cccacggccg ccaggtgacc gtgcaggaat tcgccctgtt cttcaccatc ttcgacgaga 5760
caaagtcctg gtacttcacc gagaatatgg aacggaactg cagagccccc tgcaacatcc 5820
agatggaaga tcctaccttc aaagagaact accggttcca cgccatcaac ggctacatca 5880
tggacaccct gcctggcctg gtgatggccc aggaccagag aatccggtgg tatctgctgt 5940
ccatgggcag caacgagaat atccacagca tccacttcag cggccacgtg ttcaccgtgc 6000
ggaagaaaga agagtacaag atggccctgt acaacctgta ccccggcgtg ttcgagacag 6060
tggagatgct gcccagcaag gccggcatct ggcgggtgga gtgtctgatc ggcgagcacc 6120
tgcacgctgg catgagcacc ctgtttctgg tgtacagcaa caagtgccag accccactgg 6180
gcatggcctc tggccacatc cgggacttcc agatcaccgc ctccggccag tacggccagt 6240
gggcccccaa gctggccaga ctgcactaca gcggcagcat caacgcctgg tccaccaaag 6300
agcccttcag ctggatcaag gtggacctgc tggcccctat gatcatccac ggcattaaga 6360
cccagggcgc caggcagaag ttcagcagcc tgtacatcag ccagttcatc atcatgtaca 6420
gcctggacgg caagaagtgg cagacctacc ggggcaacag caccggcacc ctgatggtgt 6480
tcttcggcaa tgtggacagc agcggcatca agcacaacat cttcaacccc cccatcattg 6540
cccggtacat ccggctgcac cccacccact acagcattag atccacactg agaatggaac 6600
tgatgggctg cgacctgaac tcctgcagca tgcctctggg catggaaagc aaggccatca 6660
gcgacgccca gatcacagcc agcagctact tcaccaacat gttcgccacc tggtccccct 6720
ccaaggccag gctgcacctg cagggccggt ccaacgcctg gcggcctcag gtcaacaacc 6780
ccaaagaatg gctgcaggtg gactttcaga aaaccatgaa ggtgaccggc gtgaccaccc 6840
agggcgtgaa aagcctgctg accagcatgt acgtgaaaga gtttctgatc agcagctctc 6900
aggatggcca ccagtggacc ctgttctttc agaacggcaa ggtgaaagtg ttccagggca 6960
accaggactc cttcaccccc gtggtgaact ccctggaccc ccccctgctg acccgctacc 7020
tgagaatcca cccccagtct tgggtgcacc agatcgccct caggatggaa gtcctgggat 7080
gtgaggccca ggatctgtac tgatgacgtc tggaacaatc aacctctgga ttacaaaatt 7140
tgtgaaagat tgactggtat tcttaactat gttgctcctt ttacgctatg tggatacgct 7200
gctttaatgc ctttgtatca tgctattgct tcccgtatgg ctttcatttt ctcctccttg 7260
tataaatcct ggttgctgtc tctttatgag gagttgtggc ccgttgtcag gcaacgtggc 7320
gtggtgtgca ctgtgtttgc tgacgcaacc cccactggtt ggggcattgc caccacctgt 7380
cagctccttt ccgggacttt cgctttcccc ctccctattg ccacggcgga actcatcgcc 7440
gcctgccttg cccgctgctg gacaggggct cggctgttgg gcactgacaa ttccgtggtg 7500

-continued

```
ttgtcgggga agctgacgtc ctttccatgg ctgctcgcct gtgttgccac ctggattctg   7560
cgcgggacgt ccttctgcta cgtcccttcg gccctcaatc cagcggacct tccttcccgc   7620
ggcctgctgc cggctctgcg gcctcttccg cgtcttcgcc ttcgccctca gacgagtcgg   7680
atctcccttt gggccgcctc cccgcctgga attaattctg cagtcgagac ctagaaaaac   7740
atggagcaat cacaagtagc aatacagcag ctaccaatgc tgattgtgcc tggctagaag   7800
cacaagagga ggaggaggtg ggttttccag tcacacctca ggtaccttta agaccaatga   7860
cttacaaggc agctgtagat cttagccact ttttaaaaga aaagaggggga ctggaagggc   7920
taattcactc ccaacgaaga caagatatcc ttgatctgtg gatctaccac acacaaggct   7980
acttccctga ttagcagaac tacacaccag ggccaggggt cagatatcca ctgacctttg   8040
gatggtgcta caagctagta ccagttgagc cagataaggt agaagaggcc aataaaggag   8100
agaacaccag cttgttacac cctgtgagcc tgcatgggat ggatgacccg gagagagaag   8160
tgttagagtg gaggtttgac agccgcctag catttcatca cgtggcccga gagctgcatc   8220
cggagtactt caagaactgc tgatatcgag cttgctacaa gggactttcc gctggggact   8280
ttccagggag gcgtggcctg ggcgggactg gggagtggcg agccctcaga tcctgcatat   8340
aagcagctgc tttttgcctg tactgggtct ctctggttag accagatctg agcctgggag   8400
ctctctggct aactagggaa cccactgctt aagcctcaat aaagcttgcc ttgagtgctt   8460
caagtagtgt gtgcccgtct gttgtgtgac tctggtaact agagatccct cagacccttt   8520
tagtcagtgt ggaaaatctc tagcagtagt agttcatgtc atcttattat tcagtattta   8580
taacttgcaa agaaatgaat atcagagagt gagaggcctt gacattgcta gcgttttacc   8640
gtcgacctct agctagagct tggcgtaatc atggtcatag ctgtttcctg tgtgaaattg   8700
ttatccgctc acaattccac acaacatacg agccggaagc ataaagtgta aagcctgggg   8760
tgcctaatga gtgagctaac tcacattaat tgcgttgcgc tcactgcccg ctttccagtc   8820
gggaaacctg tcgtgccagc tgcattaatg aatcggccaa cgcgcgggga gaggcggttt   8880
gcgtattggg cgctcttccg cttcctcgct cactgactcg ctgcgctcgg tcgttcggct   8940
gcggcgagcg gtatcagctc actcaaaggc ggtaatacgg ttatccacag aatcagggga   9000
taacgcagga aagaacatgt gagcaaaagg ccagcaaaag gccaggaacc gtaaaaaggc   9060
cgcgttgctg gcgtttttcc ataggctccg cccccctgac gagcatcaca aaaatcgacg   9120
ctcaagtcag aggtggcgaa acccgacagg actataaaga taccaggcgt ttccccctgg   9180
aagctccctc gtgcgctctc ctgttccgac cctgccgctt accggatacc tgtccgcctt   9240
tctcccttcg ggaagcgtgg cgctttctca tagctcacgc tgtaggtatc tcagttcggt   9300
gtaggtcgtt cgctccaagc tgggctgtgt gcacgaaccc cccgttcagc ccgaccgctg   9360
cgccttatcc ggtaactatc gtcttgagtc caacccggta agacacgact tatcgccact   9420
ggcagcagcc actggtaaca ggattagcag agcgaggtat gtaggcggtg ctacagagtt   9480
cttgaagtgg tggcctaact acggctacac tagaagaaca gtatttggta tctgcgctct   9540
gctgaagcca gttaccttcg gaaaaagagt tggtagctct tgatccggca aacaaaccac   9600
cgctggtagc ggtggttttt ttgtttgcaa gcagcagatt acgcgcagaa aaaaaggatc   9660
tcaagaagat cctttgatct tttctacggg gtctgacgct cagtggaacg aaaactcacg   9720
ttaagggatt ttggtcatga gattatcaaa aaggatcttc acctagatcc ttttaaatta   9780
aaaatgaagt tttaaatcaa tctaaagtat atatgagtaa acttggtctg acagttacca   9840
atgcttaatc agtgaggcac ctatctcagc gatctgtcta tttcgttcat ccatagttgc   9900
```

```
ctgactcccc gtcgtgtaga taactacgat acgggagggc ttaccatctg gccccagtgc   9960
tgcaatgata ccgcgagacc cacgctcacc ggctccagat ttatcagcaa taaaccagcc  10020
agccggaagg gccgagcgca gaagtggtcc tgcaacttta tccgcctcca tccagtctat  10080
taattgttgc cgggaagcta gagtaagtag ttcgccagtt aatagtttgc gcaacgttgt  10140
tgccattgct acaggcatcg tggtgtcacg ctcgtcgttt ggtatggctt cattcagctc  10200
cggttcccaa cgatcaaggc gagttacatg atcccccatg ttgtgcaaaa aagcggttag  10260
ctccttcggt cctccgatcg ttgtcagaag taagttggcc gcagtgttat cactcatggt  10320
tatggcagca ctgcataatt ctcttactgt catgccatcc gtaagatgct tttctgtgac  10380
tggtgagtac tcaaccaagt cattctgaga atagtgtatg cggcgaccga gttgctcttg  10440
cccggcgtca atacgggata ataccgcgcc acatagcaga actttaaaag tgctcatcat  10500
tggaaaacgt tcttcggggc gaaaactctc aaggatctta ccgctgttga gatccagttc  10560
gatgtaaccc actcgtgcac ccaactgatc ttcagcatct tttactttca ccagcgtttc  10620
tgggtgagca aaaacaggaa ggcaaaatgc cgcaaaaaag ggaataaggg cgacacggaa  10680
atgttgaata ctcatactct tcctttttca atattattga agcatttatc agggttattg  10740
tctcatgagc ggatacatat ttgaatgtat ttagaaaaat aaacaaatag gggttccgcg  10800
cacatttccc cgaaaagtgc cacctgacgt cgacggatcg ggagatcaac ttgtttattg  10860
cagcttataa tggttacaaa taaagcaata gcatcacaaa tttcacaaat aaagcatttt  10920
tttcactgca ttctagttgt ggtttgtcca aactcatcaa tgtatcttat catgtctgga  10980
tcaactggat aactcaagct aaccaaaatc atcccaaact tcccacccca taccctatta  11040
ccactgccaa ttacctgtgg tttcatttac tctaaacctg tgattcctct gaattatttt  11100
cattttaaag aaattgtatt tgttaaatat gtactacaaa cttagtagtt tttaaagaaa  11160
ttgtatttgt taaatatgta ctacaaactt agtagt                            11196
```

<210> SEQ ID NO 46
<211> LENGTH: 8303
<212> TYPE: DNA
<213> ORGANISM: Artificial Sequence
<220> FEATURE:
<223> OTHER INFORMATION: vector

<400> SEQUENCE: 46

```
tggaagggct aattcactcc caaagaagac aagatatcct tgatctgtgg atctaccaca     60
cacaaggcta cttccctgat tagcagaact acacaccagg gccaggggtc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
```

-continued

```
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aaggggggat tggggggtac agtgcagggg aaagaatagt   2100
agacataata gcaacagaca tacaaactaa agaattacaa aaacaaatta caaaaattca   2160
aaattttcgg gtttattaca gggacagcag agatccagtt tggatcgata agcttgatat   2220
cgaattcctg cgcggccgct tcgaacgcgc gcgatgcatc atatgcgtac gcggtctaga   2280
attcctgcag ggcccactag tctcccaggc atgactccaa caatgcatcc catgggattt   2340
ggggttcccc agatctgggg cttgtaggcc tgactctccc ctgtgcacac gtctcataca   2400
cgcatgcgtg cacccattgc ctgccccgcc ccttgcacag ggagtcagca gggaggactg   2460
ggttatgccc tgcttatcag cagcttccca gcttcctctg cctggattct tagaggcctg   2520
gggtcctaga acgagctggt gcacgtggct tcccaaagat ctctcagata atgagaggaa   2580
atgcagtcat cagtttgcag aaggctaggg attctgggcc atagctcaga cctgcgccca   2640
ccatctccct ccaggcagcc cttggctggt ccctgcgagc ccgtggagac tgccagtcag   2700
cgctgctgga tctcgggctc gaggccacca tggaagatgc caaaaacatt aagaagggcc   2760
cagcgccatt ctacccactc gaagacggga ccgccggcga gcagctgcac aaagccatga   2820
agcgctacgc cctggtgccc ggcaccatcg cctttaccga cgcacatatc gaggtggaca   2880
ttacctacgc cgagtacttc gagatgagcg ttcggctggc agaagctatg aagcgctatg   2940
ggctgaatac aaaccatcgg atcgtggtgt gcagcgagaa tagcttgcag ttcttcatgc   3000
ccgtgttggg tgccctgttc atcggtgtgg ctgtggcccc agctaacgac atctacaacg   3060
agcgcgagct gctgaacagc atgggcatca gccagcccac cgtcgtattc gtgagcaaga   3120
```

-continued

```
aagggctgca aaagatcctc aacgtgcaaa agaagctacc gatcatacaa aagatcatca   3180
tcatggatag caagaccgac taccagggct tccaaagcat gtacaccttc gtgacttccc   3240
atttgccacc cggcttcaac gagtacgact tcgtgcccga gagcttcgac cgggacaaaa   3300
ccatcgccct gatcatgaac agtagtggca gtaccggatt gcccaagggc gtagccctac   3360
cgcaccgcac cgcttgtgtc cgattcagtc atgcccgcga ccccatcttc ggcaaccaga   3420
tcatccccga caccgctatc ctcagcgtgg tgccatttca ccacggcttc ggcatgttca   3480
ccacgctggg ctacttgatc tgcggctttc gggtcgtgct catgtaccgc ttcgaggagg   3540
agctattctt gcgcagcttg caagactata agattcaatc tgccctgctg gtgcccacac   3600
tatttagctt cttcgctaag agcactctca tcgacaagta cgacctaagc aacttgcacg   3660
agatcgccag cggcggggcg ccgctcagca aggaggtagg tgaggccgtg gccaaacgct   3720
tccacctacc aggcatccgc cagggctacg gcctgacaga aacaaccagc gccattctga   3780
tcacccccga aggggacgac aagcctggcg cagtaggcaa ggtggtgccc ttcttcgagg   3840
ctaaggtggt ggacttggac accggtaaga cactgggtgt gaaccagcgc ggcgagctgt   3900
gcgtccgtgg ccccatgatc atgagcggct acgttaacaa ccccgaggct acaaacgctc   3960
tcatcgacaa ggacggctgg ctgcacagcg gcgacatcgc ctactgggac gaggacgagc   4020
acttcttcat cgtggaccgg ctgaagagcc tgatcaaata caagggctac caggtagccc   4080
cagccgaact ggagagcatc ctgctgcaac accccaacat cttcgacgcc ggggtcgccg   4140
gcctgcccga cgacgatgcc ggcgagctgc ccgccgcagt cgtcgtgctg gaacacggta   4200
aaaccatgac cgagaaggag atcgtggact atgtggccag ccaggttaca accgccaaga   4260
agctgcgcgg tggtgttgtg ttcgtggacg aggtgcctaa aggactgacc ggcaagttgg   4320
acgcccgcaa gatccgcgag attctcatta aggccaagaa gggcggcaag atcgccgtgt   4380
aaatgcagcc tagggtatac gatatcaagc ttatcgtcga caatcaacct ctggattaca   4440
aaatttgtga aagattgact ggtattctta actatgttgc tccttttacg ctatgtggat   4500
acgctgcttt aatgcctttg tatcatgcta ttgcttcccg tatggctttc attttctcct   4560
ccttgtataa atcctggttg ctgtctcttt atgaggagtt gtggcccgtt gtcaggcaac   4620
gtggcgtggt gtgcactgtg tttgctgacg caacccccac tggttggggc attgccacca   4680
cctgtcagct cctttccggg actttcgctt tccccctccc tattgccacg gcggaactca   4740
tcgccgcctg ccttgcccgc tgctggacag gggctcggct gttgggcact gacaattccg   4800
tggtgttgtc ggggaagctg acgtcctttc catggctgct cgcctgtgtt gccacctgga   4860
ttctgcgcgg gacgtccttc tgctacgtcc cttcggccct caatccagcg gaccttcctt   4920
cccgcggcct gctgccggct caagataggt acctttaaga ccaatgactt acaaggcagc   4980
tgtagatctt agccactttt taaaagaaaa gaggggactg gaagggctaa ttcactccca   5040
acgaagacaa gatatccttg atctgtggat ctaccacaca caaggctact tccctgatta   5100
gcagaactac acaccagggc caggggtcag atatccactg acctttggat ggtgctacaa   5160
gctagtacca gttgagccag ataaggtaga agaggccaat aaaggagaga acaccagctt   5220
gttacaccct gtgagcctgc atgggatgga tgacccggag agagaagtgt tagagtggag   5280
gtttgacagc cgcctagcat ttcatcacgt ggcccgagag ctgcatccgg agtacttcaa   5340
gaactgctga tatcgagctt gctacaaggg actttccgct ggggactttc cagggaggcg   5400
tggcctgggc gggactgggg agtggcgagc cctcagatcc tgcatataag cagctgcttt   5460
```

-continued

```
ttgcctgtac tgggtctctc tggttagacc agatctgagc ctgggagctc tctggctaac   5520
tagggaaccc actgcttaag cctcaataaa gcttgccttg agtgcttcaa gtagtgtgtg   5580
cccgtctgtt gtgtgactct ggtaactaga gatccctcag acccttttag tcagtgtgga   5640
aaatctctag cagtagtagt tcatgtcatc ttattattca gtatttataa cttgcaaaga   5700
aatgaatatc agagagtgag aggccttgac attgctagcg ttttaccgtc gacctctagc   5760
tagagcttgg cgtaatcatg gtcatagctg tttcctgtgt gaaattgtta tccgctcaca   5820
attccacaca acatacgagc cggaagcata aagtgtaaag cctggggtgc ctaatgagtg   5880
agctaactca cattaattgc gttgcgctca ctgcccgctt tccagtcggg aaacctgtcg   5940
tgccagctgc attaatgaat cggccaacgc gcggggagag gcggtttgcg tattgggcgc   6000
tcttccgctt cctcgctcac tgactcgctg cgctcggtcg ttcggctgcg gcgagcggta   6060
tcagctcact caaaggcggt aatacggtta tccacagaat caggggataa cgcaggaaag   6120
aacatgtgag caaaaggcca gcaaaaggcc aggaaccgta aaaaggccgc gttgctggcg   6180
tttttccata ggctccgccc ccctgacgag catcacaaaa atcgacgctc aagtcagagg   6240
tggcgaaacc cgacaggact ataaagatac caggcgtttc cccctggaag ctccctcgtg   6300
cgctctcctg ttccgaccct gccgcttacc ggatacctgt ccgcctttct cccttcggga   6360
agcgtggcgc tttctcatag ctcacgctgt aggtatctca gttcggtgta ggtcgttcgc   6420
tccaagctgg gctgtgtgca cgaacccccc gttcagcccg accgctgcgc cttatccggt   6480
aactatcgtc ttgagtccaa cccggtaaga cacgacttat cgccactggc agcagccact   6540
ggtaacagga ttagcagagc gaggtatgta ggcggtgcta cagagttctt gaagtggtgg   6600
cctaactacg gctacactag aagaacagta tttggtatct gcgctctgct gaagccagtt   6660
accttcggaa aaagagttgg tagctcttga tccggcaaac aaaccaccgc tggtagcggt   6720
ggtttttttg tttgcaagca gcagattacg cgcagaaaaa aaggatctca agaagatcct   6780
ttgatctttt ctacggggtc tgacgctcag tggaacgaaa actcacgtta agggattttg   6840
gtcatgagat tatcaaaaag gatcttcacc tagatccttt taaattaaaa atgaagtttt   6900
aaatcaatct aaagtatata tgagtaaact tggtctgaca gttaccaatg cttaatcagt   6960
gaggcaccta tctcagcgat ctgtctattt cgttcatcca tagttgcctg actccccgtc   7020
gtgtagataa ctacgatacg ggagggctta ccatctggcc ccagtgctgc aatgataccg   7080
cgagacccac gctcaccggc tccagattta tcagcaataa accagccagc cggaagggcc   7140
gagcgcagaa gtggtcctgc aactttatcc gcctccatcc agtctattaa ttgttgccgg   7200
gaagctagag taagtagttc gccagttaat agtttgcgca acgttgttgc cattgctaca   7260
ggcatcgtgg tgtcacgctc gtcgtttggt atggcttcat tcagctccgg ttcccaacga   7320
tcaaggcgag ttacatgatc ccccatgttg tgcaaaaaag cggttagctc cttcggtcct   7380
ccgatcgttg tcagaagtaa gttggccgca gtgttatcac tcatggttat ggcagcactg   7440
cataattctc ttactgtcat gccatccgta agatgctttt ctgtgactgg tgagtactca   7500
accaagtcat tctgagaata gtgtatgcgg cgaccgagtt gctcttgccc ggcgtcaata   7560
cgggataata ccgcgccaca tagcagaact ttaaaagtgc tcatcattgg aaaacgttct   7620
tcggggcgaa aactctcaag gatcttaccg ctgttgagat ccagttcgat gtaacccact   7680
cgtgcaccca actgatcttc agcatctttt actttcacca gcgtttctgg gtgagcaaaa   7740
acaggaaggc aaaatgccgc aaaaaaggga ataagggcga cacggaaatg ttgaatactc   7800
atactcttcc tttttcaata ttattgaagc atttatcagg gttattgtct catgagcgga   7860
```

-continued tacatatttg aatgtattta gaaaaataaa caaatagggg ttccgcgcac atttccccga 7920
aaagtgccac ctgacgtcga cggatcggga gatcaacttg tttattgcag cttataatgg 7980
ttacaaataa agcaatagca tcacaaattt cacaaataaa gcattttttt cactgcattc 8040
tagttgtggt ttgtccaaac tcatcaatgt atcttatcat gtctggatca actggataac 8100
tcaagctaac caaaatcatc ccaaacttcc caccccatac cctattacca ctgccaatta 8160
cctgtggttt catttactct aaacctgtga ttcctctgaa ttattttcat tttaaagaaa 8220
ttgtatttgt taaatatgta ctacaaactt agtagttttt aaagaaattg tatttgttaa 8280
atatgtacta caaacttagt agt 8303

<210> SEQ ID NO 47
<211> LENGTH: 8379
<212> TYPE: DNA
<213> ORGANISM: Artificial Sequence
<220> FEATURE:
<223> OTHER INFORMATION: vector

<400> SEQUENCE: 47
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560

-continued actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920
cccaaccccg aggggggacc cgacaggccc gaaggaatag aagaagaagg tggagagaga 1980
gacagagaca gatccattcg attagtgaac ggatctcgac ggtcgccaaa tggcagtatt 2040
catccacaat tttaaaagaa aaggggggat tggggggtac agtgcagggg aaagaatagt 2100
agacataata gcaacagaca tacaaactaa agaattacaa aaacaaatta caaaaattca 2160
aaattttcgg gtttattaca gggacagcag agatccagtt tggatcgata agcttgatat 2220
cgaattcctg cgcggccgct tcgaacgcgc gcgatgcatc atatggccct cacaaaggaa 2280
caataacagg aaaccatccc aggggggaagt gggccagggc cagctggaaa acctgaaggg 2340
gcgtacgcgg tctagaattc ctgcagggcc cactagtctc ccaggcatga ctccaacaat 2400
gcatcccatg ggatttgggg ttccccagat ctggggcttg taggcctgac tctcccctgt 2460
gcacacgtct catacacgca tgcgtgcacc cattgcctgc cccgcccctt gcacagggag 2520
tcagcaggga ggactgggtt atgccctgct tatcagcagc ttcccagctt cctctgcctg 2580
gattcttaga ggcctggggt cctagaacga gctggtgcac gtggcttccc aaagatctct 2640
cagataatga gaggaaatgc agtcatcagt ttgcagaagg ctagggattc tgggccatag 2700
ctcagacctg cgcccaccat ctccctccag gcagcccttg gctggtccct gcgagcccgt 2760
ggagactgcc agtcagcgct gctggatctc gggctcgagg ccaccatgga agatgccaaa 2820
aacattaaga agggcccagc gccattctac ccactcgaag acgggaccgc cggcgagcag 2880
ctgcacaaag ccatgaagcg ctacgccctg gtgcccggca ccatcgcctt taccgacgca 2940
catatcgagg tggacattac ctacgccgag tacttcgaga tgagcgttcg gctggcagaa 3000
gctatgaagc gctatgggct gaatacaaac catcggatcg tggtgtgcag cgagaatagc 3060
ttgcagttct tcatgcccgt gttgggtgcc ctgttcatcg gtgtggctgt ggccccagct 3120
aacgacatct acaacgagcg cgagctgctg aacagcatgg gcatcagcca gcccaccgtc 3180
gtattcgtga gcaagaaagg gctgcaaaag atcctcaacg tgcaaaagaa gctaccgatc 3240
atacaaaaga tcatcatcat ggatagcaag accgactacc agggcttcca aagcatgtac 3300
accttcgtga cttcccattt gccacccggc ttcaacgagt acgacttcgt gcccgagagc 3360
ttcgaccggg acaaaaccat cgccctgatc atgaacagta gtggcagtac cggattgccc 3420
aagggcgtag ccctaccgca ccgcaccgct tgtgtccgat tcagtcatgc ccgcgacccc 3480
atcttcggca accagatcat ccccgacacc gctatcctca gcgtggtgcc atttcaccac 3540
ggcttcggca tgttcaccac gctgggctac ttgatctgcg gctttcgggt cgtgctcatg 3600
taccgcttcg aggaggagct attcttgcgc agcttgcaag actataagat tcaatctgcc 3660
ctgctggtgc ccacactatt tagcttcttc gctaagagca ctctcatcga caagtacgac 3720
ctaagcaact tgcacgagat cgccagcggc ggggcgccgc tcagcaagga ggtaggtgag 3780
gccgtggcca aacgcttcca cctaccaggc atccgccagg gctacggcct gacagaaaca 3840
accagcgcca ttctgatcac cccgaaggg gacgacaagc ctggcgcagt aggcaaggtg 3900
gtgcccttct tcgaggctaa ggtggtggac ttggacaccg gtaagacact gggtgtgaac 3960

-continued

```
cagcgcggcg agctgtgcgt ccgtggcccc atgatcatga gcggctacgt taacaacccc   4020
gaggctacaa acgctctcat cgacaaggac ggctggctgc acagcggcga catcgcctac   4080
tgggacgagg acgagcactt cttcatcgtg gaccggctga agagcctgat caaatacaag   4140
ggctaccagg tagccccagc cgaactggag agcatcctgc tgcaacaccc caacatcttc   4200
gacgccgggg tcgccggcct gcccgacgac gatgccggcg agctgcccgc cgcagtcgtc   4260
gtgctggaac acggtaaaac catgaccgag aaggagatcg tggactatgt ggccagccag   4320
gttacaaccg ccaagaagct gcgcggtggt gttgtgttcg tggacgaggt gcctaaagga   4380
ctgaccggca agttggacgc ccgcaagatc cgcgagattc tcattaaggc caagaagggc   4440
ggcaagatcg ccgtgtaaat gcagcctagg gtatacgata tcaagcttat cgtcgacaat   4500
caacctctgg attacaaaat ttgtgaaaga ttgactggta ttcttaacta tgttgctcct   4560
tttacgctat gtggatacgc tgctttaatg cctttgtatc atgctattgc ttcccgtatg   4620
gctttcattt tctcctcctt gtataaatcc tggttgctgt ctctttatga ggagttgtgg   4680
cccgttgtca ggcaacgtgg cgtggtgtgc actgtgtttg ctgacgcaac ccccactggt   4740
tggggcattg ccaccacctg tcagctcctt tccgggactt tcgctttccc cctccctatt   4800
gccacggcgg aactcatcgc cgcctgcctt gcccgctgct ggacaggggc tcggctgttg   4860
ggcactgaca attccgtggt gttgtcgggg aagctgacgt cctttccatg gctgctcgcc   4920
tgtgttgcca cctggattct gcgcgggacg tccttctgct acgtcccttc ggccctcaat   4980
ccagcggacc ttccttcccg cggcctgctg ccggctcaag ataggtacct ttaagaccaa   5040
tgacttacaa ggcagctgta gatcttagcc actttttaaa agaaaagagg ggactggaag   5100
ggctaattca ctcccaacga agacaagata tccttgatct gtggatctac cacacacaag   5160
gctacttccc tgattagcag aactacacac cagggccagg ggtcagatat ccactgacct   5220
ttggatggtg ctacaagcta gtaccagttg agccagataa ggtagaagag gccaataaag   5280
gagagaacac cagcttgtta caccctgtga gcctgcatgg gatggatgac ccggagagag   5340
aagtgttaga gtggaggttt gacagccgcc tagcatttca tcacgtggcc cgagagctgc   5400
atccggagta cttcaagaac tgctgatatc gagcttgcta caagggactt tccgctgggg   5460
actttccagg gaggcgtggc ctgggcggga ctggggagtg gcgagccctc agatcctgca   5520
tataagcagc tgctttttgc ctgtactggg tctctctggt tagaccagat ctgagcctgg   5580
gagctctctg gctaactagg gaacccactg cttaagcctc aataaagctt gccttgagtg   5640
cttcaagtag tgtgtgcccg tctgttgtgt gactctggta actagagatc cctcagaccc   5700
ttttagtcag tgtggaaaat ctctagcagt agtagttcat gtcatcttat tattcagtat   5760
ttataacttg caaagaaatg aatatcagag agtgagaggc cttgacattg ctagcgtttt   5820
accgtcgacc tctagctaga gcttggcgta atcatggtca tagctgtttc ctgtgtgaaa   5880
ttgttatccg ctcacaattc cacacaacat acgagccgga agcataaagt gtaaagcctg   5940
gggtgcctaa tgagtgagct aactcacatt aattgcgttg cgctcactgc ccgctttcca   6000
gtcgggaaac ctgtcgtgcc agctgcatta atgaatcggc caacgcgcgg ggagaggcgg   6060
tttgcgtatt gggcgctctt ccgcttcctc gctcactgac tcgctgcgct cggtcgttcg   6120
gctgcggcga gcggtatcag ctcactcaaa ggcggtaata cggttatcca cagaatcagg   6180
ggataacgca ggaaagaaca tgtgagcaaa aggccagcaa aaggccagga accgtaaaaa   6240
ggccgcgttg ctggcgtttt tccataggct ccgcccccct gacgagcatc acaaaaatcg   6300
```

-continued

```
acgctcaagt cagaggtggc gaaacccgac aggactataa agataccagg cgtttccccc   6360
tggaagctcc ctcgtgcgct ctcctgttcc gaccctgccg cttaccggat acctgtccgc   6420
ctttctccct tcgggaagcg tggcgctttc tcatagctca cgctgtaggt atctcagttc   6480
ggtgtaggtc gttcgctcca agctgggctg tgtgcacgaa ccccccgttc agcccgaccg   6540
ctgcgcctta tccggtaact atcgtcttga gtccaacccg gtaagacacg acttatcgcc   6600
actggcagca gccactggta acaggattag cagagcgagg tatgtaggcg gtgctacaga   6660
gttcttgaag tggtggccta actacggcta cactagaaga acagtatttg gtatctgcgc   6720
tctgctgaag ccagttacct tcggaaaaag agttggtagc tcttgatccg gcaaacaaac   6780
caccgctggt agcggtggtt tttttgtttg caagcagcag attacgcgca gaaaaaaagg   6840
atctcaagaa gatcctttga tcttttctac ggggtctgac gctcagtgga acgaaaactc   6900
acgttaaggg attttggtca tgagattatc aaaaaggatc ttcacctaga tccttttaaa   6960
ttaaaaatga agttttaaat caatctaaag tatatatgag taaacttggt ctgacagtta   7020
ccaatgctta atcagtgagg cacctatctc agcgatctgt ctatttcgtt catccatagt   7080
tgcctgactc cccgtcgtgt agataactac gatacgggag ggcttaccat ctggccccag   7140
tgctgcaatg ataccgcgag acccacgctc accggctcca gatttatcag caataaacca   7200
gccagccgga agggccgagc gcagaagtgg tcctgcaact ttatccgcct ccatccagtc   7260
tattaattgt tgccgggaag ctagagtaag tagttcgcca gttaatagtt tgcgcaacgt   7320
tgttgccatt gctacaggca tcgtggtgtc acgctcgtcg tttggtatgg cttcattcag   7380
ctccggttcc caacgatcaa ggcgagttac atgatccccc atgttgtgca aaaaagcggt   7440
tagctccttc ggtcctccga tcgttgtcag aagtaagttg gccgcagtgt tatcactcat   7500
ggttatggca gcactgcata attctcttac tgtcatgcca tccgtaagat gcttttctgt   7560
gactggtgag tactcaacca agtcattctg agaatagtgt atgcggcgac cgagttgctc   7620
ttgcccggcg tcaatacggg ataataccgc gccacatagc agaactttaa aagtgctcat   7680
cattggaaaa cgttcttcgg ggcgaaaact ctcaaggatc ttaccgctgt tgagatccag   7740
ttcgatgtaa cccactcgtg cacccaactg atcttcagca tcttttactt tcaccagcgt   7800
ttctgggtga gcaaaaacag gaaggcaaaa tgccgcaaaa aagggaataa gggcgacacg   7860
gaaatgttga atactcatac tcttcctttt tcaatattat tgaagcattt atcagggtta   7920
ttgtctcatg agcggataca tatttgaatg tatttagaaa aataaacaaa taggggttcc   7980
gcgcacattt ccccgaaaag tgccacctga cgtcgacgga tcgggagatc aacttgttta   8040
ttgcagctta taatggttac aaataaagca atagcatcac aaatttcaca aataaagcat   8100
ttttttcact gcattctagt tgtggtttgt ccaaactcat caatgtatct tatcatgtct   8160
ggatcaactg gataactcaa gctaaccaaa atcatcccaa acttcccacc ccatacccta   8220
ttaccactgc caattacctg tggtttcatt tactctaaac ctgtgattcc tctgaattat   8280
tttcatttta aagaaattgt atttgttaaa tatgtactac aaacttagta gtttttaaag   8340
aaattgtatt tgttaaatat gtactacaaa cttagtagt                          8379
```

<210> SEQ ID NO 48
<211> LENGTH: 11272
<212> TYPE: DNA
<213> ORGANISM: Artificial Sequence
<220> FEATURE:
<223> OTHER INFORMATION: vector

<400> SEQUENCE: 48

```
tggaagggct aattcactcc caaagaagac aagatatcct tgatctgtgg atctaccaca     60
cacaaggcta cttccctgat tagcagaact acacaccagg gccaggggtc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggggacc cgacaggccc gaaggaatag aagaagaagg tggagagaga   1980
gacagagaca gatccattcg attagtgaac ggatctcgac ggtcgccaaa tggcagtatt   2040
catccacaat tttaaaagaa aaggggggat tggggggtac agtgcagggg aaagaatagt   2100
agacataata gcaacagaca tacaaactaa agaattacaa aaacaaatta caaaaattca   2160
aaattttcgg gtttattaca gggacagcag agatccagtt tggatcgata agcttgatat   2220
cgaattcctg cgcggccgct tcgaacgcgc gcgatgcatc atatggccct cacaaaggaa   2280
caataacagg aaaccatccc agggggaagt gggccagggc cagctggaaa acctgaaggg   2340
```

-continued gcgtacgcgg tctagaattc ctgcagggcc cactagtctc ccaggcatga ctccaacaat 2400
gcatcccatg ggatttgggg ttccccagat ctggggcttg taggcctgac tctcccctgt 2460
gcacacgtct catacacgca tgcgtgcacc cattgcctgc cccgcccctt gcacagggag 2520
tcagcaggga ggactgggtt atgccctgct tatcagcagc ttcccagctt cctctgcctg 2580
gattcttaga ggcctggggt cctagaacga gctggtgcac gtggcttccc aaagatctct 2640
cagataatga gaggaaatgc agtcatcagt ttgcagaagg ctagggattc tgggccatag 2700
ctcagacctg cgcccaccat ctccctccag gcagcccttg gctggtccct gcgagcccgt 2760
ggagactgcc agtcagcgct gctggatctc gggctcgagg ccaccatgca gatcgagctg 2820
tccacctgct tttttctgtg cctgctgcgg ttctgcttca gcgccacccg gcggtactac 2880
ctgggcgccg tggagctgtc ctgggactac atgcagagcg acctgggcga gctgcccgtg 2940
gacgcccggt tcccccccag agtgcccaag agcttcccct tcaacaccag cgtggtgtac 3000
aagaaaaccc tgttcgtgga gttcaccgac cacctgttca atatcgccaa gcccaggccc 3060
ccctggatgg gcctgctggg ccccaccatc caggccgagg tgtacgacac cgtggtgatc 3120
accctgaaga acatggccag ccaccccgtg agcctgcacg ccgtgggcgt gagctactgg 3180
aaggccagcg agggcgccga gtacgacgac cagaccagcc agcgggagaa agaagatgac 3240
aaggtgttcc ctggcggcag ccacacctac gtgtggcagg tgctgaaaga aaacggcccc 3300
atggcctccg acccccctgtg cctgacctac agctacctga gccacgtgga cctggtgaag 3360
gacctgaaca gcggcctgat cggcgctctg ctcgtctgcc gggagggcag cctggccaaa 3420
gagaaaaccc agaccctgca caagttcatc ctgctgttcg ccgtgttcga cgagggcaag 3480
agctggcaca gcgagacaaa gaacagcctg atgcaggacc gggacgccgc ctctgccaga 3540
gcctggccca agatgcacac cgtgaacggc tacgtgaaca gaagcctgcc cggcctgatt 3600
ggctgccacc ggaagagcgt gtactggcac gtgatcggca tgggcaccac acccgaggtg 3660
cacagcatct ttctggaagg gcacaccttt ctggtccgga accaccggca ggccagcctg 3720
gaaatcagcc ctatcacctt cctgaccgcc cagacactgc tgatggacct gggccagttc 3780
ctgctgtttt gccacatcag ctctcaccag cacgacggca tggaagccta cgtgaaggtg 3840
gactcttgcc ccgaggaacc ccagctgcgg atgaagaaca acgaggaagc cgaggactac 3900
gacgacgacc tgaccgacag cgagatggac gtggtgcggt tcgacgacga caacagcccc 3960
agcttcatcc agatcagaag cgtggccaag aagcacccca agacctgggt gcactatatc 4020
gccgccgagg aagaggactg ggactacgcc cccctggtgc tggcccccga cgacagaagc 4080
tacaagagcc agtacctgaa caatggcccc cagcggatcg gccggaagta caagaaagtg 4140
cggttcatgg cctacaccga cgagacattc aagacccggg aggccatcca gcacgagagc 4200
ggcatcctgg gccccctgct gtacggcgaa gtgggcgaca cactgctgat catcttcaag 4260
aaccaggcta gccggcccta caacatctac ccccacggca tcaccgacgt gcggcccctg 4320
tacagcaggc ggctgcccaa gggcgtgaag cacctgaagg acttccccat cctgcccggc 4380
gagatcttca agtacaagtg gaccgtgacc gtggaggacg gccccaccaa gagcgacccc 4440
agatgcctga cccggtacta cagcagcttc gtgaacatgg aacgggacct ggcctccggg 4500
ctgatcggac ctctgctgat ctgctacaaa gaaagcgtgg accagcgggg caaccagatc 4560
atgagcgaca agcggaacgt gatcctgttc agcgtgttcg atgagaaccg gtcctggtat 4620
ctgaccgaga acatccagcg gtttctgccc aaccctgccg gcgtgcagct ggaagatccc 4680
gagttccagg ccagcaacat catgcactcc atcaatggct acgtgttcga ctctctgcag 4740

```
ctctccgtgt gtctgcacga ggtggcctac tggtacatcc tgagcatcgg cgcccagacc   4800
gacttcctga gcgtgttctt cagcggctac accttcaagc acaagatggt gtacgaggac   4860
accctgaccc tgttcccttt cagcggcgag acagtgttca tgagcatgga aaaccccggc   4920
ctgtggattc tgggctgcca caacagcgac ttccggaacc ggggcatgac cgccctgctg   4980
aaggtgtcca gctgcgacaa gaacaccggc gactactacg aggacagcta cgaggatatc   5040
agcgcctacc tgctgtccaa gaacaacgcc atcgaacccc ggagcttcag ccagaacccc   5100
cccgtgctga cgcgtcacca gcgggagatc acccggacaa ccctgcagtc cgaccaggaa   5160
gagatcgatt acgacgacac catcagcgtg gagatgaaga aagaggattt cgatatctac   5220
gacgaggacg agaaccagag ccccagaagc ttccagaaga aaacccggca ctacttcatt   5280
gccgccgtgg agaggctgtg ggactacggc atgagttcta gcccccacgt gctgcggaac   5340
cgggcccaga gcggcagcgt gccccagttc aagaaagtgg tgttccagga attcacagac   5400
ggcagcttca cccagcctct gtatagaggc gagctgaacg agcacctggg gctgctgggg   5460
ccctacatca gggccgaagt ggaggacaac atcatggtga ccttccggaa tcaggccagc   5520
agaccctact ccttctacag cagcctgatc agctacgaag aggaccagcg gcagggcgcc   5580
gaaccccgga agaacttcgt gaagcccaac gaaaccaaga cctacttctg gaaagtgcag   5640
caccacatgg cccccaccaa ggacgagttc gactgcaagg cctgggccta cttcagcgac   5700
gtggatctgg aaaaggacgt gcactctgga ctgattggcc cactcctggt ctgccacact   5760
aacaccctca accccgccca cggccgccag gtgaccgtgc aggaattcgc cctgttcttc   5820
accatcttcg acgagacaaa gtcctggtac ttcaccgaga atatggaacg gaactgcaga   5880
gccccctgca acatccagat ggaagatcct accttcaaag agaactaccg gttccacgcc   5940
atcaacggct acatcatgga caccctgcct ggcctggtga tggcccagga ccagagaatc   6000
cggtggtatc tgctgtccat gggcagcaac gagaatatcc acagcatcca cttcagcggc   6060
cacgtgttca ccgtgcggaa gaaagaagag tacaagatgg ccctgtacaa cctgtacccc   6120
ggcgtgttcg agacagtgga gatgctgccc agcaaggccg gcatctggcg ggtggagtgt   6180
ctgatcggcg agcacctgca cgctggcatg agcaccctgt ttctggtgta cagcaacaag   6240
tgccagaccc cactgggcat ggcctctggc cacatccggg acttccagat caccgcctcc   6300
ggccagtacg gccagtgggc ccccaagctg gccagactgc actacagcgg cagcatcaac   6360
gcctggtcca ccaaagagcc cttcagctgg atcaaggtgg acctgctggc ccctatgatc   6420
atccacggca ttaagaccca gggcgccagg cagaagttca gcagcctgta catcagccag   6480
ttcatcatca tgtacagcct ggacggcaag aagtggcaga cctaccgggg caacagcacc   6540
ggcaccctga tggtgttctt cggcaatgtg gacagcagcg gcatcaagca caacatcttc   6600
aaccccccca tcattgcccg gtacatccgg ctgcacccca cccactacag cattagatcc   6660
acactgagaa tggaactgat gggctgcgac ctgaactcct gcagcatgcc tctgggcatg   6720
gaaagcaagg ccatcagcga cgcccagatc acagccagca gctacttcac caacatgttc   6780
gccacctggt cccccctccaa ggccaggctg cacctgcagg gccggtccaa cgcctggcgg   6840
cctcaggtca acaaccccaa agaatggctg caggtggact ttcagaaaac catgaaggtg   6900
accggcgtga ccacccaggg cgtgaaaagc ctgctgacca gcatgtacgt gaaagagttt   6960
ctgatcagca gctctcagga tggccaccag tggaccctgt tctttcagaa cggcaaggtg   7020
aaagtgttcc agggcaacca ggactccttc acccccgtgg tgaactccct ggaccccccc   7080
```

-continued

```
ctgctgaccc gctacctgag aatccacccc cagtcttggg tgcaccagat cgccctcagg   7140
atggaagtcc tgggatgtga ggcccaggat ctgtactgat gacgtctgga acaatcaacc   7200
tctggattac aaaatttgtg aaagattgac tggtattctt aactatgttg ctccttttac   7260
gctatgtgga tacgctgctt taatgccttt gtatcatgct attgcttccc gtatggcttt   7320
cattttctcc tccttgtata aatcctggtt gctgtctctt tatgaggagt tgtggcccgt   7380
tgtcaggcaa cgtggcgtgg tgtgcactgt gtttgctgac gcaaccccca ctggttgggg   7440
cattgccacc acctgtcagc tcctttccgg gactttcgct ttccccctcc ctattgccac   7500
ggcggaactc atcgccgcct gccttgcccg ctgctggaca ggggctcggc tgttgggcac   7560
tgacaattcc gtggtgttgt cggggaagct gacgtccttt ccatggctgc tcgcctgtgt   7620
tgccacctgg attctgcgcg ggacgtcctt ctgctacgtc ccttcggccc tcaatccagc   7680
ggaccttcct tcccgcggcc tgctgccggc tctgcggcct cttccgcgtc ttcgccttcg   7740
ccctcagacg agtcggatct ccctttgggc cgcctccccg cctggaatta attctgcagt   7800
cgagacctag aaaaacatgg agcaatcaca agtagcaata cagcagctac caatgctgat   7860
tgtgcctggc tagaagcaca agaggaggag gaggtgggtt ttccagtcac acctcaggta   7920
cctttaagac caatgactta caaggcagct gtagatctta gccacttttt aaaagaaaag   7980
aggggactgg aagggctaat tcactcccaa cgaagacaag atatccttga tctgtggatc   8040
taccacacac aaggctactt ccctgattag cagaactaca caccagggcc aggggtcaga   8100
tatccactga cctttggatg gtgctacaag ctagtaccag ttgagccaga taaggtagaa   8160
gaggccaata aaggagagaa caccagcttg ttacaccctg tgagcctgca tgggatggat   8220
gacccggaga gagaagtgtt agagtggagg tttgacagcc gcctagcatt tcatcacgtg   8280
gcccgagagc tgcatccgga gtacttcaag aactgctgat atcgagcttg ctacaaggga   8340
ctttccgctg gggactttcc agggaggcgt ggcctgggcg ggactgggga gtggcgagcc   8400
ctcagatcct gcatataagc agctgctttt tgcctgtact gggtctctct ggttagacca   8460
gatctgagcc tgggagctct ctggctaact agggaaccca ctgcttaagc ctcaataaag   8520
cttgccttga gtgcttcaag tagtgtgtgc ccgtctgttg tgtgactctg gtaactagag   8580
atccctcaga cccttttagt cagtgtggaa aatctctagc agtagtagtt catgtcatct   8640
tattattcag tatttataac ttgcaaagaa atgaatatca gagagtgaga ggccttgaca   8700
ttgctagcgt tttaccgtcg acctctagct agagcttggc gtaatcatgg tcatagctgt   8760
ttcctgtgtg aaattgttat ccgctcacaa ttccacacaa catacgagcc ggaagcataa   8820
agtgtaaagc ctggggtgcc taatgagtga gctaactcac attaattgcg ttgcgctcac   8880
tgcccgcttt ccagtcggga aacctgtcgt gccagctgca ttaatgaatc ggccaacgcg   8940
cggggagagg cggtttgcgt attgggcgct cttccgcttc ctcgctcact gactcgctgc   9000
gctcggtcgt tcggctgcgg cgagcggtat cagctcactc aaaggcggta atacggttat   9060
ccacagaatc aggggataac gcaggaaaga acatgtgagc aaaaggccag caaaaggcca   9120
ggaaccgtaa aaaggccgcg ttgctggcgt ttttccatag gctccgcccc cctgacgagc   9180
atcacaaaaa tcgacgctca agtcagaggt ggcgaaaccc gacaggacta taaagatacc   9240
aggcgtttcc ccctggaagc tccctcgtgc gctctcctgt tccgaccctg ccgcttaccg   9300
gatacctgtc cgcctttctc ccttcgggaa gcgtggcgct ttctcatagc tcacgctgta   9360
ggtatctcag ttcggtgtag gtcgttcgct ccaagctggg ctgtgtgcac gaaccccccg   9420
ttcagcccga ccgctgcgcc ttatccggta actatcgtct tgagtccaac ccggtaagac   9480
```

-continued acgacttatc gccactggca gcagccactg gtaacaggat tagcagagcg aggtatgtag 9540
gcggtgctac agagttcttg aagtggtggc ctaactacgg ctacactaga agaacagtat 9600
ttggtatctg cgctctgctg aagccagtta ccttcggaaa aagagttggt agctcttgat 9660
ccggcaaaca aaccaccgct ggtagcggtg gtttttttgt ttgcaagcag cagattacgc 9720
gcagaaaaaa aggatctcaa gaagatcctt tgatcttttc tacggggtct gacgctcagt 9780
ggaacgaaaa ctcacgttaa gggattttgg tcatgagatt atcaaaaagg atcttcacct 9840
agatcctttt aaattaaaaa tgaagtttta aatcaatcta aagtatatat gagtaaactt 9900
ggtctgacag ttaccaatgc ttaatcagtg aggcacctat ctcagcgatc tgtctatttc 9960
gttcatccat agttgcctga ctccccgtcg tgtagataac tacgatacgg gagggcttac 10020
catctggccc cagtgctgca atgataccgc gagacccacg ctcaccggct ccagatttat 10080
cagcaataaa ccagccagcc ggaagggccg agcgcagaag tggtcctgca actttatccg 10140
cctccatcca gtctattaat tgttgccggg aagctagagt aagtagttcg ccagttaata 10200
gtttgcgcaa cgttgttgcc attgctacag gcatcgtggt gtcacgctcg tcgtttggta 10260
tggcttcatt cagctccggt tcccaacgat caaggcgagt tacatgatcc cccatgttgt 10320
gcaaaaaagc ggttagctcc ttcggtcctc cgatcgttgt cagaagtaag ttggccgcag 10380
tgttatcact catggttatg gcagcactgc ataattctct tactgtcatg ccatccgtaa 10440
gatgcttttc tgtgactggt gagtactcaa ccaagtcatt ctgagaatag tgtatgcggc 10500
gaccgagttg ctcttgcccg gcgtcaatac gggataatac cgcgccacat agcagaactt 10560
taaaagtgct catcattgga aaacgttctt cggggcgaaa actctcaagg atcttaccgc 10620
tgttgagatc cagttcgatg taacccactc gtgcacccaa ctgatcttca gcatctttta 10680
ctttcaccag cgtttctggg tgagcaaaaa caggaaggca aaatgccgca aaaaagggaa 10740
taagggcgac acggaaatgt tgaatactca tactcttcct ttttcaatat tattgaagca 10800
tttatcaggg ttattgtctc atgagcggat acatatttga atgtatttag aaaaataaac 10860
aaataggggt tccgcgcaca tttccccgaa aagtgccacc tgacgtcgac ggatcgggag 10920
atcaacttgt ttattgcagc ttataatggt tacaaataaa gcaatagcat cacaaatttc 10980
acaaataaag catttttttc actgcattct agttgtggtt tgtccaaact catcaatgta 11040
tcttatcatg tctggatcaa ctggataact caagctaacc aaaatcatcc caaacttccc 11100
accccatacc ctattaccac tgccaattac ctgtggtttc atttactcta aacctgtgat 11160
tcctctgaat tattttcatt ttaaagaaat tgtatttgtt aaatatgtac tacaaactta 11220
gtagttttta aagaaattgt atttgttaaa tatgtactac aaacttagta gt 11272

<210> SEQ ID NO 49
<211> LENGTH: 10725
<212> TYPE: DNA
<213> ORGANISM: Artificial Sequence
<220> FEATURE:
<223> OTHER INFORMATION: Vector

<400> SEQUENCE: 49
acgcgtgtag tcttatgcaa tactcttgta gtcttgcaac atggtaacga tgagttagca 60
acatgcctta caaggagaga aaaagcaccg tgcatgccga ttggtggaag taaggtggta 120
cgatcgtgcc ttattaggaa ggcaacagac gggtctgaca tggattggac gaaccactga 180
attgccgcat tgcagagata ttgtatttaa gtgcctagct cgatacaata aacgggtctc 240

-continued

```
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggttaacttt   1800
taaaagaaaa ggggggattg gggggtacag tgcaggggaa agaatagtag acataatagc   1860
aacagacata caaactaaag aattacaaaa acaaattaca aaaattcaaa attttatcga   1920
tagcgcggcc gcttcgaacg cgcgcgatgc atcatatgcg tacgcggtct agaattcctg   1980
cagggcccac tagtctccca ggcatgactc caacaatgca tcccatggga tttggggttc   2040
cccagatctg gggcttgtag gcctgactct cccctgtgca cacgtctcat acacgcatgc   2100
gtgcacccat tgcctgcccc gccccttgca cagggagtca gcagggagga ctgggttatg   2160
ccctgcttat cagcagcttc ccagcttcct ctgcctggat tcttagaggc ctggggtcct   2220
agaacgagct ggtgcacgtg gcttcccaaa gatctctcag ataatgagag gaaatgcagt   2280
catcagtttg cagaaggcta gggattctgg gccatagctc agacctgcgc ccaccatctc   2340
cctccaggca gcccttggct ggtccctgcg agcccgtgga gactgccagt cagcgctgct   2400
ggatctcggg ctcgaggcca ccatgcagat cgagctgtcc acctgctttt ttctgtgcct   2460
gctgcggttc tgcttcagcg ccacccggcg gtactacctg ggcgccgtgg agctgtcctg   2520
ggactacatg cagagcgacc tgggcgagct gcccgtggac gcccggttcc cccccagagt   2580
gcccaagagc ttccccttca acaccagcgt ggtgtacaag aaaaccctgt tcgtggagtt   2640
```

```
caccgaccac ctgttcaata tcgccaagcc caggcccccc tggatgggcc tgctgggccc   2700
caccatccag gccgaggtgt acgacaccgt ggtgatcacc ctgaagaaca tggccagcca   2760
ccccgtgagc ctgcacgccg tgggcgtgag ctactggaag gccagcgagg gcgccgagta   2820
cgacgaccag accagccagc gggagaaaga agatgacaag gtgttccctg gcggcagcca   2880
cacctacgtg tggcaggtgc tgaaagaaaa cggccccatg gcctccgacc ccctgtgcct   2940
gacctacagc tacctgagcc acgtggacct ggtgaaggac ctgaacagcg gcctgatcgg   3000
cgctctgctc gtctgccggg agggcagcct ggccaaagag aaaacccaga ccctgcacaa   3060
gttcatcctg ctgttcgccg tgttcgacga gggcaagagc tggcacagcg agacaaagaa   3120
cagcctgatg caggaccggg acgccgcctc tgccagagcc tggcccaaga tgcacaccgt   3180
gaacggctac gtgaacagaa gcctgcccgg cctgattggc tgccaccgga agagcgtgta   3240
ctggcacgtg atcggcatgg gcaccacacc cgaggtgcac agcatctttc tggaagggca   3300
cacctttctg gtccggaacc accggcaggc cagcctggaa atcagcccta tcaccttcct   3360
gaccgcccag acactgctga tggacctggg ccagttcctg ctgttttgcc acatcagctc   3420
tcaccagcac gacggcatgg aagcctacgt gaaggtggac tcttgccccg aggaacccca   3480
gctgcggatg aagaacaacg aggaagccga ggactacgac gacgacctga ccgacagcga   3540
gatggacgtg gtgcggttcg acgacgacaa cagccccagc ttcatccaga tcagaagcgt   3600
ggccaagaag caccccaaga cctgggtgca ctatatcgcc gccgaggaag aggactggga   3660
ctacgccccc ctggtgctgg cccccgacga cagaagctac aagagccagt acctgaacaa   3720
tggcccccag cggatcggcc ggaagtacaa gaaagtgcgg ttcatggcct acaccgacga   3780
gacattcaag acccgggagg ccatccagca cgagagcggc atcctgggcc ccctgctgta   3840
cggcgaagtg ggcgacacac tgctgatcat cttcaagaac caggctagcc ggccctacaa   3900
catctacccc cacggcatca ccgacgtgcg gcccctgtac agcaggcggc tgcccaaggg   3960
cgtgaagcac ctgaaggact tccccatcct gcccggcgag atcttcaagt acaagtggac   4020
cgtgaccgtg gaggacggcc ccaccaagag cgaccccaga tgcctgaccc ggtactacag   4080
cagcttcgtg aacatggaac gggacctggc ctccgggctg atcggacctc tgctgatctg   4140
ctacaaagaa agcgtggacc agcggggcaa ccagatcatg agcgacaagc ggaacgtgat   4200
cctgttcagc gtgttcgatg agaaccggtc ctggtatctg accgagaaca tccagcggtt   4260
tctgcccaac cctgccggcg tgcagctgga agatcccgag ttccaggcca gcaacatcat   4320
gcactccatc aatggctacg tgttcgactc tctgcagctc tccgtgtgtc tgcacgaggt   4380
ggcctactgg tacatcctga gcatcggcgc ccagaccgac ttcctgagcg tgttcttcag   4440
cggctacacc ttcaagcaca agatggtgta cgaggacacc ctgaccctgt tccctttcag   4500
cggcgagaca gtgttcatga gcatggaaaa ccccggcctg tggattctgg gctgccacaa   4560
cagcgacttc cggaaccggg gcatgaccgc cctgctgaag gtgtccagct gcgacaagaa   4620
caccggcgac tactacgagg acagctacga ggatatcagc gcctacctgc tgtccaagaa   4680
caacgccatc gaaccccgga gcttcagcca gaaccccccc gtgctgacgc gtcaccagcg   4740
ggagatcacc cggacaaccc tgcagtccga ccaggaagag atcgattacg acgacaccat   4800
cagcgtggag atgaagaaag aggatttcga tatctacgac gaggacgaga accagagccc   4860
cagaagcttc cagaagaaaa cccggcacta cttcattgcc gccgtggaga ggctgtggga   4920
ctacggcatg agttctagcc cccacgtgct gcggaaccgg gcccagagcg gcagcgtgcc   4980
```

-continued ccagttcaag aaagtggtgt tccaggaatt cacagacggc agcttcaccc agcctctgta 5040
tagaggcgag ctgaacgagc acctggggct gctggggccc tacatcaggg ccgaagtgga 5100
ggacaacatc atggtgacct tccggaatca ggccagcaga ccctactcct tctacagcag 5160
cctgatcagc tacgaagagg accagcggca gggcgccgaa ccccggaaga acttcgtgaa 5220
gcccaacgaa accaagacct acttctggaa agtgcagcac cacatggccc ccaccaagga 5280
cgagttcgac tgcaaggcct gggcctactt cagcgacgtg gatctggaaa aggacgtgca 5340
ctctggactg attggcccac tcctggtctg ccacactaac accctcaacc ccgcccacgg 5400
ccgccaggtg accgtgcagg aattcgccct gttcttcacc atcttcgacg agacaaagtc 5460
ctggtacttc accgagaata tggaacggaa ctgcagagcc ccctgcaaca tccagatgga 5520
agatcctacc ttcaaagaga actaccggtt ccacgccatc aacggctaca tcatggacac 5580
cctgcctggc ctggtgatgg cccaggacca gagaatccgg tggtatctgc tgtccatggg 5640
cagcaacgag aatatccaca gcatccactt cagcggccac gtgttcaccg tgcggaagaa 5700
agaagagtac aagatggccc tgtacaacct gtaccccggc gtgttcgaga cagtggagat 5760
gctgcccagc aaggccggca tctggcgggt ggagtgtctg atcggcgagc acctgcacgc 5820
tggcatgagc accctgtttc tggtgtacag caacaagtgc cagaccccac tgggcatggc 5880
ctctggccac atccgggact tccagatcac cgcctccggc cagtacggcc agtgggcccc 5940
caagctggcc agactgcact acagcggcag catcaacgcc tggtccacca aagagccctt 6000
cagctggatc aaggtggacc tgctggcccc tatgatcatc cacggcatta agacccaggg 6060
cgccaggcag aagttcagca gcctgtacat cagccagttc atcatcatgt acagcctgga 6120
cggcaagaag tggcagacct accggggcaa cagcaccggc accctgatgg tgttcttcgg 6180
caatgtggac agcagcggca tcaagcacaa catcttcaac ccccccatca ttgcccggta 6240
catccggctg caccccaccc actacagcat tagatccaca ctgagaatgg aactgatggg 6300
ctgcgacctg aactcctgca gcatgcctct gggcatggaa agcaaggcca tcagcgacgc 6360
ccagatcaca gccagcagct acttcaccaa catgttcgcc acctggtccc cctccaaggc 6420
caggctgcac ctgcagggcc ggtccaacgc ctggcggcct caggtcaaca accccaaaga 6480
atggctgcag gtggactttc agaaaaccat gaaggtgacc ggcgtgacca cccagggcgt 6540
gaaaagcctg ctgaccagca tgtacgtgaa agagtttctg atcagcagct ctcaggatgg 6600
ccaccagtgg accctgttct ttcagaacgg caaggtgaaa gtgttccagg gcaaccagga 6660
ctccttcacc cccgtggtga actccctgga cccccccctg ctgacccgct acctgagaat 6720
ccacccccag tcttgggtgc accagatcgc cctcaggatg gaagtcctgg gatgtgaggc 6780
ccaggatctg tactgatgac gtctggaacg cgtcgacaat caacctctgg attacaaaat 6840
ttgtgaaaga ttgactggta ttcttaacta tgttgctcct tttacgctat gtggatacgc 6900
tgctttaatg cctttgtatc atgctattgc ttcccgtatg gctttcattt tctcctcctt 6960
gtataaatcc tggttgctgt ctctttatga ggagttgtgg cccgttgtca ggcaacgtgg 7020
cgtggtgtgc actgtgtttg ctgacgcaac ccccactggt tggggcattg ccaccacctg 7080
tcagctcctt tccgggactt tcgctttccc cctccctatt gccacggcgg aactcatcgc 7140
cgcctgcctt gcccgctgct ggacaggggc tcggctgttg ggcactgaca attccgtggt 7200
gttgtcgggg aaatcatcgt cctttccttg gctgctcgcc tgtgttgcca cctggattct 7260
gcgcgggacg tccttctgct acgtcccttc ggccctcaat ccagcggacc ttccttcccg 7320
cggcctgctg ccggctctgc ggcctcttcc gcgtcttcgc cttcgccctc agacgagtcg 7380
gatctccctt tgggccgcct ccccgcctgg tacctttaag accaatgact tacaaggcag 7440
ctgtagatct tagccacttt ttaaaagaaa aggggggact ggaagggcta attcactccc 7500
aacgaaaata agatctgctt tttgcttgta ctgggtctct ctggttagac cagatctgag 7560
cctgggagct ctctggctaa ctagggaacc cactgcttaa gcctcaataa agcttgcctt 7620
gagtgcttca agtagtgtgt gcccgtctgt tgtgtgactc tggtaactag agatccctca 7680
gaccctttta gtcagtgtgg aaaatctcta gcagtagtag ttcatgtcat cttattattc 7740
agtatttata acttgcaaag aaatgaatat cagagagtga gaggaacttg tttattgcag 7800
cttataatgg ttacaaataa agcaatagca tcacaaattt cacaaataaa gcattttttt 7860
cactgcattc tagttgtggt ttgtccaaac tcatcaatgt atcttatcat gtctggctct 7920
agctatcccg cccctaactc cgcccagttc cgcccattct ccgccccatg gctgactaat 7980
ttttttattt tatgcagagg ccgaggccgc ctcggcctct gagctattcc agaagtagtg 8040
aggaggcttt tttggaggcc tagacttttg cagagacggc ccaaattcgt aatcatggtc 8100
atagctgttt cctgtgtgaa attgttatcc gctcacaatt ccacacaaca tacgagccgg 8160
aagcataaag tgtaaagcct ggggtgccta atgagtgagc taactcacat taattgcgtt 8220
gcgctcactg cccgctttcc agtcgggaaa cctgtcgtgc cagctgcatt aatgaatcgg 8280
ccaacgcgcg gggagaggcg gtttgcgtat tgggcgctct tccgcttcct cgctcactga 8340
ctcgctgcgc tcggtcgttc ggctgcggcg agcggtatca gctcactcaa aggcggtaat 8400
acggttatcc acagaatcag gggataacgc aggaaagaac atgtgagcaa aaggccagca 8460
aaaggccagg aaccgtaaaa aggccgcgtt gctggcgttt ttccataggc tccgcccccc 8520
tgacgagcat cacaaaaatc gacgctcaag tcagaggtgg cgaaacccga caggactata 8580
aagataccag gcgtttcccc ctggaagctc cctcgtgcgc tctcctgttc cgaccctgcc 8640
gcttaccgga tacctgtccg cctttctccc ttcgggaagc gtggcgcttt ctcatagctc 8700
acgctgtagg tatctcagtt cggtgtaggt cgttcgctcc aagctgggct gtgtgcacga 8760
accccccgtt cagcccgacc gctgcgcctt atccggtaac tatcgtcttg agtccaaccc 8820
ggtaagacac gacttatcgc cactggcagc agccactggt aacaggatta gcagagcgag 8880
gtatgtaggc ggtgctacag agttcttgaa gtggtggcct aactacggct acactagaag 8940
gacagtattt ggtatctgcg ctctgctgaa gccagttacc ttcggaaaaa gagttggtag 9000
ctcttgatcc ggcaaacaaa ccaccgctgg tagcggtggt ttttttgttt gcaagcagca 9060
gattacgcgc agaaaaaaag gatctcaaga agatcctttg atcttttcta cggggtctga 9120
cgctcagtgg aacgaaaact cacgttaagg gattttggtc atgagattat caaaaaggat 9180
cttcacctag atccttttaa attaaaaatg aagttttaaa tcaatctaaa gtatatatga 9240
gtaaacttgg tctgacagtt accaatgctt aatcagtgag gcacctatct cagcgatctg 9300
tctatttcgt tcatccatag ttgcctgact ccccgtcgtg tagataacta cgatacggga 9360
gggcttacca tctggcccca gtgctgcaat gataccgcga gacccacgct caccggctcc 9420
agatttatca gcaataaacc agccagccgg aagggccgag cgcagaagtg gtcctgcaac 9480
tttatccgcc tccatccagt ctattaattg ttgccgggaa gctagagtaa gtagttcgcc 9540
agttaatagt ttgcgcaacg ttgttgccat tgctacaggc atcgtggtgt cacgctcgtc 9600
gtttggtatg gcttcattca gctccggttc ccaacgatca aggcgagtta catgatcccc 9660
catgttgtgc aaaaaagcgg ttagctcctt cggtcctccg atcgttgtca gaagtaagtt 9720

```
ggccgcagtg ttatcactca tggttatggc agcactgcat aattctctta ctgtcatgcc   9780

atccgtaaga tgcttttctg tgactggtga gtactcaacc aagtcattct gagaatagtg   9840

tatgcggcga ccgagttgct cttgcccggc gtcaatacgg gataataccg cgccacatag   9900

cagaacttta aaagtgctca tcattggaaa acgttcttcg gggcgaaaac tctcaaggat   9960

cttaccgctg ttgagatcca gttcgatgta acccactcgt gcacccaact gatcttcagc  10020

atcttttact ttcaccagcg tttctgggtg agcaaaaaca ggaaggcaaa atgccgcaaa  10080

aaagggaata agggcgacac ggaaatgttg aatactcata ctcttccttt ttcaatatta  10140

ttgaagcatt tatcagggtt attgtctcat gagcggatac atatttgaat gtatttagaa  10200

aaataaacaa ataggggttc cgcgcacatt tccccgaaaa gtgccacctg acgtctaaga  10260

aaccattatt atcatgacat taacctataa aaataggcgt atcacgaggc cctttcgtct  10320

cgcgcgtttc ggtgatgacg gtgaaaacct ctgacacatg cagctcccgg agacggtcac  10380

agcttgtctg taagcggatg ccgggagcag acaagcccgt cagggcgcgt cagcgggtgt  10440

tggcgggtgt cggggctggc ttaactatgc ggcatcagag cagattgtac tgagagtgca  10500

ccatatatgc ggtgtgaaat accgcacaga tgcgtaagga gaaaataccg catcaggcgc  10560

cattcgccat tcaggctgcg caactgttgg gaagggcgat cggtgcgggc ctcttcgcta  10620

ttacgccagc tggcgaaagg gggatgtgct gcaaggcgat taagttgggt aacgccaggg  10680

ttttcccagt cacgacgttg taaaacgacg gccagtgcca agctg                  10725
```

<210> SEQ ID NO 50
<211> LENGTH: 10895
<212> TYPE: DNA
<213> ORGANISM: Artificial Sequence
<220> FEATURE:
<223> OTHER INFORMATION: Vector

<400> SEQUENCE: 50

```
acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080
```

-continued ctttgttcct tgggttcttg ggagcagcag gaagcactat gggcgcagcc tcaatgacgc 1140
tgacggtaca ggccagacaa ttattgtctg gtatagtgca gcagcagaac aatttgctga 1200
gggctattga ggcgcaacag catctgttgc aactcacagt ctggggcatc aagcagctcc 1260
aggcaagaat cctggctgtg gaaagatacc taaaggatca acagctcctg gggatttggg 1320
gttgctctgg aaaactcatt tgcaccactg ctgtgccttg gaatgctagt tggagtaata 1380
aatctctgga acagattgga atcacacgac ctggatggag tgggacagag aaattaacaa 1440
ttacacaagc ttaatacact ccttaattga agaatcgcaa aaccagcaag aaaagaatga 1500
acaagaatta ttggaattag ataaatgggc aagtttgtgg aattggttta acataacaaa 1560
ttggctgtgg tatataaaat tattcataat gatagtagga ggcttggtag gtttaagaat 1620
agtttttgct gtactttcta tagtgaatag agttaggcag ggatattcac cattatcgtt 1680
tcagacccac ctcccaaccc cgaggggacc cgacaggccc gaaggaatag aagaagaagg 1740
tggagagaga gacagagaca gatccattcg attagtgaac ggatctcgac ggttaacttt 1800
taaaagaaaa ggggggattg gggggtacag tgcaggggaa agaatagtag acataatagc 1860
aacagacata caaactaaag aattacaaaa acaaattaca aaaattcaaa attttatcga 1920
tagcgcggcc gcttcgaacg cgcgcgatgc atcatatgag ggaactccct gtgctgggcc 1980
tacccagctg accccatcgc tggaaacaat gggggtcagg caacacttcc ccactctctc 2040
ccgccgggct gtgctcactt ccttcctgct ggctgcctga ggaagtgtcc ctgccctggg 2100
acagtctggc ctagcctttg tttccccgcg tacgcggtct agaattcctg cagggcccac 2160
tagtctccca ggcatgactc caacaatgca tcccatggga tttggggttc cccagatctg 2220
gggcttgtag gcctgactct cccctgtgca cacgtctcat acacgcatgc gtgcacccat 2280
tgcctgcccc gccccttgca cagggagtca gcagggagga ctgggttatg ccctgcttat 2340
cagcagcttc ccagcttcct ctgcctggat tcttagaggc ctggggtcct agaacgagct 2400
ggtgcacgtg gcttcccaaa gatctctcag ataatgagag gaaatgcagt catcagtttg 2460
cagaaggcta gggattctgg gccatagctc agacctgcgc ccaccatctc cctccaggca 2520
gcccttggct ggtccctgcg agcccgtgga gactgccagt cagcgctgct ggatctcggg 2580
ctcgaggcca ccatgcagat cgagctgtcc acctgctttt ttctgtgcct gctgcggttc 2640
tgcttcagcg ccacccggcg gtactacctg ggcgccgtgg agctgtcctg ggactacatg 2700
cagagcgacc tgggcgagct gcccgtggac gcccggttcc cccccagagt gcccaagagc 2760
ttccccttca acaccagcgt ggtgtacaag aaaaccctgt tcgtggagtt caccgaccac 2820
ctgttcaata tcgccaagcc caggcccccc tggatgggcc tgctgggccc caccatccag 2880
gccgaggtgt acgacaccgt ggtgatcacc ctgaagaaca tggccagcca ccccgtgagc 2940
ctgcacgccg tgggcgtgag ctactggaag gccagcgagg gcgccgagta cgacgaccag 3000
accagccagc gggagaaaga agatgacaag gtgttccctg gcggcagcca cacctacgtg 3060
tggcaggtgc tgaaagaaaa cggccccatg gcctccgacc ccctgtgcct gacctacagc 3120
tacctgagcc acgtggacct ggtgaaggac ctgaacagcg gcctgatcgg cgctctgctc 3180
gtctgccggg agggcagcct ggccaaagag aaaacccaga ccctgcacaa gttcatcctg 3240
ctgttcgccg tgttcgacga gggcaagagc tggcacagcg agacaaagaa cagcctgatg 3300
caggaccggg acgccgcctc tgccagagcc tggcccaaga tgcacaccgt gaacggctac 3360
gtgaacagaa gcctgcccgg cctgattggc tgccaccgga agagcgtgta ctggcacgtg 3420

-continued

```
atcggcatgg gcaccacacc cgaggtgcac agcatctttc tggaagggca cacctttctg   3480
gtccggaacc accggcaggc cagcctggaa atcagcccta tcaccttcct gaccgcccag   3540
acactgctga tggacctggg ccagttcctg ctgttttgcc acatcagctc tcaccagcac   3600
gacggcatgg aagcctacgt gaaggtggac tcttgccccg aggaacccca gctgcggatg   3660
aagaacaacg aggaagccga ggactacgac gacgacctga ccgacagcga gatggacgtg   3720
gtgcggttcg acgacgacaa cagccccagc ttcatccaga tcagaagcgt ggccaagaag   3780
caccccaaga cctgggtgca ctatatcgcc gccgaggaag aggactggga ctacgccccc   3840
ctggtgctgg cccccgacga cagaagctac aagagccagt acctgaacaa tggcccccag   3900
cggatcggcc ggaagtacaa gaaagtgcgg ttcatggcct acaccgacga gacattcaag   3960
acccgggagg ccatccagca cgagagcggc atcctgggcc ccctgctgta cggcgaagtg   4020
ggcgacacac tgctgatcat cttcaagaac caggctagcc ggccctacaa catctacccc   4080
cacggcatca ccgacgtgcg gcccctgtac agcaggcggc tgcccaaggg cgtgaagcac   4140
ctgaaggact tccccatcct gcccggcgag atcttcaagt acaagtggac cgtgaccgtg   4200
gaggacggcc ccaccaagag cgaccccaga tgcctgaccc ggtactacag cagcttcgtg   4260
aacatggaac gggacctggc ctccgggctg atcggacctc tgctgatctg ctacaaagaa   4320
agcgtggacc agcggggcaa ccagatcatg agcgacaagc ggaacgtgat cctgttcagc   4380
gtgttcgatg agaaccggtc ctggtatctg accgagaaca tccagcggtt tctgcccaac   4440
cctgccggcg tgcagctgga agatcccgag ttccaggcca gcaacatcat gcactccatc   4500
aatggctacg tgttcgactc tctgcagctc tccgtgtgtc tgcacgaggt ggcctactgg   4560
tacatcctga gcatcggcgc ccagaccgac ttcctgagcg tgttcttcag cggctacacc   4620
ttcaagcaca agatggtgta cgaggacacc ctgaccctgt tccctttcag cggcgagaca   4680
gtgttcatga gcatggaaaa ccccggcctg tggattctgg gctgccacaa cagcgacttc   4740
cggaaccggg gcatgaccgc cctgctgaag gtgtccagct gcgacaagaa caccggcgac   4800
tactacgagg acagctacga ggatatcagc gcctacctgc tgtccaagaa caacgccatc   4860
gaaccccgga gcttcagcca gaaccccccc gtgctgacgc gtcaccagcg ggagatcacc   4920
cggacaaccc tgcagtccga ccaggaagag atcgattacg acgacaccat cagcgtggag   4980
atgaagaaag aggatttcga tatctacgac gaggacgaga accagagccc cagaagcttc   5040
cagaagaaaa cccggcacta cttcattgcc gccgtggaga ggctgtggga ctacggcatg   5100
agttctagcc cccacgtgct gcggaaccgg gcccagagcg gcagcgtgcc ccagttcaag   5160
aaagtggtgt tccaggaatt cacagacggc agcttcaccc agcctctgta tagaggcgag   5220
ctgaacgagc acctggggct gctggggccc tacatcaggg ccgaagtgga ggacaacatc   5280
atggtgacct tccggaatca ggccagcaga ccctactcct tctacagcag cctgatcagc   5340
tacgaagagg accagcggca gggcgccgaa ccccggaaga acttcgtgaa gcccaacgaa   5400
accaagacct acttctggaa agtgcagcac cacatggccc ccaccaagga cgagttcgac   5460
tgcaaggcct gggcctactt cagcgacgtg gatctggaaa aggacgtgca ctctggactg   5520
attggcccac tcctggtctg ccacactaac accctcaacc ccgcccacgg ccgccaggtg   5580
accgtgcagg aattcgccct gttcttcacc atcttcgacg agacaaagtc ctggtacttc   5640
accgagaata tggaacggaa ctgcagagcc ccctgcaaca tccagatgga agatcctacc   5700
ttcaaagaga actaccggtt ccacgccatc aacggctaca tcatggacac cctgcctggc   5760
ctggtgatgg cccaggacca gagaatccgg tggtatctgc tgtccatggg cagcaacgag   5820
```

-continued

```
aatatccaca gcatccactt cagcggccac gtgttcaccg tgcggaagaa agaagagtac   5880
aagatggccc tgtacaacct gtaccccggc gtgttcgaga cagtggagat gctgcccagc   5940
aaggccggca tctggcgggt ggagtgtctg atcggcgagc acctgcacgc tggcatgagc   6000
accctgtttc tggtgtacag caacaagtgc cagaccccac tgggcatggc ctctggccac   6060
atccgggact tccagatcac cgcctccggc cagtacggcc agtgggcccc caagctggcc   6120
agactgcact acagcggcag catcaacgcc tggtccacca aagagccctt cagctggatc   6180
aaggtggacc tgctggcccc tatgatcatc cacggcatta agacccaggg cgccaggcag   6240
aagttcagca gcctgtacat cagccagttc atcatcatgt acagcctgga cggcaagaag   6300
tggcagacct accggggcaa cagcaccggc accctgatgg tgttcttcgg caatgtggac   6360
agcagcggca tcaagcacaa catcttcaac ccccccatca ttgcccggta catccggctg   6420
caccccaccc actacagcat tagatccaca ctgagaatgg aactgatggg ctgcgacctg   6480
aactcctgca gcatgcctct gggcatggaa agcaaggcca tcagcgacgc ccagatcaca   6540
gccagcagct acttcaccaa catgttcgcc acctggtccc cctccaaggc caggctgcac   6600
ctgcagggcc ggtccaacgc ctggcggcct caggtcaaca accccaaaga atggctgcag   6660
gtggactttc agaaaaccat gaaggtgacc ggcgtgacca cccagggcgt gaaaagcctg   6720
ctgaccagca tgtacgtgaa agagtttctg atcagcagct ctcaggatgg ccaccagtgg   6780
accctgttct ttcagaacgg caaggtgaaa gtgttccagg gcaaccagga ctccttcacc   6840
cccgtggtga actccctgga cccccccctg ctgacccgct acctgagaat ccacccccag   6900
tcttgggtgc accagatcgc cctcaggatg gaagtcctgg gatgtgaggc ccaggatctg   6960
tactgatgac gtctggaacg cgtcgacaat caacctctgg attacaaaat ttgtgaaaga   7020
ttgactggta ttcttaacta tgttgctcct tttacgctat gtggatacgc tgctttaatg   7080
cctttgtatc atgctattgc ttcccgtatg gctttcattt tctcctcctt gtataaatcc   7140
tggttgctgt ctctttatga ggagttgtgg cccgttgtca ggcaacgtgg cgtggtgtgc   7200
actgtgtttg ctgacgcaac ccccactggt tggggcattg ccaccacctg tcagctcctt   7260
tccgggactt tcgctttccc cctccctatt gccacggcgg aactcatcgc cgcctgcctt   7320
gcccgctgct ggacaggggc tcggctgttg ggcactgaca attccgtggt gttgtcgggg   7380
aaatcatcgt cctttccttg gctgctcgcc tgtgttgcca cctggattct gcgcgggacg   7440
tccttctgct acgtcccttc ggccctcaat ccagcggacc ttccttcccg cggcctgctg   7500
ccggctctgc ggcctcttcc gcgtcttcgc cttcgccctc agacgagtcg gatctccctt   7560
tgggccgcct ccccgcctgg tacctttaag accaatgact tacaaggcag ctgtagatct   7620
tagccacttt ttaaaagaaa aggggggact ggaagggcta attcactccc aacgaaaata   7680
agatctgctt tttgcttgta ctgggtctct ctggttagac cagatctgag cctgggagct   7740
ctctggctaa ctagggaacc cactgcttaa gcctcaataa agcttgcctt gagtgcttca   7800
agtagtgtgt gcccgtctgt tgtgtgactc tggtaactag agatccctca gaccctttta   7860
gtcagtgtgg aaaatctcta gcagtagtag ttcatgtcat cttattattc agtatttata   7920
acttgcaaag aaatgaatat cagagagtga gaggaacttg tttattgcag cttataatgg   7980
ttacaaataa agcaatagca tcacaaattt cacaaataaa gcattttttt cactgcattc   8040
tagttgtggt ttgtccaaac tcatcaatgt atcttatcat gtctggctct agctatcccg   8100
cccctaactc cgcccagttc cgcccattct ccgccccatg gctgactaat tttttttatt   8160
```

```
tatgcagagg ccgaggccgc ctcggcctct gagctattcc agaagtagtg aggaggcttt   8220
tttggaggcc tagacttttg cagagacggc ccaaattcgt aatcatggtc atagctgttt   8280
cctgtgtgaa attgttatcc gctcacaatt ccacacaaca tacgagccgg aagcataaag   8340
tgtaaagcct ggggtgccta atgagtgagc taactcacat taattgcgtt gcgctcactg   8400
cccgctttcc agtcgggaaa cctgtcgtgc cagctgcatt aatgaatcgg ccaacgcgcg   8460
gggagaggcg gtttgcgtat tgggcgctct tccgcttcct cgctcactga ctcgctgcgc   8520
tcggtcgttc ggctgcggcg agcggtatca gctcactcaa aggcggtaat acggttatcc   8580
acagaatcag gggataacgc aggaaagaac atgtgagcaa aaggccagca aaaggccagg   8640
aaccgtaaaa aggccgcgtt gctggcgttt ttccataggc tccgcccccc tgacgagcat   8700
cacaaaaatc gacgctcaag tcagaggtgg cgaaacccga caggactata aagataccag   8760
gcgtttcccc ctggaagctc cctcgtgcgc tctcctgttc cgaccctgcc gcttaccgga   8820
tacctgtccg cctttctccc ttcgggaagc gtggcgcttt ctcatagctc acgctgtagg   8880
tatctcagtt cggtgtaggt cgttcgctcc aagctgggct gtgtgcacga accccccgtt   8940
cagcccgacc gctgcgcctt atccggtaac tatcgtcttg agtccaaccc ggtaagacac   9000
gacttatcgc cactggcagc agccactggt aacaggatta gcagagcgag gtatgtaggc   9060
ggtgctacag agttcttgaa gtggtggcct aactacggct acactagaag gacagtattt   9120
ggtatctgcg ctctgctgaa gccagttacc ttcggaaaaa gagttggtag ctcttgatcc   9180
ggcaaacaaa ccaccgctgg tagcggtggt ttttttgttt gcaagcagca gattacgcgc   9240
agaaaaaaag gatctcaaga agatcctttg atcttttcta cggggtctga cgctcagtgg   9300
aacgaaaact cacgttaagg gattttggtc atgagattat caaaaaggat cttcacctag   9360
atccttttaa attaaaaatg aagttttaaa tcaatctaaa gtatatatga gtaaacttgg   9420
tctgacagtt accaatgctt aatcagtgag gcacctatct cagcgatctg tctatttcgt   9480
tcatccatag ttgcctgact ccccgtcgtg tagataacta cgatacggga gggcttacca   9540
tctggcccca gtgctgcaat gataccgcga gacccacgct caccggctcc agatttatca   9600
gcaataaacc agccagccgg aagggccgag cgcagaagtg gtcctgcaac tttatccgcc   9660
tccatccagt ctattaattg ttgccgggaa gctagagtaa gtagttcgcc agttaatagt   9720
ttgcgcaacg ttgttgccat tgctacaggc atcgtggtgt cacgctcgtc gtttggtatg   9780
gcttcattca gctccggttc ccaacgatca aggcgagtta catgatcccc catgttgtgc   9840
aaaaaagcgg ttagctcctt cggtcctccg atcgttgtca gaagtaagtt ggccgcagtg   9900
ttatcactca tggttatggc agcactgcat aattctctta ctgtcatgcc atccgtaaga   9960
tgcttttctg tgactggtga gtactcaacc aagtcattct gagaatagtg tatgcggcga  10020
ccgagttgct cttgcccggc gtcaatacgg gataataccg cgccacatag cagaacttta  10080
aaagtgctca tcattggaaa acgttcttcg gggcgaaaac tctcaaggat cttaccgctg  10140
ttgagatcca gttcgatgta acccactcgt gcacccaact gatcttcagc atcttttact  10200
ttcaccagcg tttctgggtg agcaaaaaca ggaaggcaaa atgccgcaaa aaagggaata  10260
agggcgacac ggaaatgttg aatactcata ctcttccttt ttcaatatta ttgaagcatt  10320
tatcagggtt attgtctcat gagcggatac atatttgaat gtatttagaa aaataaacaa  10380
ataggggttc cgcgcacatt tccccgaaaa gtgccacctg acgtctaaga aaccattatt  10440
atcatgacat taacctataa aaataggcgt atcacgaggc cctttcgtct cgcgcgtttc  10500
ggtgatgacg gtgaaaacct ctgacacatg cagctcccgg agacggtcac agcttgtctg  10560
```

taagcggatg ccgggagcag acaagcccgt cagggcgcgt cagcgggtgt tggcgggtgt 10620
cggggctggc ttaactatgc ggcatcagag cagattgtac tgagagtgca ccatatatgc 10680
ggtgtgaaat accgcacaga tgcgtaagga gaaaataccg catcaggcgc cattcgccat 10740
tcaggctgcg caactgttgg gaagggcgat cggtgcgggc ctcttcgcta ttacgccagc 10800
tggcgaaagg gggatgtgct gcaaggcgat taagttgggt aacgccaggg ttttcccagt 10860
cacgacgttg taaaacgacg gccagtgcca agctg 10895

<210> SEQ ID NO 51
<211> LENGTH: 11195
<212> TYPE: DNA
<213> ORGANISM: Artificial Sequence
<220> FEATURE:
<223> OTHER INFORMATION: Vector

<400> SEQUENCE: 51
acgcgtgtag tcttatgcaa tactcttgta gtcttgcaac atggtaacga tgagttagca 60
acatgcctta caaggagaga aaaagcaccg tgcatgccga ttggtggaag taaggtggta 120
cgatcgtgcc ttattaggaa ggcaacagac gggtctgaca tggattggac gaaccactga 180
attgccgcat tgcagagata ttgtatttaa gtgcctagct cgatacaata aacgggtctc 240
tctggttaga ccagatctga gcctgggagc tctctggcta actagggaac ccactgctta 300
agcctcaata aagcttgcct tgagtgcttc aagtagtgtg tgcccgtctg ttgtgtgact 360
ctggtaacta gagatccctc agaccctttt agtcagtgtg gaaaatctct agcagtggcg 420
cccgaacagg gacctgaaag cgaaagggaa accagagctc tctcgacgca ggactcggct 480
tgctgaagcg cgcacggcaa gaggcgaggg gcggcgactg gtgagtacgc caaaaatttt 540
gactagcgga ggctagaagg agagagatgg gtgcgagagc gtcagtatta agcgggggag 600
aattagatcg cgatgggaaa aaattcggtt aaggccaggg ggaaagaaaa aatataaatt 660
aaaacatata gtatgggcaa gcagggagct agaacgattc gcagttaatc ctggcctgtt 720
agaaacatca gaaggctgta gacaaatact gggacagcta caaccatccc ttcagacagg 780
atcagaagaa cttagatcat tatataatac agtagcaacc ctctattgtg tgcatcaaag 840
gatagagata aaagacacca aggaagcttt agacaagata gaggaagagc aaaacaaaag 900
taagaccacc gcacagcaag cggccactga tcttcagacc tggaggagga gatatgaggg 960
acaattggag aagtgaatta tataaatata aagtagtaaa aattgaacca ttaggagtag 1020
cacccaccaa ggcaaagaga agagtggtgc agagagaaaa aagagcagtg ggaataggag 1080
ctttgttcct tgggttcttg ggagcagcag gaagcactat gggcgcagcc tcaatgacgc 1140
tgacggtaca ggccagacaa ttattgtctg gtatagtgca gcagcagaac aatttgctga 1200
gggctattga ggcgcaacag catctgttgc aactcacagt ctggggcatc aagcagctcc 1260
aggcaagaat cctggctgtg gaaagatacc taaaggatca acagctcctg gggatttggg 1320
gttgctctgg aaaactcatt tgcaccactg ctgtgccttg gaatgctagt tggagtaata 1380
aatctctgga acagattgga atcacacgac ctggatggag tgggacagag aaattaacaa 1440
ttacacaagc ttaatacact ccttaattga agaatcgcaa aaccagcaag aaaagaatga 1500
acaagaatta ttggaattag ataaatgggc aagtttgtgg aattggttta acataacaaa 1560
ttggctgtgg tatataaaat tattcataat gatagtagga ggcttggtag gtttaagaat 1620
agtttttgct gtactttcta tagtgaatag agttaggcag ggatattcac cattatcgtt 1680

-continued

```
tcagacccac ctcccaaccc cgaggggacc cgacaggccc gaaggaatag aagaagaagg   1740
tggagagaga gacagagaca gatccattcg attagtgaac ggatctcgac ggttaacttt   1800
taaaagaaaa ggggggattg gggggtacag tgcaggggaa agaatagtag acataatagc   1860
aacagacata caaactaaag aattacaaaa acaaattaca aaaattcaaa attttatcga   1920
tagcgcggcc gcttcgaacg cgcgcgatgc atcatatgga caggcttctg agtgtaggga   1980
gctggtctgc cagtctttcg gaggtttgaa cttgtcaagg ctagggcagg atcaccatat   2040
ccagcctgga cttgcagttc tgtggggtgc ctccccatac cccataaga tgccaaacat    2100
gaggccctgt catcctccat ggtccccctc tactggctgt tcaaggccca gggctctccc   2160
atgccagata gcatcctgtc tcctaccacc actgtcccag cctgagggaa ctccctgtgc   2220
tgggcctacc cagctgaccc catcgctgga aacaatgggg gtcaggcaac acttccccac   2280
tctctcccgc cgggctgtgc tcacttcctt cctgctggct gcctgaggaa gtgtccctgc   2340
cctgggacag tctggcctag cctttgtttc cccgggggtc cccacccatg gagctttcaa   2400
ggcttctggc ccctgtgaag ccagcacacg tacgcggtct agaattcctg cagggcccac   2460
tagtctccca ggcatgactc caacaatgca tcccatggga tttggggttc cccagatctg   2520
gggcttgtag gcctgactct cccctgtgca cacgtctcat acacgcatgc gtgcacccat   2580
tgcctgcccc gccccttgca cagggagtca gcagggagga ctgggttatg ccctgcttat   2640
cagcagcttc ccagcttcct ctgcctggat tcttagaggc ctggggtcct agaacgagct   2700
ggtgcacgtg gcttcccaaa gatctctcag ataatgagag gaaatgcagt catcagtttg   2760
cagaaggcta gggattctgg gccatagctc agacctgcgc ccaccatctc cctccaggca   2820
gcccttggct ggtccctgcg agcccgtgga gactgccagt cagcgctgct ggatctcggg   2880
ctcgaggcca ccatgcagat cgagctgtcc acctgctttt ttctgtgcct gctgcggttc   2940
tgcttcagcg ccacccggcg gtactacctg ggcgccgtgg agctgtcctg ggactacatg   3000
cagagcgacc tgggcgagct gcccgtggac gcccggttcc cccccagagt gcccaagagc   3060
ttccccttca acaccagcgt ggtgtacaag aaaaccctgt tcgtggagtt caccgaccac   3120
ctgttcaata tcgccaagcc caggcccccc tggatgggcc tgctgggccc caccatccag   3180
gccgaggtgt acgacaccgt ggtgatcacc ctgaagaaca tggccagcca ccccgtgagc   3240
ctgcacgccg tgggcgtgag ctactggaag gccagcgagg gcgccgagta cgacgaccag   3300
accagccagc gggagaaaga agatgacaag gtgttccctg gcggcagcca cacctacgtg   3360
tggcaggtgc tgaaagaaaa cggccccatg gcctccgacc ccctgtgcct gacctacagc   3420
tacctgagcc acgtggacct ggtgaaggac ctgaacagcg gcctgatcgg cgctctgctc   3480
gtctgccggg agggcagcct ggccaaagag aaaacccaga ccctgcacaa gttcatcctg   3540
ctgttcgccg tgttcgacga gggcaagagc tggcacagcg agacaaagaa cagcctgatg   3600
caggaccggg acgccgcctc tgccagagcc tggcccaaga tgcacaccgt gaacggctac   3660
gtgaacagaa gcctgcccgg cctgattggc tgccaccgga agagcgtgta ctggcacgtg   3720
atcggcatgg gcaccacacc cgaggtgcac agcatctttc tggaagggca cacctttctg   3780
gtccggaacc accggcaggc cagcctggaa atcagcccta tcaccttcct gaccgcccag   3840
acactgctga tggacctggg ccagttcctg ctgttttgcc acatcagctc tcaccagcac   3900
gacggcatgg aagcctacgt gaaggtggac tcttgccccg aggaacccca gctgcggatg   3960
aagaacaacg aggaagccga ggactacgac gacgacctga ccgacagcga gatggacgtg   4020
gtgcggttcg acgacgacaa cagccccagc ttcatccaga tcagaagcgt ggccaagaag   4080
```

-continued

```
caccccaaga cctgggtgca ctatatcgcc gccgaggaag aggactggga ctacgccccc   4140
ctggtgctgg cccccgacga cagaagctac aagagccagt acctgaacaa tggcccccag   4200
cggatcggcc ggaagtacaa gaaagtgcgg ttcatggcct acaccgacga gacattcaag   4260
acccgggagg ccatccagca cgagagcggc atcctgggcc ccctgctgta cggcgaagtg   4320
ggcgacacac tgctgatcat cttcaagaac caggctagcc ggccctacaa catctacccc   4380
cacggcatca ccgacgtgcg gcccctgtac agcaggcggc tgcccaaggg cgtgaagcac   4440
ctgaaggact tccccatcct gcccggcgag atcttcaagt acaagtggac cgtgaccgtg   4500
gaggacggcc ccaccaagag cgaccccaga tgcctgaccc ggtactacag cagcttcgtg   4560
aacatggaac gggacctggc ctccgggctg atcggacctc tgctgatctg ctacaaagaa   4620
agcgtggacc agcggggcaa ccagatcatg agcgacaagc ggaacgtgat cctgttcagc   4680
gtgttcgatg agaaccggtc ctggtatctg accgagaaca tccagcggtt tctgcccaac   4740
cctgccggcg tgcagctgga agatcccgag ttccaggcca gcaacatcat gcactccatc   4800
aatggctacg tgttcgactc tctgcagctc tccgtgtgtc tgcacgaggt ggcctactgg   4860
tacatcctga gcatcggcgc ccagaccgac ttcctgagcg tgttcttcag cggctacacc   4920
ttcaagcaca agatggtgta cgaggacacc ctgaccctgt tccctttcag cggcgagaca   4980
gtgttcatga gcatggaaaa ccccggcctg tggattctgg gctgccacaa cagcgacttc   5040
cggaaccggg gcatgaccgc cctgctgaag gtgtccagct gcgacaagaa caccggcgac   5100
tactacgagg acagctacga ggatatcagc gcctacctgc tgtccaagaa caacgccatc   5160
gaaccccgga gcttcagcca gaaccccccc gtgctgacgc gtcaccagcg ggagatcacc   5220
cggacaaccc tgcagtccga ccaggaagag atcgattacg acgacaccat cagcgtggag   5280
atgaagaaag aggatttcga tatctacgac gaggacgaga accagagccc cagaagcttc   5340
cagaagaaaa cccggcacta cttcattgcc gccgtggaga ggctgtggga ctacggcatg   5400
agttctagcc cccacgtgct gcggaaccgg gcccagagcg gcagcgtgcc ccagttcaag   5460
aaagtggtgt tccaggaatt cacagacggc agcttcaccc agcctctgta tagaggcgag   5520
ctgaacgagc acctggggct gctggggccc tacatcaggg ccgaagtgga ggacaacatc   5580
atggtgacct tccggaatca ggccagcaga ccctactcct tctacagcag cctgatcagc   5640
tacgaagagg accagcggca gggcgccgaa ccccggaaga acttcgtgaa gcccaacgaa   5700
accaagacct acttctggaa agtgcagcac cacatggccc ccaccaagga cgagttcgac   5760
tgcaaggcct gggcctactt cagcgacgtg gatctggaaa aggacgtgca ctctggactg   5820
attggcccac tcctggtctg ccacactaac accctcaacc ccgcccacgg ccgccaggtg   5880
accgtgcagg aattcgccct gttcttcacc atcttcgacg agacaaagtc ctggtacttc   5940
accgagaata tggaacggaa ctgcagagcc ccctgcaaca tccagatgga agatcctacc   6000
ttcaaagaga actaccggtt ccacgccatc aacggctaca tcatggacac cctgcctggc   6060
ctggtgatgg cccaggacca gagaatccgg tggtatctgc tgtccatggg cagcaacgag   6120
aatatccaca gcatccactt cagcggccac gtgttcaccg tgcggaagaa agaagagtac   6180
aagatggccc tgtacaacct gtaccccggc gtgttcgaga cagtggagat gctgcccagc   6240
aaggccggca tctggcgggt ggagtgtctg atcggcgagc acctgcacgc tggcatgagc   6300
accctgtttc tggtgtacag caacaagtgc cagaccccac tgggcatggc ctctggccac   6360
atccgggact tccagatcac cgcctccggc cagtacggcc agtgggcccc caagctggcc   6420
```

-continued

```
agactgcact acagcggcag catcaacgcc tggtccacca aagagccctt cagctggatc   6480
aaggtggacc tgctggcccc tatgatcatc cacggcatta agacccaggg cgccaggcag   6540
aagttcagca gcctgtacat cagccagttc atcatcatgt acagcctgga cggcaagaag   6600
tggcagacct accggggcaa cagcaccggc accctgatgg tgttcttcgg caatgtggac   6660
agcagcggca tcaagcacaa catcttcaac ccccccatca ttgcccggta catccggctg   6720
caccccaccc actacagcat tagatccaca ctgagaatgg aactgatggg ctgcgacctg   6780
aactcctgca gcatgcctct gggcatggaa agcaaggcca tcagcgacgc ccagatcaca   6840
gccagcagct acttcaccaa catgttcgcc acctggtccc cctccaaggc caggctgcac   6900
ctgcagggcc ggtccaacgc ctggcggcct caggtcaaca accccaaaga atggctgcag   6960
gtggactttc agaaaaccat gaaggtgacc ggcgtgacca cccagggcgt gaaaagcctg   7020
ctgaccagca tgtacgtgaa agagtttctg atcagcagct ctcaggatgg ccaccagtgg   7080
accctgttct ttcagaacgg caaggtgaaa gtgttccagg gcaaccagga ctccttcacc   7140
cccgtggtga actccctgga cccccccctg ctgacccgct acctgagaat ccacccccag   7200
tcttgggtgc accagatcgc cctcaggatg gaagtcctgg gatgtgaggc ccaggatctg   7260
tactgatgac gtctggaacg cgtcgacaat caacctctgg attacaaaat ttgtgaaaga   7320
ttgactggta ttcttaacta tgttgctcct tttacgctat gtggatacgc tgctttaatg   7380
cctttgtatc atgctattgc ttcccgtatg gctttcattt tctcctcctt gtataaatcc   7440
tggttgctgt ctctttatga ggagttgtgg cccgttgtca ggcaacgtgg cgtggtgtgc   7500
actgtgtttg ctgacgcaac ccccactggt tggggcattg ccaccacctg tcagctcctt   7560
tccgggactt tcgctttccc cctccctatt gccacggcgg aactcatcgc cgcctgcctt   7620
gcccgctgct ggacaggggc tcggctgttg ggcactgaca attccgtggt gttgtcgggg   7680
aaatcatcgt cctttccttg gctgctcgcc tgtgttgcca cctggattct gcgcgggacg   7740
tccttctgct acgtcccttc ggccctcaat ccagcggacc ttccttcccg cggcctgctg   7800
ccggctctgc ggcctcttcc gcgtcttcgc cttcgccctc agacgagtcg gatctccctt   7860
tgggccgcct ccccgcctgg tacctttaag accaatgact tacaaggcag ctgtagatct   7920
tagccacttt ttaaaagaaa aggggggact ggaagggcta attcactccc aacgaaaata   7980
agatctgctt tttgcttgta ctgggtctct ctggttagac cagatctgag cctgggagct   8040
ctctggctaa ctagggaacc cactgcttaa gcctcaataa agcttgcctt gagtgcttca   8100
agtagtgtgt gcccgtctgt tgtgtgactc tggtaactag agatccctca gaccctttta   8160
gtcagtgtgg aaaatctcta gcagtagtag ttcatgtcat cttattattc agtatttata   8220
acttgcaaag aaatgaatat cagagagtga gaggaacttg tttattgcag cttataatgg   8280
ttacaaataa agcaatagca tcacaaattt cacaaataaa gcattttttt cactgcattc   8340
tagttgtggt ttgtccaaac tcatcaatgt atcttatcat gtctggctct agctatcccg   8400
cccctaactc cgcccagttc cgcccattct ccgccccatg gctgactaat tttttttatt   8460
tatgcagagg ccgaggccgc ctcggcctct gagctattcc agaagtagtg aggaggcttt   8520
tttggaggcc tagacttttg cagagacggc ccaaattcgt aatcatggtc atagctgttt   8580
cctgtgtgaa attgttatcc gctcacaatt ccacacaaca tacgagccgg aagcataaag   8640
tgtaaagcct ggggtgccta atgagtgagc taactcacat taattgcgtt gcgctcactg   8700
cccgctttcc agtcgggaaa cctgtcgtgc cagctgcatt aatgaatcgg ccaacgcgcg   8760
gggagaggcg gtttgcgtat tgggcgctct tccgcttcct cgctcactga ctcgctgcgc   8820
```

-continued

```
tcggtcgttc ggctgcggcg agcggtatca gctcactcaa aggcggtaat acggttatcc   8880

acagaatcag gggataacgc aggaaagaac atgtgagcaa aaggccagca aaaggccagg   8940

aaccgtaaaa aggccgcgtt gctggcgttt ttccataggc tccgcccccc tgacgagcat   9000

cacaaaaatc gacgctcaag tcagaggtgg cgaaacccga caggactata aagataccag   9060

gcgtttcccc ctggaagctc cctcgtgcgc tctcctgttc cgaccctgcc gcttaccgga   9120

tacctgtccg cctttctccc ttcgggaagc gtggcgcttt ctcatagctc acgctgtagg   9180

tatctcagtt cggtgtaggt cgttcgctcc aagctgggct gtgtgcacga accccccgtt   9240

cagcccgacc gctgcgcctt atccggtaac tatcgtcttg agtccaaccc ggtaagacac   9300

gacttatcgc cactggcagc agccactggt aacaggatta gcagagcgag gtatgtaggc   9360

ggtgctacag agttcttgaa gtggtggcct aactacggct acactagaag gacagtattt   9420

ggtatctgcg ctctgctgaa gccagttacc ttcggaaaaa gagttggtag ctcttgatcc   9480

ggcaaacaaa ccaccgctgg tagcggtggt ttttttgttt gcaagcagca gattacgcgc   9540

agaaaaaaag gatctcaaga agatcctttg atcttttcta cggggtctga cgctcagtgg   9600

aacgaaaact cacgttaagg gattttggtc atgagattat caaaaaggat cttcacctag   9660

atccttttaa attaaaaatg aagttttaaa tcaatctaaa gtatatatga gtaaacttgg   9720

tctgacagtt accaatgctt aatcagtgag gcacctatct cagcgatctg tctatttcgt   9780

tcatccatag ttgcctgact ccccgtcgtg tagataacta cgatacggga gggcttacca   9840

tctggcccca gtgctgcaat gataccgcga gacccacgct caccggctcc agatttatca   9900

gcaataaacc agccagccgg aagggccgag cgcagaagtg gtcctgcaac tttatccgcc   9960

tccatccagt ctattaattg ttgccgggaa gctagagtaa gtagttcgcc agttaatagt  10020

ttgcgcaacg ttgttgccat tgctacaggc atcgtggtgt cacgctcgtc gtttggtatg  10080

gcttcattca gctccggttc ccaacgatca aggcgagtta catgatcccc catgttgtgc  10140

aaaaaagcgg ttagctcctt cggtcctccg atcgttgtca gaagtaagtt ggccgcagtg  10200

ttatcactca tggttatggc agcactgcat aattctctta ctgtcatgcc atccgtaaga  10260

tgcttttctg tgactggtga gtactcaacc aagtcattct gagaatagtg tatgcggcga  10320

ccgagttgct cttgcccggc gtcaatacgg gataataccg cgccacatag cagaacttta  10380

aaagtgctca tcattggaaa acgttcttcg gggcgaaaac tctcaaggat cttaccgctg  10440

ttgagatcca gttcgatgta acccactcgt gcacccaact gatcttcagc atcttttact  10500

ttcaccagcg tttctgggtg agcaaaaaca ggaaggcaaa atgccgcaaa aaagggaata  10560

agggcgacac ggaaatgttg aatactcata ctcttccttt ttcaatatta ttgaagcatt  10620

tatcagggtt attgtctcat gagcggatac atatttgaat gtatttagaa aaataaacaa  10680

ataggggttc cgcgcacatt tccccgaaaa gtgccacctg acgtctaaga aaccattatt  10740

atcatgacat taacctataa aaataggcgt atcacgaggc cctttcgtct cgcgcgtttc  10800

ggtgatgacg gtgaaaacct ctgacacatg cagctcccgg agacggtcac agcttgtctg  10860

taagcggatg ccgggagcag acaagcccgt cagggcgcgt cagcgggtgt tggcgggtgt  10920

cggggctggc ttaactatgc ggcatcagag cagattgtac tgagagtgca ccatatatgc  10980

ggtgtgaaat accgcacaga tgcgtaagga gaaaataccg catcaggcgc cattcgccat  11040

tcaggctgcg caactgttgg gaagggcgat cggtgcgggc ctcttcgcta ttacgccagc  11100

tggcgaaagg gggatgtgct gcaaggcgat taagttgggt aacgccaggg ttttcccagt  11160
```

cacgacgttg taaaacgacg gccagtgcca agctg 11195

<210> SEQ ID NO 52
<211> LENGTH: 11295
<212> TYPE: DNA
<213> ORGANISM: Artificial Sequence
<220> FEATURE:
<223> OTHER INFORMATION: Vector

<400> SEQUENCE: 52
acgcgtgtag tcttatgcaa tactcttgta gtcttgcaac atggtaacga tgagttagca 60
acatgcctta caaggagaga aaaagcaccg tgcatgccga ttggtggaag taaggtggta 120
cgatcgtgcc ttattaggaa ggcaacagac gggtctgaca tggattggac gaaccactga 180
attgccgcat tgcagagata ttgtatttaa gtgcctagct cgatacaata aacgggtctc 240
tctggttaga ccagatctga gcctgggagc tctctggcta actagggaac ccactgctta 300
agcctcaata aagcttgcct tgagtgcttc aagtagtgtg tgcccgtctg ttgtgtgact 360
ctggtaacta gagatccctc agaccctttt agtcagtgtg gaaaatctct agcagtggcg 420
cccgaacagg gacctgaaag cgaaagggaa accagagctc tctcgacgca ggactcggct 480
tgctgaagcg cgcacggcaa gaggcgaggg gcggcgactg gtgagtacgc caaaaatttt 540
gactagcgga ggctagaagg agagagatgg gtgcgagagc gtcagtatta agcgggggag 600
aattagatcg cgatgggaaa aaattcggtt aaggccaggg ggaaagaaaa aatataaatt 660
aaaacatata gtatgggcaa gcagggagct agaacgattc gcagttaatc ctggcctgtt 720
agaaacatca gaaggctgta gacaaatact gggacagcta caaccatccc ttcagacagg 780
atcagaagaa cttagatcat tatataatac agtagcaacc ctctattgtg tgcatcaaag 840
gatagagata aaagacacca aggaagcttt agacaagata gaggaagagc aaaacaaaag 900
taagaccacc gcacagcaag cggccactga tcttcagacc tggaggagga gatatgaggg 960
acaattggag aagtgaatta tataaatata aagtagtaaa aattgaacca ttaggagtag 1020
cacccaccaa ggcaaagaga agagtggtgc agagagaaaa aagagcagtg ggaataggag 1080
ctttgttcct tgggttcttg ggagcagcag gaagcactat gggcgcagcc tcaatgacgc 1140
tgacggtaca ggccagacaa ttattgtctg gtatagtgca gcagcagaac aatttgctga 1200
gggctattga ggcgcaacag catctgttgc aactcacagt ctggggcatc aagcagctcc 1260
aggcaagaat cctggctgtg gaaagatacc taaaggatca acagctcctg gggatttggg 1320
gttgctctgg aaaactcatt tgcaccactg ctgtgccttg gaatgctagt tggagtaata 1380
aatctctgga acagattgga atcacacgac ctggatggag tgggacagag aaattaacaa 1440
ttacacaagc ttaatacact ccttaattga agaatcgcaa aaccagcaag aaaagaatga 1500
acaagaatta ttggaattag ataaatgggc aagtttgtgg aattggttta acataacaaa 1560
ttggctgtgg tatataaaat tattcataat gatagtagga ggcttggtag gtttaagaat 1620
agtttttgct gtactttcta tagtgaatag agttaggcag ggatattcac cattatcgtt 1680
tcagacccac ctcccaaccc cgaggggacc cgacaggccc gaaggaatag aagaagaagg 1740
tggagagaga gacagagaca gatccattcg attagtgaac ggatctcgac ggttaacttt 1800
taaaagaaaa ggggggattg gggggtacag tgcaggggaa agaatagtag acataatagc 1860
aacagacata caaactaaag aattacaaaa acaaattaca aaaattcaaa attttatcga 1920
tagcgcggcc gcttcgaacg cgcgcgatgc atcatatgga gacttttttt gaaaaacgga 1980
acatctgcct atcgcaagga ctactattat tctgaaaatc accttcttca ttagaaagta 2040

-continued atatttatca ttttattata gaactttgat cttacttctt gtgacttcat tctgcgtaga 2100
gcacactccc atccttgaat taaatgacaa agcattttat attaactgac aatgactgat 2160
gccatgggca aatcctattt ctgtaaataa ctgaattttc ttctggactg cgcatgaggg 2220
gagaaagatg tctgcagttt cggtttcctg gaaaatgaaa cctatctcat ttgttgcctg 2280
tgtcaagggg cagtgcttca gtcggggtgg agctgcttaa aaggcctggg atcacaccct 2340
ttgggaacac atccaagctt aagacggtga ggtcagcttc acattctcag gaactctcct 2400
tctttgggta agactgggag ggtgggcagg agctaccctt cccgtggccc cggaccttgg 2460
gtgggctgtg ggctcaggga gcggagggga ggccttaagc atccactctc tgcccggtgt 2520
ttttgttccg tacgcggtct agaattcctg cagggcccac tagtctccca ggcatgactc 2580
caacaatgca tcccatggga tttggggttc cccagatctg gggcttgtag gcctgactct 2640
cccctgtgca cacgtctcat acacgcatgc gtgcacccat tgcctgcccc gccccttgca 2700
cagggagtca gcagggagga ctgggttatg ccctgcttat cagcagcttc ccagcttcct 2760
ctgcctggat tcttagaggc ctggggtcct agaacgagct ggtgcacgtg gcttcccaaa 2820
gatctctcag ataatgagag gaaatgcagt catcagtttg cagaaggcta gggattctgg 2880
gccatagctc agacctgcgc ccaccatctc cctccaggca gcccttggct ggtccctgcg 2940
agcccgtgga gactgccagt cagcgctgct ggatctcggg ctcgaggcca ccatgcagat 3000
cgagctgtcc acctgctttt ttctgtgcct gctgcggttc tgcttcagcg ccacccggcg 3060
gtactacctg ggcgccgtgg agctgtcctg ggactacatg cagagcgacc tgggcgagct 3120
gcccgtggac gcccggttcc cccccagagt gcccaagagc ttccccttca acaccagcgt 3180
ggtgtacaag aaaaccctgt tcgtggagtt caccgaccac ctgttcaata tcgccaagcc 3240
caggcccccc tggatgggcc tgctgggccc caccatccag gccgaggtgt acgacaccgt 3300
ggtgatcacc ctgaagaaca tggccagcca ccccgtgagc ctgcacgccg tgggcgtgag 3360
ctactggaag gccagcgagg gcgccgagta cgacgaccag accagccagc gggagaaaga 3420
agatgacaag gtgttccctg gcggcagcca cacctacgtg tggcaggtgc tgaaagaaaa 3480
cggccccatg gcctccgacc ccctgtgcct gacctacagc tacctgagcc acgtggacct 3540
ggtgaaggac ctgaacagcg gcctgatcgg cgctctgctc gtctgccggg agggcagcct 3600
ggccaaagag aaaacccaga ccctgcacaa gttcatcctg ctgttcgccg tgttcgacga 3660
gggcaagagc tggcacagcg agacaaagaa cagcctgatg caggaccggg acgccgcctc 3720
tgccagagcc tggcccaaga tgcacaccgt gaacggctac gtgaacagaa gcctgcccgg 3780
cctgattggc tgccaccgga agagcgtgta ctggcacgtg atcggcatgg gcaccacacc 3840
cgaggtgcac agcatctttc tggaagggca cacctttctg gtccggaacc accggcaggc 3900
cagcctggaa atcagcccta tcaccttcct gaccgcccag acactgctga tggacctggg 3960
ccagttcctg ctgttttgcc acatcagctc tcaccagcac gacggcatgg aagcctacgt 4020
gaaggtggac tcttgccccg aggaacccca gctgcggatg aagaacaacg aggaagccga 4080
ggactacgac gacgacctga ccgacagcga gatggacgtg gtgcggttcg acgacgacaa 4140
cagccccagc ttcatccaga tcagaagcgt ggccaagaag caccccaaga cctgggtgca 4200
ctatatcgcc gccgaggaag aggactggga ctacgccccc ctggtgctgg cccccgacga 4260
cagaagctac aagagccagt acctgaacaa tggcccccag cggatcggcc ggaagtacaa 4320
gaaagtgcgg ttcatggcct acaccgacga gacattcaag acccgggagg ccatccagca 4380
cgagagcggc atcctgggcc ccctgctgta cggcgaagtg ggcgacacac tgctgatcat 4440
cttcaagaac caggctagcc ggccctacaa catctacccc cacggcatca ccgacgtgcg 4500
gcccctgtac agcaggcggc tgcccaaggg cgtgaagcac ctgaaggact tccccatcct 4560
gcccggcgag atcttcaagt acaagtggac cgtgaccgtg gaggacggcc ccaccaagag 4620
cgaccccaga tgcctgaccc ggtactacag cagcttcgtg aacatggaac gggacctggc 4680
ctccgggctg atcggacctc tgctgatctg ctacaaagaa agcgtggacc agcggggcaa 4740
ccagatcatg agcgacaagc ggaacgtgat cctgttcagc gtgttcgatg agaaccggtc 4800
ctggtatctg accgagaaca tccagcggtt tctgcccaac cctgccggcg tgcagctgga 4860
agatcccgag ttccaggcca gcaacatcat gcactccatc aatggctacg tgttcgactc 4920
tctgcagctc tccgtgtgtc tgcacgaggt ggcctactgg tacatcctga gcatcggcgc 4980
ccagaccgac ttcctgagcg tgttcttcag cggctacacc ttcaagcaca agatggtgta 5040
cgaggacacc ctgaccctgt tccctttcag cggcgagaca gtgttcatga gcatggaaaa 5100
ccccggcctg tggattctgg gctgccacaa cagcgacttc cggaaccggg gcatgaccgc 5160
cctgctgaag gtgtccagct gcgacaagaa caccggcgac tactacgagg acagctacga 5220
ggatatcagc gcctacctgc tgtccaagaa caacgccatc gaaccccgga gcttcagcca 5280
gaaccccccc gtgctgacgc gtcaccagcg ggagatcacc cggacaaccc tgcagtccga 5340
ccaggaagag atcgattacg acgacaccat cagcgtggag atgaagaaag aggatttcga 5400
tatctacgac gaggacgaga accagagccc cagaagcttc cagaagaaaa cccggcacta 5460
cttcattgcc gccgtggaga ggctgtggga ctacggcatg agttctagcc cccacgtgct 5520
gcggaaccgg gcccagagcg gcagcgtgcc ccagttcaag aaagtggtgt tccaggaatt 5580
cacagacggc agcttcaccc agcctctgta tagaggcgag ctgaacgagc acctggggct 5640
gctggggccc tacatcaggg ccgaagtgga ggacaacatc atggtgacct tccggaatca 5700
ggccagcaga ccctactcct tctacagcag cctgatcagc tacgaagagg accagcggca 5760
gggcgccgaa ccccggaaga acttcgtgaa gcccaacgaa accaagacct acttctggaa 5820
agtgcagcac cacatggccc ccaccaagga cgagttcgac tgcaaggcct gggcctactt 5880
cagcgacgtg gatctggaaa aggacgtgca ctctggactg attggcccac tcctggtctg 5940
ccacactaac accctcaacc ccgcccacgg ccgccaggtg accgtgcagg aattcgccct 6000
gttcttcacc atcttcgacg agacaaagtc ctggtacttc accgagaata tggaacggaa 6060
ctgcagagcc ccctgcaaca tccagatgga agatcctacc ttcaaagaga actaccggtt 6120
ccacgccatc aacggctaca tcatggacac cctgcctggc ctggtgatgg cccaggacca 6180
gagaatccgg tggtatctgc tgtccatggg cagcaacgag aatatccaca gcatccactt 6240
cagcggccac gtgttcaccg tgcggaagaa agaagagtac aagatggccc tgtacaacct 6300
gtaccccggc gtgttcgaga cagtggagat gctgcccagc aaggccggca tctggcgggt 6360
ggagtgtctg atcggcgagc acctgcacgc tggcatgagc accctgtttc tggtgtacag 6420
caacaagtgc cagaccccac tgggcatggc ctctggccac atccgggact tccagatcac 6480
cgcctccggc cagtacggcc agtgggcccc caagctggcc agactgcact acagcggcag 6540
catcaacgcc tggtccacca aagagccctt cagctggatc aaggtggacc tgctggcccc 6600
tatgatcatc cacggcatta agacccaggg cgccaggcag aagttcagca gcctgtacat 6660
cagccagttc atcatcatgt acagcctgga cggcaagaag tggcagacct accggggcaa 6720
cagcaccggc accctgatgg tgttcttcgg caatgtggac agcagcggca tcaagcacaa 6780

```
catcttcaac ccccccatca ttgcccggta catccggctg caccccaccc actacagcat   6840
tagatccaca ctgagaatgg aactgatggg ctgcgacctg aactcctgca gcatgcctct   6900
gggcatggaa agcaaggcca tcagcgacgc ccagatcaca gccagcagct acttcaccaa   6960
catgttcgcc acctggtccc cctccaaggc caggctgcac ctgcagggcc ggtccaacgc   7020
ctggcggcct caggtcaaca accccaaaga atggctgcag gtggactttc agaaaaccat   7080
gaaggtgacc ggcgtgacca cccagggcgt gaaaagcctg ctgaccagca tgtacgtgaa   7140
agagtttctg atcagcagct ctcaggatgg ccaccagtgg accctgttct ttcagaacgg   7200
caaggtgaaa gtgttccagg gcaaccagga ctccttcacc cccgtggtga actccctgga   7260
cccccccctg ctgacccgct acctgagaat ccacccccag tcttgggtgc accagatcgc   7320
cctcaggatg gaagtcctgg gatgtgaggc ccaggatctg tactgatgac gtctggaacg   7380
cgtcgacaat caacctctgg attacaaaat ttgtgaaaga ttgactggta ttcttaacta   7440
tgttgctcct tttacgctat gtggatacgc tgctttaatg cctttgtatc atgctattgc   7500
ttcccgtatg gctttcattt tctcctcctt gtataaatcc tggttgctgt ctctttatga   7560
ggagttgtgg cccgttgtca ggcaacgtgg cgtggtgtgc actgtgtttg ctgacgcaac   7620
ccccactggt tggggcattg ccaccacctg tcagctcctt tccgggactt tcgctttccc   7680
cctccctatt gccacggcgg aactcatcgc cgcctgcctt gcccgctgct ggacaggggc   7740
tcggctgttg ggcactgaca attccgtggt gttgtcgggg aaatcatcgt cctttccttg   7800
gctgctcgcc tgtgttgcca cctggattct gcgcgggacg tccttctgct acgtcccttc   7860
ggccctcaat ccagcggacc ttccttcccg cggcctgctg ccggctctgc ggcctcttcc   7920
gcgtcttcgc cttcgccctc agacgagtcg gatctccctt tgggccgcct ccccgcctgg   7980
tacctttaag accaatgact tacaaggcag ctgtagatct tagccacttt ttaaaagaaa   8040
aggggggact ggaagggcta attcactccc aacgaaaata agatctgctt tttgcttgta   8100
ctgggtctct ctggttagac cagatctgag cctgggagct ctctggctaa ctagggaacc   8160
cactgcttaa gcctcaataa agcttgcctt gagtgcttca agtagtgtgt gcccgtctgt   8220
tgtgtgactc tggtaactag agatccctca gaccctttta gtcagtgtgg aaaatctcta   8280
gcagtagtag ttcatgtcat cttattattc agtatttata acttgcaaag aaatgaatat   8340
cagagagtga gaggaacttg tttattgcag cttataatgg ttacaaataa agcaatagca   8400
tcacaaattt cacaaataaa gcattttttt cactgcattc tagttgtggt ttgtccaaac   8460
tcatcaatgt atcttatcat gtctggctct agctatcccg cccctaactc cgcccagttc   8520
cgcccattct ccgccccatg gctgactaat tttttttatt tatgcagagg ccgaggccgc   8580
ctcggcctct gagctattcc agaagtagtg aggaggcttt tttggaggcc tagacttttg   8640
cagagacggc ccaaattcgt aatcatggtc atagctgttt cctgtgtgaa attgttatcc   8700
gctcacaatt ccacacaaca tacgagccgg aagcataaag tgtaaagcct ggggtgccta   8760
atgagtgagc taactcacat taattgcgtt gcgctcactg cccgctttcc agtcgggaaa   8820
cctgtcgtgc cagctgcatt aatgaatcgg ccaacgcgcg gggagaggcg gtttgcgtat   8880
tgggcgctct tccgcttcct cgctcactga ctcgctgcgc tcggtcgttc ggctgcggcg   8940
agcggtatca gctcactcaa aggcggtaat acggttatcc acagaatcag gggataacgc   9000
aggaaagaac atgtgagcaa aaggccagca aaaggccagg aaccgtaaaa aggccgcgtt   9060
gctggcgttt ttccataggc tccgcccccc tgacgagcat cacaaaaatc gacgctcaag   9120
```

-continued

```
tcagaggtgg cgaaacccga caggactata aagataccag gcgtttcccc ctggaagctc   9180
cctcgtgcgc tctcctgttc cgaccctgcc gcttaccgga tacctgtccg cctttctccc   9240
ttcgggaagc gtggcgcttt ctcatagctc acgctgtagg tatctcagtt cggtgtaggt   9300
cgttcgctcc aagctgggct gtgtgcacga accccccgtt cagcccgacc gctgcgcctt   9360
atccggtaac tatcgtcttg agtccaaccc ggtaagacac gacttatcgc cactggcagc   9420
agccactggt aacaggatta gcagagcgag gtatgtaggc ggtgctacag agttcttgaa   9480
gtggtggcct aactacggct acactagaag gacagtattt ggtatctgcg ctctgctgaa   9540
gccagttacc ttcggaaaaa gagttggtag ctcttgatcc ggcaaacaaa ccaccgctgg   9600
tagcggtggt ttttttgttt gcaagcagca gattacgcgc agaaaaaaag gatctcaaga   9660
agatcctttg atcttttcta cggggtctga cgctcagtgg aacgaaaact cacgttaagg   9720
gattttggtc atgagattat caaaaaggat cttcacctag atccttttaa attaaaaatg   9780
aagttttaaa tcaatctaaa gtatatatga gtaaacttgg tctgacagtt accaatgctt   9840
aatcagtgag gcacctatct cagcgatctg tctatttcgt tcatccatag ttgcctgact   9900
ccccgtcgtg tagataacta cgatacggga gggcttacca tctggcccca gtgctgcaat   9960
gataccgcga gacccacgct caccggctcc agatttatca gcaataaacc agccagccgg  10020
aagggccgag cgcagaagtg gtcctgcaac tttatccgcc tccatccagt ctattaattg  10080
ttgccgggaa gctagagtaa gtagttcgcc agttaatagt ttgcgcaacg ttgttgccat  10140
tgctacaggc atcgtggtgt cacgctcgtc gtttggtatg gcttcattca gctccggttc  10200
ccaacgatca aggcgagtta catgatcccc catgttgtgc aaaaaagcgg ttagctcctt  10260
cggtcctccg atcgttgtca gaagtaagtt ggccgcagtg ttatcactca tggttatggc  10320
agcactgcat aattctctta ctgtcatgcc atccgtaaga tgcttttctg tgactggtga  10380
gtactcaacc aagtcattct gagaatagtg tatgcggcga ccgagttgct cttgcccggc  10440
gtcaatacgg gataataccg cgccacatag cagaacttta aaagtgctca tcattggaaa  10500
acgttcttcg gggcgaaaac tctcaaggat cttaccgctg ttgagatcca gttcgatgta  10560
acccactcgt gcacccaact gatcttcagc atcttttact ttcaccagcg tttctgggtg  10620
agcaaaaaca ggaaggcaaa atgccgcaaa aaagggaata agggcgacac ggaaatgttg  10680
aatactcata ctcttccttt ttcaatatta ttgaagcatt tatcagggtt attgtctcat  10740
gagcggatac atatttgaat gtatttagaa aaataaacaa ataggggttc cgcgcacatt  10800
tccccgaaaa gtgccacctg acgtctaaga aaccattatt atcatgacat taacctataa  10860
aaataggcgt atcacgaggc cctttcgtct cgcgcgtttc ggtgatgacg gtgaaaacct  10920
ctgacacatg cagctcccgg agacggtcac agcttgtctg taagcggatg ccgggagcag  10980
acaagcccgt cagggcgcgt cagcgggtgt tggcgggtgt cggggctggc ttaactatgc  11040
ggcatcagag cagattgtac tgagagtgca ccatatatgc ggtgtgaaat accgcacaga  11100
tgcgtaagga gaaaataccg catcaggcgc cattcgccat tcaggctgcg caactgttgg  11160
gaagggcgat cggtgcgggc ctcttcgcta ttacgccagc tggcgaaagg gggatgtgct  11220
gcaaggcgat taagttgggt aacgccaggg ttttcccagt cacgacgttg taaaacgacg  11280
gccagtgcca agctg                                                  11295
```

<210> SEQ ID NO 53
<211> LENGTH: 20
<212> TYPE: DNA
<213> ORGANISM: Artificial Sequence -continued

```
<220> FEATURE:
<223> OTHER INFORMATION: Primer

<400> SEQUENCE: 53

aacggctacg tgaacagaag                                                 20


<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54

gatagggctg atttccaggc                                                 20


<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55

gaaggtgaag gtcggagtc                                                  19


<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56

gaagatggtg atgggatttc                                                 20
```

ENDOTHELIUM-SPECIFIC NUCLEIC ACID REGULATORY ELEMENTS AND METHODS AND USE THEREOF

INCORPORATION BY CROSS-REFERENCE

This application is a U.S. National Phase of International Application No. PCT/EP2016/082314, filed Dec. 22, 2016, which claims priority to International Provisional Application No. PCT/EP2015/081075, filed Dec. 22, 2015, the disclosure of each of which is hereby incorporated by cross-reference in its entirety.

FIELD

The present invention relates to nucleic acid regulatory elements that are able to enhance endothelial-specific expression of genes, methods employing these regulatory elements and use thereof. The invention further encompasses expression cassettes, vectors and pharmaceutical compositions comprising these regulatory elements. The present invention is particularly useful for applications using gene therapy, more particularly endothelial-directed gene therapy, and for vaccination purposes.

BACKGROUND

Endothelial cells form a single cell layer that lines all blood vessels and regulate exchanges between the bloodstream and the surrounding tissues. Signals from endothelial cells organize the growth and development of connective tissue cells that form the surrounding layers of the blood-vessel wall. New blood vessels can develop from the walls of existing small vessels by the outgrowth of endothelial cells, which have the capacity to form hollow capillary tubes even when isolated in culture. Endothelial cells of developing arteries and veins express different cell-surface proteins, which may control the way in which they link up to create a capillary bed. (Molecular Biology of the Cell. 4th Edition). A homeostatic mechanism ensures that blood vessels permeate every region of the body. Cells that are short of oxygen increase their concentration of hypoxia-inducible factor 1 (HIF-1), which stimulates the production of vascular endothelial growth factor (VEGF). VEGF acts on endothelial cells, causing them to proliferate and invade the hypoxic tissue to supply it with new blood vessels. (Molecular Biology of the Cell. 4th Edition).

Endothelial cell phenotypes vary between different organs, between different segments of the vascular loop within the same organ, and between neighbouring endothelial cells of the same organ and blood vessel type. In addition to differences in structure, endothelial cells show remarkable heterogeneity in function. For example, the endothelial cells in the liver, called liver sinusoidal endothelial cells (LSEC), form a continuous lining of the liver capillaries, or sinusoids, separating parenchymal cells and fat-storing cells from sinusoidal blood. LSECs represent unique, highly specialized endothelial cells in the body. LSECs differ in fine structure from endothelial cells lining larger blood vessels and from other capillary endothelia in that they lack a distinct basement membrane and also contain open pores, or fenestrae, in the thin cytoplasmic projections which constitute the sinusoidal wall. This distinctive morphology supports the protective role played by liver endothelium, the cells forming a general barrier against pathogenic agents and serving as a selective sieve for substances passing from the blood to parenchymal and fat-storing cells, and vice versa.

Sinusoidal endothelial cells, furthermore, significantly participate in the metabolic and clearance functions of the liver. They have been shown to be involved in the endocytosis and metabolism of a wide range of macromolecules, including glycoproteins, lipoproteins, extracellular matrix components, and inert colloids, establishing endothelial cells as a vital link in the complex network of cellular interactions and cooperation in the liver.

In addition, LSECs have long been noted to contribute to liver regeneration after liver injury. In normal liver, the major cellular source of hepatocyte growth factor (HGF) is the hepatic stellate cell, but after liver injury, HGF expression has been thought to increase markedly in proliferating LSECs (DeLeve et al. Liver sinusoidal endothelial cells and liver regeneration J Clin. Invest. 2013). Another unexpected function of LSEC was recently reported (Shahani et al., J. Thromb. Hemost 2014), demonstrating that LSECs and not hepatocytes express coagulation factor VIII (FVIII). Moreover, endothelial cells, including LSECs, also express von Willebrand factor (vWF). It is known that secreted FVIII would be relatively unstable unless it is associated with vWF. Deficiency of FVIII, a co-factor in the intrinsic coagulation pathway, results in hemophilia A. Liver transplantation in both FVIII-deficient dogs and patients with hemophilia A corrects these disorders. Although the liver is known to be the main site of FVIII production, other organs are probably also important for the regulation of FVIII secretion. Recent studies have shown that lung endothelial cells can synthesize FVIII. Microvascular endothelial cells from lung, heart, intestine, and skin as well as endothelial cells from pulmonary artery constitutively secreted FVIII and released it after treatment with phorbol-myristate acetate and epinephrine. By contrast, endothelial cells from the aorta, umbilical artery and umbilical vein did not constitutively secrete FVIII or release it after treatment with agonists, probably because of a lack of FVIII synthesis. Extrahepatic endothelial cells from certain vascular beds therefore appear to be an important FVIII production and storage site with the potential to regulate FVIII secretion in chronic and acute conditions (Shahani et al. Blood. 2010 Jun. 10; 115(23): 4902-9). In addition, LSECs have also been reported to induce immunosuppressive IL-10-producing Th1 cells via the Notch pathway (Neumann et al. Eur J Immunol. 2015 July; 45(7):2008-16) suggesting an important immune-modulatory role. Therefore, LSEC dysfunction has been regarded as a key event in multiple liver disorders. Future studies are likely to disclose more fully the role of LSEC in the regulation of liver hemodynamics, in liver metabolism and blood clearance, in the maintenance of hepatic structure, in the pathogenesis of various liver diseases, and in the aging process in the liver (De Leeuw et al. J Electron Microsc Tech. 1990 March; 14(3):218-36).

The endothelium is involved in many disease states, either as a primary determinant of pathophysiology or as a secondary target. In particular, endothelial cell dysfunction can be caused by acquired, complex multifactorial, genetic or infectious diseases. In some cases, the underlying endothelial cell defect can be life-threatening, for which no effective cure is presently available. Dysfunction of the vascular endothelium is a hallmark of many human diseases. The endothelium is directly involved in many different diseases including peripheral vascular disease, stroke, heart disease, diabetes, insulin resistance, chronic kidney failure, tumor growth, metastasis, venous thrombosis, and severe viral infectious diseases. Consequently, the endothelium has substantial untapped potential as a therapeutic target. In particular, endothelial cells are attractive target cells for gene therapy to enable robust and/or sustained expression of the cognate therapeutic genes.

In particular, endothelial dysfunction is one of the major pathophysiological mechanisms that leads towards coronary artery disease and other atherosclerotic diseases. Atherosclerosis is a progressive vascular disease characterized by the accumulation of lipids, inflammatory cells, and fibrous elements. In Western societies, it is the underlying cause of approximately 50% of all deaths. Dysfunction or injury of vascular endothelial cells is critical for the development of atherosclerosis. The endothelium functions as a selectively permeable barrier between blood and tissues as it can regulate transcytosis and generate effector molecules such us nitric oxide (NO) that regulate thrombosis, inflammation, vascular tone and vascular remodeling. For example, over-expression of STAMP2 suppresses atherosclerosis and stabilizes plaques in diabetic mice. Similarly, it had been reported that over-expression of ABCG1 by somatic gene transfer to the atherosclerotic vessel wall results in a significant improvement of plaque morphology and composition, and of vascular function in vivo (Heart Int. 2012 Jun. 5; 7(2): e12.).

Endothelial cells also play a key role in angiogenesis and vasculogenesis. Angiogenesis is the physiological process through which new blood vessels form from pre-existing vessels. This is distinct from vasculogenesis, which is the de novo formation of endothelial cells from mesoderm cell precursors. Angiogenesis and vasculogenesis are normal and vital processes in growth and development. However, they also represent a fundamental step in cancer progression, justifying the use of angiogenesis or vasculogenesis inhibitors in the treatment of cancer. Conversely, promoting angiogenesis and vasculogenesis may benefit the treatment of ischemia which is associated with decrease in blood supply to certain organs or tissues. Consequently, the delivery of genes into endothelial cells that either promote or inhibit angiogenesis and/or vasculogenesis opens new perspectives for the treatment of cardiovascular disease and cancer, respectively. This includes a plethora of therapeutic genes including VEGF, PLGF, FGF, sFLT1, antibodies directed against these factors and their cognate receptors, cytokines, chemokines, etc.

Furthermore, endothelial cells are also promising targets for gene therapy to express therapeutic proteins that are missing or defective in genetic disorders that result from mutations in the respective genes. For example, this includes FVIII, vWF or ADAMTS13 (a disintegrin and metalloproteinase with a thrombospondin type 1 motif, member 13). As mentioned above, hemophilia A is due to a deficiency in FVIII. Moreover, deficiency in vWF causes a bleeding diathesis in patients suffering from von Willebrand disease (VWD). Conversely, a deficiency in ADAMTS13 is linked to the development of microvascular thrombosis characteristic of thrombotic thrombocytopenic purpura (TTP). Consequently, to establish an effective cure for these genetic diseases, robust expression of FVIII, vWF or ADAMTS13 in the endothelial cells is required. In addition, given their proximity to the blood, endothelial cells are also ideally suited to express other therapeutic proteins that are normally not expressed by endothelial cells but that can be directly secreted in the blood. This includes, but is not limited to, other coagulation factors (e.g. factor VII, IX, XI etc.), serum proteins (α1-antitrypsin, AAT, antibodies, growth factors etc.).

Finally, endothelial cells also play a key role in viral infection. For example, the Ebola virus is an aggressive pathogen that causes a highly lethal hemorrhagic fever syndrome in humans and nonhuman primates. The virus infects microvascular endothelial cells and compromises vascular integrity. Infection of endothelial cells also induces a cytopathic effect and damage to the endothelial barrier. Similarly, Dengue virus causes leakage of the vascular endothelium, resulting in dengue hemorrhagic fever and dengue shock syndrome. The endothelial cell lining of the vasculature regulates capillary permeability and is altered by immune and chemokine responses which affect fluid barrier functions of the endothelium. Human endothelial cells are susceptible to infection by dengue virus Following attachment to human endothelial cell receptors, dengue virus causes a productive infection that has the potential to increase viral dissemination and viremia. This provides the potential for dengue virus-infected endothelial cells to directly alter barrier functions of the endothelium, contribute to enhancement of immune cell activation, and serve as potential targets of immune responses which play a central role in dengue pathogenesis.

Hence, there is a need to establish effective cures by gene therapy to enable robust expression of the cognate therapeutic genes in the endothelial cells. This requires the development of potent expression cassettes containing the genes of interest. Consequently, there is a need to identify robust nucleic acid regulatory elements capable of substantially increasing transcription in the endothelium.

SUMMARY OF THE INVENTION

To achieve a robust and specific expression in endothelial cells, the inventors have developed a computational approach to identify robust nucleic acid regulatory elements such as cis-regulatory elements (CREs) that are capable of substantially increasing transcription in endothelial cells (also called EC-CREs or EC-REs) when combined with an endothelial specific promoter. Endothelial specific nucleic acid regulatory elements were identified in silico and subsequently validated in in vitro cell lines and also in vivo in mice.

These nucleic acid regulatory elements are critically important for the regulation of gene expression in an endothelial cell type-specific manner. They are typically composed of clusters of transcription factor binding site (TFBS) motifs. The types and arrangement of TFBS and epigenetic modification patterns influence gene expression levels and specificity. Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take into account the importance of including evolutionary conserved regulatory motifs into the expression modules. The development of nucleic acid regulatory elements that can lead to robust and specific expression in endothelial cells will be very useful for achieving safe and efficient gene delivery to endothelial cells for the treatment of disorders related to endothelial cell dysfunction.

The present inventors have relied on a computational approach (cf. FIG. 1) to identify robust nucleic acid regulatory elements that boost gene expression at the transcriptional level in endothelial cells (designated herein as "EC"). This requires the following computational steps: (1) endothelial cell-specific genes were identified that are highly and specifically expressed based on expression data from endothelial cells; (2) publicly available databases (ENSEMBL) were used for extracting the sequences upstream of the Transcriptional Start Site (TSS) of the selected genes. 3) These sequences were then submitted into UCSC Genome Browser Database for locating the transcription start site in human genome. To extract the corresponding endothelial cell nucleic acid regulatory elements, defined herein as the nucleic acid regulatory elements, the sequences were selected based on the following criteria: a) rich TFBS content, b) epigenetic signatures associated with high DNase hypersensitivity or chromatin accessibility (i.e. histone modifications), and c) evolutionary conserved clusters of TFBS associated with highly expressed endothelial cell-specific genes.

As shown in the experimental section, the inventors identified nucleic acid regulatory elements that will specifically enhance gene expression in endothelial cells.

The endothelial cell regulatory elements will subsequently be validated in vivo, yielding efficient and tissue-specific gene expression. This approach hence, allows for the use of lower and thus safer vector doses, while maximizing therapeutic efficacy.

The invention therefore provides the following aspects:

Aspect 1. A nucleic acid regulatory element for enhancing endothelial cell-specific gene expression comprising, consisting essentially of, or consisting of the sequence selected from the group consisting of: SEQ ID NO:1 to 33, or a sequence having at least 80%, preferably at least 85%, more preferably at least 90%, even more preferably at least 95%, such as 95%, 96%, 97%, 98%, or 99%, identity to any of these sequences. In a preferred embodiment of said aspect, said nucleic acid regulatory element for enhancing endothelial cell-specific gene expression comprises, consists essentially of, or consists of the sequence of SEQ ID NO.22, or a sequence having at least 80%, preferably at least 85%, more preferably at least 90%, even more preferably at least 95%, such as 95%, 96%, 97%, 98%, or 99%, identity to any of these sequences.

Aspect 2. The nucleic acid regulatory element according to aspect 1, having a maximal length of 1000 nucleotides, preferably 800 nucleotides, more preferably 700 nucleotides, most preferably of 610 nucleotides, still comprising the regulatory element defined by any one of SEQ ID Nos: 1 to 33.

Aspect 3. A nucleic acid regulatory element for enhancing gene expression in endothelial cells comprising, consisting essentially of, or consisting of the complement of a sequence as defined by any one of SEQ ID Nos: 1 to 33, or hybridizing under stringent conditions to a sequence as defined by any one of SEQ ID Nos: 1 to 33.

Aspect 4. Use of the nucleic acid regulatory element according to any one aspects 1 to 3 in a nucleic acid expression cassette, or a vector, more particularly for enhancing gene expression in endothelial cells of said nucleic acid expression cassette or vector.

Aspect 5. A nucleic acid expression cassette comprising at least one, such as one, two, three, four, five or more, nucleic acid regulatory elements according to any one of aspects 1 to 3, operably linked to a promoter.

Aspect 6. The nucleic acid expression cassette according to aspect 5, wherein the nucleic acid regulatory element is operably linked to a promoter and a transgene.

Aspect 7. The nucleic acid expression cassette according any one of aspects 5 or 6, wherein the promoter is an endothelial cell-specific promoter, such as the promotor of any one of the genes selected from the group comprising: IF127, ICAM2, VWF, EDN1, ENG, ECSCR, CDH5 (vascular endothelial cadherin promoter, cadherin 5 type 2), PECAM1, HHIP, TIE1 and HYAL2.

Aspect 8. The nucleic acid expression cassette according to any one of aspects 5 to 7, wherein the transgene encodes a therapeutic protein or an immunogenic protein.

Aspect 9. The nucleic acid expression cassette according to any one of aspects 5 to 8, wherein the transgene encodes a secretable protein or a structural protein.

Aspect 10. The nucleic acid expression cassette according to aspect 8 or 9, wherein said transgene is selected from the group comprising: hepatocyte growth factor (HGF), coagulation factor VIII (FVIII), coagulation factor VII (FVII), tissue factor (TF), tissue factor pathway inhibitor (TFPI), coagulation factor IX (FIX), coagulation factor XI (FXI), von Willebrand factor (vWF), ADAMTS13, VEGF, PLGF, FGF, sFLT1, α1-antitrypsin, AAT, apolipoprotein A-I (apoA-I), matrix metalloproteinases including but not limited to matrix metalloproteinase-3 (TIMP-3), nitric oxide synthase (NOS), antibodies, growth factors, cytokines, chemokines and antibodies, including but not limited to antibodies directed against any one of said transgenes, factors and their cognate receptors or against any secreted protein or viral protein, small interfering RNA, guide RNA, endonuclease, and Cas9.

Aspect 11. The nucleic acid expression cassette according to any one of aspects 5 to 10, further comprising a polyadenylation signal, preferably the Simian Virus 40 (SV40) polyadenylation signal, a synthetic polyadenylation signal or a bovine growth hormone polyadenylation signal.

Aspect 12. A vector comprising the nucleic acid regulatory element according to any one of aspects 1 to 3, or the nucleic acid expression cassette according to any one of aspects 5 to 11.

Aspect 13. The vector according to aspect 12, which is a viral vector, preferably a lentiviral vector (LV), an adeno-associated viral (AAV) vector, or an adenoviral vector (AV). In specific examples of said aspect, the vector is a self- or non-self inactivating lentiviral vector, preferably a self inactivating lentiviral vector.

In specific examples the LV has the following components: EC-CRE-PM-TG, with EC-CRE being one of the newly identified regulatory sequences as defined in SEQ ID Nos 1-33; PM being an endothelial cell-specific promotor such as, but not limited to, those referred to in aspect 7, and TG being a transgene such as, but not limited to, the transgenes identified herein and in particular those defined in aspect 10.

Taking the example with endothelial cell-specific promotor ICAM2, and using the self inactivating lentiviral vector backbone pCDH, the vector can be:

pCDH-CDH5-EC-CRE1a-ICAM2-TG, such as wherein the TG is any one of those identified in aspect 10, pCDH-CDH5-EC-CRE1b-ICAM2-TG, such as wherein the TG is any one of those identified in aspect 10, pCDH-CDH5-EC-CRE1c-ICAM2-TG, such as wherein the TG is any one of those identified in aspect 10, pCDH-CDH5-EC-CRE1d-ICAM2-TG, such as wherein the TG is any one of those identified in aspect 10, pCDH-CDH5-EC-CRE1e-ICAM2-TG, such as wherein the TG is any one of those identified in aspect 10, pCDH-HYAL2-EC-CRE1f-ICAM2-TG, such as wherein the TG is any one of those identified in aspect 10, pCDH-ECSCR-EC-CRE1a-ICAM2-TG, such as wherein the TG is any one of those identified in aspect 10, pCDH-ECSCR-EC-CRE1b-ICAM2-TG, such as wherein the TG is any one of those identified in aspect 10, pCDH-EDN1-EC-CRE1a-ICAM2-TG, such as wherein the TG is any one of those identified in aspect 10, pCDH-ENG-EC-CRE1a-ICAM2-TG, such as wherein the TG is any one of those identified in aspect 10, pCDH-ENG-EC-CRE1b-ICAM2-TG, such as wherein the TG is any one of those identified in aspect 10, pCDH-ENG-EC-CRE1c-ICAM2-TG, such as wherein the TG is any one of those identified in aspect 10, pCDH-HHIP-EC-CRE1a-ICAM2-TG, such as wherein the TG is any one of those identified in aspect 10, pCDH-HHIP-EC-CRE1b-ICAM2-TG, such as wherein the TG is any one of those identified in aspect 10, pCDH-HYAL2-EC-CRE1a-ICAM2-TG, such as wherein the TG is any one of those identified in aspect 10, pCDH-HYAL2-EC-CRE1b-ICAM2-TG, such as wherein the TG is any one of those identified in aspect 10, pCDH-HYAL2-EC-CRE1c-ICAM2-TG, such as wherein the TG is any one of those identified in aspect 10, pCDH-ICAM2-EC-CRE1a-ICAM2-TG, such as wherein the TG is any one of those identified in aspect 10, pCDH-ICAM2-EC-CRE1b-ICAM2-TG, such as wherein the TG is any one of those identified in aspect 10, pCDH-ICAM2-EC-CRE1c-ICAM2-TG, such as wherein the TG is any one of those identified in aspect 10, pCDH-IF127-EC-CRE1a-ICAM2-TG, such as wherein the TG is any one of those identified in aspect 10, pCDH-IF127-EC-CRE1b-ICAM2-TG, such as wherein the TG is any one of those identified in aspect 10, pCDH-PECAM1-EC-CRE1a-ICAM2-TG, such as wherein the TG is any one of those identified in aspect 10, pCDH-TIE1-EC-CRE1a-ICAM2-TG, such as wherein the TG is any one of those identified in aspect 10, pCDH-TIE1-EC-CRE1b-ICAM2-TG, such as wherein the TG is any one of those identified in aspect 10, pCDH-VWF-EC-CRE1a-ICAM2-TG, such as wherein the TG is any one of those identified in aspect 10, or pCDH-VWF-EC-CRE1b-ICAM2-TG, such as wherein the TG is any one of those identified in aspect 10.

In anyone of said VL constructs, the ICAM2-promotor can be replaced by another endothelial cell specific promotor, such as, but not limited to those exemplified in aspect 7. In anyone of said VL constructs, the vector backbone can be exchanged by another suitable backbone such as those known to the person skilled in the art.

Aspect 14. The vector according to aspect 12, which is a non-viral vector, preferably a plasmid, a minicircle, an episomal vector, or a transposon-based vector, such as a PiggyBac-based vector or a Sleeping Beauty-based vector.

Aspect 15. A pharmaceutical composition comprising the nucleic acid expression cassette according to any one of aspects 5 to 11, or the vector according to any one of aspects 12 to 14, and a pharmaceutically acceptable carrier.

Aspect 16. The nucleic acid regulatory element according to any one of aspects 1 to 3, the nucleic acid expression cassette according to any one of aspects 5 to 11, the vector according to any one of aspects 12 to 14, or the pharmaceutical composition according to aspect 15 for use in medicine, more preferably for use in gene therapy, in particular for use in treating endothelial cell dysfunction, preferably such as any one of the diseases or disorders selected from the group comprising: liver diseases, hemophilia A, von Willebrand disease, microvascular thrombosis, thrombotic thrombocytopenic purpura, peripheral vascular disease, coronary artery diseases, atherosclerotic diseases, stroke, heart disease, diabetes, insulin resistance, chronic kidney failure, tumor growth, metastasis, venous thrombosis, ischemia, tumour growth, tumour vascularisation, cancer and viral infectious diseases such as Ebola, Dengue and Dengue hemorrhagic fever.

Aspect 17. The nucleic acid regulatory element according to any one of aspects 1 to 3, the nucleic acid expression cassette according to any one of aspects 4 to 11, the vector according to any one of aspects 12 to 14, or the pharmaceutical composition according to aspect 15 for use as a vaccine, preferably a prophylactic vaccine, or for use in vaccination therapy, preferably prophylactic vaccination. Alternatively, said nucleic acid regulatory element according to any one of aspects 1 to 3, the nucleic acid expression cassette according to any one of aspects 4 to 11, the vector according to any one of aspects 12 to 14, or the pharmaceutical composition according to aspect 15 can be for use in induction of immunotolerance to the transgene.

Aspect 18. A method, preferably an in vivo method, for expressing a transgene product in endothelial cells, comprising:

introducing the nucleic acid expression cassette according to any one of aspects 4 to 11, or the vector according to any one of aspects 12 to 14, comprising the nucleic acid regulatory element according to any one of aspects 1 to 3, into the cells; and Aspect 19. A method, preferably an in vitro or ex vivo method, for expressing a transgene product in endothelial cells, comprising:

introducing the nucleic acid expression cassette according to any one of aspects 4 to 11, or the vector according to any one of aspects 12 to 14, comprising the nucleic acid regulatory element according to any one of aspects 1 to 3, into the cells; and expressing the transgene product in the cells.

Aspect 20. A method for treating an endothelial cell-related disease or disorder comprising the administration of a therapeutically effective amount of the nucleic acid expression cassette according to any one of aspects 5 to 11, the vector according to any one of aspects 12 to 14, or the pharmaceutical composition according to aspect 15, each comprising the nucleic acid regulatory element according to any one of aspects 1 to 3, to a subject in need thereof.

Aspect 21. The method according to aspect 20, wherein said endothelial cell-related disease or disorder is selected from the group comprising: endothelial cell dysfunction, preferably such as any one of the diseases or disorders selected from the group comprising: liver diseases, hemophilia A, von Willebrand disease, microvascular thrombosis, thrombotic thrombocytopenic purpura, peripheral vascular disease, coronary artery diseases, atherosclerotic diseases, stroke, heart disease, diabetes, insulin resistance, chronic kidney failure, tumor growth, metastasis, venous thrombosis, ischemia, tumour growth, tumour vascularisation, cancer and viral infectious diseases such as Ebola Dengue and Dengue hemorrhagic fever.

As shown in the experimental section (Example 1), the inventors identified nucleic acid regulatory elements that will specifically enhance gene expression in endothelial cells. The endothelial specific regulatory elements were subsequently be validated in vitro and in vivo assays in mice. The details of the in vitro and in vivo validation are described in Example 2 to 6 below. The successful use of the endothelial CREs will hence, allows for the use of lower and thus safer vector doses, while maximizing therapeutic efficacy.

Figure 2:
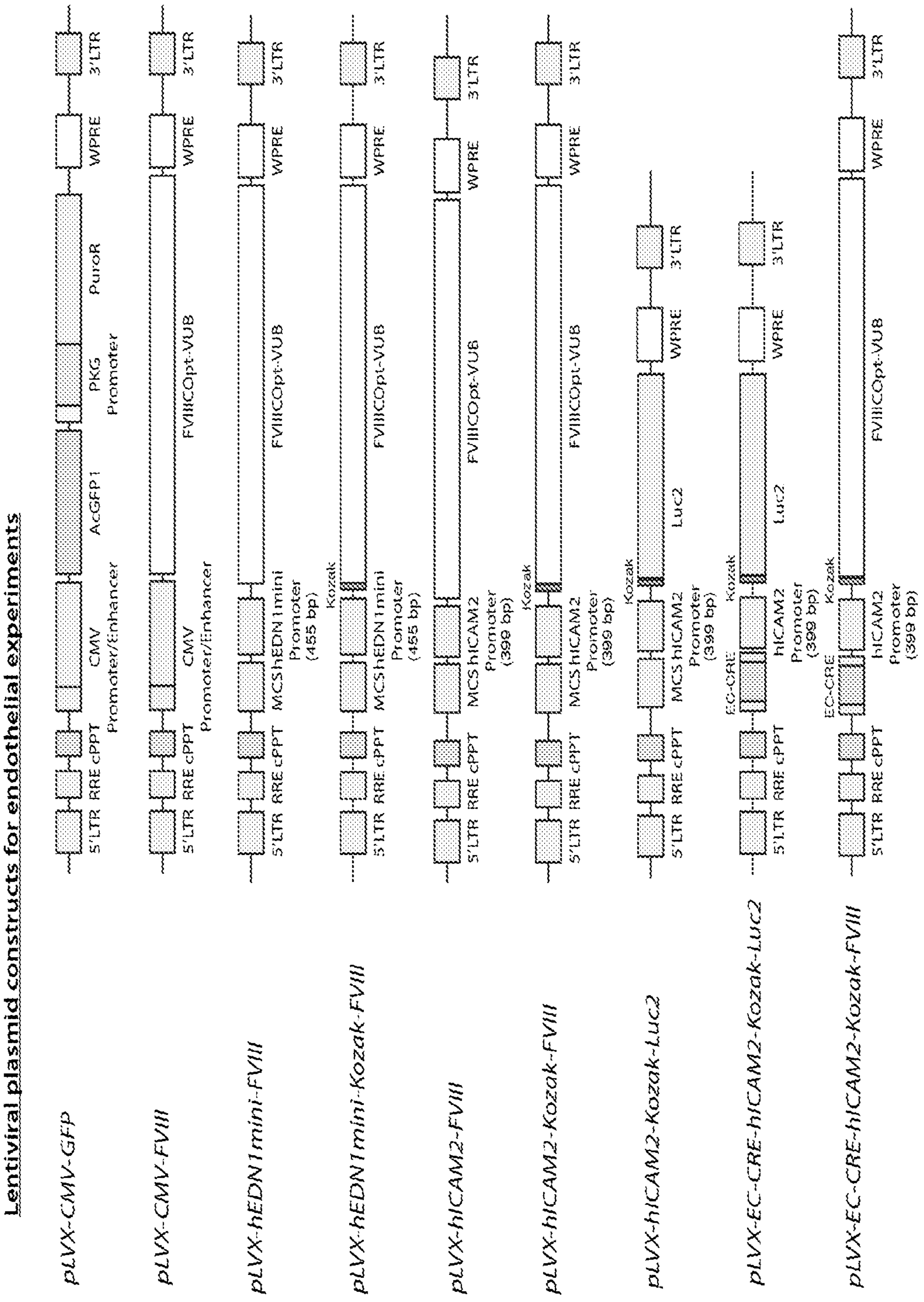

FIG. 2: Lentiviral vector design

Lentiviral vectors were produced as described previously (VandenDriessche et al., Blood 2002). Briefly, the lentiviral vector-containing plasmids were cotransfected with a VSV-G expression plasmid, a gag-pol and Rev expression plasmid. Lentiviruses were produced by transient co-transfection of HEK293T (293T) cells using supplemented Dulbecco modified Eagle medium (Invitrogen) with 10% heat-inactivated fetal bovine serum (Invitrogen) and 1% penicillin/streptomycin. A total of 60 μg lentiviral plasmid was used for transfection of one double-tray culture chamber: 60 μg lentiviral plasmid, 30 μg pRSV-REV, 30 μg pMDLg/pRRE and 30 μg pCMV-VSV-G. Plasmid was pre-complexed with calcium phosphate (Calcium phosphate transfection kit, Invitrogen) for 30 minutes at room temperature. Transfection media was added to the cells for 16 hours and then replaced by fresh medium containing NU-serum (Invitrogen) and Sodium Butyrate (Sigma). Viral supernatant was harvested 48 and 72 hours after transfection and concentrated using a Centricon concentrator (Millipore) (2000 rpm for 1 hours at 4° C.). Aliquots of viruses were stored at −80° C. The physical titer in nanograms per microliter of all LVs was determined using a p24 colorimetric enzyme-linked immunosorbent assay (ELISA) kit (Cell Biolabs) according to the manufacturer's instructions. This value was then used to calculate an estimated vector titer equivalent in transducing units (TU) per milliliter. Polybrene (8 μg/mL) was added to the concentrated vectors to enhance transduction.

Figure 3A:
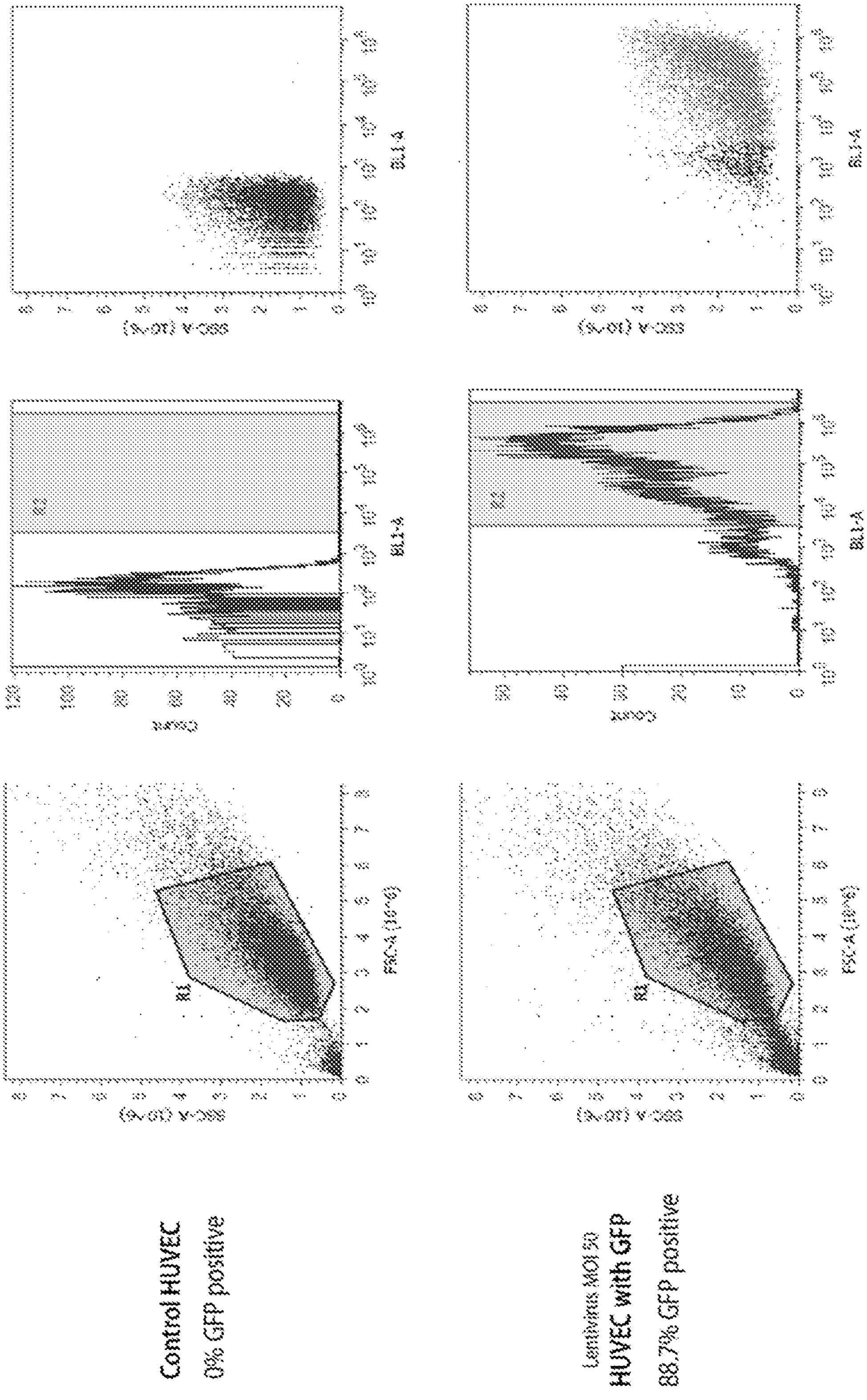
Figure 3B:
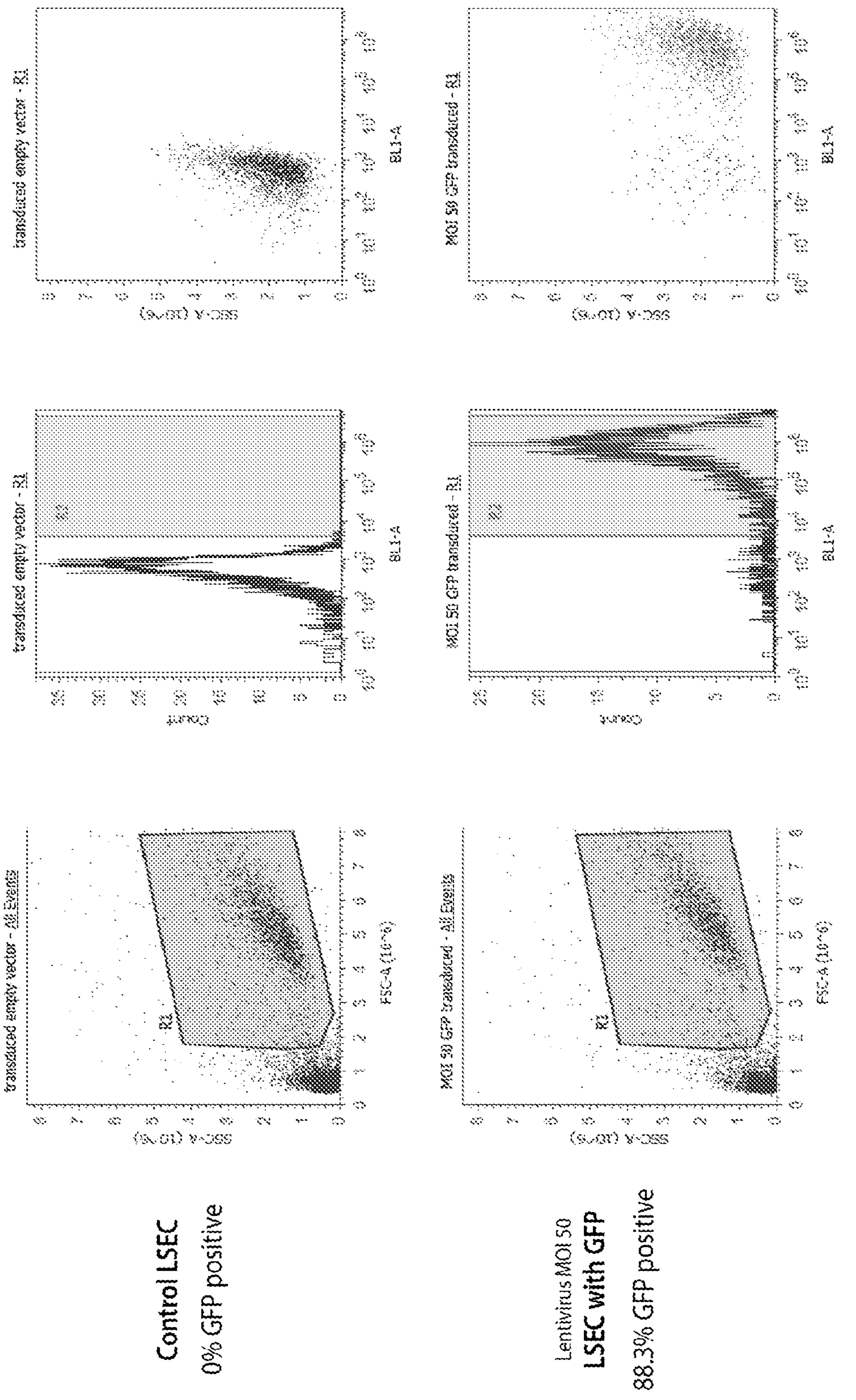

FIG. 3: Flow cytometry analysis of HUVECs and LSECs transduced with LV CMV-GFP vector (MOI 50) at 72 hr timepoint post transduction.

Figure 4:
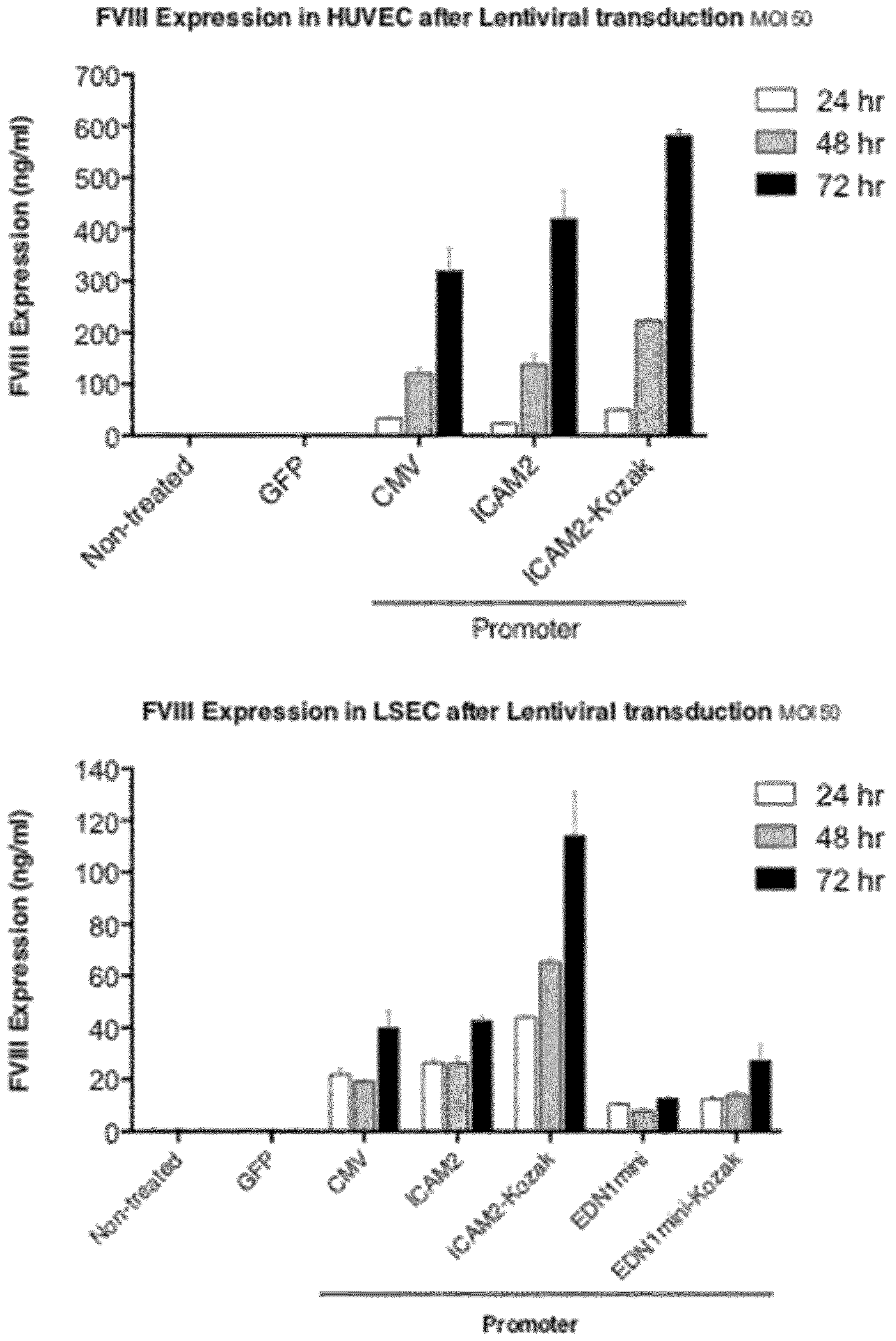

FIG. 4: FVIII antigen expression expressed in ng/ml in HUVECs and LSECS transduced with different lentiviral vector designs. FVIII antigen expression levels were determined at 24, 48 and 72 hrs after transduction.

Figure 5:
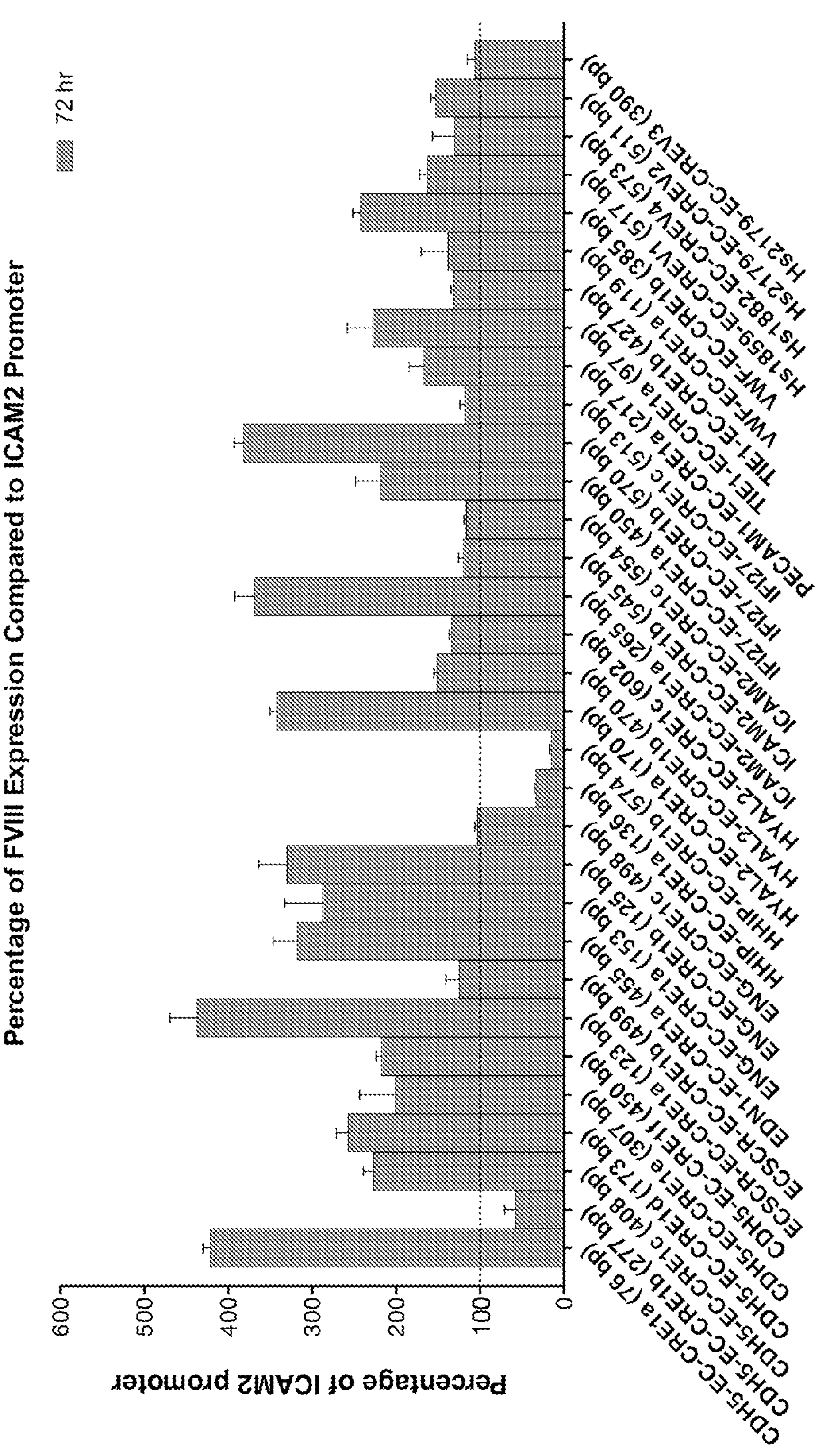

FIG. 5: The FVIII expression levels of each EC-CRE-ICAM2-FVIII construct in HUVECs. The percentage compared to the ICAM2 construct without EC-CREs. The expression values were represented as mean with standard error of mean (SEM; n=3 for each group).

Figure 6:
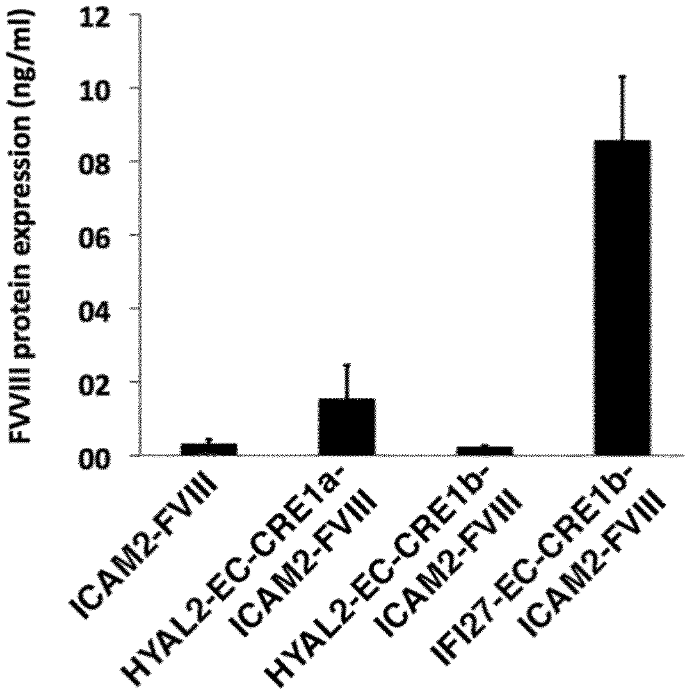

FIG. 6: FVIII expression after lentiviral in vivo transduction. FVIII protein expression was determined using a human FVIII-specific ELISA on the plasma samples collected 5 weeks after lentiviral vector injection. The mice cohorts (n=4 mice per cohort) include ICAM2-FVIII (no CRE control), HYAL2-EC-CRE1a-ICAM2-FVIII, HYAL2-EC-CRE1b-ICAM2-FVIII & IF127-EC-CRE1b-ICAM2-FVIII.

Figure 7:
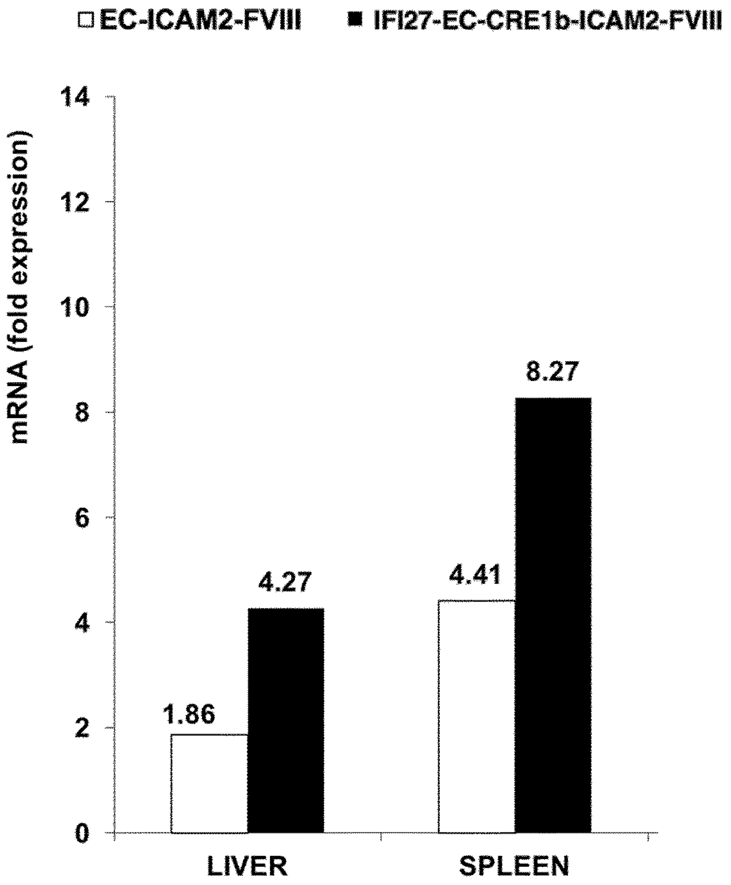

FIG. 7: mRNA analysis of the CD146-positive endothelial cells isolated from liver and spleen. The human FVIII expression encoded by the lentiviral vector was normalized to endogenous mouse GAPDH expression.

FIG. 8: plasmid maps of lentiviral vectors

All endothelial CRE's were cloned, in a self inactivating the lentiviral vectors called pCDH as shown in the map. A: pCDH-HYAL2-EC-CRE1a-ICAM2-FVIII (SEQ ID NO. 50); B: pCDH-ICAM2-FVIII (SEQ ID NO. 49); C: pCDH-IF127-EC-CRE1b-ICAM2-FVIII (SEQ ID NO. 52); D: pCDH-HYAL2-EC-CRE1b-ICAM2-FVIII (SEQ ID NO. 51).

DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any or etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

For general methods relating to the invention, reference is made inter alia to well-known textbooks, including, e.g., “Molecular Cloning: A Laboratory Manual, 2nd Ed.” (Sambrook et al., 1989), “Current Protocols in Molecular Biology” (Ausubel et al., 1987).

In one aspect, the invention relates to a nucleic acid regulatory element for enhancing gene expression in endothelial cells or tissue comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of: a sequence selected from the group consisting of: SEQ ID NO:1 to 33, a sequence having at least 80%, preferably at least 85%, more preferably at least 90%, even more preferably at least 95%, such as 95%, 96%, 97%, 98%, or 99%, identity to any of these sequences, or a functional fragment of a sequence selected from the group consisting of: SEQ ID NO:1 to 33.

Tables 2 and 3 below depict the core nucleotide sequence of the different nucleic acid regulatory elements for enhancing gene expression in endothelial cells or tissue. Table 1 lists the corresponding genes and lengths.

A ‘nucleic acid regulatory element’, ‘cis-acting regulatory element’, ‘ORE’ or ‘regulatory element’ as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for an endothelial cell-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory elements hence have a sequence which is only a small part of the naturally occurring genomic sequence and hence is not naturally occurring as such, but is isolated therefrom.

The term “nucleic acid” as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term “nucleic acid” further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A “nucleic acid” can be double-stranded, partly double stranded, or single-stranded. Where single-stranded, the nucleic acid can be the sense strand or the antisense strand. In addition, nucleic acid can be circular or linear.

As used herein “transcription factor binding site”, “transcription factor binding sequence” or “TFBS” refers to a sequence of a nucleic acid region to which transcription factors bind. Non-limiting examples of TFBS include binding sites for or such as: POLR2A, Pol2(b), GATA2, GATA-2, FOS, c-Fos, NR3C1, Freac-2, MAX, FOX2P, MYC, SRY, SOX9, SRF, JUN, TEAD4, EZH2, TBP, TCF7L2, SPI1, RELA, JUND, MXI1, JUNB, BHLHE40, RCOR1, TCF12, TALI, EP300, HDAC2, GTF2F1, SIN3AK20, FOSL2, ETS1, CTBP2, GATA3, CEBPB, FOXA1, YY1, RFX5, TAF1, REST, ELF1, CTCF, SMC3, FOXP2, RUNX3, NRF1, HDAC6, IRF4, PAX5, RAD21, WRNIP1, ERalpha_a, PU.1, TCF4, TALI, HDAC2, GATA3, Mxi1, GTF2F1, ELF1, NRSF, CTCF, SMC3, Ini1, IRF4, PAX5, CTCF, Pol2-4H8, YY1, CTCF, FOXO1, FOXJ2, GATA-X, Gfi-1, Hand1/E47, MAZ, USF1, REST, TFAP2A, TFAP2C, CHD2, ZNF274, BACH1, EBF, EBF1, ATF2:c-Jun, CREB1, ATF, Tax/CREB, CREB1, EGR1, NF-kappaB, c-Rel, Pax-3, FOXO4, SOX5, GR, ZNF263, Lmo2 complex, AP-4, HEN1, E2F6, PML, TRIM28, SMARCA4, RBBP5, NRF2F, TBL1XR1, STAT5A, MAFF, REST, JUND, IRF1, MAFK, eGFP-JunDATF1, ARID3A, ATF3, E2F6, GATA2, GATA-1, Brg1, TALI, JunB, NR2F2, HDAC8, BCL3, ATF2, CBX3, HNF4, FOXA2, KAP1, UBTF, GABP, GABPA, BCLAF1, SP1, FOXM1, MEF2A, ZNF143, ZBTB7A, NANOG, CTCFL, NFKB, CCNT2, EBF1, FOXA1, Max, c-Myc, STAT1, STAT2, MZF1, SMARCC1, E2F4, FOSL1, STAT3, P300, AP2gamma, MafF1, JunD, AP2alpha, FOXA2, HMGN3, ZBTB33, P300, Nkx2-2, Nkx2-5, SRF, YY1, HTF, CHX10, HNF1, OCT, Ncx, AP-2rep, Lmo2 complex, SOX5, GATA-1, CDP CR1, Cart-1, NFIV, RXRA, SREBP1, MYBL2, HNF4G, HNF4A, HEY1, ZEB1, PHF8, CHD1, PU-1, RSRFC4, MEF-2, and/or Lyf-1. The nucleic acid regulatory elements described herein can comprise any one or more of said TFBS, or combinations thereof. Transcription factor binding sites may be found in databases such as Transfac®.

Sequences disclosed herein may be part of sequences of regulatory elements capable of controlling transcription of endothelial cell-specific genes in vivo. Particular examples for endothelial-specific regulatory elements may in particular be controlling the following genes: IF127, ICAM2, VWF, EDN1, ENG, ECSCR, CDH5, PECAM1, HHIP, TIE1 or HYAL2.

Accordingly, in embodiments, the nucleic acid regulatory elements disclosed herein comprise a sequence from CDH5 regulatory elements, i.e. regulatory elements that control expression of the CDH5 gene (Cadherin 5 or VE-cadherin gene) in vivo, e.g. regulatory elements comprising any one or more of SEQ ID NOs: 1 to 6, or functional fragments thereof. In other embodiments, the nucleic acid regulatory elements disclosed herein comprise a sequence from ECSCR regulatory elements, i.e. regulatory elements that control expression of the ECSCR gene (Endothelial Cell-Specific Chemotaxis Regulator gene) in vivo, e.g. regulatory elements comprising any one or more of SEQ ID NOs: 7 or 8, or functional fragments thereof. In other embodiments, the nucleic acid regulatory elements disclosed herein comprise a sequence from EDN1 regulatory elements, i.e. regulatory elements that control expression of the EDN1 gene (Endothelin 1 gene) in vivo, e.g. regulatory elements comprising SEQ ID NO: 9, or functional fragments thereof. In other embodiments, the nucleic acid regulatory elements disclosed herein comprise a sequence from ENG regulatory elements, i.e. regulatory elements that control expression of the ENG gene (Endoglin gene) in vivo, e.g. regulatory elements comprising any one or more of SEQ ID NOs: 10 to 12, or functional fragments thereof. In other embodiments, the nucleic acid regulatory elements disclosed herein comprise a sequence from HHIP regulatory elements, i.e. regulatory elements that control expression of the HHIP gene (Hedgehog Interacting Protein gene) in vivo, e.g. regulatory elements comprising any one or more of SEQ ID NOs: 13 or 14, or functional fragments thereof. In other embodiments, the nucleic acid regulatory elements disclosed herein comprise a sequence from HYAL2 regulatory elements, i.e. regulatory elements that control expression of the HYAL2 gene (Hyaluronoglucosaminidase 2 gene) in vivo, e.g. regulatory elements comprising any one or more of SEQ ID NOs: 15 to 17, or functional fragments thereof. In other embodiments, the nucleic acid regulatory elements disclosed herein comprise a sequence from ICAM2 regulatory elements, i.e. regulatory elements that control expression of the ICAM2 gene (Intercellular Adhesion Molecule 2 gene) in vivo, e.g. regulatory elements comprising any one or more of SEQ ID NOs: 18 to 20, or functional fragments thereof. In other embodiments, the nucleic acid regulatory elements disclosed herein comprise a sequence from IF127 regulatory elements, i.e. regulatory elements that control expression of the IF127 gene (Interferon, Alpha-Inducible Protein 27 gene) in vivo, e.g. regulatory elements comprising any one or more of SEQ ID NOs: 21 to 23, or functional fragments thereof. In other embodiments, the nucleic acid regulatory elements disclosed herein comprise a sequence from PECAM1 regulatory elements, i.e. regulatory elements that control expression of the PECAM1 gene (Platelet/Endothelial Cell Adhesion Molecule 1 gene) in vivo, e.g. regulatory elements comprising SEQ ID NO: 24, or functional fragments thereof. In other embodiments, the nucleic acid regulatory elements disclosed herein comprise a sequence from TIE1 regulatory elements, i.e. regulatory elements that control expression of the TIE1 gene (Tyrosine Kinase With Immunoglobulin-Like And EGF-Like Domains 1 gene) in vivo, e.g. regulatory elements comprising any one or more of SEQ ID NOs: 25 or 26, or functional fragments thereof. In other embodiments, the nucleic acid regulatory elements disclosed herein comprise a sequence from VWF regulatory elements, i.e. regulatory elements that control expression of the VWF gene (Von Willebrand Factor gene) in vivo, e.g. regulatory elements comprising any one or more of SEQ ID NOs: 27 or 28, or functional fragments thereof. In other embodiments, the nucleic acid regulatory elements disclosed herein comprise a sequence comprising any one or more of SEQ ID NOs: 29 to 33, or functional fragments thereof.

As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term 'functional fragment' as used in the application refers to fragments of the regulatory element sequences disclosed herein that retain the capability of regulating endothelial cell-specific expression, i.e. they can still confer tissue specificity and they are capable of regulating expression of a (trans)gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, or at least 400 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived.

"endothelial cell-specific expression" as used in the application, refers to the preferential or predominant expression of a (trans)gene (as RNA and/or polypeptide) in endothelial cells and tissue comprising or built from endothelial cells, as compared to other (i.e. non-endothelial) cells or tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within endothelial cells or endothelial tissue.

The term “endothelial cell” as used herein encompasses all endothelial cell types, such as the cells forming a single cell layer that lines all blood vessels and regulates exchanges between the bloodstream and the surrounding tissues. Many endothelial cell types exist and their phenotypes vary between different organs, between different segments of the vascular loop within the same organ, and between neighbouring endothelial cells of the same organ and blood vessel type. Non-limiting examples of such endothelial cells are: liver sinusoidal endothelial cells (LSEC), (micro)vascular endothelial cells from e.g. lung, heart, intestine, skin, retina, arterial endothelial cells, such as endothelial cells from pulmonary artery, the aorta, umbilical artery and umbilical vein, extrahepatic endothelial cells from certain vascular beds, blood-brain barrier ECs, bone marrow ECs, and high endothelial venule cells (HEVs).

According to a particular embodiment, endothelial cell specific expression entails that there is less than 10%, less than 5%, less than 2% or even less than 1% ‘leakage’ of expressed gene product to other organs or tissue than those comprising or built by endothelial cells, such as muscle, heart, lung, liver, brain, kidney and/or spleen.

The same applies mutatis mutandis for endothelial progenitor cell (EPC)-specific expression, which may be considered as a particular form of endothelial cell-specific expression. Hence, throughout the application, where endothelial cell-specific is mentioned in the context of expression, endothelial progenitor cell (EPC)-specific expression is also explicitly envisaged.

In embodiments, the invention relates to a nucleic acid regulatory element for enhancing gene expression in endothelial cells or tissue derived therefrom comprising, consisting essentially of, or consisting of a sequence selected from the group consisting of: SEQ ID NO:1 to 33; a sequence having at least 80%, preferably at least 85%, more preferably at least 90%, even more preferably at least 95%, such as 95%, 96%, 97%, 98%, or 99%, identity to any of the sequences selected from the group consisting of SEQ ID NO: 1 to 33; or a functional fragment thereof, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 2, 3, 4, or 5, more preferably at least 10 or at least 15 transcription factor binding sites (TFBS) such as those TFBS that are present in the sequence from which it is derived.

It is also possible to make nucleic acid regulatory elements that comprise an artificial sequence by combining two or more identical or different sequences disclosed herein or functional fragments thereof. Accordingly, in certain embodiments a nucleic acid regulatory element for enhancing gene expression in endothelial cells is provided comprising at least two sequences selected from the group consisting of: SEQ ID NO:1-33.

For example, disclosed herein is a nucleic acid regulatory element comprising, consisting essentially of, or consisting of 2, 3, 4, or 5 repeats, e.g. tandem repeats, of any one of SEQ ID NOs:1 to 33, or combinations thereof.

Particular examples of nucleic acid regulatory elements that comprise an artificial sequence include the regulatory elements that are obtained by rearranging the transcription factor binding sites (TFBS) that are present in the sequences disclosed herein. Said rearrangement may encompass changing the order of the TFBSs and/or changing the position of one or more TFBSs relative to the other TFBSs and/or changing the copy number of one or more of the TFBSs. For example, also disclosed herein is a nucleic acid regulatory element for enhancing endothelial cell-specific gene expression, in particular endothelial cell-specific gene expression, comprising binding sites for e.g. Sp1, EGR-1, ETS and GATA. Further for example, also disclosed herein is a nucleic acid regulatory element for enhancing endothelial cell-specific gene expression, in particular comprising binding sites for one or more of: Sp1, EGR-1, ETS and GATA and combinations thereof. In some embodiments, these nucleic acid regulatory elements comprise at least two, such as 2, 3, 4, or more copies of any one or more of the recited TFBSs.

In some embodiments, the vector used is a lentiviral vector. In other embodiments, the vector used is an adeno-associated viral vector. In yet other embodiment, the vector used is an adenoviral vector. In case a lentiviral vector is used, it can be a self inactivating or a non self-inactivating lentiviral vector. A self inactivating lentiviral vector is sometimes preferred for clinical use since it is considered safer.

In case the regulatory element is provided as a single stranded nucleic acid, e.g. when using a single-stranded AAV vector, the complement strand is considered equivalent to the disclosed sequences. Hence, also disclosed herein is a nucleic acid regulatory element for enhancing endothelial cell-specific gene expression comprising, consisting essentially of, or consisting of the complement of a sequence described herein, in particular a sequence selected from the group consisting of: SEQ ID NOs:1 to 33; a sequence having at least 80%, preferably at least 85%, more preferably at least 90%, even more preferably at least 95%, such as 95%, 96%, 97%, 98%, or 99%, identity to any of these sequences; or a functional fragment thereof as defined herein.

Also disclosed herein is a nucleic acid regulatory element for enhancing endothelial cell-specific gene expression hybridizing under stringent conditions to a nucleic acid regulatory element described herein, in particular to the nucleic acid regulatory element comprising, consisting essentially of, or consisting of a sequence selected from the group consisting of: SEQ ID NOs:1 to 33; a sequence having at least 90%, preferably at least 95%, such as 95%, 96%, 97%, 98%, or 99%, identity to any of these sequences; a functional fragment thereof as defined herein; or to its complement. Said nucleic acid regulatory elements do not need to be of equal length as the sequence they hybridize to. In preferred embodiments, the size of said hybridizing nucleic acid regulatory element does not differ more than 25% in length, in particular 20% in length, more in particular 15% in length, most in particular 10% in length from the sequence it hybridizes to.

The expression ‘hybridize under stringent conditions’ refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature (Tm) of the native duplex. Methods of calculating Tm are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours.

Preferably the regulatory elements as described herein are fully functional while being only of limited length. This allows their use in vectors or nucleic acid expression cassettes without unduly restricting their payload capacity. Accordingly, in embodiments, the regulatory element disclosed herein is a nucleic acid of 1500 nucleotides or less, 1000 nucleotides or less, 900 nucleotides or less, 800 nucleotides or less, 700 nucleotides or less, more preferably 610 nucleotides or less, such as 550 nucleotides or less, 500 nucleotides or less, 450 nucleotides or less, 400 nucleotides or less, 350 nucleotides or less, or 300 nucleotides or less (i.e. the nucleic acid regulatory element has a maximal length of 1500 nucleotides, 1000 nucleotides, 900 nucleotides, 800 nucleotides, 700 nucleotides, preferably 610 nucleotides, such as 550 nucleotides, 500 nucleotides, 450 nucleotides, 400 nucleotides, 350 nucleotides, or 300 nucleotides).

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 150 nucleotides, 200 nucleotides, 250 nucleotides, 300 nucleotides, 350 nucleotides or 400 nucleotides.

In certain embodiments, the invention provides for a nucleic acid regulatory element of 1000 nucleotides or less, preferably 900 nucleotides or less, preferably 800 nucleotides or less, preferably 700 nucleotides or less of a sequence selected from the group consisting of: SEQ ID NOs:1 to 33; a sequence having at least 80%, preferably at least 85%, more preferably at least 90%, even more preferably at least 95%, such as 95%, 96%, 97%, 98%, or 99%, identity to any of said sequences; or a functional fragment thereof as defined herein.

The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term 'operably linked' as used herein refers to the arrangement of various nucleic acid molecule elements relative to each other such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By "modulate" is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this need not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one nucleic acid regulatory element as described herein. In alternative embodiments, the nucleic acid expression cassette comprises two or more, such as, e.g., 2, 3, 4, 5, 6, 7, 8, 9, or 10, nucleic acid regulatory elements as described herein, i.e. they are combined modularly to enhance their regulatory (and/or enhancing) effect. In further embodiments, at least two of the two or more nucleic acid regulatory elements are identical or substantially identical. In yet further embodiments, all of the two or more regulatory elements are identical or substantially identical. The copies of the identical or substantially identical nucleic acid regulatory elements may be provided as tandem repeats in the nucleic acid expression cassette. In alternative further embodiments, at least two of the two or more nucleic acid regulatory elements are different from each other, that is to say, are defined by a different SEQ ID NO:. The nucleic acid expression cassette may also comprise a combination of identical and substantially identical nucleic acid regulatory elements and non-identical nucleic acid regulatory elements.

For example, the nucleic acid expression cassette may comprise a nucleic acid regulatory element comprising SEQ ID NO:1, and a nucleic acid regulatory element comprising any one or more of SEQ ID Nos: 2 to 33. Alternatively, this can be done for remaining regulatory elements defined by SEQ ID NOs:2 to 33, which can be combine with any one or more of the other regulatory elements.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of endothelial cell-specific expression in vivo (and/or in vitro in cell lines derived from endothelial cell- or tissue) of the transgene, and/or (2) can increase the level of expression of the transgene in endothelial cells (and/or in vitro in cell lines derived from endothelial cells or tissue).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus, any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

Non-limiting exemplary endothelial cell-specific promoters are: the promotors of the genes depicted in Table 1 below, more preferably the In particularly preferred embodiments, the promoter is a mammalian promoter, in particular a murine or human promoter.

In preferred embodiments, the promoter is from the vascular-endothelial cadherin gene, in particular the murine or human cadherin-5 gene, such as the promoter as defined in SEQ ID NO: 34 (cf. Table 4).

In preferred embodiments, the promoter is from the endothelin-1 gene, in particular the murine or human endothelin-1 gene, such as the promoter as defined in SEQ ID NO: 35 (cf. Table 4).

In preferred embodiments, the promoter is from the endoglin gene, in particular the murine or human endoglin gene, such as the promoter as defined in SEQ ID NO: 36 (cf. Table 4).

In preferred embodiments, the promoter is from the Fms-Related Tyrosine Kinase 1 gene, in particular the murine or human Fms-Related Tyrosine Kinase 1 gene, such as the promoter as defined in SEQ ID NO: 37 (cf. Table 4).

In preferred embodiments, the promoter is from the Intercellular Adhesion Molecule 2 gene, in particular the murine or Intercellular Adhesion Molecule 2 gene (ICAM2), such as the promoter as defined in SEQ ID NO: 38 (cf. Table 4).

Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A 'minimal promoter' (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Preferably, the promoter contained in the nucleic acid expression cassette disclosed herein is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less. One particular non-limiting example of such a minimal promotor is the EDN1mini promoter (cf. Table 4).

The term 'transgene' as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), catalytic RNA, antisense RNA, RNA aptamers, ZFN, TALEN, CRISPR/Cas9 or similar DNA or RNA cutters, etc.

How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular mammal, in which it is introduced, e.g. in cases where the nucleic acid expression cassette is used for gene therapy).

The transgene may be a full length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e. e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein typically encodes a gene product such as RNA or a polypeptide (protein).

In embodiments, the transgene encodes a therapeutic protein. The therapeutic protein may be a secretable protein. Non-limiting examples of secretable proteins, in particular secretable therapeutic proteins, include hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin, AAT, apolipoprotein A-I (apoA-I), matrix metalloproteinases including but not limited to matrix metalloproteinase-3 (TIMP-3), insulin, erythropoietin, lipoprotein lipase, nitric oxide synthase (NOS), antibodies or nanobodies, including but not limited to antibodies directed against any one of said transgenes, factors and their cognate receptors or against any secreted protein or viral protein, small interfering RNA, guide RNA, endonuclease, and Cas9, growth factors, cytokines, chemokines, plasma factors etc. The therapeutic protein may also be a structural protein. Non-limiting examples of structural proteins, in particular structural therapeutic proteins, include proteins modulating vascular relaxation and vasoconstriction, atherosclerosis. In preferred embodiments, the transgene comprises the nitric oxide synthase (NOS).

In embodiments, the transgene encodes an immunogenic protein. Non-limiting examples of immunogenic proteins include epitopes and antigens derived from a pathogen.

As used herein, the term "immunogenic" refers to a substance or composition capable of eliciting an immune response.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein, but may not be necessary. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron. Preferably, the intron is MVM intron.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit β-globin (mRBG) gene, and the synthetic polyA s(SPA) site as described in Levitt et al. (1989, Genes Dev 3:1019-1025). Preferably, the polyadenylation signal is derived from SV40 (i.e. SV40 pA).

In particular embodiments, the invention provides a nucleic acid expression cassette comprising, consisting essentially of, or consisting of a nucleic acid regulatory element selected from the group consisting of SEQ ID NO: 1 to 33 or a sequence having 95% identity to said sequence, operably linked to a promoter, preferably a promoter selected from the group consisting of the promoter from the cadherin-5, endothelin-1, endoglin, Fms-Related Tyrosine Kinase 1, or Intercellular Adhesion Molecule 1 gene or the promoter, and a transgene, preferably a transgene encoding a luciferase. In yet further embodiments the nucleic acid expression cassette further comprises a polyadenylation signal, preferably a polyadenylation signal derived from SV40.

In particular embodiments, the invention provides a nucleic acid expression cassette comprising, consisting essentially of, or consisting of a nucleic acid regulatory element selected from the group consisting of SEQ ID NO: 1 to 33 or a sequence having 95% identity to said sequence, operably linked to a promoter, preferably the promoter from the cadherin-5, endothelin-1, endoglin, Fms-Related Tyrosine Kinase 1, or Intercellular Adhesion Molecule 1 gene, and a transgene, preferably a transgene encoding a therapeutic or structural protein as defined herein. In yet further embodiments, the nucleic acid expression cassette further comprises a polyadenylation signal. In particular embodiments, any one of the following transgenes can introduced: secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin (AAT), matrix metalloproteinases including but not limited to matrix metalloproteinase-3 (TIMP-3) (TIMP-3), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, modulating vascular relaxation and vasoconstriction, atherosclerosis. In preferred embodiments, the transgene comprises the nitric oxide synthase (NOS).

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term 'vector' as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably a lentiviral vector. Lentiviral vectors are preferably derived from the human immune deficiency virus (HIV) though other lentiviral vectors based on other lentiviruses could also be used (including but not limited to Equine infectious anemia virus). Lentiviral vectors can transduce endothelial cells. Production of lentiviral vectors can be achieved by (VandenDriessche et al. J. Thromb Hemostasis, 2007) transient co-transfected of lentiviral vector plasmids encoding the gene of interest with the gag-pol, rev and env-encoding helper constructs. Typically, a heterologous envelope is used such as the vesicular stomatitis virus G glycoprotein (VSV-G) or an endotheliotropic envelope including but not limited to envelopes that confer antibody or nanobody (i.e. single chain antibody)-mediated endothelial retargeting targeting specific endothelial cell surface markers (VandenDriessche & Chuah, Blood. 2013 Sep. 19; 122(12):1993-4; Abel et al., Blood. 2013 Sep. 19; 122(12):2030-8; Buchholz et al. Trends Biotechnol. 2015 December; 33(12):777-90; Munch et al., Mol Ther. 2011 April; 19(4):686-93; Anliker et al., Nat Methods. 2010 November; 7(11):929-35).

In another embodiment the vector is an adeno-associated viral (AAV) vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), although the use of single-stranded AAV vectors (ssAAV) are also encompassed herein.

Production of AAV vector particles can e.g. be achieved by transient co-transfection of AAV-vector and AAV helper constructs, encoding AAV capsids into HEK293 cells, followed by a purification step based on cesium chloride (CsCl) density gradient ultracentrifugation, as described (Vanden Driessche et al., 2007). Capsids can also be derived from different serotypes or are specifically modified to enhance endothelial cell transduction either by evolution or selection, antibody (nanobody engineering) or the use of DARPin (Work et al., Mol Ther. 2006 April; 13(4):683-93; Munch et al., Nat Commun. 2015 Feb. 10; 6:6246; Buchholz et al., Trends Biotechnol. 2015 December; 33(12):777-90; White et al. Circulation. 2004 Feb. 3; 109(4):513-9.)

In yet another embodiment the vector is an adenoviral vector. Adenoviral vectors are preferably derived from the human adenovirus 5 serotype or from other serotypes that display increased tropism to endothelial cells, including but not limited to Ad5T*F35++(White et al., J Cardiothorac Surg. 2013 Aug. 9; 8:183. doi: 10.1186/1749-8090-8-183). Alternatively, the capsid can be engineered to enhance the endotheliotropic properties of the adenoviral vectors including but not limited to the references below (Nicol et al., FEBS Lett. 2009 Jun. 18; 583(12):2100-7; Nicklin and Baker, Mol Ther. 2008 December; 16(12):1904-5; Work et al., Methods Mol Med. 2005; 108:395-413; Work et al., Genet Vaccines Ther. 2004 Oct. 8; 2(1):14). They can be derived from either early-generation or helper-dependent adenoviral vectors (Mol Ther. 2010 December; 18(12): 2121-9). Production of these vectors has after transfection of adenoviral vector and helper constructs in HEK293T cells has been described previously (Mol Ther. 2010 December; 18(12):2121-9).

Since the nucleic acid regulatory elements are de facto modular, also combinations of the best endothelial cell-specific nucleic acid regulatory elements with any other endothelial cell-specific nucleic acid regulatory elements to maximize expression in the desired target tissue are tested. Consequently, this can lead to the generation of a versatile endothelial cell-specific nucleic acid regulatory element platform tailor-made for diseases that affect endothelial cells and tissues encompassing those. Furthermore, the endothelial cell-specific nucleic acid regulatory elements can also be combined with other promoters or nucleic acid regulatory elements active in other target tissues.

In other embodiments, the vector is a non-viral vector, preferably a plasmid, a minicircle, or a transposon-based vector, such as a Sleeping Beauty(SB)-based vector or piggyBac(PB)-based vector.

In yet other embodiments, the vector comprises viral and non-viral elements.

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 33, a promoter, preferably the promoter from the cadherin-5, endothelin-1, endoglin, Fms-Related Tyrosine Kinase 1, or Intercellular Adhesion Molecule 1 gene, a transgene, preferably a transgene encoding a therapeutic structural or secretable protein, and a polyadenylation signal. In particular, any one of the following transgenes can introduced: secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin (AAT), apolipoprotein A-I (apoA-I), matrix metalloproteinases including but not limited to matrix metalloproteinase-3 (TIMP-3) (TIMP-3), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, including proteins modulating vascular relaxation, vasoconstriction or atherosclerosis. In preferred embodiments, the transgene comprises the nitric oxide synthase (NOS).

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 33, a promoter, preferably the promoter from the cadherin-5, endothelin-1, endoglin, Fms-Related Tyrosine Kinase 1, or Intercellular Adhesion Molecule 1 gene, a transgene, preferably a transgene encoding secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin (AAT), apolipoprotein A-I (apoA-I), matrix metalloproteinases including but not limited to matrix metalloproteinase-3 (TIMP-3) (TIMP-3), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, including proteins modulating vascular relaxation, vasoconstriction or atherosclerosis. In preferred embodiments, the transgene comprises the nitric oxide synthase (NOS).

The nucleic acid expression cassettes and vectors disclosed herein may be used, for example, to express proteins that are normally expressed and utilized in endothelial cells (i.e. structural proteins), or to express proteins that are expressed in endothelial cells and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors disclosed herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, a further aspect of the invention relates to a pharmaceutical composition comprising a nucleic acid expression cassette or a vector described herein.

The use of nucleic acid regulatory elements described herein for the manufacture of these pharmaceutical compositions is also disclosed herein.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In a further aspect, the invention relates to the nucleic acid regulatory elements, the nucleic acid expression cassettes, the vectors, or the pharmaceutical compositions described herein for use in medicine.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder such as a disease or disorder related to endothelial cells.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. "Preventing" also encompasses preventing the recurrence or relapse-prevention of a disease or disorder for instance after a period of improvement. In embodiments, the nucleic acid regulatory elements according to any one of SEQ ID Nos: 1-33, the nucleic acid expression cassettes, the vectors, or the pharmaceutical compositions described herein may be for use in gene therapy, in particular endothelial cell-directed gene therapy.

Also disclosed herein is the use of the nucleic acid regulatory elements according to any one of SEQ ID Nos:

1-33, the nucleic acid expression cassettes, the vectors, or the pharmaceutical compositions described herein for the manufacture of a medicament for gene therapy, in particular endothelial cell-directed gene therapy.

Also disclosed herein is a method for gene therapy, in particular endothelial cell-directed gene therapy in a subject in need of said gene therapy comprising:

introducing in the subject, in particular in endothelial cells or tissue of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID Nos: 1-33, operably linked to a promoter and a transgene; and expressing a therapeutically effective amount of the transgene product in the subject, in particular in endothelial tissue or cells of the subject.

The transgene product may be any one of the following transgenes can introduced: secretable proteins, in particular secretable therapeutic proteins, including hepatocyte growth factor (HGF), coagulation factor VIII (FVIII), coagulation factor VII (FVII), coagulation factor IX (FIX), coagulation factor XI (FXI), tissue factor (TF), tissue factor pathway inhibitor (TFPI), von Willebrand factor (vWF), ADAMTS13, VEGF, PLGF, FGF, sFLT1, α1-antitrypsin (AAT), apolipoprotein A-I (apoA-I), insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, including proteins modulating vascular relaxation, vasoconstriction or atherosclerosis, In preferred embodiments, the transgene comprises the nitric oxide synthase (NOS).

Alternatively, the transgene product may be RNA, such as siRNA, or a nuclease such as ZFN, TALEN, CRISPR/Cas9 or similar DNA or RNA editing systems.

Exemplary diseases and disorders that may benefit from gene therapy using the nucleic acid regulatory elements, the nucleic acid expression cassettes, the vectors, or the pharmaceutical compositions described herein include: liver diseases, hemophilia A, von Willebrand disease, microvascular thrombosis, thrombotic thrombocytopenic purpura, peripheral vascular disease, coronary artery diseases, atherosclerotic diseases, stroke, heart disease, diabetes, insulin resistance, chronic kidney failure, tumor growth, metastasis, venous thrombosis, ischemia, tumour growth, tumour vascularisation, cancer and viral infectious diseases such as Ebola, Dengue fever and dengue hemorrhagic fever.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993). In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of medicament or a vaccine, in particular for the manufacture of a prophylactic vaccine.

Also disclosed herein is a method of vaccination, in particular prophylactic vaccination, of a subject in need of said vaccination comprising:

introducing in the subject, in particular in endothelial tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID Nos: 1 to 33, operably linked to a promoter and a transgene; and expressing an immunologically effective amount of the transgene product in the subject, in particular in endothelial cells or tissue of the subject.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one nucleic acid regulatory element) are higher than when an identical expression cassette or vector is used but without a nucleic acid regulatory element therein. More particularly, the expression is at least double as high, at least five times as high, at least ten times as high, at least 20 times as high, at least 30 times as high, at least 40 times as high, at least 50 times as high, or even at least 60 times as high as when compared to the same nucleic acid expression cassette or vector without nucleic acid regulatory element. Preferably, the higher expression remains specific to endothelial tissues or cells. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, and in some instances 300 days or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

Also disclosed herein is the use of the nucleic acid regulatory elements according to SEQ ID Nos: 1 to 33, or the nucleic acid expression cassettes, or the vectors disclosed herein comprising said nucleic acid regulatory elements, for transfecting or transducing endothelial cells.

Further disclosed herein is the use of the nucleic acid expression cassettes or the vectors disclosed herein comprising the nucleic acid regulatory elements according to SEQ ID Nos: 1 to 33, for expressing a transgene product in endothelial cells, wherein the nucleic acid expression cassette or the vector comprises said nucleic acid regulatory element disclosed herein operably linked to a promoter and a transgene.

Further disclosed herein is a method for expressing a transgene product in endothelial cells, comprising:

transfecting or transducing said cells with a nucleic acid expression cassette or a vector disclosed herein, wherein the nucleic acid expression cassette or the vector comprises a nucleic acid regulatory element according to any one of SEQ ID Nos: 1 to 33, operably linked to a promoter and a transgene; and expressing the transgene product in said cells.

Non-viral transfection or viral vector-mediated transduction of endothelial cells may be performed by in vitro, ex vivo or in vivo procedures. The in vitro approach requires the in vitro transfection or transduction of endothelial cells, e.g. cells previously harvested from a subject, cell lines or cells differentiated from e.g. induced pluripotent stem cells or embryonic cells. The ex vivo approach requires harvesting of the endothelial cells from a subject, in vitro transfection or transduction, and optionally re-introduction of the transfected cells into the subject. The in vivo approach requires the administration of the nucleic acid expression cassette or the vector disclosed herein into a subject. In preferred embodiments, the transfection of the endothelial cells is performed in vitro or ex vivo.

It is understood by the skilled person that the use of the nucleic acid regulatory elements, the nucleic acid expression cassettes and vectors disclosed herein has implications beyond gene therapy, e.g. coaxed differentiation of stem cells into endothelial cell precursors or endothelial cells, transgenic models for over-expression of proteins in endothelial cells or their precursors, etc.

The invention is further explained by the following non-limiting examples

EXAMPLES

Example 1: Identification of Endothelial Cell-Specific Nucleic Acid Regulatory Elements To identify the endothelial cell genes that are highly expressed, we followed several steps. First, we obtained the list of genes that are highly expressed in endothelial cells from the publication of Bhasin et al., 2010 (Genomics 2010, 11:342) showing 104 genes that were identified as endothelial-restricted genes. Subsequently, the specificity and robustness of expression of the endothelial-restricted genes was compared to that of 6 types of endothelial cells (i.e. LSEC: Liver Sinusoid Endothelial cells, HCAEC: Coronary Artery Endothelial cells, HMVEC: Dermal Microvascular Endothelial cells, HUVEC: Human Umblilical Vein Endothelial cells, IEn: Iliac Artery Endothelial cells, RE: Retinal Endothelial cells) based on the Reference Database of Gene Expression Analysis (RefExA). We identified 11 genes (Table 1) from this endothelial-restricted gene list that are highly expressed and specific among these quintessential endothelial cell types. Consequently, these 11 genes were then used for designing the endothelial-specific cis-regulatory elements (CREs: Table 2)

TABLE 1

Highly expressed genes in endothelial cells

| Highly expressed genes in endothelial cells | ENSEMBL Acc. No |
|---|---|
| IFI27 | ENSG00000165949 |
| ICAM2 | ENSG00000108622 |
| VWF | ENSG00000110799 |
| EDN1 | ENSG00000078401 |
| ENG | ENSG00000106991 |
| ECSCR | ENSG00000279686 |
| CDH5 | ENSG00000179776 |
| PECAM1 | ENSG00000261371 |
| HHIP | ENSG00000164161 |
| TIE1 | ENSG00000066056 |
| HYAL2 | ENSG00000068001 |

Figure 1:
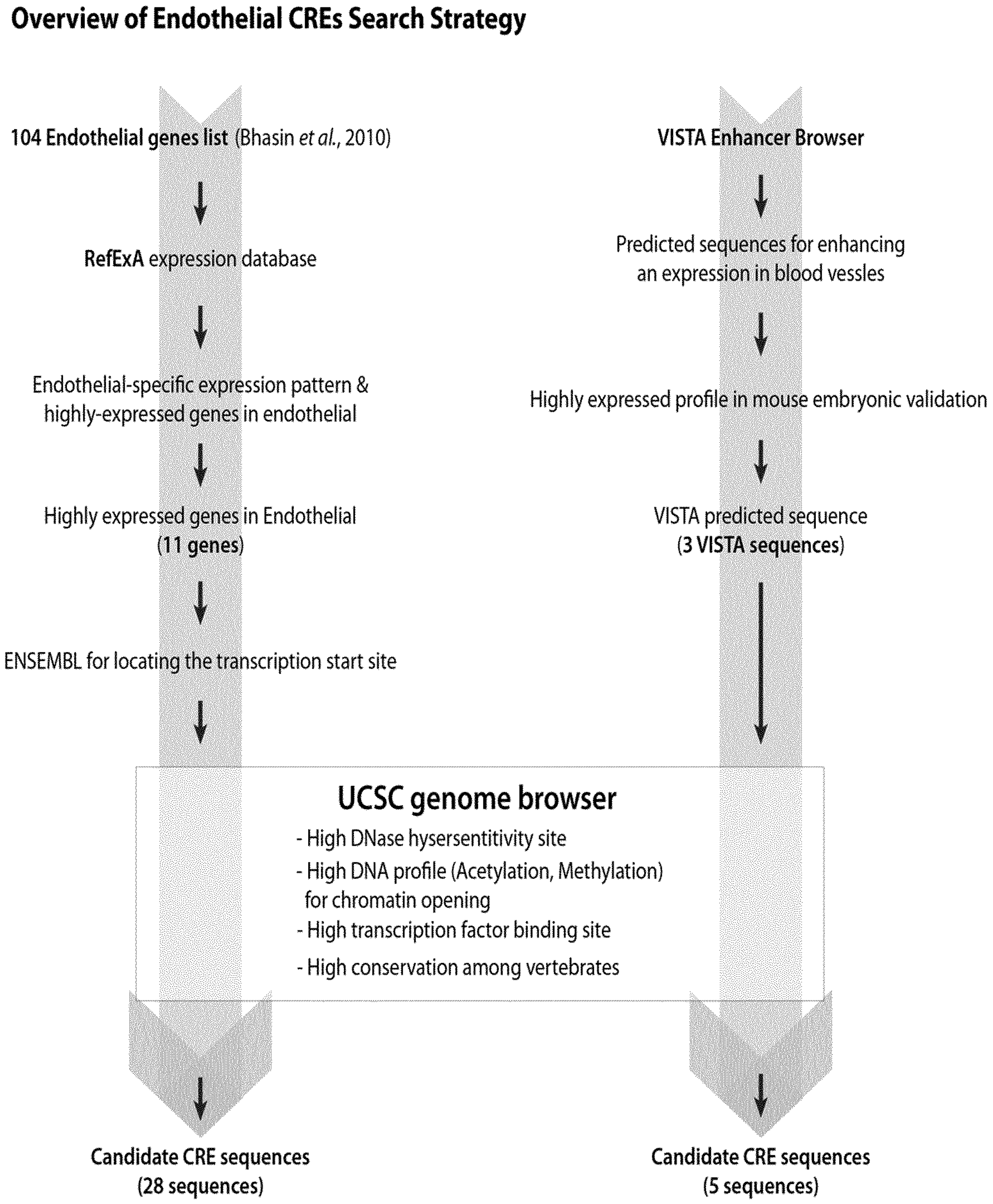
FIG. 1: The selection strategies of endothelial-specific CREs

Candidate CREs were selected using the University of California Santa Cruz (UCSC) Genome Browser database based on i) high DNase hypersensitivity sites; ii) high content of epigenetic markers associated with open chromatin (acetylation, methylation); iii) high content of transcription factor binding sites; iv) strong evolutionary conservation. The ideal CREs were expected to exhibit co-existence of predicted motifs together with DNase clusters, high conservation level in vertebrates, and explicit histone modification patterns. Therefore, 28 potential CRE sequences were selected based on those criteria (FIG. 1 and Table 2).

TABLE 2

The EC-CREs sequence for highly expression in endothelial cells.

| Gene | EC-CRE | Size (bp) | Sequence |
|---|---|---|---|
| CDH5 | EC-CRE1a | 76 | GCCCTCACAAAGGAACAATAACAGGAAACCATCCCA GGGGGAAGTGGGCCAGGGCCAGCTGGAAAACCTGA AGGGG (SEQ ID NO: 1) |
| CDH5 | EC-CRE1b | 277 | GGCCGAGGCAGCCGCCCACCGCAGGGCCTGCCTAT CTGCAGCCAGCCCAGCCCTCACAAAGGAACAATAAC AGGAAACCATCCCAGGGGGAAGTGGGCCAGGGCCA GCTGGAAAACCTGAAGGGGAGGCAGCCAGGCCTCC CTCGCCAGCGGGGTGTGGCTCCCCTCCAAAGACGGT CGGCTGACAGGCTCCACAGAGCTCCACTCACGCTCA GCCCTGGACGGACAGGCAGTCCAACGGAACAGAAAC ATCCCTCAGCCCACAGGCACGGTGAGTG (SEQ ID NO: 2) |
| CDH5 | EC-CRE1c | 408 | GCTTCCTCCTCTGCTACTAATCTGGTCTCACAGACCA TCCCATTTCCTGCTAGCCCACCAGCCGCCTTCCTTGC TCCCAATGACACTTCCTGGCCTTGTGCCCTCCTGTTA CCTCCTTTGCCTCCAGAGAGGTTGGAGCAGAGGCTG GGCAGTGCCAGAAATCAGGCATGAAATCCTCAGGGG GACCAAGGAGGCACCAGCCTCCCTCCCACAGTCTCA GCTACCTCTGCTACGGTGACCCCCAGCCCCACCCCT GGGGCCCACAGCTCATGCCTGGCTCACCATTCCTTT GTTTATGGACCACAGGAACAGTCGTTTTCAGGGCAGA GTCAACTTCCTCATGGACTGGGAGTACAAAGGGAATT GGCAGATGGTGCCAGGACAGGCCCTGTCCCCATCTG CCACAGC (SEQ ID NO: 3) |
| CDH5 | EC-CRE1d | 173 | GCTTCCTCCTCTGCTACTAATCTGGTCTCACAGACCA TCCCATTTCCTGCTAGCCCACCAGCCGCCTTCCTTGC TCCCAATGACACTTCCTGGCCTTGTGCCCTCCTGTTA CCTCCTTTGCCTCCAGAGAGGTTGGAGCAGAGGCTG GGCAGTGCCAGAAATCAGGCATGAAA (SEQ ID NO: 4) |
| CDH5 | EC-CRE1e | 307 | CCCAGCTGAGGGCTGGTGCCAGAGCCGTGTCTGCTT GCCCCATCAAGAGGTGGGAGGGATTGATCCACCTTC CTGCCCCACAGATGGTGCAGCCTCCAACCTATTGTTT TCCAGGACGCTTCGGTGGAGAGCACAAGGAATGTAG GGTCTAGAAACAGGAAGCCCTGGCTTCCGCTGGACA AGGTTTCCTCCAGACTCAGGCCTGCCCTCCAGACAA CAAGGCAGGGCCCTTGGTCCCACCCTGCCCTGCCTG GCTCACTGGGCCACCCCAAGGAAGGCCTTGCCCTCT CTGGGCTTCTGCATGTGA (SEQ ID NO: 5) |
| CDH5 | EC-CRE1f | 450 | AGGTATCCACCAAGGGGCCCAAGAGCTGCTGAGCCC CTGAGCAGCCCTACCAATTTCAGCTTATGGTGGTGAG GGGTAGGGGAGGTGTATACTGGCCTGGAAGGGGTTA AGCTGCCCGCCTGCAGCCTCAGCCTGAGCTATTGTG TTGCCAAACAAGGGCCGGACATGAGGGCAGGAAGCC AGCAGGGGCCACACATTTTCTGCAAAGTTGGATGATT CACTGCTGACTTGGGGACACCCAGGGGACAGAGGG GACACCATCCCAGGAAGAATCTTAGGCTCATTTTGCC CACATGGACCCATGACTGTTCCCTGTATCCTCTCTCT GCACCCCCTCAGTCACACTGAAGCAACTATGAGAATT CCCATTTGACAGATGGGACCATCGAGGCTGAGGGAA GCTGTGCAGCCAGTCCAAGGTCACACAACCAACACA AGGTAGAAGCAGGG (SEQ ID NO: 6) |
| ECSCR | EC-CRE1a | 123 | AGGGCCCCTGGAGCTGGTCCCAATGTGTTTCCTTCTA TTCTTTTGACAGGAAGCTCCTGGAGAGCCAGTCCCCA CCCCCATCCCGCCCCAGCACTCCCTCTCTCTTCTCCA CTATGGACAGAG (SEQ ID NO: 7) |
| ECSCR | EC-CRE1b | 499 | TAGGGCCTCTCTGAAAGATGTGGGGAGTCCTATCTG CATTGGGATCCCTGAGGAGGGAGAGGAATGTGGAGA ATTCAGGGTCCAGGGAGCATGGGTGACTGGTGGGCT GGGCTTCCAGGCTGAATCATGGGAAAGGAGAACCTG GTCTGAAACAGTACTGGGCGGGATTGGTGTTAGATTC CAGGAAAACCCCCAGGCGGTCTGTGGTGGAACCTGA TGGACCCTCAGAAGGGAAGAGAATGGGGATGGGGC CAGGTTGCCATGGTTGGTCATTGTGCATAGGCACTAG AGGCCATGCTGGGTGGGCACAGTCGCTGCTGCAGC CTCACATCCTCATCTGGACATGGCTGAGCAGGGCCC CTGGAGCTGGTCCCAATGTGTTTCCTTCTATTCTTTTG ACAGGAAGCTCCTGGAGAGCCAGTCCCCACCCCCAT |

TABLE 2-continued

The EC-CREs sequence for highly expression in endothelial cells.

| Gene | EC-CRE | Size (bp) | Sequence |
|---|---|---|---|
| | | | CCCGCCCCAGCACTCCCTCTCTCTTCTCCACTATGGA CAGAGCCTCCACTGAGCTGCTGCCTGCC (SEQ ID NO: 8) |
| EDN1 | EC-CRE1a | 455 | GAGACATAAAAGGAAAATGAAGCGAGCAACAATTAAA AAAAATTCCCCGCACACAACAATACAATCTATTTAAAC TGTGGCTCATACTTTTCATACCAATGGTATGACTTTTT TTCTGGAGTCCCCTCTTCTGATTCTTGAACTCCGGGG CTGGCAGCTTGCAAAGGGGAAGCGGACTCCAGCACT GCACGGGCAGGTTTAGCAAAGGTCTCTAATGGGTATT TTCTTTTTCTTAGCCCTGCCCCCGAATTGTCAGACGG CGGGCGTCTGCCTCTGAAGTTAGCAGTGATTTCCTTT CGGGCCTGGCCTTATCTCCGGCTGCACGTTGCCTGT TGGTGACTAATAACACAATAACATTGTCTGGGGCTGG AATAAAGTCGGAGCTGTTTACCCCCACTCTAATAGGG GTTCAATATAAAAAGCCGGCAGAGAGCTGTCCAAGTC AGACGCGCCTC (SEQ ID NO: 9) |
| ENG | EC-CRE1a | 153 | TGTCCACTTCTCCTGACCCCTCGGCCGCCACCCCAG AAGGCTGGAGCAGGGACGCCGTCGCTCCGGCCGCC TGCTCCCCTCGGGTCCCCGTGCGAGCCCACGCCGG CCCCGGTGCCCGCCCGCAGCCCTGCCACTGGACAC AGGATAAGGCCC (SEQ ID NO: 10) |
| ENG | EC-CRE1b | 125 | GGGCCCCCCACCCAGTGACAAAGCCCGTGGCACTTC CTCTACCCGGTTGGCAGGCGGCCTGGCCCAGCCCCT TCTCTAAGGAAGCGCATTTCCTGCCTCCCTGGGCCG GCCGGGCTGGATGAGCC (SEQ ID NO: 11) |
| ENG | EC-CRE1c | 498 | GGGATGGGAGGGTGGGGTGCTTGGGGAGACAAGCC TAGAGCCTGGGCCCTCCCACCCCACTGCCTCCCCCC ATCCCAGGGCCCCCCACCCAGTGACAAAGCCCGTGG CACTTCCTCTACCCGGTTGGCAGGCGGCCTGGCCCA GCCCCTTCTCTAAGGAAGCGCATTTCCTGCCTCCCTG GGCCGGCCGGGCTGGATGAGCCAGGAGCTCCCTGC TGCCGGTCATACCACAGCCTTCATCTGCGCCCTGGG GCCAGGACTGCTGCTGTCACTGCCATCCATTGGAGC CCAGCACCCCCTCCCCGCCCATCCTTCGGACAGCAA CTCCAGCCCAGCCCCGCGTCCCTGTGTCCACTTCTC CTGACCCCTCGGCCGCCACCCCAGAAGGCTGGAGC AGGGACGCCGTCGCTCCGGCCGCCTGCTCCCCTCG GGTCCCCGTGCGAGCCCACGCCGGCCCCGGTGCCC GCCCGCAGCCCTGCCACTGGACACAGGATAAGGC (SEQ ID NO: 12) |
| HHIP | EC-CRE1a | 136 | AGCGGTGACGTCAAGGGGCGCGCTGTGGCAGCACC TCCCCGCGCGCTAGTTAAAAAGAAGAAGAAAAGAGG GAACGAAACATGAGAGGCTGTGTGAGAAGCTGCAGC CGCCGGCAGAGGAGACCTCAGCATCATCT (SEQ ID NO: 13) |
| HHIP | EC-CRE1b | 574 | CTGGGCGGGGGCGCGCGAGAAGCGGTGACGTCAAG GGGCGCGCTGTGGCAGCACCTCCCCGCGCGCTAGT TAAAAAGAAGAAGAAAAGAGGGAACGAAACATGAGA GGCTGTGTGAGAAGCTGCAGCCGCCGGCAGAGGAG ACCTCAGCATCATCTAGAGCCCAGCGCTGGCCCTGC CTCCGCCTGCCCCGCCGCCGCCGTCGCCGTTTCTGT TCCTGCTACTGTCCCACCTAAACAACTCCCGTTACAC GGACAAGTGAACATCTGTGGCTGTCCTCTCCTTTTCT TCCTCCTCTTCCAACTCCTTCTCCTCCTCCCACTTCC CAGCCGCAGCAGAAAGCCCCCAACCCAACTGACACT GGCACAACTGCAAACGGTGTCATCCGCACAACTTTAT CTCGCTCCTCGGGCTCCCCTAAGGCATTGGACCCAT CGCCGCGTCTTTTATTTTTTGCAAAGTTGCATCGCTG TACATATTTTTGTCCCCGCCACCTCCCTCTGTCTCTG GAGTGCCCTACAGCCCCGCAAACTCCTCCTGGAGCT GCGCCCTAGTGCCCCTGCTGGGCAGTGGCGT (SEQ ID NO: 14) |
| HYAL2 | EC-CRE1a | 170 | AGGGAACTCCCTGTGCTGGGCCTACCCAGCTGACCC CATCGCTGGAAACAATGGGGGTCAGGCAACACTTCC CCACTCTCTCCCGCCGGGCTGTGCTCACTTCCTTCCT GCTGGCTGCCTGAGGAAGTGTCCCTGCCCTGGGACA GTCTGGCCTAGCCTTTGTTTCCCCG (SEQ ID NO: 15) |

TABLE 2-continued

The EC-CREs sequence for highly expression in endothelial cells.

| Gene | EC-CRE | Size (bp) | Sequence |
|---|---|---|---|
| HYAL2 | EC-CRE1b | 470 | GACAGGCTTCTGAGTGTAGGGAGCTGGTCTGCCAGT CTTTCGGAGGTTTGAACTTGTCAAGGCTAGGGCAGG ATCACCATATCCAGCCTGGACTTGCAGTTCTGTGGGG TGCCTCCCCATACCCCCATAAGATGCCAAACATGAGG CCCTGTCATCCTCCATGGTCCCCCTCTACTGGCTGTT CAAGGCCCAGGGCTCTCCCATGCCAGATAGCATCCT GTCTCCTACCACCACTGTCCCAGCCTGAGGGAACTC CCTGTGCTGGGCCTACCCAGCTGACCCCATCGCTGG AAACAATGGGGGTCAGGCAACACTTCCCCACTCTCTC CCGCCGGGCTGTGCTCACTTCCTTCCTGCTGGCTGC CTGAGGAAGTGTCCCTGCCCTGGGACAGTCTGGCCT AGCCTTTGTTTCCCCGGGGGTCCCCACCCATGGAGC TTTCAAGGCTTCTGGCCCCTGTGAAGCCAGCACA (SEQ ID NO: 16) |
| HYAL2 | EC-CRE1c | 602 | CAGTGGAAAAAAACGGACTCAGCTACTGGAAGTCCC CCCGACCCTCCCCCCAAGGCTAGTTCCCTTCTTGGG CACCTGCTCTGGGGGACCATCAGCTGAACGACCCCC AAGTATTTTGACTCCCAAAAGCACCACCACCTGACCC CATCCTCTCACACCCTACTGGATTTGAGGATGGGCCC CAATCCTAGGGAAGGAGTGAAGAGGTTCCCTAGTGT TGGAAGCTGTGGGTGTGGGGGAGATTGGCACCTGAT CCTGAGCCCATAGCCTTCCTGTCACCTGGCGCAGCT GGCGGGGCCAGATCCTACTCGGGAAGGGTGGGGAG GGCAGCCAGCCAGCAGGGCATTCTGGAGGGAAACA GGGTCAAGGCGATCTCCTCCCCCACGCCTGTTCCTG GCCCTTTCCTCTCAGGGGGCAGCAGGAAGTGAGGAG AAAGGGCTGGGATGGGAGGCGGGAGCGGATGGGAG GGAATGGGGTTTATCAAGTCCTCGGCGAGCTGCCCA ACGGGCAGCAGCTGGCGCAAGTAGCCTAGCTGGAG AGGCTCACCCCAGGAAGGAGGGAGGCCACCGACCT ACTGGGCCGACGGACTCCCACACAGGTGA (SEQ ID NO: 17) |
| ICAM2 | EC-CRE1a | 265 | CTTGCATAGATGGCCAGCGTTCATACTTTCTGCTTGT TTGTACAAAGTCATTCTTCTAGAGTAATTGTTGTAAAA TTGCTAGGCAAGGTGGCAGGTCTGATAAGATTTGATG ACGTAATGGCTCTTAGTCGCTAATAAGAGGCTTTTGT GGAGTGGCGTGTCACAGCCAGCGAAGGCTCAGCTCT GTGATCTTCGCCTGCCTCACTTGGGGGACCAGAAGG CAGCTTGTCTTGGAACTGCCTCATTCACAGAAGACCC CATTGAG (SEQ ID NO: 18) |
| ICAM2 | EC-CRE1b | 545 | TTTACCTAGCATGATCTTGGCAGTTCAAAGAGGAATG TGCCAGAAACCAAGCAAAGAAGAAAAAGAAATAAATG GAAATGGAAAGTGATCTGCTCAGAGGCCACAAAGTT GAGGGAGGAGGTTTCCAGAGTGGGATTTGGCCCAAA TGTTGCCTGAGGAAGTACGTAAAGGGGTCTCAACTCT GGCTACACAACAGAACAGCAGGACTGTGTGTGCAGC TCACGAAGTGGGTACACAGGGTAATCTGCAAGTTCTG GGTGGATCTAGCACCTGGATTGTTAAAACTTGCATAG ATGGCCAGCGTTCATACTTTCTGCTTGTTTGTACAAA GTCATTCTTCTAGAGTAATTGTTGTAAAATTGCTAGGC AAGGTGGCAGGTCTGATAAGATTTGATGACGTAATGG CTCTTAGTCGCTAATAAGAGGCTTTTGTGGAGTGGCG TGTCACAGCCAGCGAAGGCTCAGCTCTGTGATCTTC GCCTGCCTCACTTGGGGGACCAGAAGGCAGCTTGTC TTGGAACTGCCTCATTCACAGAAGACCCCAT (SEQ ID NO: 19) |
| ICAM2 | EC-CRE1c | 554 | ATGGCAGCTGGCAGGTGCCTTCACGTCCAGGGTTTC CAGAGAGAAAGCATCTCTCCTCCGCAGAGACCCTCC CACGCTCTCCCTCCCTCAAATTAGTGCATCTACATAG ACCGCCCTCCTTATAAACAGTCTCTCAGGGGATCCTA GCCCATTCCAAATCTACCTGTGATTGCAGAATCGCAA GGAATGTGATTTACCGCAGATCGCGGGGCGTCGTGT CTTTTAGGGGACCTGCTCACTTTGGCCACTAGGTGG CGGGCAGTGCAGCCCCTGCTCCTGTCGACCCTGAGC GTTCAGCGTTTCCGCCGCCTCCGCCCCACTCCGTAG GGGGAGCTGATGAGATGAGGTTGAGGTCCAGGAAGA CGTCAAGGGCTTGGTTTTGTAAACAACTCCATTCCTC GCTCGCTGATAAGTTTTCTAAGTGATGCATATTCACAA CCTTGTCCCATCCAAGGACCCAAGAATTAACACATTA |

TABLE 2-continued

The EC-CREs sequence for highly expression in endothelial cells.

| Gene | EC-CRE | Size (bp) | Sequence |
|---|---|---|---|
| | | | CATAATATGGACAGCCCCCTCCTGTCCAACGGGCAT GATTTTGGGGTCTGATATTCTGTGGATCTGTGCAATA GTCAAC (SEQ ID NO: 20) |
| IFI27 | EC-CRE1a | 450 | AGACTTTTTTTGAAAAACGGAACATCTGCCTATCGCA AGGACTACTATTATTCTGAAAATCACCTTCTTCATTAG AAAGTAATATTTATCATTTTATTATAGAACTTTGATCTT ACTTCTTGTGACTTCATTCTGCGTAGAGCACACTCCC ATCCTTGAATTAAATGACAAAGCATTTTATATTAACTG ACAATGACTGATGCCATGGGCAAATCCTATTTCTGTA AATAACTGAATTTTCTTCTGGACTGCGCATGAGGGGA GAAAGATGTCTGCAGTTTCGGTTTCCTGGAAAATGAA ACCTATCTCATTTGTTGCCTGTGTCAAGGGGCAGTGC TTCAGTCGGGGTGGAGCTGCTTAAAAGGCCTGGGAT CACACCCTTTGGGAACACATCCAAGCTTAAGACGGTG AGGTCAGCTTCACATTCTCAGGAACTCTCCTTCTTTG GGT (SEQ ID NO: 21) |
| IFI127 | EC-CRE1b | 570 | GAGACTTTTTTTGAAAAACGGAACATCTGCCTATCGC AAGGACTACTATTATTCTGAAAATCACCTTCTTCATTA GAAAGTAATATTTATCATTTTATTATAGAACTTTGATCT TACTTCTTGTGACTTCATTCTGCGTAGAGCACACTCC CATCCTTGAATTAAATGACAAAGCATTTTATATTAACT GACAATGACTGATGCCATGGGCAAATCCTATTTCTGT AAATAACTGAATTTTCTTCTGGACTGCGCATGAGGGG AGAAAGATGTCTGCAGTTTCGGTTTCCTGGAAAATGA AACCTATCTCATTTGTTGCCTGTGTCAAGGGGCAGTG CTTCAGTCGGGGTGGAGCTGCTTAAAAGGCCTGGGA TCACACCCTTTGGGAACACATCCAAGCTTAAGACGGT GAGGTCAGCTTCACATTCTCAGGAACTCTCCTTCTTT GGGTAAGACTGGGAGGGTGGGCAGGAGCTACCCTT CCCGTGGCCCCGGACCTTGGGTGGGCTGTGGGCTC AGGGAGCGGAGGGGAGGCCTTAAGCATCCACTCTCT GCCCGGTGTTTTTGTTC (SEQ ID NO: 22) |
| IFI27 | EC-CRE1c | 513 | AGGTGGGGATGAGGGGCTAAGTATGAACCAAGGAGC TAGAAATACAGCACTGGAAGCTGGAAGCAGGGGGCT TGGAGACTGGGAGCTGGAGTGCGTGTGGGCAGGGT GTGGCAGCAGCCGGCAGAGGCCATTTCCCCTTGGCA GAACATTCACCATGTGACCCTGAGCATGTCTTTGAAC TCCTCTGAGCTCCTGTTTCCTCTCCAGAGAAAAGGCT GGTAATGCCCATTCAGGGTTATGGTCAGGATTGCATA GGGTGAAACAATAGAGATTGAACACAGTAGACATGAA AGAGATGCCAGGGCTCAGCTCCCTTTGGTTTAGTTGC TTCCAGTGTGCTCTGTGGCAACACCACGGAGCCCTA GAGCTGTCTCTTTGAGCCGCTCTGAATGTGCCTCTTA CATAATCTCCTGGGCAACATCTGCTCCCCTAATGAGA TTTGCTCCCCAGCAAAGATAAGAAACTTGCCAACCAC TCCCCTGGTCCAGCATTTGGCCAAGGCAGACACTGA GG (SEQ ID NO: 23) |
| PECA M1 | EC-CRE1a | 217 | ACCTCACTCAATGCATGGAAGTTGACACAATGGCTCA ACATTAGCGTTGGGCTGATTCATCATTTGGCTGTTGA CACCAGCCTCTGGCCCAGCCAGGACAGAAAAAGGGC CCCTGAGGAACTTCTGGCTCTGTTCCCTCTATGGGG GAGGGGCAGTGGACTTGTGATAAGACAGGGTGTTAG GGTGAGGTGGACTTGGGGAAACAGGATATTTCTAA (SEQ ID NO: 24) |
| TIE1 | EC-CRE1a | 97 | GGGGGGAGGGGAGACCCCAGAACAATGTCCCCCAC CCCACCCCCCTCCTCAATAGGCGGAAGCCACTGGCT TCCTCCCTTTCCTGCCTCCTGCCTCC (SEQ ID NO: 25) |
| TIE1 | EC-CRE1b | 427 | GTGTGTTTGTGCCGGGGGGAGGGGAGACCCCAGAA CAATGTCCCCCACCCCACCCCCCTCCTCAATAGGCG GAAGCCACTGGCTTCCTCCCTTTCCTGCCTCCTGCCT CCTTTGTGCCAGCAAGACTGAGTACTGGAGAGAGAC AGGGGATGGGAAAAATCAGTCCAGCTGTCCCCAGGT CTGCCCTTACCATAACCTTCCCCCCACCTCAAGTGAC TCCTCCCAGGCCACACCCATCCCCAGCCTTGTGGGG GCCAGATTGGGGGGCCTAGAGGCTCAAAGGCAGAAT GAGTCCTCCCACCCCCTACCCTGCCACCCCTCCCAC CCAAGCCACCTCATTTCCTCTTCCTCCCCAGCACCGA |

TABLE 2-continued

The EC-CREs sequence for highly expression in endothelial cells.

| Gene | EC-CRE | Size (bp) | Sequence |
|---|---|---|---|
| | | | CCCACACTGACCAACACAGGCTGAGCAGTCAGGCCC ACAGCATCTGACCCCAGGCCCAGCTCGTC (SEQ ID NO: 26) |
| VWF | EC-CRE1a | 119 | CTACAAAGCTTTATCAGCTTGGAGGTACTTCTAATAC CATTTCCTTTCATTGTTTCCTTTTGGTAATTAAAAGGA GGCCAATCCCCTGTTGTGGCAGCTCACAGCTATTGT GGTGGGAA (SEQ ID NO: 27) |
| VWF | EC-CRE1b | 385 | CTGCCAGGAGGTCTCCCTCCAAACTCTACAAAGCTTT ATCAGCTTGGAGGTACTTCTAATACCATTTCCTTTCAT TGTTTCCTTTTGGTAATTAAAAGGAGGCCAATCCCCT GTTGTGGCAGCTCACAGCTATTGTGGTGGGAAAGGG AGGGTGGTTGGTGGATGTCACAGCTTGGGCTTTATCT CCCCCAGCAGTGGGGACTCCACAGCCCCTGGGCTAC ATAACAGCAAGACAGTCCGGAGCTGTAGCAGACCTG ATTGAGCCTTTGCAGCAGCTGAGAGCATGGCCTAGG GTGGGCGGCACCATTGTCCAGCAGCTGAGTTTCCCA GGGACCTTGGAGATAGCCGCAGCCCTCATTTGCAGG GGAAGGTATGGCCTTTGGAA (SEQ ID NO: 28) |

Alternatively, the VISTA enhancer browser (enhancer.lbl.gov) was also applied, a central resource for experimentally validated human and mouse non-coding fragments with gene enhancer activity. This also provided the predicted DNA elements associated with high expression in blood vessels. The predicted sequences from VISTA were selected based on the validated data using mouse embryonic staining. Up to 3 VISTA sequences were selected from these validated data. However, since the DNA fragment sizes were too large to be accommodated into a viral vector, the selected sequences were further trimmed down or separated into sub-fragments using the UCSC genome browser using the aforementioned criteria. This resulted in 5 CREs derived from the 3 selected VISTA sequences (Table 3). All of the endothelial-specific CREs sequences were further validated both in vitro and in vivo to investigate their specificity and robustness in endothelial cells.

TABLE 3

The EC-CREs sequence for highly expression in endothelial cells from VISTA Enhancer browser.

| VISTA code | EC-CRE | Size (bp) | Sequence |
|---|---|---|---|
| Hs185 9 | EC-CRE-V1 | 517 | GCCATTGGCTGGTCCTTCACTGACAGCAGAAACT TGGCCAATGGCAATCAATCAGGGGGCCCGCGCT GCCTTAAATACCAGCAGAGCAAACAGCCTCAGAC AAAGCTGCGCCGTGTATCAATTACCGAGAGGCT GCGTGCTCCTCTGGGCGGAGGGAGCCGGAGCG AGCGGCCAGGGCTGCTGCCCCAGCTGATAAGG GCCCGCATTGTTCGGGGACAGCTGGCAGCCCGA TAAGGGCCTGCTCGCCCGAGATAATGGCAGTGG GCAGGCGCCTCGCGGCAGTTTAGAATTTCTTGG GTCTCCAAGAAAGGTTCTATTAAGCCCACTGACC CCAATTGAATATTAATTAGCTAATTAACGGATTTA TTGTTCCACGCCATTTCTGGAGAGGCCATTTTTTT TCGAGTGCCATTATTTTTGTAAATGATTTTTCGCA TTGTTCATAATTGAATCTTTGCAGCTGCCAGCATC TTCTGCATGATTTGGCAAAAAAAAGGAAGCAGAA GCACTTAGGGTT (SEQ ID NO: 29) |
| Hs217 9 | EC-CRE-V2 | 511 | CCCCTAATAAACAGGAAGGCATCCGCGCCATTA GTATCCATCCTTTTCAGAGCATCTGAGACCTGTC TGGACCATCAAAGCCATCCCCAGCCCCCAGGAG CCTACTGGAGGAGACACCAGCCTCGCCAAAACA ATTCTCCATTGTGTTCTTCCCCTTAGAAATCATGG GTTTGTAAACAGGCCCTTACATTTCAGCAGGTCC TGCCCTGGCTTTGTGCTGGTGTGTTGTTTTTTCTT CCCTGAACAATGTCCTTTCCAGTAGGGCCAGCC GTTCACACCATTGTCTGAGACCCTTGGACTACAG GAAACATCACCAGATTCTTATCAGTTGGGGGCAG GAGTGGGGGGGTGAACAGATGAGATCATGTCCA CAGAGCAAGTGGCTGGTGTGCCACGTCATTCCC CATGCCTTCATCTGTGAGAGCAGAGCCCGCTCG |

TABLE 3-continued

The EC-CREs sequence for highly expression in endothelial cells from VISTA Enhancer browser.

| VISTA code | EC-CRE | Size (bp) | Sequence |
|---|---|---|---|
| | | | CCCTCCATCAATCTGGGCTTCATGTGTCCAGAGT CCAGTCCCCTCTATTTGGTGGTAGACACCTGGAC TCTGTT (SEQ ID NO: 30) |
| Hs2179 | EC-CRE-V3 | 390 | TCCTACAGTTATGGGTCTGTCTTTCCTGCTAGAT CAGAAGCTCCAGGGACCTGTCTGTCTTATTAACC TTTCTTCCCCTCATGATGCCTGGCCCAGGACTCC ACGTTCAGAGGCAGTTTAATGTCTACAGAACTGA TGGATGCTCCATACCCTGTATTCATAAGCCTGTG TTTTGCTGCCAAACACCAGAGGGCACTGTTAGCA TGTCGATGAAGATTATAAACCCTCAGACCTGGAA GGCTGGGAAAGGCTTATGAAAATCTTGCTTCTGT TTTGGGATTACATAAGACTTATTGCGCCTCAATTG TTCTAAACACATCTGTTCGAGTTTATTCATGAGGC ACGTTCCTGTTGGGGTTAGAGATGAGTTTGAAAG CTCCCCGTCACAGG (SEQ ID NO: 31) |
| Hs1882 | EC-CRE-V4 | 573 | AGGGACTGTTGGGCAGCCCCAGACTGGCACAGG TGGATCGGGTGCCTAGGCAGGGGGTGGTGAGTT ATGGCGCAGCTGTCTTGGTGGCTGGGGGGAGCA GGGATAAGGGTGGACTTCTTAGTGACCGCTCTCT GCCCCAGGAGGTAGAGTCCTGGGGGCTGGGCT GGCCTGAGAGACGCCCCCTCATCCTTTCCAGGG TGAGGTACGAGGGCTCCGCCCCCTCCTGATATC ACCAGGCCTAGGGCAGCATCCTGATGGGGGAG GGGCAAGTGACCCGGGCCCTGGACTGCAGGAA CAGCCCCTCCTCCACTGGTGGAGTTCCCACTTC CTGCGGAAGGAACTATGTTAGAAGTTGTGTATAT GGGGTGGGGGTTGGGTGTGGGTGGCGGGGGG CCTGGGTGGGGTCCACTGAGTCGCCTCCCCTGT CTCCCTGCACTTCCTCCTGGAGGAAATGGGGAC AACAGGATGAAGTGAGGGCCTGCTGAGCCCAGG GCTGCCACCTGGGAGTGAAGCCGGGGCAGGCT GCAGGGTCCGGGCCCTTCTGTGTGGGCAGGTG GAAGTGGTGGGGATGCA (SEQ ID NO: 32) |
| Hs1882 | EC-CRE-V5 | 441 | GGGGAGAGGGTGTGGGGTGGGGTGGGGAGAG GGTGTGGGGTGGGGTGGGGAGAGGGGATGGGA TGGCATGGGGGGATGTGGCAGTGAGGAGGCTG GGCCCTTGGAGCTGCCGAGTGCAGGGGCCTGG AGGACTCCGGGAAGGCGTCCTAGTGCATCAAGC GTGGGCTTGGCCTGCTTGGGTCTCCCCTCCTGG CCCCCCTAGCAATGGGCGGACTTGGGCCCGCTC TGGGAGGATTCCAGGAACGGCTCCTGCCTGGTT ATAAATAGACTTCTCCGAAAGGCCTGGGGCTGTG CCAGCTGCAGCAGGTGCCTCCCAGGCCCGGCC AGAGGGCCCCAGGCAAGGGGGTGGAGCCCGGG TGGGGGTGATGAGGATGCTGGGGTCCACTTTTG TAGCGCCAGAGGCGACGGGCTCTGTCTGGTTGT AGCATCACAGAGCTTGAT (SEQ ID NO: 33) |

Example 2: Lentiviral Transduction of Human Endothelial Cells In Vitro

To validate the potential endothelial cell-specific CREs, we first validated a robust endothelial-specific promoter. The selected endothelial cell-specific CREs were cloned upstream of this promoter. We identified several human endothelial-specific promoter such as the human CDH5 promoter (1,303 bp) and human EDN1 promoter (455 bp) (The sequence of the CDH5 was obtained from Genecopoeia (www.genecopoeia.com) and for EDN1mini promoter, we selected the promoter sequence using the same concept as we select the CREs from UCSC). In addition, we also identified several endothelial promoters that are commercially available (Invivogen, USA) such as the as ENG promoter (888 bp), FLT1 promoter (1,037 bp), and ICAM2 promoter (399 bp). The sequences of these promoters are provided in Table 4. The endothelial-specific promoters were cloned into the lentiviral vector plasmid upstream of the FVIII or GFP reporter gene (FIG. 2). Nine different lentiviral constructs were generated (designated as:

1) pLVX-CMV-GFP (SEQ ID NO:40),
2) pLVX-CMV-FVIII (SEQ ID NO:41),
3) pLVX-hEDNlmini-FVIII (SEQ ID NO:42),
4) pLVX-hEDNlmini-Kozak-FVIII (SEQ ID NO:43),
5) pLVX-hICAM2-FVIII (SEQ ID NO:44),
6) pLVX-hICAM2-Kozak-FVIII (SEQ ID NO:45)
7) pLVX-hICAM2-Kozak-Luc2 (SEQ ID NO:46)
8) pLVX-EC-CRE-h(uman)ICAM2-Kozak-Luc2 (SEQ ID NO:47)
9) pLVX-EC-CRE-h(uman)ICAM2-Kozak-FVIII (SEQ ID NO:48), by conventional cloning. pLVX can also be a pCDH backbone or another (lenti)viral backbone.

TABLE 4

| Endothelial-specific promoter sequences | | | | |
|---|---|---|---|---|
| Promoter | Host Species | Size (bp) | Sequence | Source |
| CDH5 | Human | 1303 | GCTTGCCCAGCTATATAATAAAACAAGTTTGGGACTTCC CAACCATTCACCCATGGAAAAACAGAAGCAACTCTTCAA AGGACAGATTCCCAGGATCTGCCCTGGGAGATTCCAAA TCAGTTGATCTGGGGTGAGCCCAGTCCTCTGTAGTTTTT AGAAGCTCCTCCTATGTCTCTCCTGGTCAGCAGAATCTT GGCCCCTCCCTTCCCCCCAGCCTCTTGGTTCTTCTGGG CTCTGATCCAGCCTCAGCGTCACTGTCTTCCACGCCCC TCTTTGATTCTCGTTTATGTCAAAAGCCTTGTGAGGATG AGGCTGTGATTATCCCCATTTTACAGATGAGGAAACTGT GGCTCCAGGATGACACAACTGGCCAGAGGTCACATCAG AAGCAGAGCTGGGTCACTTGACTCCACCCAATATCCCT AAATGCAAACATCCCCTACAGACCGAGGCTGGCACCTT AGAGCTGGAGTCCATGCCCGCTCTGACCAGGAGAAGC CAACCTGGTCCTCCAGAGCCAAGAGCTTCTGTCCCTTT CCCATCTCCTGAAGCCTCCCTGTCACCTTTAAAGTCCAT TCCCACAAAGACATCATGGGATCACCACAGAAAATCAA GCTCTGGGGCTAGGCTGACCCCAGCTAGATTTTTGGCT CTTTTATACCCCAGCTGGGTGGACAAGCACCTTAAACC CGCTGAGCCTCAGCTTCCCGGGCTATAAAATGGGGGTG ATGACACCTGCCTGTAGCATTCCAAGGAGGGTTAAATG TGATGCTGCAGCCAAGGGTCCCCACAGCCAGGCTCTTT GCAGGTGCTGGGTTCAGAGTCCCAGAGCTGAGGCCGG GAGTAGGGGTTCAAGTGGGGTGCCCCAGGCAGGGTCC AGTGCCAGCCCTCTGTGGAGACAGCCATCCGGGGCCG AGGCAGCCGCCCACCGCAGGGCCTGCCTATCTGCAGC CAGCCCAGCCCTCACAAAGGAACAATAACAGGAAACCA TCCCAGGGGGAAGTGGGCCAGGGCCAGCTGGAAAACC TGAAGGGGAGGCAGCCAGGCCTCCCTCGCCAGCGGG GTGTGGCTCCCCTCCAAAGACGGTCGGCTGACAGGCT CCACAGAGCTCCACTCACGCTCAGCCCTGGACGGACA GGCAGTCCAACGGAACAGAAACATCCCTCAGCCCACAG GCACGGTGAGTGGGGGCTCCCACACTCCCCTCCACCC CAAACCCGCCACCCTGCGCCCAAGATGGGAGGGTCCT CAGCTTCCCCATCTGTAGAATGGGCATCGTCCCACTCC CATGACAGAGAGGCTC (SEQ ID NO: 34) | *Genecopoeia* |
| EDN1 | Human | 455 | GAGACATAAAAGGAAAATGAAGCGAGCAACAATTAAAAA AAATTCCCCGCACACAACAATACAATCTATTTAAACTGT GGCTCATACTTTTCATACCAATGGTATGACTTTTTTTCTG GAGTCCCCTCTTCTGATTCTTGAACTCCGGGGCTGGCA GCTTGCAAAGGGGAAGCGGACTCCAGCACTGCACGGG CAGGTTTAGCAAAGGTCTCTAATGGGTATTTTCTTTTTCT TAGCCCTGCCCCCGAATTGTCAGACGGCGGGCGTCTG CCTCTGAAGTTAGCAGTGATTTCCTTTCGGGCCTGGCC TTATCTCCGGCTGCACGTTGCCTGTTGGTGACTAATAAC ACAATAACATTGTCTGGGGCTGGAATAAAGTCGGAGCT GTTTACCCCCACTCTAATAGGGGTTCAATATAAAAAGCC GGCAGAGAGCTGTCCAAGTCAGACGCGCCTC (SEQ ID NO: 35) | UCSC |
| ENG | Human | 888 | CGCCTTGCTGTGCCACTTTGGGACTTCCCTCCCTAGCC TGAGCTTCAGTTTTCCTGCCTGTTAGGCAGCCCCATGT CAACTGCACTTAGTAGGCCGGGTTTGATGCCCGACAAG ACGTGAAGTGGTGGAGGTGGGCAGGATCCCAGCGCTA CCATCTTCTTGAACCAGTGATCTCAACACATCGGATTTC TGTTTCCTCATCTGCAAAATGGGATCAGTGAGCTCAGGT GGGTCACAAATTCTACAGGAACTACTTTAGCCAAGCCC GGCCCCCTGAAAGTTCCCCTCGGTGGGCTGTTAGGGT GATTGTTTTCATCTGTGGGGCTCCCTGATGCGTCCCAC CCACCAGCCTTGGAGAGGGTGGGATGGGAGGGTGGG GTGCTTGGGGAGACAAGCCTAGAGCCTGGGCCCTCCC ACCCCACTGCCTCCCCCCATCCCAGGGCCCCCCACCC AGTGACAAAGCCCGTGGCACTTCCTCTACCCGGTTGGC AGGCGGCCTGGCCCAGCCCCTTCTCTAAGGAAGCGCA TTTCCTGCCTCCCTGGGCCGGCCGGGCTGGATGAGCC GGGAGCTCCCTGCTGCCGGTCATACCACAGCCTTCATC TGCGCCCTGGGGCCAGGACTGCTGCTGTCACTGCCAT CCATTGGAGCCCAGCACCCCCTCCCCGCCCATCCTTCG GACAGCAACTCCAGCCCAGCCCCGCGTCCCTGTGTCC ACTTCTCCTGACCCCTCGGCCGCCACCCCAGAAGGCTG GAGCAGGGACGCCGTCGCTCCGGCCGCCTGCTCCCCT CGGGTCCCCGTGCGAGCCCACGCCGGCCCCGGTGCC CGCCCGCAGCCCTGCCACTGGACACAGGATAAGGCCC AGCGCACAGGCCCCCACGTGGACACC (SEQ ID NO: 36) | Invivogen Inc. |

TABLE 4-continued

| Endothelial-specific promoter sequences | | | | |
|---|---|---|---|---|
| Promoter | Host Species | Size (bp) | Sequence | Source |
| FLT1 | Human | 1037 | TTTGCTTCTAGGAAGCAGAAGACTGAGGAAATGACTTG GGCGGGTGCATCAATGCGGCCAAAAAAGACACGGACA CGCTCCCCTGGGACCTGAGCTGGTTCGCAGTCTTCCCA AAGGTGCCAAGCAAGCGTCAGTTCCCCTCAGGCGCTCC AGGTTCAGTGCCTTGTGCCGAGGGTCTCCGGTGCCTTC CTAGACTTCTCGGGACAGTCTGAAGGGGTCAGGAGCG GCGGGACAGCGCGGGAAGAGCAGGCAAGGGGAGACA GCCGGACTGCGCCTCAGTCCTCCGTGCCAAGAACACC GTCGCGGAGGCGCGGCCAGCTTCCCTTGGATCGGACT TTCCGCCCCTAGGGCCAGGCGGCGGAGCTTCAGCCTT GTCCCTTCCCCAGTTTCGGGCGGCCCCCAGAGCTGAG TAAGCCGGGTGGAGGGAGTCTGCAAGGATTTCCTGAG CGCGATGGGCAGGAGGAGGGGCAAGGGCAAGAGGGC GCGGAGCAAAGACCCTGAACCTGCCGGGGCCGCGCTC CCGGGCCCGCGTCGCCAGCACCTCCCCACGCGCGCTC GGCCCCGGGCCACCCGCCCTCGTCGGCCCCCGCCCCT CTCCGTAGCCGCAGGGAAGCGAGCCTGGGAGGAAGAA GAGGGTAGGTGGGGAGGCGGATGAGGGGTGGGGGAC CCCTTGACGTCACCAGAAGGAGGTGCCGGGGTAGGAA GTGGGCTGGGGAAAGGTTATAAATCGCCCCCGCCCTC GGCTGCTCTTCATCGAGGTCCGCGGGAGGCTCGGAGC GCGCCAGGCGGACACTCCTCTCGGCTCCTCCCCGGCA GCGGCGGCGGCTCGGAGCGGGCTCCGGGGCTCGGGT GCAGCGGCCAGCGGGCGCCTGGCGGCGAGGATTACC CGGGGAAGTGGTTGTCTCCTGGCTGGAGCCGCGAGAC GGGCGCTCAGGGCGCGGGGCCGGCGGCGGCGAACAA GAGGACGGACTCTGGCGGCCGGGTCGTTGGCCGCGG GGAGCGCGGGCACCGGGCGAGCAGGCCGCGTCGCGC TCACC (SEQ ID NO: 37) | Invivogen Inc. |
| ICAM2 | Human | 399 | GTCTCCCAGGCATGACTCCAACAATGCATCCCATGGGA TTTGGGGTTCCCCAGATCTGGGGCTTGTAGGCCTGACT CTCCCCTGTGCACACGTCTCATACACGCATGCGTGCAC CCATTGCCTGCCCCGCCCCTTGCACAGGGAGTCAGCA GGGAGGACTGGGTTATGCCCTGCTTATCAGCAGCTTCC CAGCTTCCTCTGCCTGGATTCTTAGAGGCCTGGGGTCC TAGAACGAGCTGGTGCACGTGGCTTCCCAAAGATCTCT CAGATAATGAGAGGAAATGCAGTCATCAGTTTGCAGAA GGCTAGGGATTCTGGGCCATAGCTCAGACCTGCGCCC ACCATCTCCCTCCAGGCAGCCCTTGGCTGGTCCCTGCG AGCCCGTGGAGACTGCCAGTC (SEQ ID NO: 38) | Invivogen Inc. |

The Kozak consensus sequence is present in eukaryotic mRNA and is known to improve expression by enhancing translation initiation. Consequently, we introduce the Kozak consensus sequence (i.e. GCCACC, SEQ ID NO:39) upstream of the FVIII or LUC2 gene within the lentiviral vector plasmids.

HUVECs or LSECs were transduced at a multiplicity of infection (MOI)=50. Culture medium was collected at 24, 48, and 72 hrs and FVIII levels were subsequently measured in the conditioned medium using a human FVIII-specific ELISA, according to the manufacturer's instructions (Asserachrome). Using flow cytometry, the results showed that more than nearly 90% of HUVEC and LSEC cells were transduced compared to non-transduced HUVECs (FIG. 3). Relatively robust FVIII expression could be achieved in transduced HUVECs and LSECs with CMV, ICAM2 and EDN1mini. The Kozak translational consensus sequence significantly enhanced FVIII expression levels (FIG. 4). In particular, the Kozak consensus optimized ICAM2 construct yielded the highest FVIII expression in both HUVECs and LSECs. These results confirmed the robustness of the selected promoters in endothelial cells.

Figure 8A:
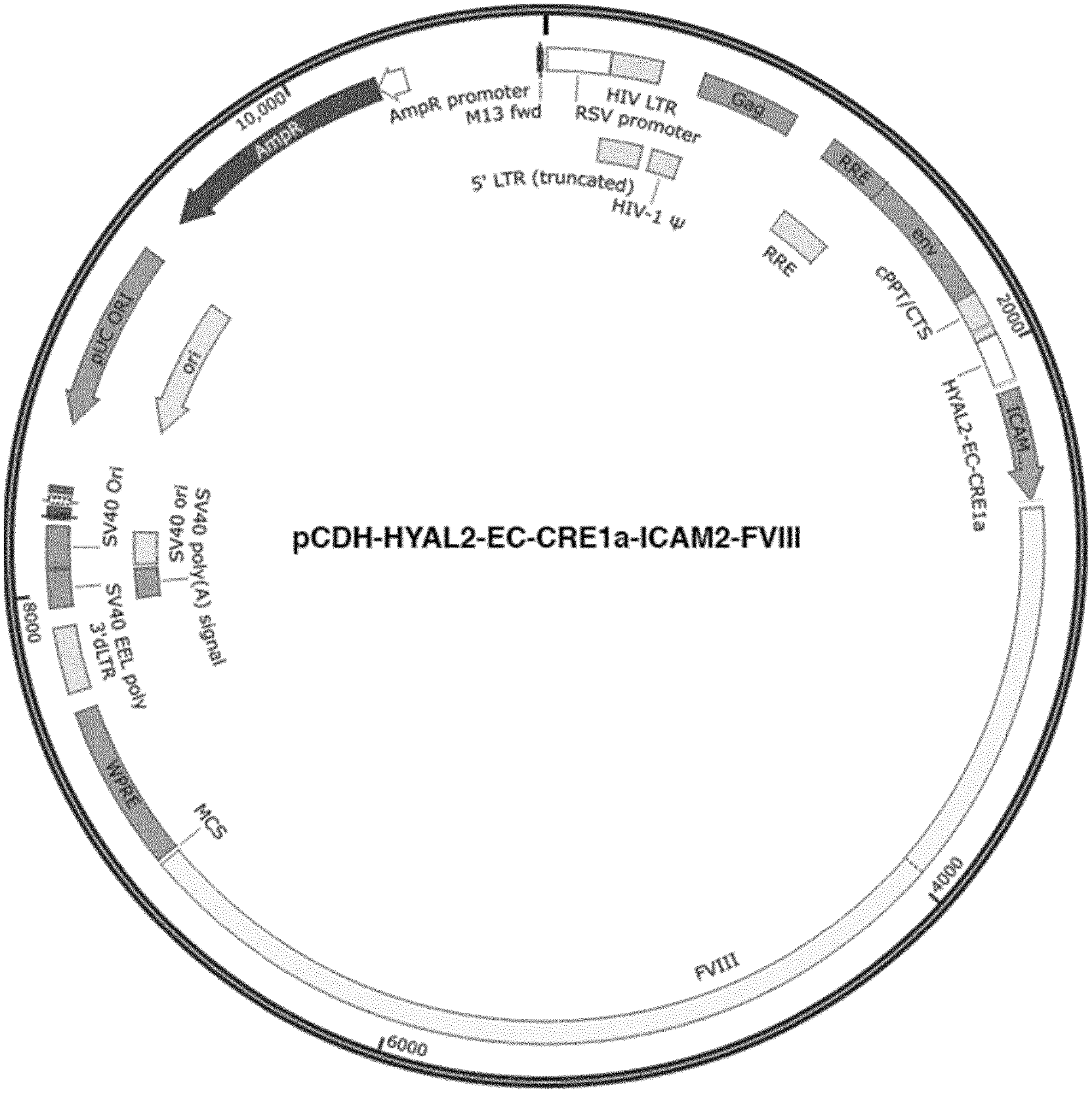
Figure 8B:
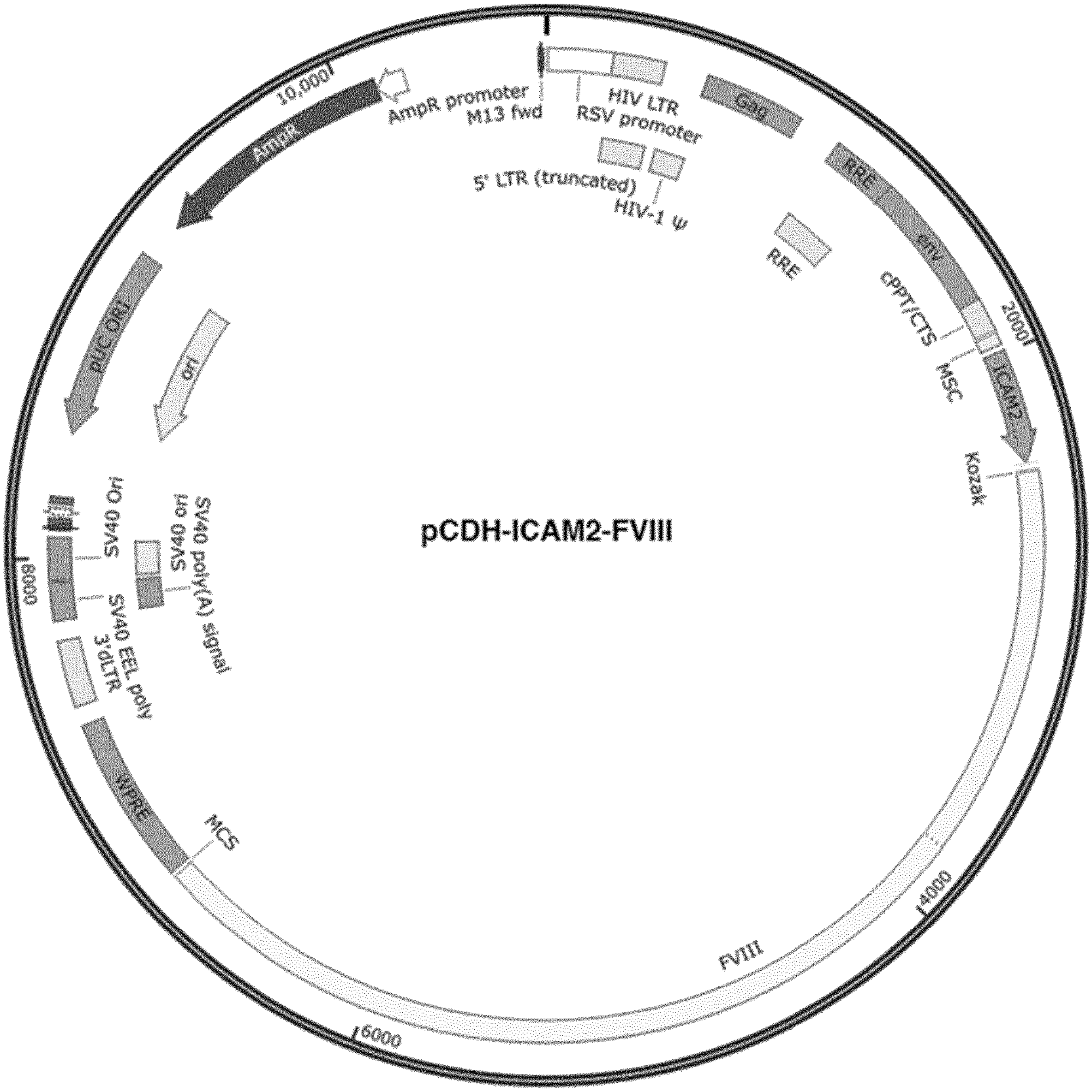
Figure 8C:
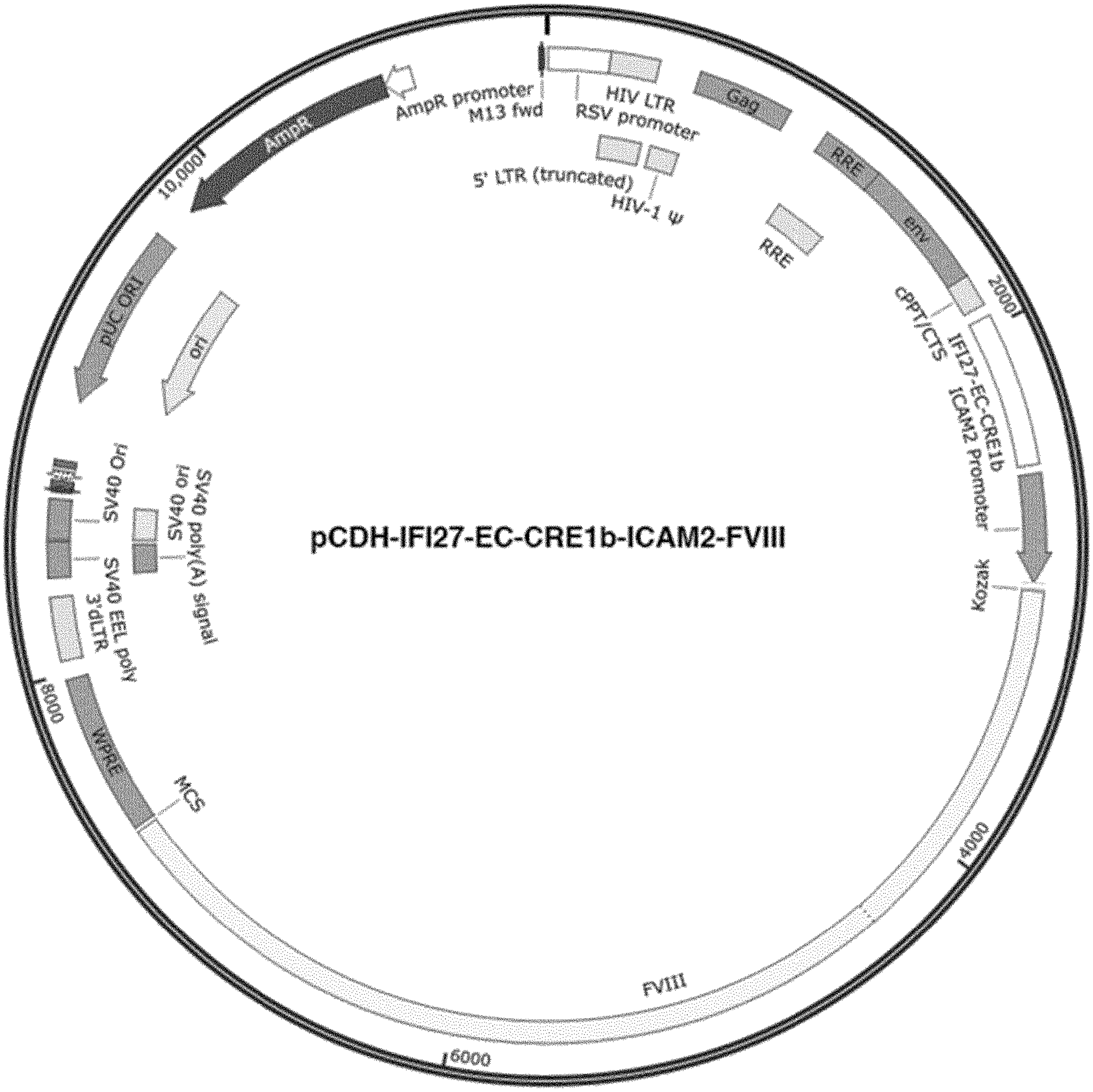
Figure 8D:
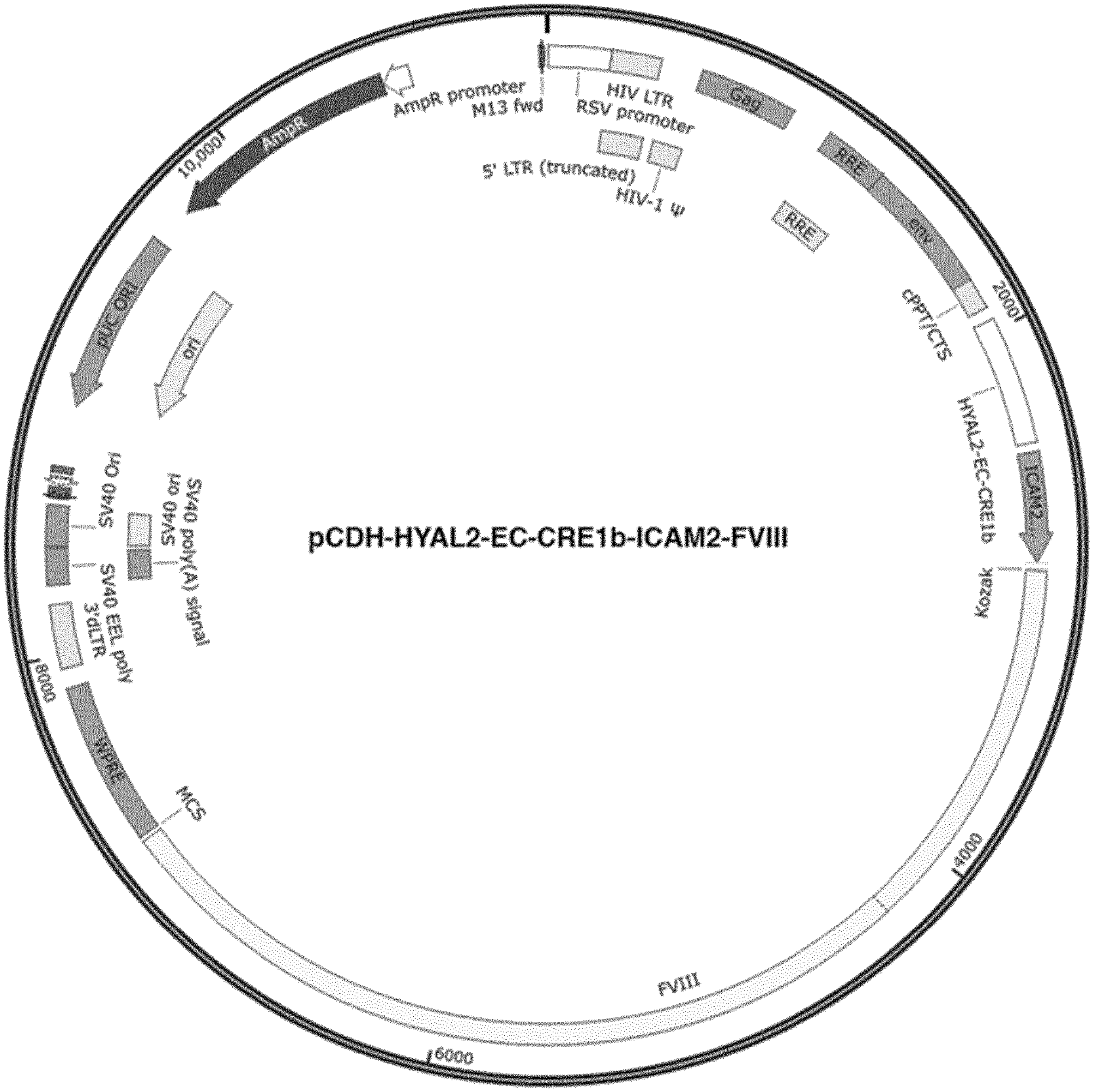

Example 3: In Vitro Validation of Endothelial-Specific (EC) CREs in Transfected HUVECs To validate whether the different EC-CREs identified by genome-wide computational analysis, led to enhanced FVIII expression when coupled to an EC-specific human ICAM2 promoter, human umbilical vein endothelial cells (HUVECs) were transfected in vitro with the corresponding lentiviral vector constructs: pCDH-EC-CRE-ICAM2-FVIII, with EC-CRE representing the respective regulatory elements named in FIG. 5, which were cloned upstream of the ICAM2 promoter driving the human FVIII gene in a pCDH lentiviral self-inactivating backbone. FIG. 8 shows 4 examples of such expression cassettes comprising HYAL2-EC-CRE1a (FIG. 8*a*—SEQ ID NO. 50), HYAL2-EC-CRE1b (FIG. 8*d*—SEQ ID NO. 51) and IF127-EC-CRE1b (FIG. 8*c*—SEQ ID NO. 52). The control vector (without EC-CRE) is depicted in FIG. 8*b* (SEQ ID NO. 49). Analogously, the person skilled in the art would be capable of cloning the other EC-CRE's in a similar manner in the expression vector backbone.

HUVECs were seeded at $1.5\times10^5$ cells/well of 6-well plate transfected 24 hr later with cationic lipid-based Lipofectamine 3000 (Invitrogen, USA). For HUVECs, 2.5 microgram of each plasmid were mixed with 3.75 microliter of Lipofectamine reagents. The P3000 reagent was mixed with each plasmid at 2 microliter per 1 microgram of plasmid and incubated at room temperature for 5 mins before adding to the HUVECs. Sixteen hours after transfection, the cell culture medium was removed and then replaced with fresh medium. 72 hrs later 100 microliter of the culture medium was collected and stored in −80° C. for FVIII quantification using a human FVIII-specific ELISA (Asserachrome). The results showed that about 70% of the CRMs resulted in increased FVIII expression in transfected HUVECs in vitro, relative to the control lentiviral vector without CRE (i.e. 23 out of 32). (FIG. 5).

Example 4: In Vivo Validation of Endothelial-Specific (EC) CREs Following Lentiviral Transduction in Mice Next, it was validated whether the EC-CREs identified by genome-wide computational analysis, led to enhanced FVIII expression in mice in vivo. Self-inactivating lentiviral vectors were used to express the human codon usage optimized B-domain deleted FVIII from an EC-specific human ICAM2 promoter. To test the impact of the EC-CRE on FVIII expression, the HYAL2-EC-CRE1a (SEQ ID NO. 50), HYAL2-EC-CRE1b (SEQ ID NO. 51) and IF127-EC-CRE1b (SEQ ID NO. 52) elements were cloned upstream of the ICAM2 promoter driving the human FVIII gene. Said expression cassettes comprise respectively the EC-CRE's HYAL2-EC-CRE1a, HYAL2-EC-CRE1b and IF127-EC-CRE1b. Analogously, the person skilled in the art would be capable of cloning the other EC-CRE's in a similar manner in an expression vector backbone. In these examples the pCDH-ICAM2-FVIII backbone is used. A lentiviral vector identical in design but without any upstream EC-CRE was used as control (SEQ ID NO. 49) to compare FVIII expression levels. Lentiviral vector particles were manufactured by transient cotransfection of HEK293 packaging cells with lentiviral vector and helper plasmids (Cyagen, USA). Vector titer was determined and expressed in Transducing Units per ml (TU/ml). Lentiviral vectors were retro-orbitally injected in 2 day-old neonatal CB17-SCID mice (Taconic). The vector preparation was supplemented with 40 microgram/ml polybrene in a total volume of 80 microliter. A total vector dose of $1\times10^8$TU was used. Plasma was collected 5 weeks post-injection and FVIII was measured using a human FVIII-specific ELISA.

A significant increase was detected in FVIII expression in vivo when the EC-CRE were present compared to a control lentiviral vector without EC-CRE (FIG. 6). In particular, a 27-fold increase in FVIII could be detected following in vivo transduction with lentiviral vectors containing the IF127-EC-CRE1b compared to a control lentiviral vector without EC-CRE (ICAM2-FVIII). Similarly, the HYAL2-EC-CRE1a also boosted FVIII expression, but to a lesser extent (5-fold). This is consistent with the increased FVIII expression following in vitro HUVEC transfection with the IF127-EC-CRE1b and HYAL2-EC-CRE1a vectors compared to controls without EC-CRE (ICAM2-FVIII) (FIG. 5). HYAL2-EC-CRE1b did not increase FVIII expression in vivo, consistent with the lower levels of FVIII expression in transfected HUVECs in vitro (FIG. 5).

Example 5: Confirmation of Increased Gene Expression by EC-CRE in Organ-Derived Endothelial Cells Isolated from Lentivirally Transduced Mice The mice were injected with the lentiviral vectors containing the ICAM2-FVIII (no CRE control—SEQ ID NO. 49) or IF127-EC-CRE1b-ICAM2-FVIII (SEQ ID NO. 52) expression cassette. After euthanization, the liver and spleen were processed to obtain their respective endothelial populations (i.e. liver sinusoidal endothelial cells, splenic endothelial cells). First, a single cell suspension was obtained from the liver and spleen tissue using the GentleMACS dissociator (Product no—130-093-235, Miltenyi Biotec) according to the manufacturer's protocol (Liver Dissociation Kit: Product code: 130-105-807; Miltenyi Biotec.—http://www.miltenyibiotec.com/en/products-and-services/macs-sample-preparation/sample-dissociation/tissue-dissociation-kits/liver-dissociation-kit-mouse.aspx), spleen (Spleen Dissociation Kit: Product code: 130-095-926; Miltenyi Biotec.—http://www.miltenyibiotec.com/en/products-and-services/macs-sample-preparation/sample-dissociation/tissue-dissociation-kits/liver-dissociation-kit-mouse.aspx).

Subsequently, the single cell suspension from each organ was subjected to MACS cell separation technology (Miltenyi Biotec) to sort out the respective endothelial populations. The single cell suspension obtained from liver and spleen were therefore tagged with CD146 microbeads, according to the manufacturer's instructions (Product code: 130-092-007; Miltenyi Biotec.—http://www.miltenyibiotec.com/en/products-and-services/macs-sample-preparation/sample-dissociation/tissue-dissociation-kits/liver-dissociation-kit-mouse.aspx), allowing positive selection of the respective liver-derived and splenic endothelial cells. One to $1.6\times10^6$ CD146-positive endothelial cells were obtained from the liver and $6.9\text{-}8.1\times10^5$ CD146-positive endothelial cells were obtained from the spleen. The isolated cells were plated at a density of 25000 cells/well of 48 well plates in 200 microliterof Endothelial Basal Medium supplemented with growth factors.

Total RNA was isolated from the cells using RNeasy Micro Kit (Qiagen) according to manufacturer's instruction. Isolated RNA concentrations were measured using Nanodrop 1000 (Thermo scientific, MA, USA). Complementary DNA (cDNA) was synthesized from 75 ng-35 ng isolated RNA using Superscript III First-Strand synthesis system (Invitrogen) according to manufacturer's instructions. The qRT-PCR was performed using SYBR Green qPCR mix (Life technology) in a qPCR ABI Prism 7900HT (Applied Biosystems, Foster City/CA, USA) using FVIII specific primers 5'-AACGGCTACGTGAACAGAAG-3' (forward—SEQ ID NO. 53) and 5'-GATAGGGCTGATTTCCAGGC-3' (reverse—SEQ ID NO. 54). The expression levels were normalized to GAPDH (glyceraldehyde-3-phosphate dehydrogenase) mRNA expression, obtained by using the forward primer 5'-GAAGGTGAAGGTCGGAGTC-3' (SEQ ID NO. 55) and reverse primer 5'-GAAGATGGTGATGGGATTTC-3' (SEQ ID NO. 56).

The results showed that the IF127-EC-CRE1b element enhanced FVIII expression in CD146-positive endothelial cells obtained from liver or spleen, as reflected by increased FVIII mRNA levels in mice injected with the lentiviral vector containing the IF127-EC-CRE1b-ICAM2-FVIII cassette compared to the ICAM2-FVIII control (FIG. 7).

The invention claimed is:

1. A nucleic acid regulatory element for enhancing endothelial cell specific gene expression consisting of a sequence selected from the group consisting of SEQ ID NOS: 3, 4, 5, 6, 7, 9, 10, 11, 15, 18, 21, 22, 24, 25, 28, 29 and 30.

2. A nucleic acid regulatory element for enhancing endothelial cell-specific gene expression consisting of the sequence of SEQ ID NO: 1.

3. A nucleic acid regulatory element for enhancing gene expression in endothelial cells consisting of a complement of a sequence as defined by any one of SEQ ID NOS: 3, 4, 5, 6, 7, 9, 10, 11, 15, 18, 21, 22, 24, 25, 28, 29 or 30.

4. A nucleic acid expression cassette comprising one or more nucleic acid regulatory elements according to claim 1 or 2, operably linked to a promoter.

5. The nucleic acid expression cassette according to claim 4, wherein the nucleic acid regulatory element is operably linked to a promoter and a transgene.

6. The nucleic acid expression cassette according to claim 4, wherein the promoter is an endothelial cell-specific promoter selected from the group consisting of 1F127, ICAM2, VWF, EDN1, ENG, ECSCR, CDH5, PECAM1, HHIP, TIE1 and HYAL2.

7. The nucleic acid expression cassette according to claim 5, wherein the transgene encodes a therapeutic protein or an immunogenic protein.

8. The nucleic acid expression cassette according to claim 5, wherein the transgene encodes coagulation factor VIII (FVIII).

9. The nucleic acid expression cassette according to claim 4, further comprising a polyadenylation signal.

10. A vector comprising the nucleic acid regulatory element according to claim 1 or 2.

11. The vector according to claim 10, wherein the vector is a lentiviral vector, an adeno-associated viral (AAV) vector, or a adenoviral vector.

12. The vector according to claim 10, wherein the vector is a plasmid, a minicircle, an episomal vector, or a transposon-based vector.

13. A pharmaceutical composition comprising a nucleic acid expression cassette or a vector each comprising the nucleic acid regulatory element according to claim 1 or 2, and a pharmaceutically acceptable carrier.

14. A method for expressing a transgene product in endothelial cells, comprising:

i) introducing a nucleic acid expression cassette or a vector each comprising the nucleic acid regulatory element according to claim 1 or 2 operably linked to a promoter and a transgene, into the cells; and ii) expressing a transgene product in the cells.

15. The nucleic acid expression cassette according to claim 9, wherein the polyadenylation signal is the Simian Virus 40 (SV40) polyadenylation signal.

16. The vector according to claim 12, wherein the transposon-based vector is a PiggyBac-based vector or a Sleeping Beauty-based vector.

17. The nucleic acid expression cassette according to claim 5, wherein the transgene encodes von Willebrand factor (vWF).

18. The nucleic acid expression cassette according to claim 5, wherein the transgene encodes small interfering RNA.

19. The nucleic acid expression cassette according to claim 5, wherein the transgene encodes VEGF.

20. The nucleic acid expression cassette according to claim 5, wherein the transgene encodes PLGF.

21. The nucleic acid regulatory element according to claim 1, consisting of the sequence set forth in SEQ ID NO:22.

* * * * *